United States Patent
Zalev et al.

(10) Patent No.: US 9,743,839 B2
(45) Date of Patent: Aug. 29, 2017

(54) PLAYBACK MODE IN AN OPTOACOUSTIC IMAGING SYSTEM

(71) Applicant: Seno Medical Instruments, Inc., San Antonio, TX (US)

(72) Inventors: Jason Zalev, Thornhill (CA); Bryan Clingman, Chandler, AZ (US)

(73) Assignee: Seno Medical Instruments, Inc., San Antonio, TX (US)

( * ) Notice: Subject to any disclaimer, the term of this patent is extended or adjusted under 35 U.S.C. 154(b) by 242 days.

(21) Appl. No.: 13/842,225

(22) Filed: Mar. 15, 2013

(65) Prior Publication Data

US 2013/0296701 A1 Nov. 7, 2013

Related U.S. Application Data

(63) Continuation-in-part of application No. 13/793,808, filed on Mar. 11, 2013, now Pat. No. 9,330,452, (Continued)

(51) Int. Cl.
 *G06K 9/00* (2006.01)
 *A61B 5/00* (2006.01)
 *A61B 8/00* (2006.01)

(52) U.S. Cl.
 CPC .......... *A61B 5/0095* (2013.01); *A61B 8/4281* (2013.01); *A61B 8/463* (2013.01);
 (Continued)

(58) Field of Classification Search
 CPC .................................................. A61B 5/0095
 (Continued)

(56) References Cited

U.S. PATENT DOCUMENTS

| 4,651,850 A | 3/1987 | Matsuo |
| 5,062,715 A | 11/1991 | Nakata et al. |

(Continued)

FOREIGN PATENT DOCUMENTS

| EP | 0282234 A1 | 9/1988 |
| JP | 2003126091 A | 5/2003 |

(Continued)

OTHER PUBLICATIONS

"MATLAB: Programming Fundamentals", The Math Works, Inc., R2011 b, 2011.

(Continued)

*Primary Examiner* — Andrew Moyer
(74) *Attorney, Agent, or Firm* — Harness, Dickey & Pierce, P.L.C.

(57) ABSTRACT

An optoacoustic imaging system includes a handheld probe and a computing subsystem. The probe includes an ultrasound transducer array, the array being capable of receiving an acoustic return signal. The system further includes a light source capable of generating pulses of light and delivering the pulses to the handheld probe. The computing subsystem generates images from the acoustic return signal, and the subsystem is configured to store raw data frames in a buffer. Upon actuation of a playback mode via the user input device, the computing subsystem is caused to switch from a live mode wherein images from the acoustic return signal are displayed substantially in real time to the playback mode wherein images are generated from the frames stored in the buffer. One or more parameters affecting processing of the frames into an output image displayed upon the display can be enabled during the playback mode such that the output image varies from an image generated from the frame when the system is not in the playback mode. In this manner, the user can play back an area of interest using alternative filters (Continued)

that highlight different physiological features of the region of interest, alternative modes of display, and other alternative parameters.

13 Claims, 37 Drawing Sheets

Related U.S. Application Data which is a continuation-in-part of application No. 13/507,217, filed on Jun. 13, 2012, now Pat. No. 9,289,191, application No. 13/842,225, which is a continuation-in-part of application No. 13/507,223, filed on Jun. 13, 2012, and a continuation-in-part of application No. 13/341,950, filed on Dec. 31, 2011, now Pat. No. 8,686,335, and a continuation-in-part of application No. 13/287,759, filed on Nov. 2, 2011, now abandoned, and a continuation-in-part of application No. 13/746,905, filed on Jan. 22, 2013.

(52) U.S. Cl.
CPC ............ *A61B 8/465* (2013.01); *A61B 8/466* (2013.01); *A61B 2560/0431* (2013.01); *A61B 2562/16* (2013.01)

(58) Field of Classification Search
USPC ........................................................ 382/128
See application file for complete search history.

(56) References Cited

U.S. PATENT DOCUMENTS

| | | | |
|---|---|---|---|
| 5,293,873 A | | 3/1994 | Fang |
| 5,341,204 A | | 8/1994 | Grant et al. |
| 5,348,002 A | | 9/1994 | Caro |
| 5,460,182 A | | 10/1995 | Goodman et al. |
| 5,504,281 A | | 4/1996 | Whitney et al. |
| 5,840,023 A | | 11/1998 | Oraevsky et al. |
| 5,935,288 A | | 8/1999 | DiGiovanni et al. |
| 5,946,081 A | | 8/1999 | Lai et al. |
| 5,977,538 A | | 11/1999 | Unger et al. |
| 6,126,605 A | | 10/2000 | Washburn et al. |
| 6,263,094 B1 * | | 7/2001 | Rosich et al. ............... 382/128 |
| 6,617,559 B1 | | 9/2003 | Emery et al. |
| 6,650,928 B1 | | 11/2003 | Gailly et al. |
| 6,716,172 B1 | | 4/2004 | Kerby et al. |
| 6,979,292 B2 | | 12/2005 | Kanayama et al. |
| 7,741,900 B1 | | 6/2010 | Li |
| 8,298,144 B2 | | 10/2012 | Burcher |
| 8,784,318 B1 | | 7/2014 | Napolitano et al. |
| 2004/0147842 A1 | | 7/2004 | Desmarais |
| 2004/0167619 A1 | | 8/2004 | Case et al. |
| 2004/0253572 A1 | | 12/2004 | Chosack et al. |
| 2005/0004458 A1 | | 1/2005 | Kanayama et al. |
| 2005/0105877 A1 | | 5/2005 | Nappi et al. |
| 2005/0187471 A1 | | 8/2005 | Kanayama et al. |
| 2006/0167531 A1 | | 7/2006 | Gertner et al. |
| 2006/0262903 A1 | | 11/2006 | Diebold |
| 2007/0093702 A1 | | 4/2007 | Yu et al. |
| 2007/0106146 A1 | | 5/2007 | Altmann et al. |
| 2007/0161898 A1 | | 7/2007 | Hao et al. |
| 2007/0236492 A1 | | 10/2007 | Ahn et al. |
| 2008/0051655 A1 | | 2/2008 | Sato et al. |
| 2008/0114910 A1 * | | 5/2008 | He ..................... G01S 7/52017 710/52 |
| 2008/0177183 A1 | | 7/2008 | Courtney et al. |
| 2008/0242988 A1 | | 10/2008 | Yoshida et al. |
| 2008/0255433 A1 | | 10/2008 | Prough et al. |
| 2009/0000383 A1 | | 1/2009 | Knowles et al. |
| 2009/0124902 A1 | | 5/2009 | Herrmann |
| 2009/0171195 A1 | | 7/2009 | Barbour |
| 2009/0187099 A1 | | 7/2009 | Burcher |
| 2009/0295941 A1 | | 12/2009 | Nakajima et al. |
| 2010/0049044 A1 * | | 2/2010 | Burcher ............... A61B 5/0059 600/437 |
| 2010/0080427 A1 * | | 4/2010 | Yeluri et al. .................. 382/128 |
| 2010/0094134 A1 | | 4/2010 | Zhu et al. |
| 2010/0127171 A1 | | 5/2010 | Jonsson et al. |
| 2010/0137715 A1 * | | 6/2010 | Kakee ............................ 600/443 |
| 2010/0154547 A1 | | 6/2010 | Fukada et al. |
| 2010/0249562 A1 | | 9/2010 | Zhang et al. |
| 2010/0249570 A1 | | 9/2010 | Carson et al. |
| 2010/0285518 A1 | | 11/2010 | Viator et al. |
| 2011/0098572 A1 | | 4/2011 | Chen et al. |
| 2011/0144495 A1 | | 6/2011 | Wilkening et al. |
| 2011/0201914 A1 * | | 8/2011 | Wang et al. .................. 600/407 |
| 2011/0238618 A1 | | 9/2011 | Valdiserri et al. |
| 2011/0303015 A1 | | 12/2011 | Ichihara et al. |
| 2011/0319743 A1 | | 12/2011 | Satoh |
| 2011/0319744 A1 | | 12/2011 | Tsujita et al. |
| 2012/0029829 A1 | | 2/2012 | Li et al. |
| 2012/0054619 A1 * | | 3/2012 | Spooner et al. .............. 715/723 |
| 2013/0041267 A1 | | 2/2013 | Ntziachristos et al. |
| 2013/0060140 A1 | | 3/2013 | Sinelnikov |
| 2013/0190589 A1 | | 7/2013 | Chen et al. |
| 2013/0190591 A1 | | 7/2013 | Hirson et al. |
| 2013/0190595 A1 | | 7/2013 | Oraevsky et al. |
| 2013/0289381 A1 | | 10/2013 | Oraevsky et al. |
| 2013/0301380 A1 | | 11/2013 | Oraevsky et al. |
| 2014/0194723 A1 | | 7/2014 | Herzog et al. |

FOREIGN PATENT DOCUMENTS

| | | |
|---|---|---|
| WO | 0110295 A1 | 2/2001 |
| WO | 01-78009 A2 | 10/2001 |
| WO | 2004010866 A1 | 2/2004 |
| WO | 2006061829 A1 | 6/2006 |
| WO | 2011098101 A1 | 8/2011 |
| WO | 2011137385 A1 | 11/2011 |

OTHER PUBLICATIONS

Beard, Paul, "Biomedical photoacoustic Imaging", Interface Focus rsfs20110028; published ahead of print Jun. 21, 2011, doi:10.1098/rsfs.2011.0028 2042-8901.

Castelino, Robin; "Biomedical Applications of Photoacoustics for Thermal Therapy", 2008.

Dahl, Jeremy J. and Trahey, Gregg E., "Off-Axis Scatterer Filters for Improved Aberration Measurements", 2003 IEEE Ultrasonics Symposium—344, 2003.

Ermilov et al., "Development of Laser Optoacoustic and Ultrasonic Imaging System for breast cancer utilizing handheld array probes", Photons Plus Ultrasound Imaging and Sensing 2009, SPIE vol. 7177.

Intel, Intel Integrated Performance Primitives for Intel Architecture, Reference Manual, vol. 2: Image and Video Processing, Sep. 2007.

Kingsbury, "Complex Wavelets for Shift Invariant Analysis and Filtering of Signals", Journal of Applied and Computational Harmonic Analysis, vol. 10, No. 3, May 2001, pp. 234-253.

Kuchment, P. et al., "Mathematics of Photoacoustic and Thermoacoustic Tomography", Mathematics Dept., Texas A&M University, Dec. 10, 2009.

Ma, Rui, et al. "Multispectral optoacoustic tomography (MSOT) scanner for whole-body small animal imaging." Optics express 17.24 (2009): 21414-21426.

Misiti, Michel et al., "Wavelet Toolbox", The MathWorks, Inc., User's Guide, Version 1, 1996.

Munch, Beat et al., "Stripe and ring artifact removal with combined wavelet—Fourier filtering", Optics Express 8567, vol. 17, No. 10, May 11, 2009.

Nguyen, "A Family of Inversion Formulas in Thermoacoustic Tomography", Department of Mathematics, Texas A&M University, Mar. 5, 2009.

O'Donnell, Matthew et al., "Correlation-Based Aberration Correction in the Presence of Inoperable Elements", IEEE Transactions of Ultrasonics, Ferroelectrics, and Frequency Control, vol. 39, No. 6, Nov. 1992.

(56) References Cited

OTHER PUBLICATIONS

Otto et al., "Coregistration of Angiogenesis Related Hemoglobin and Tissue Density in breast tumors using opto-acoustic imaging combined with ultrasound", 2009.

Robert J Talbert et al, "Photoacoustic discrimination of viable and thermally coagulated blood using a two-wavelength method for burn injury monitoring; Photoacoustic blood discrimination", Physics in Medicine and Biology, Institute of Physics Publishing, Bristol GB, (Apr. 7, 2007), vol. 52, No. 7.

Sendur et al., "Bivariate Shrinkage Functions for Wavelet-Based Denoising Exploiting Interscale Dependency", IEEE Transactions on Signal Processing, vol. 50, No. 11, Nov. 2002.

\* cited by examiner

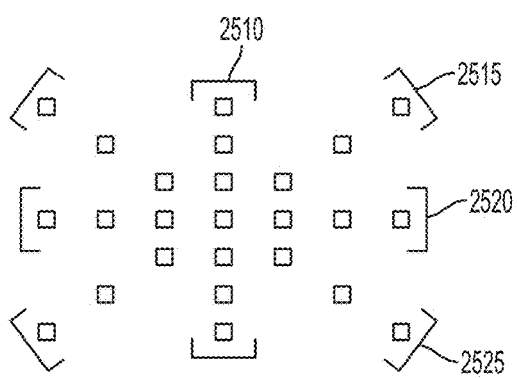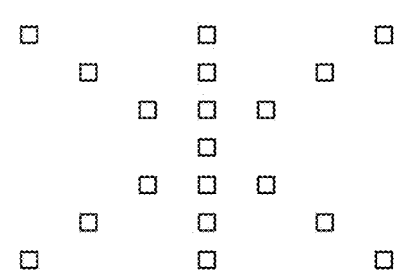
FIG. 25A        FIG. 25B
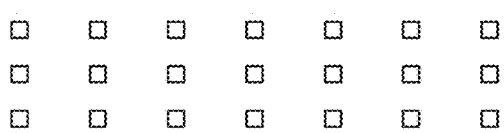
FIG. 25C

PLAYBACK MODE IN AN OPTOACOUSTIC IMAGING SYSTEM

This application is a continuation-in-part of U.S. patent application Ser. No. 13/793,808 filed Mar. 11, 2013, entitled "Statistical Mapping In An Optoacoustic Imaging System," which is a continuation-in-part of U.S. patent application Ser. No. 13/507,217 filed Jun. 13, 2012 entitled "System and Method for Acquiring Optoacoustic Data and Producing Parametric Maps Thereof." This application is also a continuation-in-part of U.S. patent application Ser. No. 13/507,223, filed Jun. 13, 2012, entitled "System and Method for Storing Data Associated With the Operation of a Dual Modality Optoacoustic/Ultrasound System" and U.S. patent application Ser. No. 13/341,950, filed Dec. 31, 2011, entitled "System and Method for Adjusting the Light Output of an Optoacoustic Imaging System" and U.S. patent application Ser. No. 13/287,759 entitled "Handheld Optoacoustic Probe" filed Nov. 2, 2011. This application is also a continuation-in-part of U.S. patent application Ser. No. 13/746,905 filed Jan. 22, 2013, entitled "Probe With Optoacoustic Isolator." The entire disclosures of those applications, including the CD-ROM Appendix to U.S. patent application Ser. No. 13/507,217, are incorporated herein by reference.

This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The present invention relates in general to the field of medical imaging, and in particular to system relating to optoacoustic imaging.

BRIEF DESCRIPTION OF THE DRAWINGS

The foregoing and other objects, features, and advantages of the invention will be apparent from the following more particular description of preferred embodiments as illustrated in the accompanying drawings, in which reference characters refer to the same parts throughout the various views. The drawings are not necessarily to scale, emphasis instead being placed upon illustrating principles of the invention.

FIGS. 25A-25C show a representation of several examples of various organizations of two dimensional arrays of transducer elements.

Figure 1:
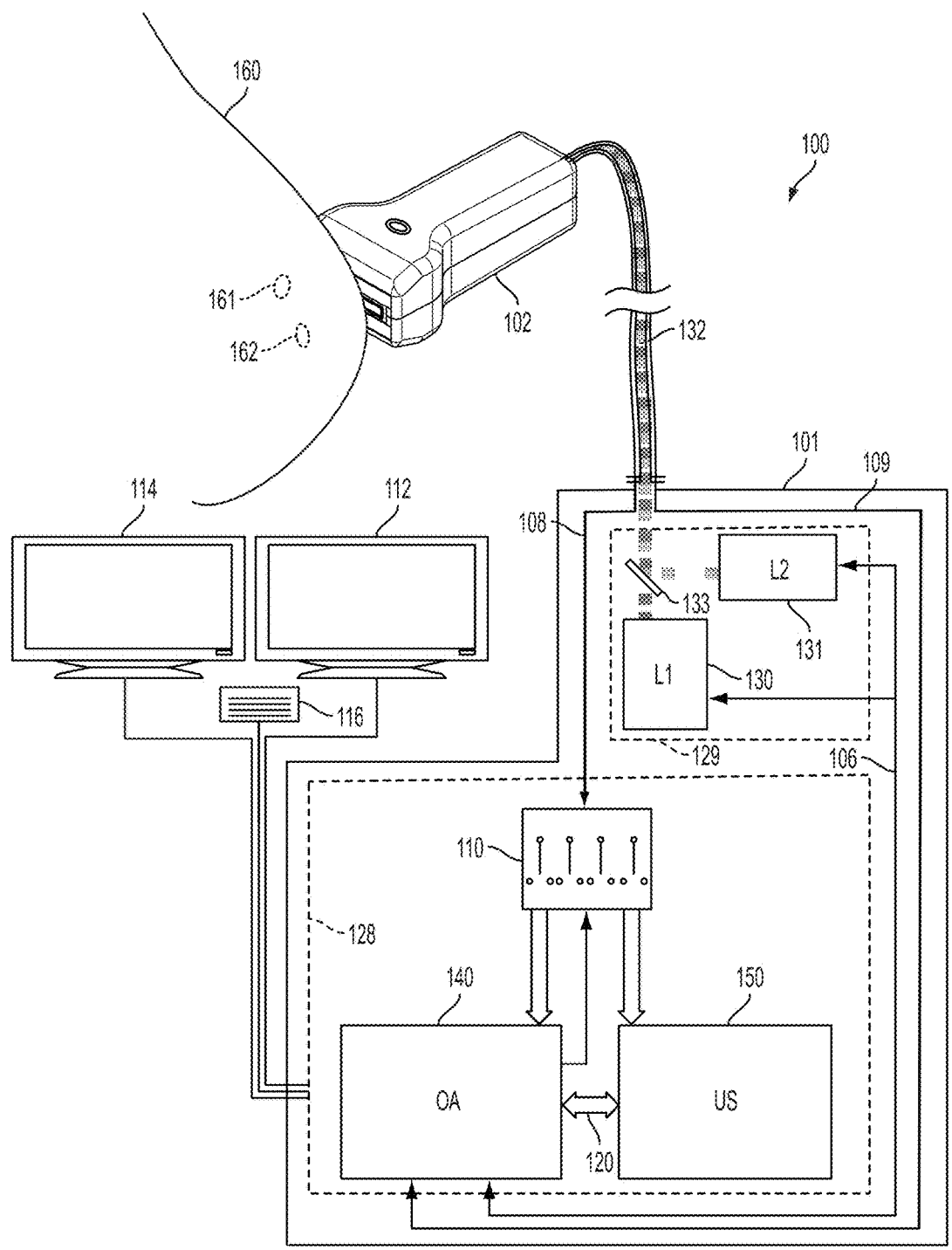
FIG. 1 shows a schematic block diagram illustrating an embodiment of a combined optoacoustic and ultrasound system that may be used as a platform for the methods and devices disclosed herein.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description and drawings are illustrative and are not to be construed as limiting. Numerous specific details are described to provide a thorough understanding. However, in certain instances, well-known or conventional details are not described in order to avoid obscuring the description. References to one or an embodiment in the present disclosure are not necessarily references to the same embodiment; and, such references mean at least one.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The systems and methods are described below with reference to, among other things, block diagrams, operational illustrations and algorithms of methods and devices to process optoacoustic imaging data. It is understood that each block of the block diagrams, operational illustrations and algorithms and combinations of blocks in the block diagrams, operational illustrations and algorithms, can be implemented by means of analog or digital hardware and computer program instructions.

These computer program instructions can be provided to a processor of a general purpose computer, special purpose computer, ASIC, or other programmable data processing apparatus, such that the instructions, which execute via the processor of the computer or other programmable data processing apparatus, implements the functions/acts specified in the block diagrams, operational block or blocks and or algorithms.

In some cases frequency domain based algorithms require zero or symmetric padding for performance. This padding is not essential to describe the embodiment of the algorithm so it is sometimes omitted from the description of the processing steps. In some cases, where padded is disclosed in the steps, the algorithm may still be carried out without the padding. In some cases padding is essential, however, and cannot be removed without corrupting the data.

In some alternate implementations, the functions/acts noted in the blocks can occur out of the order noted in the operational illustrations. For example, two blocks shown in succession can in fact be executed substantially concurrently or the blocks can sometimes be executed in the reverse order, depending upon the functionality/acts involved.

Reference will now be made in more detail to various embodiments of the present invention, examples of which are illustrated in the accompanying drawings and the Appendix filed in related U.S. patent application Ser. No. 13/507,217, filed Jun. 13, 2012. As will be apparent to one of skill in the art, the data structures described in the Appendix and processing steps described in the Appendix (including in pseudo-code) may be implemented in a variety of other ways without departing from the spirit of the disclosure and scope of the invention herein. The Appendix is intended to provide one manner of implementing the concepts disclosed herein the purpose of illustration and to facilitate understanding.

System and Method for Presenting Optoacoustic Data

Turning to FIG. 1, and as described generally below under the heading Optoacoustic System and Method is a device 100, including a probe 102 connected via a light path 132 and an electrical path 108 to a system chassis 101. Within the system chassis 101 is housed a light subsystem 129 and a computing subsystem 128. The computing subsystem 128 includes one or more computing components for, among other things, optoacoustic control and analysis. In an embodiment, through the sampling of transducers in the probe 102, the device 100 can obtain data received in response to: stimulation caused by pulsed light sources 130, 131 (i.e., the optoacoustic return signal); and to stimulation caused by acoustic output of the ultrasound transducer elements.

In an embodiment, to obtain an optoacoustic return signal corresponding to a single light event occurring in a volume of tissue, the transducers in the probe 102 can be sampled for a period of time after the light event. In an embodiment, the transducers in the probe 102 can be sampled for a period of time after the light event approximately equal to the time it would take sound to travel a desired distance in the tissue. In an embodiment, the desired distance may be at least one centimeter. In an embodiment, the desired distance may be at least two centimeters. In an embodiment, the period of sampling would correspond to the amount of time it would take sound to travel at least one, but not more than 15 centimeters in tissue. In an embodiment, the period of sampling would correspond to the amount of time it would take sound to travel at least five, but not more than 12 centimeters in tissue. In an embodiment, the desired distance may be less than one centimeter. The sampling rate should be sufficient to obtain sufficient information in the optoacoustic return signal. In an embodiment, the sampling rate is above 20 Mhz, in another embodiment, the sampling rate is above about 30 Mhz. In an embodiment the sampling is at least 8 bits, and more preferably more than 12 bits. In an embodiment, sampling is done at 14 bits. In an embodiment, sampling is done at resolutions higher than 14 bits.

In an exemplary embodiment, to obtain the optoacoustic return signal, 128 or 256 transducers (i.e., channels) in a probe 102 are sampled at 14 bits for approximately 65 microseconds (μs) at a sampling rate of 31.25 Mhz. The 65 us of sampling at 31.25 Mhz results in over 2,000 samples. In an embodiment, 2,045 14 bit samples may be stored for each transducer or channel. For efficiency, the 14 bit samples can be stored in a 16 bit computer word. The samples associated with a single light event, along with additional header information relating to the light event, can be stored in a frame of about 512 KB (kilobytes) for 128 channels, or 1 MB (megabyte) for 256 channels. Thus, in an exemplary embodiment, the optoacoustic return signal from a light event, including header information, can be stored in either 512 KB, or 1 MB. As discussed further below, in an embodiment, the device 100 comprises at least two light sources 130, 131 operating at different light wavelengths. In an embodiment with two light sources 130, 131 operating at different light wavelengths, the optoacoustic return signal from one light event from each of the light sources can be used in the method and system for presenting the optoacoustic data. In an embodiment, the device 100 comprises a single light source that may be operated at different wavelengths, such as a tunable laser that can change wavelengths quickly enough for use as described herein. In an embodiment, the device 100 comprises at least two light sources 130, 131, each being capable of tuning to a plurality of different wavelengths. In an embodiment, the device 100 comprises one light source 130 operating a one light wavelength, and at least one additional light source 131 capable of being tuned to a plurality of different wavelengths.

As used herein, the term sinogram refers to sampled data or processed sampled data corresponding to a single light event. The term sinogram is also used at times to refer to an image presented by using the original or filtered sampled data as gray scale or color data, wherein there is a correspondence between the samples in the data and the voxels in the image. In an embodiment using optoacoustic return signals from two different light events, each corresponding to a different wavelength of light, the term short sinogram refers to the sinogram corresponding to the shorter wavelength of light generating a light event, and the term long sinogram refers to the sinogram corresponding to the longer wavelength of light generating a light event. Because more than two different wavelengths may be used, the use of the terms short and long wavelength are intended to embody the extended context of a system with an arbitrary number of wavelengths.

In an embodiment, as discussed in more detail below, sinograms are processed to produce an envelope image. As used herein the term short envelope image refers to an envelope image corresponding to the short sinogram, and the term long envelope image refers to an envelope image corresponding to the long sinogram. In an embodiment, the short sinogram and long sinogram are each processed separately to produce a short envelope image and a long envelope image, respectively. The short and long envelope images are then used together to generate parametric images. From the parametric images, maps can be created of oxygenation, hemoglobin and masked oxygenation. These maps can be co-registered data representing an ultrasound image of substantially the same volume, and can thereafter produce one or more of an oxygenation image, a hemoglobin image and a masked oxygenation image. In an embodiment, the oxygenation image, hemoglobin image and masked oxygenation image reflect information about the composition of the volume of tissue. The terms parametric map and parametric image are in some instances used interchangeably. The use of the term map generally relates to the correspondence between the image and a volume. Parametric maps may be represented in numerous ways, including, for example, as a single-channel (i.e., grayscale) representation, as a color (i.e., RGB) representation, or as a color with transparency (RGBA) representation. Parametric maps may be used to convey qualitative or quantitative information about one or more parameters. A parametric map or parametric image may be represented in computer memory or presented as a displayed representation, thus, as used herein, the term "image" or "map" do not necessarily imply a visual representation.

Storing Sinogram and Other System Data

In an embodiment, the sinogram, along with other data recorded relating to the use of the optoacoustic device, may be recorded in a laser optic movie file or LOM. The LOM is not, as the name would suggest, a movie file, but rather, the LOM is a collection of recorded data that may be recorded in group of related files, or more preferably, in a single data file. One consideration for the format of the LOM is the differing and likely asynchronous processes that generate data requiring storage in the LOM. In an embodiment, the LOM can be used to store a variety of information concerning the use of the optoacoustic device, including, without limitation, the long and short optoacoustic sinograms, ultrasound frames, configuration data, annotations made by a user, or at a later time, an audio and/or video recording made during the use of the optoacoustic device and information concerning version information as reported by the optoacoustic system and its software.

In an embodiment, the LOM may be structured in blocks of 1024 bytes (1K) each. Each collection of information (e.g., a sinogram) may comprise a header, and, where additional data is required, one or more additional blocks of information associated with the header. In an embodiment, the header may include an identifier that is used to identify the block as a header. In an embodiment, the header may also include a value for a synchronization counter to permit the collection of information to be placed in proper order when the LOM is used, even if it is recorded in the LOM out of order, as may be the case with the varied types of inputs and I/O systems in a particular implementation. In an embodiment, the header further comprises a CRC of itself and any additional data associated with the collection, thus permitting an integrity check or validation of the entire collection within the LOM. A data structure for an exemplary LOM is provided in the Appendix.

Processing Sinograms

For a variety of reasons, sinograms may contain unwanted, inaccurate or insufficiently scaled data. These maladies of sinogram data may result from myriad reasons, including characteristics of the measuring instrument (e.g., the probe) or the light used, characteristics of the volume (i.e., the tissue), characteristics of the interaction between the volume and the probe or light, external stimuli, or other sources. Regardless of the source, a variety of processes can be used to remove unwanted aspects of the sinogram data.

In an exemplary embodiment, where the sinogram data is sampled as an integer, e.g., as a 14 bit integer, prior to performing the processing steps on the sinogram, the sinogram data may be converted from integer form to a floating point number. Conversion from integer to floating point is performed to increase accuracy and expand the dynamic range of the calculations. In an embodiment, the sinogram may be processed as integer data. In an embodiment, the sinogram may be processed as integer data, but the integers are enlarged to a sufficient size to accommodate the appropriate range of data, e.g., 64 bits, or 96 bits, or 128 bits.

Generally in each of the following steps for processing the sinogram, the processing is performed on the time domain signal. In a preferred embodiment (and as discussed below) the probe 102 includes an acoustic lens that enables the sinogram data to be more focused on what is on the plane below that of the transducers—the image plane. In an embodiment, the probe comprises an acoustic lens having a focal length of between 10 and 40 millimeters. In an illustrative embodiment, the probe comprises an acoustic lens having a focal length of 20 millimeters. In an embodiment, the probe may comprises an acoustic lens having a focal length that can be zoomed in or out, in hardware, or in software.

As discussed above, in an illustrative embodiment, each channel of the sinogram data represents approximately 100 millimeters of distance in the volume. The acoustic lens generally rejects at least some portion of a signal propagating from points outside (e.g., orthogonal) to the image plane. Each transducer, however, receives signal from substantially all points of the image plane that lie within the approximately 100 millimeters distance. The received signal for a channel can be thought of as comprising the area of a semicircle of radius 100 on the image plane.

Figure 2:
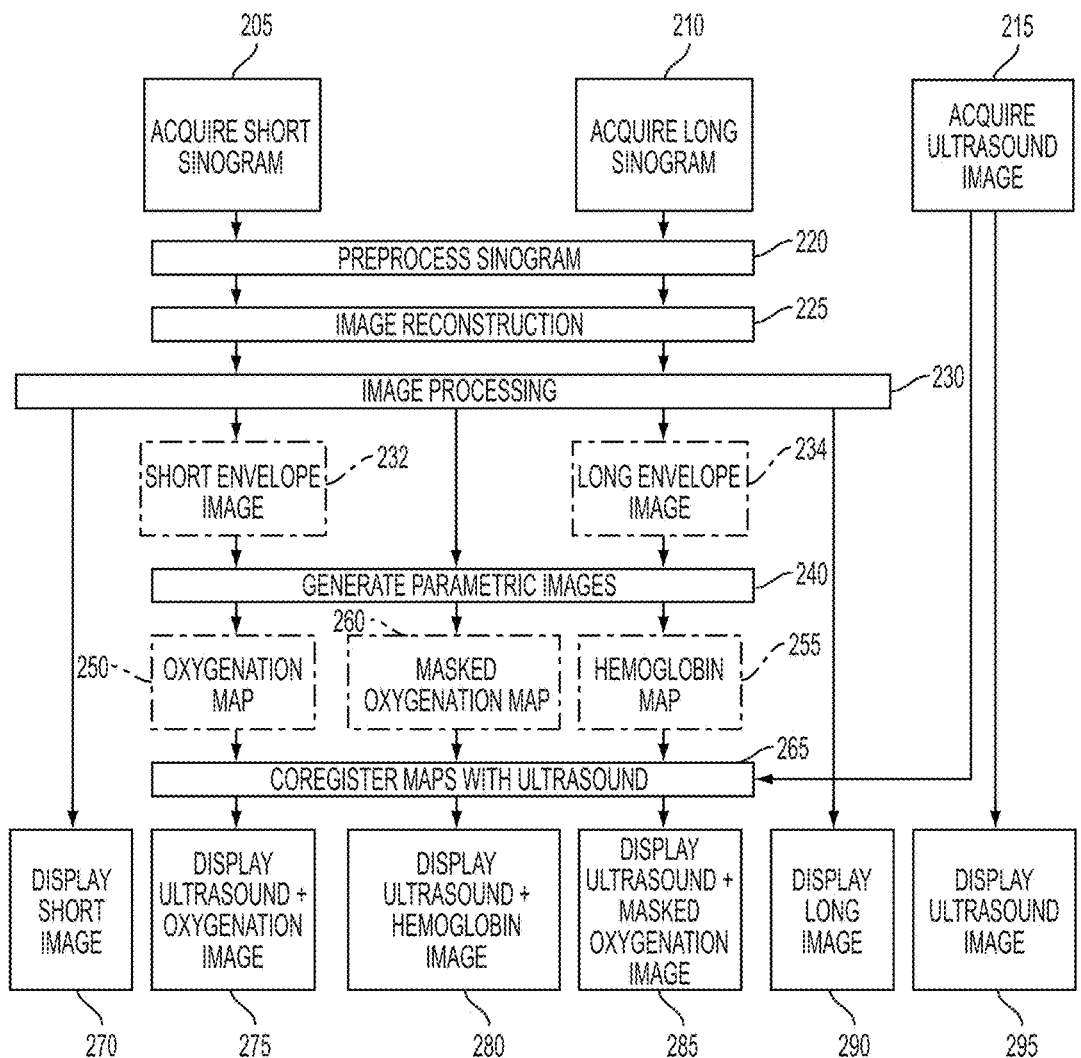
FIG. 2 shows a flow for an illustrative embodiment of a method of providing output images resulting from optoacoustic data, and from optoacoustic data combined with ultrasound data.

Turning to FIG. 2, an overview of an exemplary process is shown, beginning with the acquisition of three sets of data, namely, a short sinogram (step 205), a long sinogram (step 210) and an ultrasound image (step 215), and processing the data to produce up to six separate images that may be useful in viewing various aspects of that acquired data. In an exemplary embodiment, the three sets of acquired data may be acquired using a handheld optoacoustic probe 102 (FIG. 1). For the purposes of illustration herein, it may be presumed that probe 102 movement is minimal, if any, between the acquisition of the three sets of data in steps 205, 210 and 215. In an exemplary embodiment, a reasonable frame rate (e.g., 10 hz), coupled with a reasonably steady hand used in handholding the probe may yield the three data sets having substantially minimal movement occurring there-between. It should be noted that the process described herein is not limited to being used with the three identified data sets. Use of additional data sets, such as, for example, data sets from additional wavelengths of light, may be used to further improve the resulting images.

As will be discussed in more detail below, the short and long sinogram data are preprocessed (step 220) in one or more separate manners to reduce or compensate for undesired data in the sinogram, including characteristics of the measuring instrument (e.g., the probe) or the light used, characteristics of the volume (i.e., the tissue), characteristics of the interaction between the volume and the probe or light, external stimuli, or other sources. After the preprocessing, separate short and long images are reconstructed (step 225). In an embodiment, separate real and imaginary components of complex short and long images result from the reconstruction step. In an embodiment, the processing (step 230) of the reconstructed images is performed. The processing (step 230) may remove additional artifacts that can be identified in the reconstructed images, and in any event creates a short envelope image (232) and a long envelope image (234). In an embodiment, the short and long envelope images (232, 234) are used to generate parametric images (step 240) process. The generate parametric images (step 240) process outputs an oxygenation map (250), a hemoglobin map (255) and a masked oxygenation map (260). In an embodiment, any or all of the three maps are coregistered with, and overlaid on an ultrasound image (step 265). A display can be provided for display of one or more of the displayable images displayed in steps 270, 275, 280, 285, 290 and 295. In an embodiment, a group of two or more of the images may be displayed on the same screen, and may be commonly scaled and sized. In an embodiment, the group of all six images may be displayed on the same screen, and may be commonly scaled and sized.

In an embodiment, the system performing processing on the optoacoustic data, and/or the system displaying the optoacoustic output—which may, but need not be the same as the system acquiring the sinogram—would provide the operator the ability to vary parameters used in processing, when processing or viewing optoacoustic images. In an embodiment, the system performing processing on the optoacoustic data, and/or the system displaying the optoacoustic output would provide the operator the ability to switch on and off, and potentially vary the order of, the processing steps used to process the optoacoustic images.
Preprocess (220)

Figure 3:
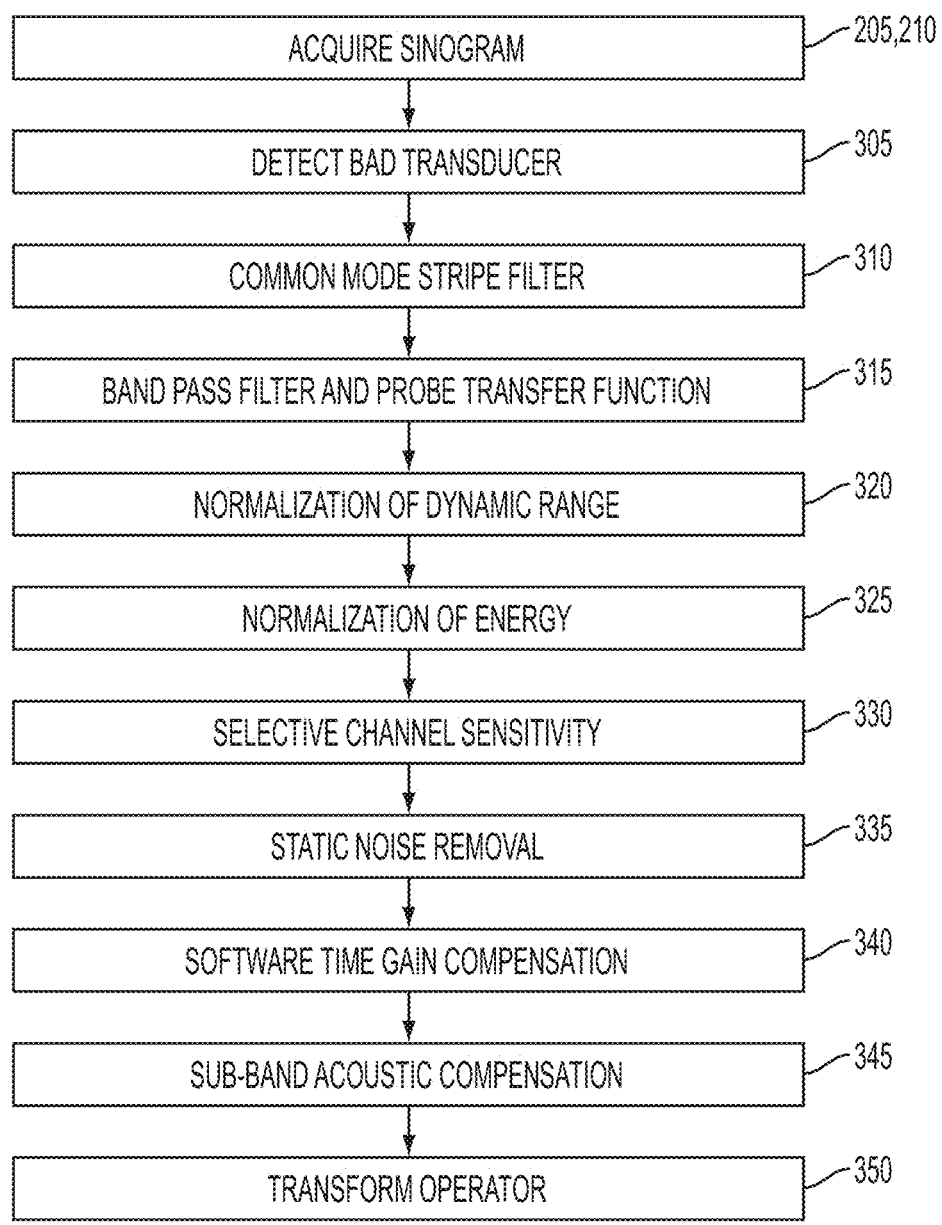
FIG. 3 shows a flow for an illustrative embodiment of a method for preprocessing sinograms to remove unwanted information.

Turning to FIG. 3, an overview of an exemplary sinogram preprocessing is shown. After acquisition of sinogram data (step 205, 210), that data is preprocessed (step 220, FIG. 2) in one or more separate manners to reduce or compensate for undesired data in the sinogram, including, without limitation, artifacts of the device itself, artifacts of the device-subject interaction, and external sources of unwanted information. In an embodiment, preprocessing may consist of one or more of the following steps: detecting bad transducers (step 305), common mode stripe filtering (step 310), band pass filtering and/or applying of a probe transfer function (step 315), normalization of the dynamic range (step 320), normalization for energy (step 325), selective channel sensitivity (step 330), interframe persistent artifact removal (step 335) and software time gain compensation step (340). One or more additional preprocessing steps may also be used to reduce or compensate for undesired data in the sinogram. Notably, the steps identified in FIG. 3 do not need to be performed in the order presented, and may be performed in any order. Moreover, not all of the steps presented in FIG. 3 are required for any implementation of an exemplary system, rather, preprocessing consists of the use of any one or more steps to reduce or compensate for undesired data in the sinogram.
Preprocess (220)—Detect Bad Transducer (305)

One potential source of malady in the sinogram is a transducer that fails to accurately reflect the optoacoustic return signal incident thereon during the sampling process. The failure may be temporary, or may be permanent. Moreover, the failure may be partial, such as where the sampled data reflecting too high or too low a signal, or reflecting noise, or the failure may be complete, such as where the sampled data are all zeros or nominal values. A bad transducer could also present inconsistent or flakey output, even within a single sinogram. Bad transducer channels may also result, for example, from poor contact with the tissue beneath one or more transducer elements.

In an embodiment, when a consistently bad transducer is identified, its identity is noted, and thereafter the data provided from that transducer may be ignored, replaced or separately pre-processed. For example, in an embodiment, to compensate for the misbehavior of a transducer, a preprocessor is run to remove the transducer's abnormal response characteristics. In another embodiment, to compensate for the misbehavior of a transducer, the transducer's data is replaced with an average of the data from the two adjacent channels.

In an embodiment, sinogram data is analyzed for the presence of bad channels. A bad channel may be detected by the fact that the sinogram has a "skin" signal—that is an optoacoustic response signal reflected from at or near the surface of the volume—that is significantly weaker than the average across the other channels. A weaker skin signal may result from a bad acoustic contact right above the channel or some problems, e.g., with electronics that significantly reduced the gain of that channel. When a channel exhibits this behavior, it may be identified as "bad" and, in an embodiment, the data in that channel is zeroed out following the processing with a stripe filter (discussed below) to avoid artifacts.

In an illustrative embodiment, the algorithm below may be used for identifying bad data channels and zeroing that part of data, thereby avoiding inaccurate image artifacts.

In this illustrative embodiment, an algorithm assumes that a strong optoacoustic skin signals is supposed to be received by each transducer. The strong optoacoustic skin signal is expected to dominate over noise and are expected to be close in magnitude from channel to channel.

The illustrative algorithm is described as follows: each connected data channel is analyzed and labeled "bad" if the average of a group of several consecutive samples of absolute channel data (containing the optoacoustic signal from the skin) is very small and considered to be a statistical outlier when compared across all the connected channels. The outlier determination is based on the weighted standard deviation across all the channels.

An illustrative algorithm may be executed as follows:
a. Absolute values of the signals are calculated.
b. Average values of the first several samples in absolute signals are calculated.
c. Small outliers of the average values are identified using the average across all the connected channels minus weighted standard deviation as a threshold.
d. Identified outliers are labeled as bad channels.

Pseudo-code in the Appendix will provide a guide for a person of ordinary skill in the art in implementing illustrative algorithms discussed herein. The algorithm presented is merely an example of one way to remove bad channels that can adversely affect the later calculations and operations made upon the optoacoustic data. In view of the foregoing, it will be apparent to a person of skill in the art, and within the scope of this disclosure, that other methods can be used for detecting bad channels, including, without limitation, methods that use an autocorrelation between channels, or between sets of channels.

Preprocess (220)—Common Mode Stripe Filter (310)

Other potential sources of unwanted information in the sinogram may appear in the form of noise or other unwanted signal that affects all channels simultaneously. There may be a variety of causes of this kind of noise or unwanted signal, including, for example, external interference or probe characteristics. Regardless of the cause, however, the noise or unwanted signal may be removed or mitigated. When the sinogram is oriented with channels corresponding to columns, and samples according to rows, this type of filter removes horizontal stripes from the sinogram. In an embodiment, horizontal stripes may be removed using a method based on the 2-Dimensional Discrete Wavelet Transform (2D-DWT). In an embodiment, horizontal stripes may be removed using a method based on a frequency domain filter (e.g., a 1-dimensional or 2-dimensional frequency domain filter) or FIR filter. In an embodiment, an average across a row or other set of data is subtracted from each sample in that row or set of data.

In an illustrative embodiment, the algorithm below may be used for removing horizontal stripes from a sinogram. In an embodiment, the illustrative algorithm may be executed as follows:
a. Precompute the sizes of the wavelet coefficients for the horizontal coefficients at each subband level.
b. Precompute the even-symmetric zero-phase transfer function of the 1-Dimensional (1D) frequency domain stripe filter for each wavelet subband.
c. Compute a 2D wavelet transform using the highpass and lowpass wavelet coefficients, which may be defined by the input parameters, and by applying forward wavelet decomposition for some number of levels.
d. With the vertical coefficients from each subband level, apply the 1D transfer function filter to each line along the vertical direction, where the 1D transfer function smoothly suppresses low frequencies for each of the lines.
e. Take the inverse wavelet transform by applying wavelet reconstruction to the modified wavelet coefficients Pseudo-code in the Appendix will provide a guide for a person of ordinary skill in the art in implementing this illustrative algorithm. The algorithm presented is merely an example of one way to implement a stripe filter to remove data that can adversely affect the later calculations and operations made upon the optoacoustic data. In an embodiment, common mode stripe filtering can be performed by using principal component analysis on the channels of the sinogram to remove interference that is common to each channel. In an embodiment, common mode stripe filtering can be performed by using principal component analysis on the channels of the complex analytic sinogram to remove interference that is common to each channel where interference may be subject to different complex phase on each channel. In view of the foregoing, it will be apparent to a person of skill in the art, and within the scope of this disclosure, that other methods can be used for removing this type of errant data.

As a wave travels along the surface of the tissue, illustratively, the wave's crest may meet each element of the transducer in sequence; accordingly, such a wave may produce diagonal artifacts in the sinogram when measurement is acquired using a linear-array probe. In an embodiment, the stripe filter may be used to remove these and other such diagonal artifacts. In an embodiment, to remove such diagonal artifacts, each channel of the sinogram may be shifted based on the perceived travelling speed of the surface wave prior to application of the stripe filter and then unshifted after the stripe filter has been applied. In an embodiment, diagonal stripes may be removed using a 2D band-reject stripe filter.

Preprocess (220)—Band Pass Filter and Probe Transfer Function (315)

The acquired channels of optoacoustic return signal data captured by the transducers and stored in a sinogram comprise a sampling of the data the transducers detect (during the sampling period). As discussed above, the sinogram-resident samples are acquired in the time domain. As also discussed below, the optoacoustic return signal transducer may have a wider band than a traditional ultrasound transducer. Thus, in an embodiment, an optoacoustic return signal transducer may have a band width from 10 Khz or lower, to as high as 20 Mhz or more. In an illustrative embodiment, an optoacoustic return signal transducer may have a bandwidth from about 50 Khz to 20 Mhz.

Selected portions of the optoacoustic return signal have been more suitable for use in image reconstruction. Thus, in an embodiment, portions of the optoacoustic return signal are eliminated without materially detracting from the resulting optoacoustic image. In an embodiment, a one dimensional FFT (Fast Fourier Transform) band pass filter may be used to reduce or remove the high and low frequency components without material detraction from the resulting optoacoustic image. Thus, in an illustrative embodiment, a one dimensional FFT band pass filter can be employed that, on the low frequency side, provides substantially complete attenuation at less than 10 Khz, while on the high frequency side, provides substantially complete attenuation after 12 Mhz. In an embodiment, a one dimensional FFT band pass filter can be employed that, on the low frequency side, starts to roll off at 50 Khz, while on the high frequency side, starts to roll of at 6 Mhz. In an embodiment, the roll off rate is steeper for the low frequency side than the high frequency side. Thus, in an illustrative embodiment, a one dimensional FFT band pass filter can be employed that, on the low frequency side, starts to roll off (downwardly) at 50 Khz, and provides substantially complete attenuation at less than 10 Khz, while on the high frequency side, starts to roll of at 6 Mhz, and provides substantially complete attenuation after 12 Mhz.

In addition to filtering frequency portions of the optoacoustic return signal that have no material effect on the resulting optoacoustic image, in an illustrative embodiment, an algorithm may provide an approximation of the transfer function of the probe and the electronics, i.e., a function that substantially approximates the system's transfer function. As used in this section, the system's transfer function (i.e., the function that substantially approximates the system's transfer function) is a transfer function that reflects at least some of the system's own response characteristics, such as the probe geometry, the way the probe itself affects a light event or the resulting optoacoustic return signal at varying frequencies, including changes in, e.g., attenuation, delay, spatial response, noise or other aspects of the signal. In an embodiment, spatial frequency response characteristics of the tissue and/or the coupling medium may also affect the system's own response characteristics. The frequency domain response characteristics, or impulse response characteristics of the system electronics also may be included in the system response. Examples of the kind of response characteristics that could be introduced by a system response may include: filtration of frequencies such that, e.g., sound at 1 Mhz comes through louder than sound at 100 Khz; delay such that, e.g., sound at 1 Mhz comes through sooner than sound at 100 Khz; and/or spatial effects, such that, e.g., a sound arriving at the transducer from a location 45 degrees from normal with respect to the transducer sounds different than it would if it arrived from a direction normal to the transducer.

In an illustrative embodiment, an overall system filter (i.e., a filter to compensate for, among other things, the system transfer function) may formed by steps including deconvolution of the acousto-electric impulse response, bandpass filtering, and an additional arbitrary transfer function to support filtration of other factors. The sinogram data can then be processed using the system filter function.

In this illustrative embodiment, the system's complex transfer function is formed out of three parts, which are later multiplied together. The first part is the frequency domain representation for deconvolution of acousto-electric impulse response, which may be determined using Wiener deconvolution with a regularization parameter that pertains to the noise-to-signal power spectral ratio. The second part of the transfer function is the bandpass filter, which is designed with a raised cosine apodization function, using provided information on the band pass/stop regions. The third part of the transfer function is an optional arbitrary frequency response. The system filter only needs to be recalculated if one of its parameters changes. Otherwise the filter may be determined, stored, and loaded from the storage as needed. In short, the sinogram data is conditioned and transformed into the frequency domain, where it is multiplied by the system's filter function before it is transformed back into the time domain.

An illustrative algorithm for making the system filter may be described as follows: If none of the parameters were modified since the last run, the system's transfer function is the previously calculated input system's transfer function. Otherwise the system filter may be calculated according to the following steps. In step one, the deconvolution Wiener filter is formed. (A Wiener deconvolution filter as follows may be used:

$$G(f) = \frac{H^*(f)}{|H(f)|^2 + \alpha(f)}$$

where f—frequency (Hz), G—transfer function of the filter, H—system's frequency response, α—noise-to-signal spectral power density ratio.) In the step two, the bandpass filter is calculated using a raised cosine apodization function and input band pass/stop frequency parameters. If specified by the parameters, the bandpass filter may be unity (a constant value of 1), and hence, no bandpass filtering is applied. As a last step, those two complex transfer functions are multiplied together with another defined arbitrary transfer function (optional) to get the output system filter function. One purpose for multiplying the two complex transfer functions with another defined arbitrary transfer function is to allow frequency domain filtering that is not readily susceptible to filtering using the other two methods.

An illustrative algorithm for processing data according to the system filter function may be described (for a single channel of data) as follows: The input data is zero-padded (or symmetrically padded) to double the length and is transformed to the frequency domain via the Fast Fourier Transform (FFT), complex-multiplied by the system's transfer function, and then the Inverse Fast Fourier Transform (IFFT) applied, to return the data to the time domain. Once returned to the time domain, the padding is removed.

Pseudo-code in the Appendix will provide a guide for a person of ordinary skill in the art in implementing this illustrative algorithm.

In an embodiment, overall system compensation may be performed and used to mitigate, eliminate or enhance portions of a sinogram. In an embodiment, overall system compensation may be used to account for situations that are not limited to ideal lab situations or factors based solely on the probe and the electronics; rather the characteristics of the sinogram may be affected by the physiology and characteristics of a typical subject and embody non-ideal situations that do not strictly occur in the lab. Difficult-to-model interactions may occur in real-world situations that differentiate in-vivo optoacoustic measurements from models. These can include interactions involving geometry of a probe that is part of the system; the manner in which the probe affects a light event caused by the system; the way in which the probe affects attenuation, delay, spatial response, noise or other aspects of an optoacoustic return signal; spatial frequency response characteristics of a tissue being imaged, and a coupling medium used in connection with recording the sinogram. In many cases these situations may also be anticipated and be replicable, though they may result from combination of factors that would have be unlikely to foresee even when using simulated environments, e.g., phantoms. Accordingly, in an embodiment, overall system compensation or calibration can encompass accounting for these factors by performing analysis based on a multitude of acquired datasets; the process to determine the overall system compensation can be based on empirically tuning the overall system compensation to meet a performance objective. In an embodiment, tuning can be based on collecting a multitude of datasets and performing a statistical regression analysis, the objective of the statistical regression may involve optimizing a cost function, or using manual operator adjustment; performing an offline computation to determine parameters for computation; fitting parameters to match the objective; determining spatial or temporal weights for a table, the table used in reconstruction to account for factors including geometry; or using the statistical or manual analysis to determine the weights of an optimal filter. In an embodiment, the statistical analysis may involve using specialized computer software for performing the analysis. In an embodiment, the statistical analysis may yield different optimal tuning parameters for different types of tissue or for subjects of different physiology. A method for tuning may account for these factors. In an embodiment, a method for tuning may have, as its objective, the yield of optimal results, or the enhancement of features for different tissues. For example, enhancement or optimal results may be sought for dense or fatty breast tissue or other known types of tissue as may be differentiable; likewise, enhancement or optimal results may be sought for any types of characteristics, including, without limitation: thick or thin layers of skin; the mechanism by which light is absorbed separately based on the tone of skin; the emphasis of a tumor or lesion, including where the tumor or lesion has different frequency characteristics than the background tissue; the differences between a cellular or non-cellular fibroadenoma (or other such determinable condition) and sets of parameters to make this more apparent optoacoustically; the differences between classes of malignant and benign lesions and other indeterminate structures yielding an optoacoustic signature (e.g. lymph nodes, fat necrosis) and a system or method for discriminating such; features of different scales or sizes; tuning parameters such as packet wavelet coefficients or vector support coefficients involving feature detection classification; or adjustable parameters in a deconvolution process. The method for tuning may include acquiring data under strictly controlled measurement conditions according to a measurement procedure, wherein the probe is manipulated to according to specific or specialized motions (e.g. sweeping or fanning) and specific portions of tissue are captured (e.g. parenchyma). In an embodiment, the method for optoacoustic tuning may comprise: collection of measurements; statistical or manual analysis involving optimizing an objective; adjusting parameters to obtain the desired system compensation; and applying the compensation to the sinogram thus affecting the resulting diagnostic overlay. In an embodiment, the compensation may be performed separately for two or more wavelengths. In an embodiment, the tuning analysis may be used to generate a set of rules that can be applied to an optoacoustic image or other system data to develop a prognosis or histology. The rules so generated may be applied by an operator, by the system, or by another system, and once applied, may provide a report of the prognosis or histology. In an embodiment, multiple sets of pre-tuned parameters may be user-adjustable or enable-able by a user interface, which user interface may include a set of pre-tuned parameters.

Preprocess (220)—Normalization of Dynamic Range (320)

As discussed below, time gain compensation may be applied in hardware to achieve higher dynamic range and/or improve the signal to noise ratio (SNR) for a given depth or distance. Hardware applied time gain compensation may improve the overall dynamic range of the optoacoustic return signal. Analog hardware applied time gain compensation may increase the precision of the data captured by the analog-to-digital conversion device by amplifying low magnitude signals from deep tissue that would otherwise not effectively use the full bitwise representation of the data. In addition, analog hardware applied time gain compensation may improve the signal-to-noise ratio by bringing weak signals at depth above an analog noise limit in the pathway between the hardware TGC amplifier and the analog-to-digital conversion device. In an embodiment, time gain compensation may compensate for the attenuation that occurs to the light as it transmits from a surface of a volume of e.g., tissue to areas within the volume of tissue, and/or for attenuation to the optoacoustic return signal as it transmits through the volume of tissue. In an embodiment, the image reconstruction algorithms utilized presume, however, that there has been no change in gain, e.g., amplifying later or deeper signals. Accordingly, in an embodiment, to normalize the data, the hardware time gain compensation is mathematically reversed, thus removing its impact from the image calculation.

In an embodiment, the sampled data is a relatively modest sized integer, such as a 14 bit integer, which e.g., can represent values from 0 to 16,383. In an embodiment, the data in the sinogram is converted from integer to floating point prior to the processing discussed in this section; conversion from integer to floating point may be performed to increase accuracy and expand the dynamic range of the calculations. Generally, care should be exercised to prevent the loss of dynamic range when reversing the hardware time gain compensation. In an embodiment, the normalization of dynamic range filters the sinogram to reflect substantially flat gain without loss of dynamic range. It permits each sample in the sinogram to sum its proper contribution when used in connection with forming the resulting optoacoustic image.

In an embodiment, to renormalize the dynamic range, the time dependent hardware TGC curves may be factored out of each channel. In an embodiment, hardware TGC curves may be stored as a set of data points that are linearly interpolated by the system firmware and sent to the hardware TGC amplifier. A TGC curve may be computed from stored data points.

An illustrative algorithm for renormalizing the dynamic range of a sinogram follows: generate the TGC curve, send the TGC curve to the hardware TGC amplifier, if necessary, linearly interpolate the TGC curve to create a piecewise linear curve equal in length to the number of samples, map the computed curve from a numeric representation as may be required by the hardware to the amplifier gain, compute the reciprocal of the gain curve, and finally, multiply the corresponding samples in the reciprocal curve by the samples of each channel and store the result as output.

Pseudo-code in the Appendix will provide a guide for a person of ordinary skill in the art in implementing illustrative this algorithm.

In an embodiment, the system includes adjustable amplifiers and a probe having an array of transducer elements, each of the adjustable amplifiers being associated with one or more of the transducer elements. The transducer elements are acoustically coupled with a surface of a volume. The gain on the adjustable amplifiers is changed as a function of the passage of time during a predetermined period of time after a pulse of light. A sinogram is recorded by sampling the adjustably amplified plurality of transducer elements for the predetermined period of time. The sinogram is processed by substantially reversing the changing step mathematically, and storing the results in an expanded dynamic range sinogram. The expanded dynamic range sinogram provides sufficient numeric precision to permit the reversal of the changing step without materially decreasing the dynamic range of the information in the sinogram. An optoacoustic image is generated based upon the information contained in the expanded dynamic range sinogram.

The function of the passage of time noted above may account for at least one of: acoustic wave propagation attenuation of tissue, optical fluence attenuation of tissue and geometry of the plurality of transducer elements. The process of generating an image may include generating a complex-valued array that includes an analytic representation of the expanded dynamic range sinogram, an imaginary component of the complex-valued array representing a quadrature, and a real component of the complex-valued array representing an in-phase component. The optoacoustic image may be generated based upon the complex-valued array, the optoacoustic image being a positive, real valued, non-complex image. The quadrature component may be formed by computing the Hilbert transform of the real component. Processing of the sinogram may include generating at least one time gain compensation curve reflecting the changing gain on the adjustable amplifiers as a function of the passage of time, computing a reciprocal of the mapped time gain compensation curve, and multiplying corresponding samples in the reciprocal time gain compensation curve by samples of each of a plurality of channels of data in the sinogram. The processing step may further include the step of mapping the time gain compensation curve from logarithmic units into linear units. The step of generating a time gain compensation curve may include generating a complex-valued array comprising an analytic representation of the expanded dynamic range sinogram, the imaginary component of the complex-valued array representing a quadrature, and a real component of the complex-valued array representing the in-phase component. The generating step may also include generating an optoacoustic image based upon the complex-valued array, the optoacoustic image being a positive, real valued, non-complex image. Each adjustable amplifier may be associated with one of the transducer elements, or may be associated with two or more of the transducer elements.

Preprocess (220)—Energy Normalization (325)

In an embodiment, the sinograms contain optoacoustic return signal data correspond to a single light event such as the firing of a laser. In use, the system 100 may produce a plurality of sinograms, each corresponding to a separate light event. For example, in an embodiment, a single light source can be used repetitively, with the system generating a separate sinogram to capture optoacoustic return signal data from each. In another embodiment, two or more light sources can be used to generate discrete light events, such as, for example, by interleaving them so that one is used and then the other, with the system generating a separate sinogram to capture optoacoustic return signal data from each. In an illustrative embodiment, an ND:YAG laser and an Alexandrite laser are used in an interleaved manner, with one causing a light event and then the other. In each of the foregoing multiple light event situations, the energy of one light event may deviate from the total energy of another. Deviation from one light event to another may, or may not be intended, and may be the result of external influences or system design or a combination of factors. For example, most lasers fluctuate in energy, at least to some degree and often to a large degree, each time they are used in the manner described in more detail below.

Regardless of the cause, in an embodiment, it may be desirable to reduce or eliminate the shot-to-shot variance. Such shot-to-shot variance can, for example, create problems in using the sinogram data to produce consistent images. Moreover, when images are shown in sequence, shot-to-shot variance can cause flicker, not unlike that seen in an old time movie. As a result, shot-to-shot variance can inhibit or prevent adequate review of image sequences, or inhibit or prevent adequate interpretation of images created by different lights in two separate light events such as of the image pairs created using an ND:YAG laser and an Alexandrite laser as discussed.

In an embodiment, energy normalization can be accomplished by dividing each sample by a value proportional to a measured energy of the light event so that each sample in the sinogram would thereafter represent a normalized value. In an embodiment, energy normalization can be used in conjunction with a calibration procedure, for example, by setting the initial energy of laser output to a specified level and normalizing the energy deviation against that level.

In an embodiment, an optoacoustic imaging system includes a handheld probe and first and second pulsed light sources having a common output. The first and second light sources generate pulses of light at first and second predominant wavelengths, respectively. The handheld probe includes an ultrasound transducer array having an active end located at the distal end of the handheld probe for receiving an optoacoustic return signal. A sensor measures a portion of the light transmitted along the light path. A data acquisition samples the ultrasound transducer array during a predetermined period of time after a pulse of light from the first light source and during a predetermined period of time after a pulse of light from the second light source. The sampled data is stored. An image processing unit reconstructs a first optoacoustic image based on the sampled data corresponding to a pulse of light from the first light source and reconstructs a second optoacoustic image based on the sampled data corresponding to a pulse of light from the second light source. An energy normalizing unit computes a normalization factor based on a measurement from each sensor in the array and applies the normalization factor to data corresponding to the pulse of light. The energy normalization unit may comprise, for example, the computing subsystem 128 (FIG. 1), the computer, the optoacoustic processing and overlay system 140 (FIG. 1), the digital acquisition and processing board 2818 (FIG. 28), and/or any other electronics capable of digital signal processing.

In an embodiment, the sampled data is stored in a sinogram, and the energy normalizing unit applies the normalization factor to data stored in a sinogram. The normalization factor may be computed, for example, by dividing a nominal light source energy by the measurement from the sensor times a constant, and may be applied by multiplying each sample in the sinogram by the normalization factor. The energy normalizing unit may be programmed to apply the normalization factor to the reconstructed image. The sampled data may be processed prior to being reconstructed into an optoacoustic image, and the energy normalizing unit may be programmed to apply the normalization factor to processed sampled data. The sensor that measures a portion of the light transmitted along the light path may be adapted to measure light reflected by the optical window, and may comprise a sensor input that is filtered using an optical filter. Such optical filter may be adapted to provide more attenuation at the second predominant wavelength than at the first predominant wavelength.

In an embodiment, the system includes first and second sensors to measure at least a portion of the light. The first sensor measures light having a first predominant wavelength transmitted along an auxiliary light path, and the second sensor measures light having a second predominant wavelength transmitted along the auxiliary light path. The first and second sensors may be adapted to measure light reflected from the optical window. The first and second sensors are the same sensor. The auxiliary light path may be configured to direct light from the common output to the first and second sensors. The main light path and the auxiliary light path may be common. A data acquisition unit may be provided for sampling the ultrasound transducer array during a period of time after a pulse of light and for storing the sampled data as a sinogram. A data processing unit may be provided for reconstructing an optoacoustic image based on sampled data stored as a sinogram, the data processing unit. In this respect, the data processing unit can include software for computing a normalization factor based on a measurement made by at least one of the first sensor and the second sensor during a pulse of light and applying the normalization factor to data corresponding to the pulse of light. The data processing unit may comprise, for example, the computing subsystem 128 (FIG. 1), the computer, the optoacoustic processing and overlay system 140 (FIG. 1), the digital acquisition and processing board 2818 (FIG. 28), and/or any other electronics capable of digital signal processing.

The data processing unit may include software for generating a complex-valued array comprising an analytic representation based on data stored as a sinogram, an imaginary component of the complex-valued array representing a quadrature, and a real component of the complex-valued array representing an in-phase component. The data processing unit may additionally include software for reconstructing the optoacoustic image based upon the complex-valued array, the optoacoustic image being a positive, real valued, non-complex image. The data processing unit may additionally include software for generating a map overlay based on at least portions of two optoacoustic images, the map overlay being reflective of areas within at least a portion of the images which have a difference in absorption in response to the different pulses of light. The data processing unit may also include software for generating another map overlay based on at least a portion of the two optoacoustic images, the another map being reflective of areas within at least a portion of the images which have stronger absorption in response to both pulses of light than other areas within the images. The data processing unit may further include software for generating a mask reflective of a combination of information in the map and information in the another map, the mask adapted to exclude areas of an image, and for generating a masked parametric map by applying the mask to an auxiliary map, thus forming a parametric map. The auxiliary map may be another map and/or an image.

Pseudo-code in the Appendix will provide a guide for a person of ordinary skill in the art in implementing this illustrative algorithm.

Preprocess (220)—Selective Channel Sensitivity (330)

The sinogram data may contain variations that are related to the performance of specific components of the system. Such variations can cause inaccuracy and/or unwanted or undesired results in images reconstructed therefrom. In an embodiment, information is stored concerning such variations and the information is used to process the sinogram and remove variations that are related to the performance of specific components of the system such as a channel-to-channel variation. In an embodiment, the channel sensitivity process may be performed in a manner to account for variations in signal strength resulting from signal variation related to contact, the coupling medium and other such issues (e.g., performed adaptively or dynamically). In an embodiment, dynamic compensation may be performed by using channels in close proximity to each other, which may be presumed to have similar content, to determine a dynamic compensation factor of each channel. In an embodiment, the sinogram is filtered prior to performing dynamic selective channel sensitivity.

In an illustrative embodiment, an optoacoustic device comprises a probe having 128 or 256 transducer elements. Each of the transducer elements are electrically connected to one amplifier. Each of the amplifiers may handle, e.g., 8 individual transducers, thus, a total of 1 or 8 amplifiers may be required in this illustrative embodiment. A DAP board (i.e., data acquisition processor board) may contain 8 such amplifiers, and thus be used to acquire data from all 128 or 256 transducer elements. Variations may occur between the response of the several transducer elements. Generally, for example, each amplifier has a single gain control that may affect the gain on all 8 transducers it is handling. Accordingly, if one or more of the transducer elements responds differently, e.g., more quietly, than the other transducer elements connected to the same amplifier, it cannot be compensated for using the gain control. Similarly, variations may occur between the response of the several amplifiers, leading to variation in what would otherwise be identical transducer element responses. Variations in may also occur due to the amount of pressure applied to the probe, including different amounts of pressure being applied to different regions or elements on the probe. Variation may additionally occur due to the quality or amount of skin or surface contact with the probe, or the amount of coupling medium used. Surface features, such as roughness, physiological structures near the surface, or focusing aberrations may also produce variations in the signals received on a per-channel basis. In an embodiment, variations can be detected using an automatic method or a fixed method that is determined by measuring and calibrating a particular transducer.

In an embodiment, calibration data for a probe indicative of the relative or absolute performance of the transducer elements may be maintained. Similarly, calibration data for a DAP board indicative of the relative or absolute performance of the amplifiers may be maintained. Such calibration data may be acquired at the factory at manufacture time by using known inputs or tests, or alternatively, may be acquired later, e.g., in the field, using calibration equipment. A "dummy" probe that is calibrated to transmit specific output signals may be used to help determine calibration information for the amplifiers. A known phantom may be used to help determine calibration information for the transducer elements. In an embodiment, the probe holder contains an object having a known acoustic or optoacoustic response that can be used to run calibration tests, or to confirm that the system is functioning in a consistent manner.

In an embodiment, a test sample is provided that is expected to produce a given output X from each transducer element. When the test sample is tested, the response from most channels is indeed X, but from several channels is 0.9X, and from one channel 0.85X. In an embodiment, the sinogram column corresponding to the 0.9X channels are enlarged by a factor of 1/0.9, while the sinogram column corresponding to the 0.85X channel is enlarged by a factor of 1/0.85. Where a channel responds with 1.1X it can similarly be multiplied by a factor of 1/1.1.

The foregoing presumes that any channels that differ from the expected output will do so in a linear manner. Where this presumption is insufficient to accommodate the actual deviation, a more complex transfer function can be used to compensate for the actual sensitivity of a channel.

Preprocess (220)—Interframe Persistent Artifact Removal (335)

For the purpose of the following discussion, the optoacoustic return signal data can be thought of to include three components: the desired coupled response; the undesired coupled response; and noise. Interframe persistent artifact as used in this section refers to the undesired coupled response, not to other noise. Unless compensated for, interframe persistent artifacts may be present in images created from an optoacoustic return signal created using a handheld probe that provides both the light and the transducer elements. The interframe persistent artifact is generally not the same from one tissue or volume to another, however, a sub-component of the interframe persistent artifact may remain the same between all data collected using a given set of hardware, or even a given probe. More generally, while two similar phantoms may create similar interframe persistent artifacts, tissue creates different interframe persistent artifacts than a phantom, and one person's tissue creates different interframe persistent artifacts from another person's tissue. Moreover, generally, the amount of interframe persistent artifacts present in most common phantoms may be lower than, or different than, the interframe persistent artifacts present in most tissue.

It has been found that interframe persistent artifacts are relatively stable for a given individual, and more so, when collecting data around nearby locations. Thus, for example, the shot-to-shot variance in interframe persistent artifacts are relatively low shots of a single individual, but relatively much higher for shots of different individuals. The interframe persistent artifacts may also remain relatively stable when similar amounts of coupling medium are used, and where the pressure applied to the probe, and thus the probe contact, remains consistent. A method of mitigating interframe persistent artifacts from sinogram data comprises the removal of common data from separate, spatially distinct frames. In an embodiment, common data can be removed from separate, spatially distinct frames using singular value decomposition (SVD) algebra, principal component analysis (PCA), or other similar methods. In an embodiment, common data can be removed from separate, spatially distinct frames using a principal component removal algorithm. Typically, the singular value decomposition and principal component removal will require a sufficient number of independent frames where the interframe persistent artifact remains substantially constant and the collected data is changing and uncorrelated at a given sample or pixel. In an embodiment, more than 3 uncorrelated frames, and preferably more than 20 to 30 frames form the data set for analysis to remove the interframe persistent artifacts. In an embodiment, at least about 50 frames are analyzed in connection with an algorithm to remove interframe persistent artifacts.

In an embodiment, Interframe persistent artifact removal is performed on a per-light-source basis, meaning that where, for example, both YAG and Alexandrite lasers are used for different frames, YAG frames only are analyzed for Interframe persistent artifact removal from the YAG frames, and Alexandrite frames only are analyzed for Interframe persistent artifact removal from the Alexandrite frames. It should be noted that the expression per-light source is substantially directed at the wavelengths for the light source. Generally, lasers do not operate at a single wavelength, but rather, lasers produce light in a narrow range of wavelengths, often characterized by a dominant wavelength, which wavelength is used as a reference to for that laser. Thus, for example, a Nd:YAG laser output is often tuned to, and described as a 1,064 nm wavelength, not because the laser output is solely and precisely at that wavelength, but rather, because that is its predominant wavelength of light output. Similarly, an Alexandrite laser, which can be tuned to a variety of wavelengths from about 700 to 820 nm, and as used herein is generally tuned to, and often described as a 757 nm wavelength, is not intended to describe a precise wavelength, but rather a predominant wavelength in a narrow-band output of such a laser. Accordingly, as the term "per-light-source basis" is used above, if a tunable (rather than pre-tuned) laser were used, it would be considered one light-source for all frames created at substantially the same wavelength setting.

In an embodiment, where the total light energy for each frame is known or can be estimated, it may be advantageous to perform Interframe persistent artifact removal on frames having similar total light energy. Thus for example, in an embodiment, Interframe persistent artifact removal may be performed on a per-light-source basis for frames having more than average light energy, separately from the frames having less than average light energy. In an embodiment, the frames for a given light-source are divided into a plurality of groupings based on the total light energy for the frame, and Interframe persistent artifact removal is performed on each of the plurality of groupings. In an embodiment, the plurality of groupings is determined based on dividing the frames equally into the desired number of groupings, i.e., ⅓ in the first group, ⅓ in the second group, ⅓ in a third group. In an embodiment, the total light energy for the frames can be analyzed and the frames divided statistically, with those falling within a statistical grouping being analyzed together. For example, frames having total light energy of within one standard deviation of the mean may fall into a first category, frames more than one standard deviation above the mean fall into a second category and the remainder fall into a third category.

In an embodiment, an estimate of the interframe persistent artifacts is created from an average for each sample, for each channel, across a relatively large set of sinograms, e.g., 50 or more. In an embodiment, an estimate of the interframe persistent artifacts for each wavelength is created from an average for each sample, for each channel, for a given wavelength, across a relatively large set of sinograms, e.g., 50 or more. In an embodiment, the sinograms forming the set comprising the estimate set are spatially distinct from each other—i.e., captured from a differing regions of tissue. In an embodiment, each sinogram being a candidate for addition to the set of sinograms used in forming the estimate is rejected if it is not spatially distinct from the previous sinogram. In an embodiment, a test is run on a frame to ensure that it is spatially distinct from the previously used frame before it is mathematically embodied in the estimate. In an embodiment, the estimate is updated with each subsequent frame, or each new frame for the given wavelength. In an embodiment, the estimate is updated with a predetermined number of new frames (or new frames for the wavelength), and then remains consistent for the reading, or for some longer period. In an embodiment, the estimate is updated with each subsequent frame, or each new (spatially distinct) frame for the given wavelength. In an embodiment, the estimate is updated with a predetermined number of new (spatially distinct) frames (or new (spatially distinct) frames for the wavelength), and then remains consistent for the reading, or for some longer period.

In an embodiment, the estimate is updated using a moving window of frames representing a fixed number of the most recent frames taken in a reading. In an embodiment, an estimate for a specific individual is associated with that individual and retained for future use with the individual. In an embodiment, as estimate for a specific individual created with a given probe is associated with both the individual and the probe, and retained for future use with the same individual and probe.

In an embodiment, the detection of motion of the probe is used to discriminate and ensure that the frames collected for estimating the interframe persistent noise are independent or not correlated; i.e., when zero or little motion is occurring, the frames are correlated. In an embodiment and automatic motion detection algorithm may be performed on a sinogram, or on a reconstructed image, to determine if motion is occurring. In an embodiment, phase correlation may be used on two or more reconstructed images to determine the extent of motion that has occurred there-between. In an embodiment, a frequency-domain filter may be applied to two or more sinograms or images, and the correlation or difference between frames, may be used to determine if substantial motion has occurred between the frames; the more similar the frames, the less motion that has occurred. In an embodiment, low frequencies may be filtered out prior to motion detection since dominant interframe persistent artifacts are found in lower frequencies, whereas many structures in the tissue, such as blood vessels and tissue boundaries correspond to higher frequencies. In an embodiment, the interframe persistent noise estimate may be filtered in the frequency domain (or in another domain) to prevent structures such as the skin layer—which remain constant but is not considered unwanted—from inadvertent removal.

In an embodiment, where a "live" display is provided, an estimate can be formed using a plurality of prior frames. In an embodiment, where a "live" display is provided, an estimate can be formed using a plurality of prior spatially distinct frames. In an embodiment, where a "live" display is provided and the system comprises a satisfactory frame rate, the estimate can comprise past frames and future frames, provided that the display is delayed in time to permit the use of such frames. Thus, for example, where the frame rate for a given laser is, e.g., 5 frames per second, and the display is about one second behind real time, it may be possible to use four or five "future" frames to estimate the interframe persistent artifacts in the current frame. It will be apparent to one of skill in the art that "future" frame data can be incorporated into an estimate where the display is provided in an offline (e.g., non-live) playback system.

In an embodiment where a display output is provided after a reading is complete, all of the spatially distinct frames (or all of the spatially distinct frames of a give wavelength) can be used in creating a post-reading estimate of interframe persistent artifacts, and then entire reading can be reconstructed and output with the post-reading estimate of interframe persistent artifacts eliminated from the sinograms prior to their reconstruction.

In an embodiment, interframe persistent artifact estimation and removal is performed post-reconstruction, on the reconstructed image, or on an intermediate image formed after reconstruction, rather than performing this step on the sinogram data. In an embodiment, interframe persistent artifact estimation and removal is performed post-reconstruction on the real, imaginary or both components of complex images reconstructed from complex sinograms; complex images and sinograms are discussed in more detail below.

In an embodiment, the estimate of interframe persistent artifacts is used as a basis to modify sinograms prior to image reconstruction. In an embodiment, the estimate of interframe persistent artifacts is used to subtract artifacts out of the sinogram prior to image reconstruction.

In an embodiment, an estimate for the interframe persistent artifact can be computed by using the first principal component of the independent analysis frames. In an embodiment, independent component analysis can be used to estimate the interframe persistent artifact from the independent analysis frames in a similar fashion.

The following processing steps are illustrative of an embodiment of the Interframe persistent artifact removal algorithm.

a. compute the interframe persistent artifact estimate;
b. compute the scalar product "P" of the interframe persistent artifact estimate on the input data containing the artifact;
c. from each element of the input, subtract the projection of the interframe persistent artifact on the input from the input, by subtracting each corresponding element in the interframe persistent artifact estimate multiplied by P from the input and storing the result in the output.

Pseudo-code in the Appendix will provide a guide for a person of ordinary skill in the art in implementing this illustrative algorithm.

Preprocess (220)—Software Time Gain Compensation (340)

After a light event in tissue produces sound via an optoacoustic effect, the sound attenuates as it travels through the surrounding tissue. As the acoustic wave propagates through the tissue, its energy is absorbed by the tissue. In general, the further the sound has traveled, the more of its energy will have been lost, i.e., into the tissue or other propagation medium. In addition, the longer it takes sound to reach the transducer, the father it has traveled (assuming a constant speed of sound). For example, in the illustrative embodiment above, more than 2,000 samples are taken at a frequency of 31.25 Mhz, thus sampling for about 65 microseconds of time, which corresponds to a distance of somewhere around 100 millimeters, depending on the speed of sound in the particular tissue. Thus, later samples in the sinogram have greatly attenuated high frequencies as compared to the earlier samples, which have less attenuated high frequencies. The tissue structures and material constituents of the propagating medium (including, e.g., the acoustic lens and/or transducers), as well as physical boundaries or layers found within the medium may play a role in the attenuation, and thus the received energy of the optoacoustic return signal. In an embodiment, attenuation in an homogenous medium can be modeled as an exponential decay curve (e.g., as ideal), but the degree to which this holds true depends on the particular tissue or other volume being imaged. In an embodiment, compensation is performed on a per channel basis. In an embodiment, the samples are amplified by a factor related to the time they were received.

An illustrative embodiment of the software time gain compensation algorithm is provided below:
  a. Compute a 1D compensation curve based on a function of time corresponding to the sample number in the measured channel data. (In an embodiment, the 1D compensation curve may be based on an exponential decay curve with nominal acoustic attenuation corresponding to the one-way propagation of the acoustic wave from the optoacoustic source to the transducer.)
  b. For each channel in the sinogram
     i. Multiply each sample in the input sinogram by the corresponding compensation value in the 1D compensation curve
     ii. Place the resultant multiplied value into the output sinogram at the corresponding sample and channel Pseudo-code in the Appendix will provide a guide for a person of ordinary skill in the art in implementing this illustrative algorithm.

Preprocess (220)—Sub-band Acoustic Compensation (345)

Typically, as between the higher and lower frequencies information contained in the optoacoustic return signal, the higher frequencies may correspond to smaller sources and boundaries, and the lower frequencies may correspond to larger sized objects. During acoustic wave propagation in tissue, however, higher frequencies typically attenuate more and lower frequencies typically attenuate less. In other words, higher frequency acoustic waves are more attenuated than lower frequency acoustic waves traveling the same distance, and thus, received at (or near) the same time. This difference in attenuation can create distortion in a reconstructed optoacoustic image. Moreover, the higher frequency acoustic waves travel in tissue at a somewhat differing rate than lower frequency acoustic waves counterparts. Accordingly, to provide more accurately reconstructable data (e.g., sinogram), compensation may be made for time on a per frequency basis, and for amplitude on a per time basis.

To perform compensation for frequency dependent attenuation, the higher frequency information may be amplified, or may be amplified more than lower frequency information. In an embodiment, such amplification may be performed by applying compensation separately to sub-bands of the data, each sub-band corresponding to a filtered range of frequencies from the data. Applying the compensation to sub-bands rather than individual frequency components reduces computational load, and thus the need for computational resources. In an embodiment, in each sub-band, older samples (i.e., samples received later in time) are amplified more than newer samples. Compensation values can be estimated for tissue generally, or for specific tissue of interest, by measuring attenuation and speed of sound in tissue samples at varying frequencies.

Thus, in an embodiment, frequency domain sub-bands are identified which associate sub-band compensation factors, approximately, to the frequency dependent attenuation of the signal. In an exemplary embodiment of a sub-band acoustic compensation method, the compensation factors associated with a particular sub-band may be calculated in relation to depth and the center frequency associated with the sub-band. In an embodiment, to account for effects of depth related distortion as a function of a particular depth, d, and center frequency, fc, the compensation factor f(d, fc) may be calculated as f(d, fc)=exp(d*fc/1,000,000). In an embodiment, the compensation factor f(d, fc) may be calculated as f(d, fc)=exp(d*fc^g/a0), where g and a0 are parameters. In an embodiment, g equals 1.0 and a0 equals 1,000,000. In another embodiment, g and a0 are configurable parameters. In an embodiment, the system performing processing on the optoacoustic data, and/or the system displaying the optoacoustic output—which may, but need not be the same as the system acquiring the sinogram—would provide the operator the ability to vary the g and/or a0 parameters when processing or viewing optoacoustic images.

The following processing steps are an illustrative embodiment of a Sub-band Acoustic Compensation (345) algorithm as implemented to process sinogram data:
  a. Compute a list of frequencies corresponding to each sample in the frequency domain.
  b. Compute an array corresponding to the distance of an optoacoustic source to a transducer pertaining to each sample in the received optoacoustic signal. This may be done by multiplying the known time delay for each sample (i.e., based upon when it is received) with the nominal speed of sound for the volume of tissue.
  c. Compute a sub-band filter for each sub-band.
  d. Create an array to store an output sinogram and initialize each element to zero.
  e. Compute the Fourier transform of the input sinogram for each channel to create the frequency domain data
  f. For each sub-band filter, for each channel,
     i. multiply the frequency domain data by the sub-band filter
     ii. compute the inverse Fourier transform of the result
     iii. multiply the result element-wise by the compensation factor for the sub-band
     iv. accumulate the result in an output sinogram In processing the optoacoustic return signal, information in the signals from as much of the acoustic spectrum as may be detected by the transducer may contain potentially valuable information concerning the volume of tissue. Thus, in an embodiment, (as discussed in more detail below) the transducer used to receive the optoacoustic return signal is sensitive to a broad band of acoustic frequencies. Because of the broadband sensitivity, certain undesired information may also be captured in the optoacoustic return signal, including, without limitation, electronic interference, acoustic interference and mechanical interference. This undesired information is not easily identified in, and thus not easily filtered out of, the optoacoustic return signal. Furthermore, frequency dependent attenuation and the frequency dependent speed of sound are more pronounced in the optoacoustic return signal because of the broadband nature of the transducer sensitivity.

Because of its wideband nature, in an embodiment, the optoacoustic return signal is subjected to one or more techniques to process distortions across all frequencies. In an embodiment, some narrowband simplifications may be applied to optoacoustic data in sub-bands, where such simplifications may not prove reasonable for the entire wideband optoacoustic return signal.

Thus, in an embodiment, a Sub-band Acoustic Compensation (345) algorithm may employ a narrowband simplification of having fixed acoustic attenuation coefficient; although the simplification would not be valid across the broadband optoacoustic return signal, the algorithm can apply this simplification separately for each of the sub-bands. In another embodiment, a narrow-band simplification can be performed by computing a small time shift between two demodulated narrow-band signals in the time domain; the shift being found by using phase of the inner product of the two complex signals rather than using a less efficient computation involving normalized moments of the cross-correlation function. Other narrowband simplifications may also be employed after breaking the optoacoustic return signal into a plurality of sub-bands, such simplifications reducing the computational load required for processing the optoacoustic return signal. Following is an illustrative embodiment of a method for applying narrowband simplifications to optoacoustic data:

i) a filter bank of multiple filters can be formed to encompass a set of sub-bands of the frequency domain so that the energy summation (i.e., the sum of the squares) of the filters for each frequency will have a constant value of one (i.e. "partition of unity" property of the filter bank in the frequency domain), and, each filter in the filter bank may conform to a band-limited frequency range, thus, in context, the filter being referred to as a sub-band filter;

ii) each sub-band filter from the filter bank is applied separately to the optoacoustic return signal to create a filtered representation of the optoacoustic data for each sub-band;

iii) a narrow-band simplification is applied separately to each filtered representation of the optoacoustic data to create processed data for each sub-band;

iv) the processed data for each sub-band may then be re-assembled, with the processed data for the other sub-bands, into a final processed form, the re-assembly comprising additively combining the contributions from all of the processed data for each sub-band.

In an embodiment, a narrowband simplifications may be applied to optoacoustic data by using a wavelet packet transform which uses convolutional cascaded filter banks and downsampling operations. In an embodiment, the wavelet packet transform may be a dual-tree complex wavelet packet transform. In another an embodiment, narrowband simplifications may be applied in the time domain on demodulated filtered sub-bands where the demodulation is performed directly in the frequency domain. Where narrowband simplifications are applied in the time domain on demodulated filtered sub-bands, arbitrary sub-band filters may be used. In an embodiment, the system performing processing on the optoacoustic data, and/or the system displaying the optoacoustic output—which may, but need not be the same as the system acquiring the sinogram—may provide the operator the ability to vary the sub-band filters used in the narrowband simplification, when processing or viewing optoacoustic images. In an embodiment, applying the processing method using a suitable narrowband simplification may reduce the amount of necessary computation.

In an illustrative embodiment, an optoacoustic data processing method is described below, where the narrowband simplification is performed in the time-domain on data demodulated in the frequency domain. In an embodiment, the FFT size of the sub-bands can be significantly smaller than the FFT size of the full signal, by having a significantly smaller FFT size in the sub-bands, processing may be substantially faster, while achieving substantially the same result. The following processing steps are illustrative:

a. if appropriate, pad the signal with zero padding or symmetric padding (optional);
b. convert the input signal to the frequency domain;
c. remove the "negative" frequencies (i.e. in the range [−fs/2, 0−]) and double the "positive" frequencies (i.e. in the range [0+, fs/2]) to create an analytic signal in the frequency domain;
d. for each sub-band, create a temporary complex-valued array filled with zeros, with a length of at least twice the bandwidth of the corresponding sub-band filter to store the demodulated signals in the frequency domain. Ideally, the length of the temporary array will be much less than the original frequency domain signal, and thus, corresponds to a downsampling operation;
e. for each sub-band, copy the values of the positive frequency coefficients in the frequency-domain signal (within a range that encompasses the first non-zero value of the sub-band filter to the last non-zero value of the sub-band filter) into the corresponding temporary array, such that a frequency domain demodulation is performed by aligning the lowest frequency component of the copied range with the position of the DC frequency component in the temporary array, (note that the temporary array will contain zeros for coefficients corresponding to negative frequency components), the temporary array may also be padded with additional zeros beyond the range of copied frequency components corresponding to time domain interpolation, which may further increase the number of samples in the demodulated signal so the length is an optimal power-of-two for fast Fourier transformation;
f. with each sub-band, apply the sub-band filter to the corresponding temporary array by multiplying the sub-band filter values with the temporary array values corresponding to the aligned frequency components, and storing the result in the temporary array as the frequency domain demodulated signal;
g. convert each frequency domain demodulated signal to the time domain using the inverse fast Fourier transform (IFFT);
h. apply the narrowband simplification in the time domain to each time domain demodulated signal;
i. covert each time-domain demodulated signal back to the frequency domain by applying the fast Fourier transform (FFT);
j. modulate and sum each processed signal together in the frequency domain and store the result as a new full-length frequency domain signal (the modulation may be performed implicitly by aligning the frequency domain values of the processed signal with the positive frequency component positions corresponding the original full-length frequency domain signal);
k. perform the inverse Fourier transform on the resulting frequency domain signal;
l. if padding was used, remove the padding.

The time domain signal resulting from the foregoing method is the output of this embodiment of a method of applying a narrowband simplification to an optoacoustic data processing.

When using sub-band methods, demodulated signals may leak into other sub-bands. Such leakage may cause distortion and aliasing. The prevention of leakage each demodulated signal into other sub-bands may reduce distortion, aliasing and/or maintain partition-of-unity for mathematical reasons. To mitigate leakage, then an additional step may be applied for each processed demodulated sub-band in the frequency domain prior to performing an FFT transform, namely, either:

a. apply a multiplicative windowing filter (e.g., the original filter bank filter, or an inverse for such filter); or
b. apply a thresholding shaping function such that the magnitude of each complex coefficient will not exceed the value defined by the shaping function for each coefficient.

In an embodiment, a wavelet packet transform or a the dual-tree complex wavelet packet transform (DTCWPT)

algorithm may be applied, an thus, a cascaded filter bank implementation can be used rather than operating directly in the frequency domain. The following steps illustrate such an embodiment:

a. apply the wavelet packet transform;
b. apply a narrow band simplification to time-domain sub-band; and
c. then apply the inverse wavelet packet transform.

In an embodiment, a spectrogram or another method of time-frequency domain processing can be applied to the narrow-band simplification rather than sub-band filters. Use of a spectrogram uses time-domain based windowing rather than sub-band filters. Regardless of whether time-domain based windowing or sub-band filters (e.g., frequency based windowing) is employed, a Sub-band Acoustic Compensation (345) algorithm may implemented to process the optoacoustic data (e.g., sinogram data) to reduce complexity and permit narrow-band simplification.

Pseudo-code in the Appendix will provide additional details of an illustrative embodiment of a Sub-band Acoustic Compensation (345) algorithm.

Preprocess (220)—Transform Operator (350)

As discussed in more detail in the reconstruction section below, for a variety of reasons, the two dimensional sinogram data as discussed herein is not susceptible to closed form reconstruction. In an embodiment, a transform operation is performed in advance of or during reconstruction. The transform operation is used to yield more accurate results. In an embodiment, the transform operator can be used to account for the geometry of the system using the propagation model of the Helmholtz equation to approximate a closed form inversion formula, thereby yielding an accurate numerical results for the case of ideal reconstruction. In an embodiment, the transform operator may consist of discrete operations to match or resemble mathematical operations inside of the integrand of a closed-form inversion equation, or a similar equation, for the system geometry. In an embodiment, the transform operator may be separated from the weights of the equation because both the transform operator and the weights may be tuned separately. In an embodiment, a tuning procedure of the transform operator and of the weights may be carried out by comparison to a phantom, or to tissue, and identifying (subjectively or objectively) the best result. In an embodiment, a tuning procedure of the transform operator and of the weights may be carried out by comparison against a known equation, matching the weights to the transducer and patient geometry, typical fluence, etc.

In an embodiment, a transform operator may implemented by the following equation:

$$v_{out}(t) = a(t) d/dt [b(t) v_{in}(t)],$$

where vin(t) is the input signal, vout(t) is the output signal, d/dt is a derivative operation, and a(t) and b(t) are constant functions. In an embodiment, $a(t)=(t)^2$ and $b(t)=1/(t)$ to approximately represent a simplification for the integrand for a three dimensional case for a full view reconstruction formula with part of the geometry weights folded into the a(t) term. Thus, the transform operator amplifies high frequencies while not eliminating low frequencies in the signal. In an embodiment, $a(t)=(t+\alpha)^2$ and $b(t)=1/(t+\alpha)$, where α is a small number to prevent division by zero. In an embodiment, the transform operator may consist of a sequence of convolution and signal multiplication operations in (or building upon) the form described above to approximate a closed-form inversion or similar equation. In an embodiment, the transform operator alone may be applied on the acquired data as a pre-conditioner for a reconstruction method or for other processing. In an embodiment, the transform operator is used as a non-linear pre-conditioner prior to a sparse or quadratic minimization based reconstruction algorithm, which may bring the data closer to the reconstructed form of the solution with the frequency components matching the reconstructed geometry for faster convergence.

In an embodiment, to implement the transform operator formula in discrete time, the derivative operation may be replaced with a finite difference operation. In an embodiment, the value of t may be replaced with kT, where T is the sample period (inverse sample rate), and k ranges from 1 to the number of samples. In an embodiment, the transform operation is performed on each channel.

The following processing steps are an illustrative embodiment of applying the transform operator to a set of data such as a sinogram:

a. Create a floating point time values squared array (TV2[ ]), the array size being as large as the number of samples. The elements in the time values squared array are populated with the square of kT, where T is the inverse of the sample rate and k ranges from 1 to the number of samples (i.e., the first value TV2[0]=T*T, the second value is TV2[1]=2T*2T, etc.). For example, with a sample rate of 100 Hz, this array would have [0.0001, 0.0004, 0.0009, etc.].

b. Create a floating point time values reciprocal array (TVR[ ]) of the same size. The elements of the time values reciprocal array are populated as the reciprocal of the corresponding time values array entry (i.e., the first value TVR[0]=1/T, the second value TVR[1]= (½T), etc.).

c. Create two floating point temporary arrays (T1[ ] and T2[ ]) of the same size.

d. Iterating over each channel:
  i. Multiply each sample in the input signal (i.e., channel) by the corresponding entry in the time values reciprocal array (e.g., T1[n]=Input[n]×TVR[n]; then
  ii. Form the finite difference between each multiplied sample and preceding multiplied sample (e.g., T2[n]=T1[n]−T1[n−1], note, T2[0] may be set to zero as there is no preceding sample)
  iii. Form an output array by multiplying each finite difference by the time value squared (e.g., Output[n]=T2[n]×TV2[n]

Image Reconstruction (225)

Above were discussed several optional processing steps for processing the time domain optoacoustic return signal. For a variety of reasons, the two dimensional sinogram data as discussed herein is not susceptible to closed form reconstruction because, among other reasons, complexities involving: tissue attenuation; frequency dependent tissue attenuation; in-homogeneities of propagation speed; and in-homogeneities for other tissue properties. Moreover, the transducer elements used to acquire the sinogram data are not ideal, i.e., perfect, but rather, have an electro-mechanical frequency response that distorts the data. The transducer elements also have directivity and finite-aperture which affects the weighting of the measured signal strength corresponding to each pixel, and the transducer array has a limited view. Further, in some circumstances, as discussed herein, the acquisition probe uses an acoustic lens to limit the opto-acoustic signal of 3D tissue to a 2D imaging plane—suppressing out-of-plane signals—and thus, changing the mathematical geometry. The dimensionality of the geometry represented by the sinogram data does not conform neatly to a 3D case, a 2D case or a case with cylindrical symmetry.

Figure 4:
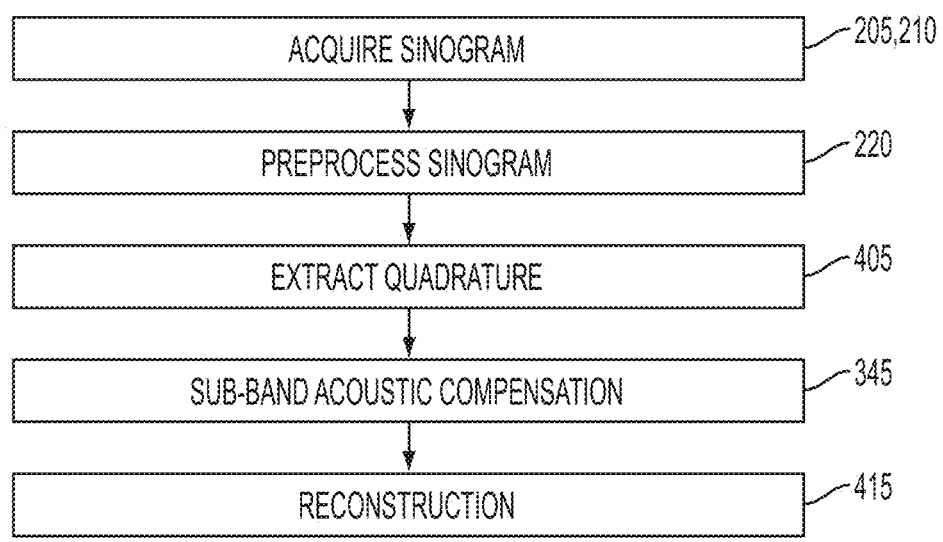
FIG. 4 shows a flow for an illustrative embodiment of a method for image reconstruction.

Turning now to FIG. 4, an illustrative image reconstruction process is shown, including several optional steps. Several time-domain processing functions are discussed as part of image reconstruction, however, it should be noted that there is no bright-line distinction to when preprocessing ends and image reconstruction begins. In other words, one can consider preprocessing part of the image reconstruction process. The distinctions made herein between preprocessing and image reconstruction are merely for organizational convenience.

In an embodiment, raw or preprocessed sinograms may be further processed in the time domain, and an image reconstructed there-from. Further processing may, but need not include, extract quadrature (405) and sub-band acoustic compensation (345). Sub-band acoustic compensation was discussed above, and will not be discussed again in detail— as discussed above, the pre-reconstruction time domain signal processing order is generally flexible, and the various processes may be rearranged for a variety of reasons, including, without limitation, optimization, image quality, coding convenience and processing considerations. Accordingly, in an exemplary embodiment, the transform operator (350) may be considered, and included, within the reconstruction block. The re-ordering of the blocks may, or may not, yield identical results, accordingly, in an embodiment, the system described herein may be flexible enough to permit the operation of one or more of the blocks in varying sequences.

In an embodiment, each of the sinograms, e.g., each long and short sinogram, is reconstructed. In an embodiment, as discussed in more detail below, the long and short sinograms each result in two images, one processed from the real component of a complex sinogram, and one from the imaginary component of a complex sinogram. Once reconstruction (414), and thus image reconstruction (225), is complete, post-processing, i.e., image processing (230), as discussed further below, is performed on the resulting image or images.

Image Reconstruction (225)—Extract Quadrature (405)

When measurements are taken with a probe 102, the response of the transducer may change the frequency domain phase of the optoacoustic return signal. As an example, if there is a shift in phase of a particular frequency component of the optoacoustic return signal, it may invert (negative) the corresponding portion of the signal in time domain, and in effect, cancel a portion of the signal during a back-projection or other reconstruction process. Generally, however, a probe can be calibrated by measuring how it changes the phase of a signal. Despite knowledge of how the probe changes the frequency domain phase, the phase of the optoacoustic return signal from tissue is unknown, and substantially unpredictable. The transfer functions of the acoustic paths between the locations of each acoustic source and each transducer element will change under varying mechanical conditions, and upon scanning different regions or types of tissue or between subjects. Thus, in this regard, frequency domain phase cannot be predicted even where the probe's effect on phase were known precisely. The frequency domain amplitude response from each acoustic source in the volume to the transducer is also an unknown, however distortions resulting from the miscalibrated frequency domain amplitude response of the tissue are of a different nature, and in some cases may not cause the same degree of problems, or can be compensated for using other methods. In addition, the response function is different for the path from each position in the tissue volume to each transducer. In all, there exist a large number of unknown transfer functions for which to compensate.

Although it is not necessary to rectify the complex-valued analytic signal prior to reconstruction, in an embodiment, to counteract the potential unwanted distortions and cancellations that may affect the reconstruction process, the sinogram can be processed into an analytic representation and stored as complex-valued array. With the negative frequencies removed, the complex-valued analytic signal in the time-domain will permit reconstruction of images that show instantaneous energy representing the acoustic sources in the tissue more accurately. The result of a rectification prior to reconstruction is different from a post-reconstruction rectification (i.e., $|z_1|+|z_2|+ \ldots +z_N|>=|z_1+z_2+ \ldots +z_N|$ where $z_n$ is a complex number and N is the number of transducers). Said differently, if beamforming (i.e., reconstruction) is performed on band-limited signals without taking the envelope, ringing may occur in the reconstructed image. When the complex analytic signal is used for reconstruction, however, the same ringing does not occur.

When the rectification is performed prior to reconstruction, no destructive mechanism exists to cancel the signals, which tends to result in high-contrast but also high streaking of the image, especially where the view is limited. When the complex analytic signal is reconstructed, however, there is a destructive mechanism (which may operate based on coherence). Thus, in the formation of any pixel, when the contributing components of the signals line up, they will add constructively but when signals are random or incoherent, which tends to occur under a variety of circumstances (including when the sources have not resulted from an acoustic source associated with the pixel being reconstructed), they will tend to cancel out. In an embodiment, this effect may be used to produce higher quality images. In an embodiment, a real-valued non-analytic sinogram may also be used to form the image, the envelope of which may be extracted, if desired, post-reconstruction. In such embodiment, ringing associated with a real-valued band-limited or filtered reconstruction may have occurred.

In an embodiment, an envelope can be extracted from the non-analytic reconstructed real image post-reconstruction. The envelope may be extracted by taking the envelope of a monogenic representation of the image, which may be carried out by computing the Hilbert-transformed directional derivative surfaces of the horizontal and vertical lines of the image and then computing for each pixel the square root of the square of the horizontal component plus square of the vertical component plus the square of the original image.

In an embodiment, an envelope image/auxiliary image can be formed by computing the envelope from every vertical line of the image post-reconstruction.

In an embodiment, to produce the analytic representation, the sinogram may be transformed to the frequency domain, multiplied by a coefficient array where the negative frequency components are zeroed and the positive frequency components are doubled, and then returned to the time domain, to form the complex-valued analytic representation. The imaginary portion of the complex-valued time domain signal represents the "quadrature" component and the real portion of the complex-valued time domain signal represents the "in-phase" component. The "quadrature" (i.e., imaginary) component, Q, is a function of the "in-phase" component, I, as follows: Q=H (I), where H is the Hilbert transform. In an embodiment, the Hilbert transform operator can be used to extract an analytic signal representation from the real-valued data. In an embodiment, the Hilbert transform may be performed in the time domain or in the frequency domain. Transfer from the time domain to the frequency domain may be done using a Fourier transform such as the Fast Fourier Transform, and the return to the time domain may be accomplished by an inverse operation such as the Inverse Fast Fourier Transform.

In an embodiment, the in-phase and quadrature sinograms can go through the reconstruction process separately, each treated as an independent, real-valued constructions. In an embodiment, the in-phase and quadrature components can be treated as a single, complex-value sinogram, with a single reconstruction stage operating on complex data. In an embodiment, weighted delay-and-sum reconstruction (415) may be used to implement the reconstruction step. In an embodiment, the output of reconstruction (415) is treated as complex-value data, with in-phase and quadrature reconstructed components. In an embodiment, the Extract Quadrature (405) step uses as the real component input the (processed or unprocessed) sinogram, and returns an imaginary (quadrature) component sinogram having the same dimensions as the input sinogram, thus, together with the source sinogram, forming a complex sinogram; each of the two sinograms may then be used to form a separate image, one of the real sinogram and one of the imaginary (quadrature) sinogram. In an embodiment, the complex sinogram may be used to form an image from the complex modulus of each complex value of the reconstructed complex image, or, the square root of the real (in-phase) image component squared plus the imaginary (quadrature) image component squared.

In an embodiment, a two dimensional frequency domain transform comprising a filtering operation is used to create a secondary image from the complex image. In an embodiment the secondary image is created from the complex image using a convolutional or FIR filter. As discussed in more detail below, in an embodiment, a series of processing steps may be performed on the complex image prior to converting it, or rectifying it, to a real valued image.

In an embodiment, the analytic representation of sinogram (with negative frequencies removed) may undergo a shift in the frequency domain, corresponding to complex demodulation. In an embodiment, such demodulation may be used to further prevent ringing by bringing the optoacoustic frequency content remaining after filtering towards DC. In an embodiment, such demodulation may be used in conjunction with a bandpass or smoothing filter to perform feature size selection, the operation of demodulation assisting in the display of features associated with a particular range of frequencies or scale. In an embodiment, frequency size selection may be tunable by an operator or selectable from a predefined list of settings.

Image Reconstruction (225)—Reconstruction (415)

Reconstruction (415) is a term used to signify the process of converting the processed or unprocessed data in the sinogram into an image representing localized features in a volume of tissue. In an exemplary embodiment, reconstruction (415) can be based on a weighted delay-and-sum approach. As discussed above, the weighted delay-and-sum algorithm may optionally be preceded by a transform operator (350). In an embodiment, the weighted delay-and-sum algorithm can operate on complex-valued data. In an embodiment, weights may be used by reconstruction (415) to represent the contributions from each sample to be used for each pixel, and organizationally, the method used to generate the weights may be considered part of image reconstruction (225). In an embodiment, the weights may be tuned based on an analysis of the collected data.

Generally, reconstruction (415) takes as input, processed or unprocessed channel data, i.e., a sinogram, and uses this information to produce a two dimensional image of a predetermined resolution.

The dimensions of an individual pixel (in units of length) determine the image resolution. If the maximum frequency content in the sinogram data is too high for the selected resolution, aliasing can occur during reconstruction. Thus, in an embodiment, the resolution and sampling rate may be used to compute limits for the maximum frequency content that will be used in reconstruction, and thus to avoid frequency content that is too high for the selected resolution. In an embodiment, the sinogram can be low-pass filtered to an appropriate cutoff frequency to prevent the aliasing from occurring.

Conversely, if the sampling rate is too low to support the image resolution, then, in an embodiment, the sinogram can be upsampled and interpolated so to produce a higher quality images. While the two dimensional image can be any resolution, in an exemplary embodiment, the image can comprise 512×512 pixels. In an another exemplary embodiment, the image can comprise 1280×720 pixels. In yet another exemplary embodiment, the image may comprise 1920×1200 pixels. In an embodiment, the horizontal resolution is at least 512 pixels wide, but not more than 2560 pixels wide, and the vertical resolution is at least 512 pixels high, but not more than 1600 pixels high.

A two dimensional image may represent variations in the volume, such as structures, blood, or other inhomogeneities in tissue. The reconstruction may be based upon the first propagation time from each location in the tissue to each transducer and the contribution strength of each sample to each pixel. The signal intensities contributing to each pixel in the image are combined to generate the reconstruction.

The following processing steps are an illustrative embodiment of a reconstruction algorithm using a weighted delay-and-sum technique:

a. Allocate an output image array and set all values to zero
b. For each transducer channel:
  i. For each pixel in the output image array:
    1. Access the delay (in samples) from Sample Delay Table for that channel and pixel, and then retrieve the sample (from the sinogram) corresponding to the channel and delay
    2. Access the weight from Weights Table corresponding to the channel and pixel
    3. Multiply the sample by the corresponding weight
    4. Add and store the result with in location of the output image array corresponding to the destination pixel.

The weights table is a table representing the relative contribution of each sample in the sinogram to each pixel in the resulting image. In an exemplary embodiment, for relative computational efficiency, the same weights table can be used for the real and imaginary components of a complex sinogram. In an embodiment, separate weights table can be used for each of the components of a complex sinogram. In an embodiment, one complex weights table can be used for the real and imaginary components of a complex sinogram. In an embodiment, separate complex weights table can be used for each of the components of a complex sinogram. In an embodiment, a complex weights table can be used to account for standing-wave type patterns in the image that are the result of the system geometry.

The weights table can be used to establish something akin to an aperture in software. Thus, in an embodiment, where a wider aperture is desired, more weight is given to off-center samples. Stated in other words, for example, for a given transducer, usually no sample would be given more weight than the sample directly beneath the transducer, and for the purposes of illustration, consider that the weight for a given sample directly beneath the transducer is 1. Consider further the relative contribution of samples that are at 15, 30 and 45 degrees from center, but equidistant from the transducer. To narrow the aperture, those samples could be weighted 0.5, 0.25 and 0.12 respectively, while to widen the aperture, those same samples could be weighted 0.9, 0.8 and 0.7 respectively. The former would provide only a slight (12%) weight to samples received from a source at 45 degrees from center, while the latter would provide the same sample much higher (70%) weighting. In an embodiment, the system displaying the optoacoustic output—which may, but need not be the same as the system acquiring the sinogram—would provide the operator the ability to vary this parameter (i.e., the software aperture) when viewing optoacoustic images.

In an embodiment, a very large table contains a mapping of relative weight and delay for each pixel and transducer. Thus, in an embodiment where a target image is 512×512 pixels and the probe 102 has 128 channels (i.e., transducers), there are 33,554,432 weight entries and the same number of delay entries. Similarly, in an embodiment where a target image is 1280×720 pixels and the probe 102 has 128 channels (i.e., transducers), there are 117,964,800 of each type of entry. In an embodiment where a target image is 1920×1200, and the probe has 256 channels, there are almost 600 million entry of each type.

As discussed above, the extract quadrature step (405) provides an imaginary component sinogram, and in an embodiment, each of the real and the imaginary component sinograms may be reconstructed into an image, thus producing two images, one for each component of the complex sinogram. In an embodiment, delay and weight tables are the same for each component of the complex sinogram. In an embodiment, the delay table is the same for each component of the complex sinogram, but the weight table is different for the real and imaginary component sinograms. In an embodiment, the weight table is the same for each component of the complex sinogram, but the delay table is different for the real and imaginary component sinograms.

Image Reconstruction (225)—Calculate Weights and Delays

As discussed above, in the illustrative embodiment of a delay-and-sum reconstruction algorithm, a Weights Table may be employed. An algorithm may be used to calculate the Sample Delay Table and Weights Table for each transducer. In an embodiment, the data comprising Sample Delay Table(s) correlates the estimated contribution of each transducer to each pixel, while the data comprising the Weight Table(s) provides an estimate of the relative weighting of the contribution of each transducer to each pixel as compared to the other contributions to that pixel. In an embodiment, the Weights Table may be used to account for angular apodization with respect to the transducer's norm, power of the laser, time gain control, light attenuation within the tissue, skin thickness, coupling medium characteristics, patient specific variables, wavelength specific variables and other factors.

In an embodiment, each of the tables corresponds in size (in pixels) to the two dimensional image output by image reconstruction, and a plurality of each table are created, one for each channel. In the illustrative embodiment above, each Sample Delay Table correlates the pixels of the target image with the samples in an sinogram, thus, one Sample Delay Table (which is specific to a channel) will identify for each pixel in the image, the specific sample number in that channel that is to be used in calculating that pixel. Similarly, in the illustrative embodiment above, each Weights Table correlates the pixels of the target image with the weight given to the sample that will be used; thus, one Weights Table (which is specific to a channel) will identify for each pixel in the image, the weight to be given to the sample from that channel when calculating the pixel.

X- and Y-coordinates of the image pixels are calculated using the input information on the image size and location. The time delays are calculated for each transducer and each pixel by knowing the distance between pixel and transducer and the speed of sound. If an acoustic matching layer with different speed of sound is used, then separate time delays are calculated inside and outside of the matching layer and added together, resulting in the overall transducer-pixel delay. The weights are calculated for each transducer and each pixel, depending on their relative location. The distance and angle between the transducer-pixel vector and transducer's norm are taken into account, as well as the depth position of an individual pixel. In an embodiment, the system calculating the weights and/or delays—which may, but need not be the same as the system acquiring the sinogram or displaying the images reconstructed therefrom—would provide the operator the ability to vary parameters used in processing. In an embodiment, the system calculating the weights would provide the operator the ability to vary the bases for the weight calculation, thus, e.g., giving more or less weight to off-center acoustic data. In an embodiment, the system calculating the weights would provide the operator the ability to controls whether linear or power relationships are be used in calculation of the weights.

Pseudo-code in the Appendix will provide a guide for a person of ordinary skill in the art in implementing an illustrative algorithm to calculate weights and delays.

Once reconstruction (414), and thus image reconstruction (225), is complete, post-processing, i.e., image processing (230), may be performed on the resulting image or images.

In an embodiment, image reconstruction may be based on Adaptive Beamforming, Generalized Sideband Cancellation, or other methods as are known in the art. In an embodiment, techniques for reconstruction may be based on determining cross-correlations functions between channels and/or maximizing the sharpness objective of the image.

In an embodiment, a method to reconstruct a volume may consist of decomposing a cross-section or volume into radial wavelets, the radial wavelets representing optoacoustic sources (the measured optoacoustic return signal of radial optoacoustic sources in particular are presumed to obey a simple closed form equation), the technique of Wavelet-Vaguelette decomposition may be used to relate the wavelets and vaguelettes between the image domain and the sinogram and to thereby determine the intensities of the radial wavelets in the image, and thus to reconstruct the image. In an embodiment, the projection of radial wavelets from the image domain into the sinogram domain (i.e., vaguelettes) can be used in conjunction with other image formation techniques prior to determining the intensities of the of the radial wavelets. In an embodiment, adaptive beamforming, or wavelet de-noising involving thresholding can be performed on the radial-wavelet projections as a stage such a reconstruction.

In an embodiment, reconstruction may be based on Iterative Minimization or Iterative Maximization, such as, for example, L1-minimization or L2-minimization. Iterative Minimization algorithms for reconstruction and enhancement require high computational load and thus, are not considered applicable for real-time imaging. Real-time optoacoustic reconstruction of a cross-section of a volume can be performed using an L1-minimization algorithm. In an exemplary embodiment for performing L1-minimization reconstruction in real-time on a 2D cross-section of a volume, the Fast Wavelet Iterative Thresholding Algorithm is used, and combined with the Helmholtz wave equation in the frequency-domain, which can be efficiently used to represent optoacoustic wave propagation yielding a diagonalizable (or nearly diagonalizable) system matrix. In an embodiment, the pixels of the image may be decomposed into radial wavelets, the decomposition represented in the frequency domain as radial subbands, and the radial subbands used in the iterative thresholding. In an embodiment, the Fast Wavelet Iterative Thresholding Algorithm may be used where the system matrix is found empirically rather than through using an ideal equation.

When the laser illuminates the volume of tissue with at least a portion of the surface being adjacent to a medium that is not perfectly matched to the acoustic properties of the volume, the propagating acoustic wave may reflect—at least in part—off the unmatched surface and propagate into the volume as an incident wave-front. The incident wave-front can further reflect off acoustic discontinuities in the tissue and interfere with the optoacoustic return signal creating an artifact. This artifact can be separated from the optoacoustic return signal using, e.g., an interactive minimization technique. In an embodiment, an image mapping the intensity of this artifact can be produced.

In an embodiment, a pattern detection classifier can be applied to an optoacoustic return signal, wherein the classifier output reflects the strength of a particular indicator as a function of time (or distance). Accordingly, upon obtaining measurements from multiple transducer positions, the classifier output can be beam-formed to localize the source (i.e., phenomenon) causing the pattern detected. An image produced from the beam-formed classifier output may suffer from blurring, reconstruction artifacts, and streak artifacts, which may be particularly acute in a limited-view case. These artifacts may result at least in part because the pattern classified signal may lack information concerning signal strength that is part of a non-pattern classified sinogram, and its intensity is related to the presence of the pattern, not necessarily on the distance that the transducer is located from the source of the pattern. The classifier output of a classified optoacoustic signal, however, can be "fit" into the propagation model of the Helmholtz equation where the classifier output is characterized as originating from an instantaneous source term at a given position. Thus, to reduce the streaking, blurring and artifacts a parametric map of the pattern classified signal can be formed using techniques for reconstruction and deconvolution other than simple beamforming. Application of, e.g., an iterative minimization technique can be used to reduce streaking and thus better localize the source of the pattern. Different types of classifiers and reconstruction techniques may have different considerations that apply. In an exemplary embodiment, a parametric map of the classified quantity can be produced by using an iterative minimization technique, where the system matrix is formed as it would be had the source been an optoacoustic signal. In an embodiment, the sparse basis representation used by, e.g., L1 minimization, may serve to localize the source of the pattern and hence reduce artifacts. Thus, rather than applying the reconstruction technique to an optoacoustic return signal, it may be applied to classifier output, where the classifier output is represented in the form of a sinogram. In an embodiment, the reconstruction technique is applied as though the classifier output were an optoacoustic return signal. In an embodiment, further processing, such as taking a complex envelope of the classifier output, filtering, or deconvolving the classifier output may be performed prior to reconstruction. In an embodiment, the classifier may be designed to discriminate between normal and abnormal branching blood vessels in tissue.

Image Processing (230)

Figure 5:
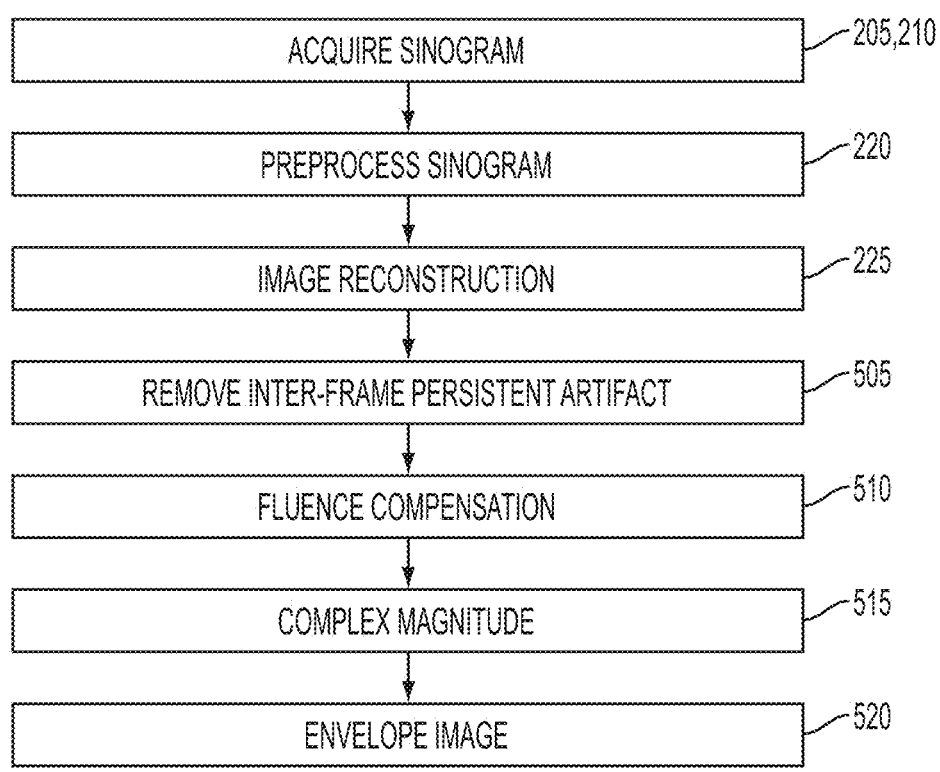
FIG. 5 shows a flow for an illustrative embodiment of a method of post-processing to produce an envelope image.

As discussed above, after the long and short sinogram are acquired (205, 210), optionally preprocessed (220) and then image reconstructed (225) to form images, certain post processing may be performed on the resulting images. Turning now to FIG. 5, optional post-processing steps are shown, including remove inter-frame persistent artifact (505), fluence compensation (510) and complex magnitude (515). In an embodiment, image processing produces an envelope image (520) that is positive real valued (not complex-valued).

Image Processing (225)—Remove Inter-Frame Persistent Artifact (505)

The optoacoustic return signal comprises both desirable and undesirable information, among the information that may be undesirable is what will be referred to herein as the undeired coupled response. The undesired coupled response may include artifacts that result from light striking a person's skin as it penetrates into the tissue. More generally, the undesired coupled response being addressed by this step is inter-frame persistent signal or inter-frame persistent artifact. Inter-frame persistent signal, as used herein, refers to an interfering signal that remains constant, or changes very slowly, and which is therefore presumed to produce similar interference in each of a plurality of images that are spatially and/or temporally related. Inter-frame persistent artifact refers to the same phenomenon, but when it appears in a reconstructed image. Thus, the terms inter-frame persistent signal and inter-frame persistent artifact may sometimes be interchanged herein because they represent the same phenomenon. The problem of removing inter-frame persistent signal is complicated by the fact that the similar interference found in separate frames may be scaled in amplitude by a constant factor. The scaling may be related to a number of factors, including, without limitation variation in the total light energy used to cause the optoacoustic return signal. Moreover, generally, inter-frame persistent signal varies sufficiently from person to person, that it is not readily identifiable except by examination of a plurality of frames for a given individual. In an embodiment, a plurality of frames taken in relatively close spatial and/or temporal proximity to each other, but generally not in an identical location, are analyzed with the goal of removing inter-frame persistent signal.

In an embodiment, in a first process directed to the removal of inter-frame persistent signal, a step is performed to estimate its composition. In an embodiment, an inter-frame persistent signal is taken as the first principal component from a set of independent frames. The first principal component can be computed using any method, although, in an embodiment, the first principal component can be computed using SVD (singular value decomposition) or an equivalent iterative method.

In an exemplary embodiment, the set of independent frames is selected such that each frame has independent background noise. In other words, generally, independent frames taken when the probe 102 is not moving should not be included in the set. Accordingly, in an embodiment, each sequential frame that may be considered for use in the set may be flagged to indicate its suitability (or to indicate its non-suitability) for inclusion in the set. To analyze a frame for suitability or non-suitability for inclusion in the set, the frame may be compared to one or more frames preceding it in sequence. The flagging of a frame (as suitable or non-suitable) may be done at capture-time, or thereafter, but prior to the step estimating the inter-frame persistent signals. In an embodiment, the flagging of a frame (as suitable or non-suitable) is performed prior to writing that frame to the LOM file. In an embodiment, the process of estimating the inter-frame persistent signals may include a frames selection sub-step.

The following processing steps are an illustrative embodiment of an inter-frame persistent signal estimator:
a. Initialization (enter if sizeOfFrameBuffer has changed, or Nr (number of rows in frame) or Nc (number of columns in frame) has changed)
   i. For each channel, allocate a frameBuffer as a circular buffer to have sizeOfFrameBuffer frames.
   ii. Set frameBuffer.start[channel] to 0 and frameBuffer.end[channel] to 0 for each channel. These two variables keep track of the active frames in the circular buffer.
   iii. For each channel allocate estimate[channel][Nr][Nc] and set all elements to 0.
b. If captureFrame is true (thus the frame is flagged as suitable for inclusion in the set) then
   i. Optionally, apply an image transform to frame_in (e.g., a two dimensional wavelet transform, a two dimensional FFT, or another similar transform; a band pass filter may be applied to remove certain frequencies from the computation)
   ii. Add frame_in to the frameBuffer for the current channel. If the buffer is full overwrite the oldest frame in the buffer.
c. If computeFrame is true then
   i. Map all of the data in frameBuffer into a matrix where each frame in the buffer is treated as a column and each row is a value of the same pixel index.
   ii. Compute the principal component (or independent components) of frameBuffer for the current channel.
   iii. (If an image transform was applied to frame_in, apply the inverse transform to the results of the previous calculation.
d. Output estimate out for the current channel as the selected principal component (or independent component), absent an alternative selection, the first principal component is selected.

In connection with the foregoing process steps it should be noted that for optimization of step c(ii), computation of the full SVD may not be real-time. It is not necessary that the persistent frame estimation process run on every frame. In an embodiment, the persistent frame estimation process may be re-updated periodically, e.g., based on a trigger external to the algorithm. In an embodiment, it may be beneficial to run persistent frame estimation process in a thread and utilize the most recently finished estimate only. In an embodiment, the first principal component is found in the complex domain, thus, the SVD (or other) function should accept complex-valued input. In an embodiment, the inter-frame persistent signal estimate should have a zero mean, and unit L2-norm. In an embodiment, only the first principal component is computed. In an exemplary embodiment, the first principal component is computed for the estimate on the complex image using a power iterative method for efficiency. In an embodiment, the interframe persistent signal estimate is the first several principal components. In an embodiment, the interframe persistent signal estimate is the first several independent components. In an embodiment, when multiple estimates are generated, each is removed from the signal. In an embodiment, the inter-frame persistent estimate can be performed in an image transform domain, such as a two dimensional wavelet transform domain or two dimensional FFT transform domain, as discussed above. In an embodiment, the inter-frame persistent estimate can be performed on a band-passed set of data.

Once the inter-frame persistent signal is estimated, it can be removed from the frames. In an embodiment, the inter-frame persistent signal may be subtracted from the frame. As discussed above, although the interference may be identical from frame to frame, it may be scaled in amplitude. Thus, in an embodiment, prior to subtraction of the inter-frame persistent signal estimate from the source frame, a scaling factor should be computed, and the scaling factor may be used to scale the estimate so that it can be subtracted from the source frame. The scaling factor is the projection of the inter-frame persistent signal component. In an embodiment, multiple inter-frame persistent signals may be estimated. In an embodiment each of the multiple inter-frame persistent signals may correspond to the highest energy components in the decomposition method used to perform the computation (e.g., first 3 SVD components).

Image Processing (230)—Fluence Compensation (510)

Because skin and tissue characteristics vary from patient to patient, light distribution in the tissue of a specific patient cannot be predicted. The fluence profile of the light can be broken down into a spatially-dependent common light penetration profile component and two spatially-dependent wavelength-specific fluence-ratio profiles, which relate the true fluence to the common light penetration profile. In an embodiment, the common light penetration profile and wavelength-specific fluence-ratios may be used to compensate for patient specific variations that affect the distribution of light within the tissue. In an embodiment, 1-dimensional curves based on a model of fluence behavior for the common profile and specific profile may be used, with a single patient specific parameter, to generate the two dimensional fluence compensation curves. In an embodiment, any of the following equations may be used without limitation as for compensation curves:

| Type | Equation |
| --- | --- |
| LINEAR | $f(x, g) = 1 + g * x$ |
| EXPONENTIAL | $f(x, g) = \exp(g * x)$ |
| EXPONENTIAL_DIV | $f(x, g) = x * \exp(g * x)$ |
| IDENTITY | $f(x, g) = 1$ |

Other equations or simulated curves may be used for the compensation curves. In an embodiment, experimentally measured fluence distribution curves can be used as a method of compensation. In an embodiment, a separate device or a separate sensor (that may use optoacoustic principles) can be employed to measure the fluence curves in real-time during the light event. In an embodiment, the fluence compensation curves can be derived (i.e., estimated) from simulations. In an embodiment, the reciprocal (or modified reciprocal) of a measured or simulated curve may be used as a one dimensional fluence compensation curve. In embodiment, a measured or simulated curve may be filtered prior to being used in fluence compensation. In an embodiment, fluence compensation curves based on statistical features may be computed as a function of depth in a single image or in a set of images dynamically acquired.

Figure 6:
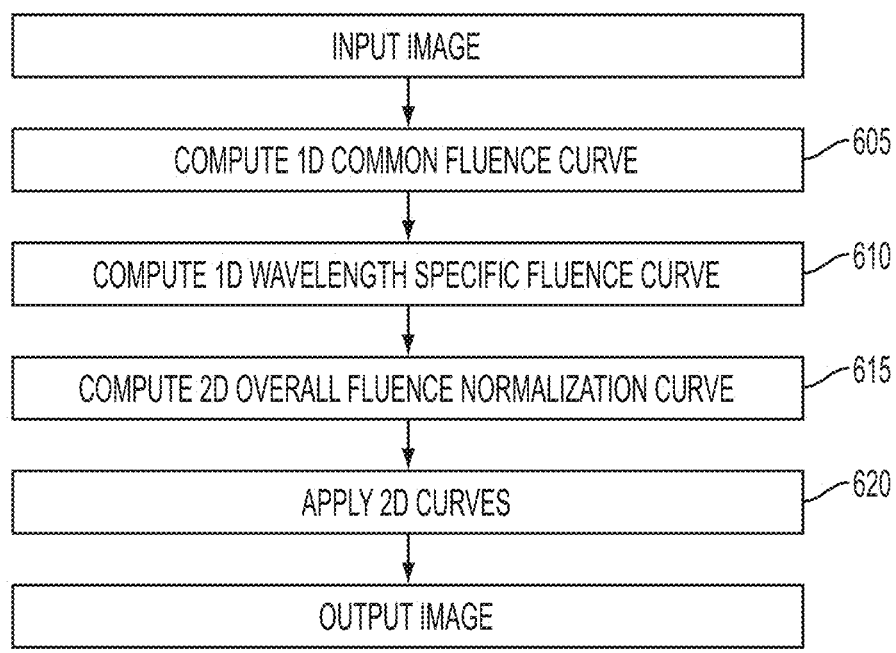
FIG. 6 shows a flow for an illustrative embodiment of a method of performing fluence compensation.

Turning now to FIG. 6, a set of process steps for fluence compensation (510) is shown. In an embodiment, the system performing processing on the optoacoustic data, and/or the system displaying the optoacoustic output—which may, but need not be the same as the system acquiring the sinogram—would provide the operator the ability to select between available equations, and select a parameter used for processing an optoacoustic image or its derivative for viewing. Thus, in an embodiment, an operator may select a curve, such as the exponential curve, and/or a parameter, such as the exponent. In an embodiment, the curve, and possibly the parameter, are selected from a finite list of selections presented to the operator in a user interface. Once the curve and parameter are selected, the common fluence curve (605) and wavelength specific curves (610) are calculated. Thereafter, in an embodiment, a two dimensional (e.g., a curve for each pixel column) overall fluence normalization curve (615) is computed. The two dimensional overall fluence normalization curve is then applied to the image (620). In an embodiment, the compensation curves are automatically selected from a set of compensation curves based on image statistics or statistics of a region of interest within the reconstructed image. In an embodiment, the fluence compensation curve may be computed based on a region-of-interest identified in real-time by a system operator, the fluence compensation curve being dependent on a measure of depth of the identified region-of-interest. In an embodiment, a region-of-interest may be identified by selecting a rectangular region-of-interest of a target object, the center of the region corresponding to the depth used to determine the compensation curve.

The following processing steps are an illustrative embodiment of producing a two dimensional fluence compensation curve from a selected one dimensional equation applicable for an ideal linear array and applying it to an uncompensated image:

a. Compute one dimensional array containing the depths for each pixel in the image starting at the minimum image depth until the maximum image depth. Store the result in the vector "x".
b. Calculate one dimensional common fluence compensation curve based on the common gain parameter "$g_0$" using a selected compensation function for $f_0(x,g_0)$ for the fluence compensation.
c. Calculate one dimensional channel-specific compensation curves for each channel
  i. The channel 1 curve is based gain parameter "$g_1$" using a selected compensation function for $f_1(x,g_1)$ for the fluence compensation.
  ii. The channel 2 curve is based gain parameter "$g_2$" using a selected compensation function for $f_2(x,g_2)$ for the fluence compensation.
d. Calculate the overall two dimensional normalization curves from the one dimensional common curve and channel specific curve.
  i. For each channel, create an overall one dimensional curve by multiplying the common curve with the channel specific curve
  ii. Set each vertical column in the two dimensional normalization curve equal to overall one dimensional curve
e. For the current channel reconstructed image
  i. for each pixel in the image, multiply the value of the pixel by the corresponding pixel in overall two dimensional normalization curve belonging to the current channel In an embodiment, Fluence Compensation (510) may process the complex image, and provides a new complex image as its output. In an embodiment, Fluence Compensation (510) may process a real image, and provides a modified real image as its output.

Image Processing (230)—Complex Magnitude (515)

In an embodiment, the complex magnitude (515) step takes as input the complex image (or a real image where the imaginary component is not available), and produces an envelope image that has the same number of rows and columns as the input image. The envelope image may be determined by taking the complex magnitude of each element of the input. Where the real image alone is available, the envelope image is the absolute value of the information in that image. In an embodiment, the envelope can be computed alternately from the real image alone by producing an image in substitute for the imaginary component image where each vertical line in the imaginary image is the Hilbert transform of the corresponding line in the real image; the complex magnitude being applied in the same way.

Generate Parametric Images (240)

As discussed above, after the long and short sinogram are acquired (steps 205, 210), optionally preprocessed (step 220) reconstructed (step 225) to form images, and processed (step 230) to produce short (232) and long (234) envelope images, the envelope images are used to generate parametric images (step 240), and more specifically, to generate one or more of the following parametric images: an oxygenation map (250), a hemoglobin map (255) and a masked oxygenation map (260). In an embodiment, parametric images are presented by providing a colorized image reflective of qualitative information obtained from within the short and long envelope images (232, 234).

Figure 7:
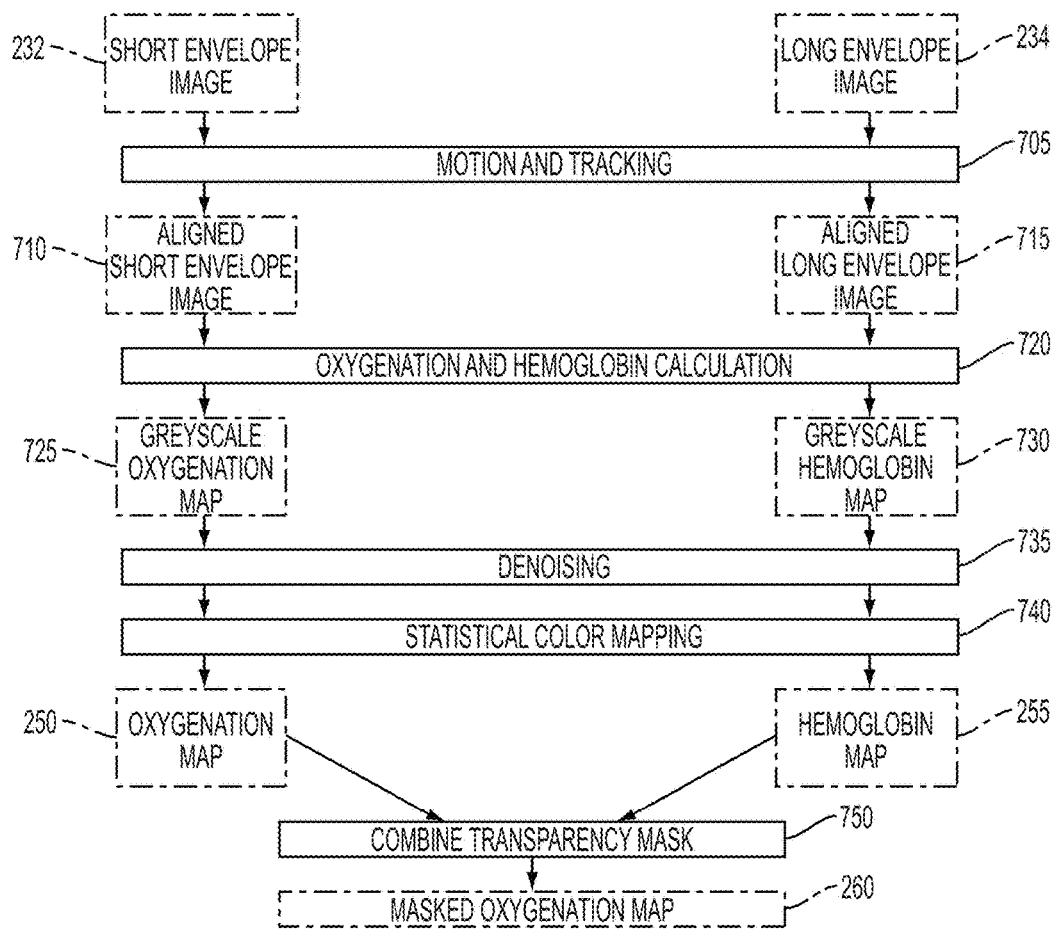
FIG. 7 shows a flow for an illustrative embodiment of a method of creating color parametric maps from the envelope image information.

Turning now to FIG. 7, the short envelope image (232) and long envelope image (234) are processed to provide at least one of the parametric images (250, 255, 260). In an embodiment, the short envelope image (232) and long envelope image (234) may be processed by motion and tracking (705) to improve the signal to noise ratio and/or provide better alignment between the images. In an embodiment, the short envelope image (232) and long envelope image (234) are processed by oxygenation and hemoglobin calculation (720) to produce grayscale maps of oxygenation and hemoglobin. More generally, a plurality of parametric maps (i.e., two or more) may each be formed from the information in a plurality of images (i.e., two or more), and another parametric map may be formed from the information in at least two of the plurality of parametric maps. It is within the scope of this disclosure that, rather than forming another parametric map from the information in at least two of the plurality of parametric images, such latter parametric map may be created directly from the information in the plurality of images. In other words, in cases where mathematics does not require the creation of the intermediate parametric maps, should the only reason to do so be to combine them into the latter combined parametric map, the separate step of producing the intermediate maps may, in an embodiment, be omitted.

Once created, parametric maps may be denoised (735). In an embodiment the grayscale maps are statistically color mapped to produce color maps of oxygenation (250) and hemoglobin (255). The hemoglobin map (255) may thereafter be in combination with the oxygenation map (250) to provide a masked oxygenation map (260) in the combine transparency mask (750). In an embodiment, the result of Generate Parametric Images (240) is an RGBA oxygenation map an RGBA hemoglobin map and an RGBA HgO masked oxygenation map. As discussed above, in an embodiment, the color mapped quantity similar to the masked oxygenation map may be generated directly from the data in the two envelope images, rather than passing through the intermediate stage of combining the transparency channels of the oxygenation map and hemoglobin map.

Generate Parametric Images (240)—Motion and Tracking (705)

Motion and tracking (705) may be necessary because, as successive images of a static (or slow moving) scene are generated, motion in the sensor will cause the position of content of the scene to "move" relative to each other. Thus, a subsequent image, $g_b$, taken a short time (e.g., 100 ms) after a previous image, $g_a$, may be offset by a number of image pixels in the horizontal and vertical dimension from the previous image, $g_a$. Similarly, subsequent images may also be subject to non-rigid deformations that can occur between frames. In an embodiment, corrections may be made for non-rigid deformations. Moreover, in an embodiment, further motion and tracking may be employed to determine how the probe is moving, thus providing a basis to generate a 3D image of the tissue structures. In an embodiment, and as discussed in more detail below, the system may include sensors (e.g., accelerometers, or fixed positions sensors and targets, or otherwise) that will provide data concerning the position or movement of the probe during imaging. Such information concerning position or movement may be taken into account in making correction for translation, rotation, angular deflection, or other probe movement that may cause deformations from frame to frame.

Figure 8:
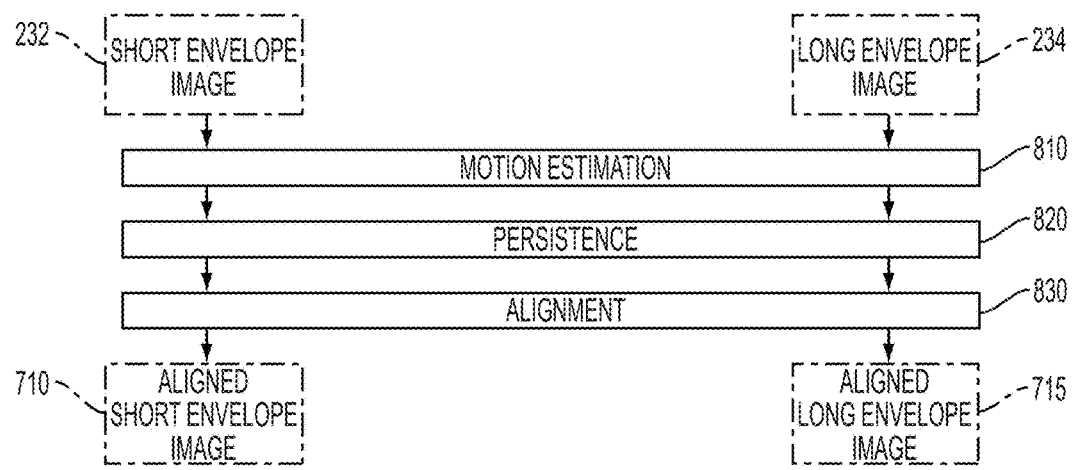
FIG. 8 shows a flow for an illustrative embodiment of a method of motion and tracking processing.

Turning briefly to FIG. 8, in an embodiment, the step of motion and tracking (705) is broken out into component parts, which may include motion estimation (810), persistence (820) and alignment (830). In an embodiment, the motion estimation (810) process may be used to estimate motion between two images. In an embodiment, the rigid motion between the images is assumed to have no rotational component of motion. In an embodiment, the rigid motion between the images may be assumed to have a rotational component of motion. In an embodiment, the persistence (820) process may be used to improve the signal to noise ratio. In an embodiment, the alignment (830) process aligns two images, such as a short envelope image (232) and a long envelope image (234).

Motion estimation (810) can provide information that may support one or more methods of removing the effect of probe motion between successive image acquisitions. In an illustrative embodiment, motion estimation (810) estimates motion that occurred between a short envelope image (232) and a long envelope image (234). In an embodiment, the motion estimation (801) process requires input of the number of rows and columns in the image, as well as cutoff values for a raised cosine apodized bandpass filter. In an embodiment, a filter array is created on startup, or whenever there is a change to the input parameters. The filter array may be created by determining the 2D frequency components, and then using a raised cosine apodization function to smoothly shape the bandpass characteristics of the filter and/or o that the bandpass range corresponds to frequencies relevant to features that are tracking. In an embodiment, using a raised cosine apodization function creates a radial 2D bandpass filter in the frequency domain to suppress components that are less likely to correlate in the motion estimation procedure, which may depend on the specific nature of optoacoustic scans. A correlation array computed using a buffered image and another image may then be determined, and correlation determined there-from. In an embodiment, a phase correlation algorithm may provide a frequency domain approach to estimate the relative positions of the content of two images. In an embodiment, given two input images, ga and gb, taken a short time apart, and where Ga=F{ga}, and Gb=F{gb}, and where F{g}=2D Fourier Transform if image g, the cross-power spectrum of the phase, R can be formed as follows:

$$R = \frac{G_a G_b^*}{|G_a G_b^*|}$$

a normalized cross-correlation, r, can be provided by using the inverse Fourier Transform:

$$r = F^{-1}\{R\}$$

and the offset, in pixels, is equal to the location of the peak in r:

$$(\Delta x, \Delta y) = \operatorname{argmax}_{x,y}\{r\}$$

In an embodiment, filtering (2-D) or zero padding in the edges may be applied to the images (before the Fourier transform) to compensate for edge effects. In an embodiment, a small constant may be added to the denominator of the cross-power spectrum term R, to serve as a filter for weak values, and/or to prevent division by zero. In an embodiment a bandpass filter (i.e. the 2D radial raised-cosine apodized frequency domain bandpass filter described above) may be multiplied with the numerator of the cross-power spectrum.

In an embodiment, the motion is expressed in horizontal and vertical pixels, and may be provided along with additional correlation values. The correlation values may be expressed in a variety of ways, and in an embodiment, is expressed by providing a mean value of the absolute value of the cross correlation array along with the maximum value of the absolute value of the cross correlation array. In an embodiment, the pixel motion between successive frames, by knowing the timing of when frames are collected, may be used to estimate the velocity of the motion along an axis. In an embodiment, the estimated velocity of the motion may be filtered to remove error, to produce a filtered estimate of velocity. In an embodiment, the estimates of velocity may be used to estimate the position of the probe at a given time. In an embodiment, the estimate of the position of the probe at a given time may be used in co-registration with ultrasound, such that during co-registration, the position of the optoacoustic parametric map or opto-acoustic image is shifted to correspond with the anticipated position for the overlay based upon the known time at which the ultrasound frame gets collected; accordingly, when ultrasound and optoacoustic information is collected in an interleaved fashion, a smoothly tracking motion of the co-registered overlay can be produced, that can also reduce positional misalignment between co-registered frames.

The following processing steps are an illustrative embodiment of motion estimation:
 a. Create (or recreate) a filter array based on the input parameters, by:
   i. Getting the radial frequency components, ii. Using a raised cosine apodization function to create a bandpass filter array;
b. Determine the correlation between the previous frame (stored in prior iteration of algorithm) and the current frame, and calculate the translation offset vector;
c. If the value of the correlation is lower than a threshold, and the translation is also lower than a threshold, the motion can be assumed perpendicular to the imaging plane;
d. Store the current frame as the "previous" frame;
e. The probe velocity may be estimated from the translation using the time elapsed between the frames;
f. In an embodiment, the translation or velocity outputs may be low pass filtered to have a smoother estimate of velocity.

In an embodiment, once motion is estimated, a persistence (820) process may be run to filter out noise and strengthen the true signal in the image. The persistence (820) process presumes that unwanted signal, e.g., noise, may be present in the image, than the unwanted signal will change from frame to frame. In an embodiment, the unwanted signal may be modeled as Gaussian white noise. In an embodiment, it is assumed that the two images upon which the persistence (820) process is run will be highly correlated, making the change in true image content from frame to frame small. It will be apparent to a person of skill in the art that the lower the change in true image content, the better the results that will be achieved.

In an embodiment, the persistence (820) process performs a weighted moving averaging (WMA) on image data, where one or more previous frames are weighted and considered with the image. In an embodiment, the weight given to previous frame or frames may depend on a single input parameter. In an embodiment, the weight given to previous frames may depend on a plurality of parameters. In an embodiment, the persistence (820) process performs exponentially weighted moving averaging (EWMA) on image data, which is a type of (infinite impulse response) IIR filter. Using an IIR filter, instead of a finite impulse response (FIR) filter permits storing less data in memory for calculation, such as, for example, having only an array of the image, and an array for previous frames in memory.

In an embodiment, for a sample, n, the output value, y[n] is calculated from an input value x[n] and the previous output value y[n−1] as y[n]=(1−α)x[n]+αy[n−1]. If n<0 then y[n]=0.

The following processing steps are an illustrative embodiment of persistence:
a. During initialization or if the image size has changed Allocate and initialize an array called persistence buffer
b. If translational motion has been detected (and the buffer is not being flushed)
 i. shift the persistence buffer for the current channel using linear translation the detected amount
c. For each pixel in the input image

--- i. If the persistence buffer is not being flushed, then
 persistence_buffer[channel][pixel] = (1-alpha) * input_image[pixel] + alpha * persistence_buffer[channel][pixel];
else
 flush the persistence buffer for the channel by setting the value of the input image pixel e.g., persistence_buffer[channel][pixel] = input_image[pixel];
ii. output_image[pixel] = persistence_buffer[channel][pixel]

---

In an embodiment, once the persistence (820) process is run, an alignment (830) process may be used to align the present image and the prior one. In an embodiment, the alignment (830) process may rely upon the results (e.g., horizontal and vertical pixel calculations) of motion estimation (810). In an embodiment, the alignment (830) process may estimate the movement between the previous frame and the frame under consideration. The alignment (830) process provides an output image shifted by a vertical and/or horizontal offset. In an embodiment, the vertical and/or horizontal offset is provided in pixels. In an embodiment, the motion estimate for the persistence process uses phase correlation information from the images of similar wavelength channels, since images from similar channels will have the most similar features for performing motion estimation. In an embodiment, the alignment process runs on images of dissimilar wavelength channels since the images from dissimilar channels should be aligned prior to calculation.

In an embodiment, the motion estimate and correlation are used to automatically detect frames used by the interframe persistent artifact estimation procedure.

Generate Parametric Images (240)—Oxygenation and Hemoglobin Calculation (720)

After motion and tracking (705) an aligned short envelope image (710) and an aligned long envelope image (715) can be processed using oxygenation and hemoglobin calculation (720) to produce a grayscale oxygenation map (725) and a grayscale hemoglobin map (730). Generally, optical absorption in blood is different at differing wavelengths of light. Moreover, optical absorption in blood is affected by blood oxygenation. Because of the coefficient of absorption, at some wavelengths of light, blood of a given oxygenation is more optoacoustically responsive than blood at a lower oxygenation, while at other wavelengths of light, the reverse is true. For example, oxygenated blood is less optoacoustically responsive than deoxygenated blood in response to stimulus from an Alexandrite laser, which has predominant output at about a 757 nm wavelength, while blood oxygenated blood is more optoacoustically responsive than deoxygenated blood in response to stimulus from an Nd:YAG laser, which has predominant output at about a 1,064 nm wavelength.

Figure 9:
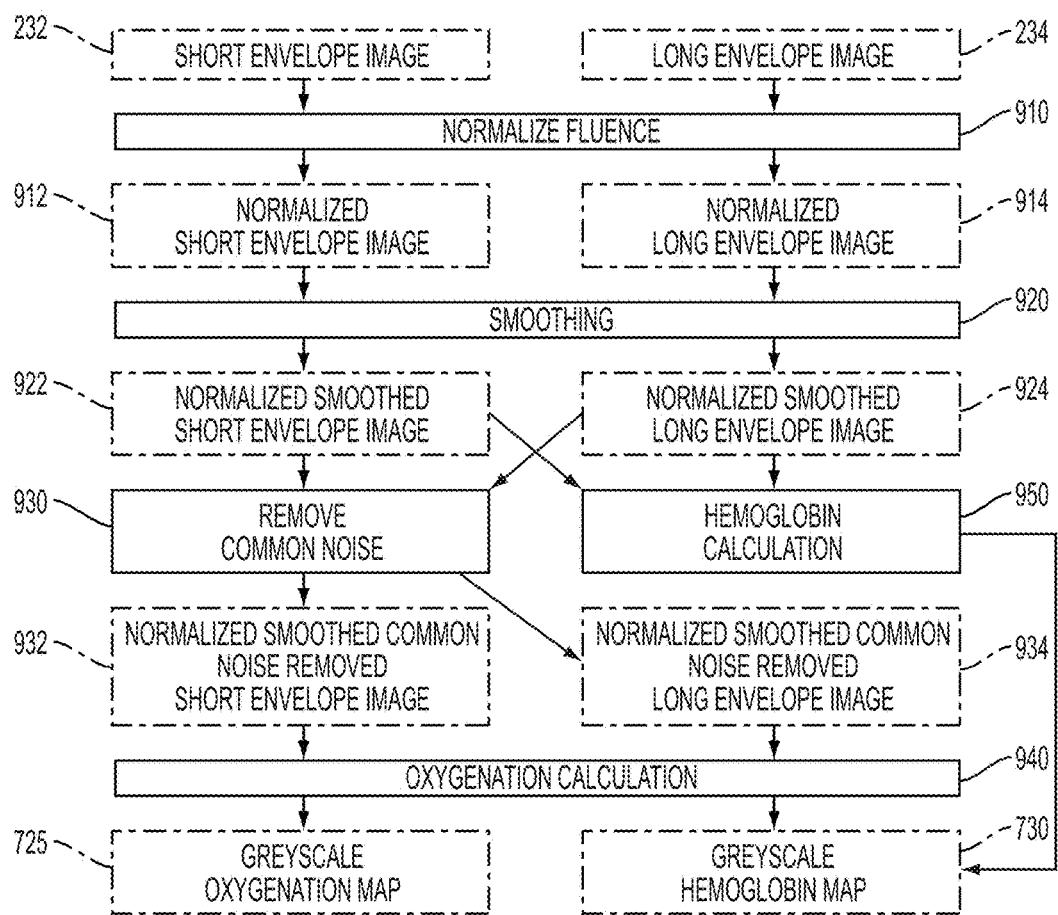
FIG. 9 shows a flow for an illustrative embodiment of a method of producing grayscale parametric maps from envelope image information.

Turning to FIG. 9, and as discussed in more detail below, a hemoglobin map and an oxygenation may be computed using information about the absorption coefficients for deoxy-hemoglobin and oxy-hemoglobin at the short and long wavelengths. Because the penetration of light into tissue can vary, in an embodiment, the light penetration may be statistically normalized (normalize fluence (910)), In an embodiment, light penetration may be statistically normalized within a region of interest (ROI). In an embodiment, smoothing (920) may be applied. In addition, in an embodiment, oxygenation calculation (940) (but not hemoglobin calculation (950)) may be enhanced by a noise removal (930) process. In an embodiment, either hemoglobin and/or oxygenation calculations may be enhanced by a noise removal process In an embodiment, the system performing processing on the optoacoustic data, and/or the system displaying the optoacoustic output—which may, but need not be the same as the system acquiring the sinogram—would provide the operator the ability to select a region of interest. In an embodiment, a graphical user interface would permit the user to identify a region of interest within, e.g., an ultrasound or optoacoustic image. In an embodiment, the ROI is a rectangular region. In an embodiment, the ROI may be non-rectangular. In an embodiment, the ROI is specified by a value, e.g., a Boolean value, for each pixel in the image and/or in the resulting parametric map to indicate if that pixel is part of the computational region of interest; in this way, the calculation is not limited to performing on rectangular shapes. In an embodiment, a separate ROI may be used for display purposes, thus, for example, one ROI may be used computationally, and a separate ROI may be used as a boundary display in the displayed image. In other words, the computational ROI and the display ROI need to be the same ROI.

In an embodiment, the fluence in the ROI within the short envelope image (232) and the long envelope image (234) may be statistically normalized. In an embodiment, the fluence in the ROI within the short envelope image (232) and the long envelope image (234) may be statistically normalized using a mathematical function. In an embodiment, to statistically normalize each pixel with the ROI of an envelope image, the value of that pixel is divided by the standard deviation for pixel values in the ROI. This normalization method is used to compensate for variation in the actual fluence of light on a specific target within the tissue, because the actual fluence is unknown, and may vary from person to person as well as from laser event to laser event. Once statistically normalized the ROI generally reflects qualitative information concerning the target tissue or volume. The physical justification for the normalization is not based on OA principles, but rather, the effect of the operation is to normalize the histogram of each of wavelength in the region of interest, based on an observation that the width (standard-deviation) of the histograms for each wavelength tend to be invariant under certain conditions. Moreover, although the laser fluence may not be accurately quantified at depth, the histogram width between wavelengths is believed to have some general stability with regard to other unknowns.

In an embodiment, smoothing (920) may be performed on the images via a two dimensional convolutional filter. In an embodiment, the two dimensional convolutional filter kernel may be based on an adjustable parameter. In an embodiment, the filter kernel parameter defaults to Gaussian. In an embodiment, the Gaussian or other filter kernel is separable which may permit more efficient implementation. In an embodiment, the smoothing kernel may provide a facility to permit focus on objects of a particular size or scale, which may be related to a feature-size selection. In an embodiment, a feature-size selection kernel may be a bandpass filter. In an embodiment, the system performing processing on the optoacoustic data, and/or the system displaying the optoacoustic output—which may, but need not be the same as the system acquiring the sinogram—would provide the operator the ability to select the adjustable parameter upon which the two dimensional convolutional filter kernel is based. The filter kernel may be applied to parametric images or to the envelope images or to the complex-valued image. In an embodiment, the filter kernel may be applied at any stage of processing.

The following processing steps are an illustrative embodiment of smoothing:
  a. Compute a filter kernel according to the dimensions of the image, the kernel type and the scaling parameter, sigma;
  b. Use the kernel to perform two dimensional symmetric convolution with the data.

A hemoglobin calculation (950) process may be performed using the short and long envelope images. In an embodiment, the normalized, smoothed short and long envelope images (922, 924) are used in the hemoglobin calculation (950) process along with a 2×2 matrix of hemoglobin coefficients. The hemoglobin coefficients, referred to following as k11, k12, k21 and k22, are in proportion to the pseudo-inverse absorption coefficients for hemoglobin or blood. In an embodiment, the forward absorption coefficients may be used in the derivation of the hemoglobin coefficients and would pertain to the absorption of oxygenated and deoxygenated blood or hemoglobin at each of the short and long wavelengths and may also account for the absorption of water and other absorbers. In an embodiment, the pseudo-inverse coefficients may instead be arrived at directly or may be empirically tuned or adjusted. In an embodiment, the pseudo-inverse absorption coefficients may also take into account expected values of other absorption material in the tissue. This methodology can be extended to situations where more absorbing materials exist or where more laser wavelengths are used. The computation can also be applied for different absorbers. This methodology can be extended to situations where more absorbing materials exist or where more laser wavelengths are used. As further illustrated in the Appendix, in an embodiment, the pixels of the grayscale hemoglobin map (730) may be computed on a pixel by pixel basis as (k11+k21)*short_image+(k21+k22)*long_image.

A remove common noise (930) process may be performed using the short and long envelope images. In an embodiment, the normalized, smoothed short and long envelope images (922, 924) are used in the remove common noise (930) process. An illustrative embodiment of a process to remove common noise is presented in pseudo code in the Appendix. In an embodiment, the remove common noise (930) process produces normalized, smoothed, common noise removed, short and long envelope images (932, 934). In an embodiment, these images (932, 934) are then used by the oxygenation calculation (950) process along with a 2×2 matrix of oxygenation coefficients. The oxygenation coefficients, referred to following as k11, k12, k21 and k22, are in proportion to the pseudo-inverse absorption coefficients for hemoglobin or blood. In an embodiment, the forward absorption coefficients may be used in the derivation of the hemoglobin coefficients and would pertain to the absorption of oxygenated and deoxygenated blood or hemoglobin at each of the short and long wavelengths and may also account for the absorption of water and other absorbers. In an embodiment, the pseudo-inverse coefficients may instead be arrived at directly or may be empirically tuned or adjusted. In an embodiment, as discussed above for a hemoglobin calculation process, the pseudo-inverse absorption coefficients may also take into account expected values of other absorption material in the tissue. As above, the computation can also be applied for different absorbers. As with the methodology for performing a hemoglobin calculation process, this methodology as well can be extended to situations where more absorbing materials exist or where more laser wavelengths are used. As further illustrated in the Appendix, in an embodiment, the pixels of the grayscale hemoglobin map (730) may be computed on a pixel by pixel basis as (k11+k21)*short_image/((k11+k21)*short_image+(k12+k22)*long_image). In an embodiment, this equation may further be modified with the constant terms k01 and k02 such that the computation on a pixel basis becomes (k01+(k11+k21)*short_image)/(k01+(k11+k21)*short_image+k02+(k12+k22)*long_image). In an embodiment, the terms k01 and k02 are computed from a statistical function of a region of interest.

Other methods for computing parametric maps may be used in place of the methods described above. In an embodiment, multiple laser wavelengths can be fired at the same moment in a single frame, with the frame in its entirety corresponding to a measurement event. The molecular concentrations may be decoded by analyzing several measurement events with different combinations of fired laser wavelengths in each measurement event by using Frequency-Hopping Spread Spectrum or other similar techniques. In an embodiment, multiple laser wavelengths can be fired in a single frame, but not at the same moment, wherein molecular concentrations can be determined by analyzing the frame using Blind Source Separation or similar techniques. The multiple wavelength single frame approach can improve sensitivity to motion. In an embodiment, the analyzing steps may include solving systems of absorption equations from laser wavelengths to determine molecular concentrations in one or more portions of the volume.

Generate Parametric Images (240)—Denoising (735)

Returning to FIG. 7, applying a denoising (735) process may remove noise having characteristics similar to Gaussian white noise. In an embodiment, with the grayscale oxygenation and hemoglobin maps (725, 730) created, a denoising (735) process is applied to the maps in the wavelet domain. In an embodiment, a denoising (735) process may be alternatively, or additionally, applied to real or complex sinograms and/or real or complex images. Regardless of the subject (e.g., maps, images or sinograms), the denoising (735) process may be applied to different areas of processing.

In an embodiment, a multi-spectral denoising procedure may be used, which uses information from more than one optical wavelength to reduce noise. In an embodiment, multi-spectral denoising may denoise using information from different sampled datasets, such as, for example, two sequential maps, images or sinograms, two non-sequential maps, images or sinograms, or from maps, images or sinograms resulting from different wavelength light events.

In an embodiment, a denoising (735) process may operate in the two dimensional wavelet transform domain. In an embodiment, the wavelet denoising is based on a thresholding operation in the wavelet domain coefficients. In an embodiment, a complex-valued two dimensional wavelet transform may be used. In an embodiment, wavelet thresholding via the bivariate shrinkage method may be applied for noise reduction.

The following processing steps are an illustrative embodiment of denoising:

a. Optionally, extend the boundaries of the image, (e.g., by using a symmetric extension)
b. Compute the two dimensional wavelet transform of the image, (e.g., a two dimensional complex dual-tree wavelet transform)
c. Threshold the coefficients in the wavelet domain according to an adaptive or fixed thresholding function, the thresholding function may be based on characteristics of the image, signal, wavelet coefficients and/or statistical properties thereof,
d. Compute the inverse two dimensional wavelet transform of the modified coefficients,
e. Delete any extended boundaries of the image to return an image of the original size.

In an embodiment, the denoising (735) process will return a denoised version of the input, having the same dimensions as the input, such as, for example, a denoised grayscale oxygenation map or a denoised grayscale hemoglobin map.

Generate Parametric Images (240)—Statistical Color Mapping (740)

The statistical color mapping (740) process is performed in an embodiment to take a grayscale (e.g., single-image-channel (as compared with, for example, a 3-image-channel RGB image)) map, and provide color to highlight data believed to be more meaningful, and in an additional embodiment provide a transparency mask that can be used to obscure the visibility of specific pixels. In an embodiment, the statistical color mapping (740) consists of four stages, namely calculating statistics for the ROI, generating a color mapping, interpolating the map, and generating a transparency mask. In an embodiment, the statistical color mapping (740) consists of three stages, namely calculating statistics for the ROI, generating a color mapping and generating a transparency mask, as the stage of interpolating the map being optional, particularly where the map has sufficient color depth (i.e., a sufficient number of colors) to render the stage reasonably superfluous.

In the calculating statistics stage, statistics of the computational region of interest are calculated to be used as calibration or reference points in the color calculation. In an embodiment, the mean and the standard deviation are calculated in this stage. As discussed above, the ROI may be any shape. In an embodiment, the ROI is specified by a value, e.g., Boolean value, for each pixel in the parametric map to indicate if that pixel is part of the computational region of interest; thus calculation is not limited to rectangular shapes, nor even to a contiguous ROI. In an embodiment, the ROI may correspond to specific pixels in the image that meet one or more criteria, such as, e.g., pixels determined to have at least a threshold level of hemoglobin content, or other such molecular or physiological indicator based on criteria. The criteria for such ROI pixels may include those criteria which may be useful for computation or to enhance the contrast or other aspects of the display.

In the generating a color mapping stage, a color mapping is generated from the grayscale (e.g., single-image-channel) image to a predefined color map. The color map determines an ordered list of colors (e.g., RGB colors) that will be used to represent information in the output image. In an embodiment, a color reference point is initially taken as the mean of the computational ROI, plus an offset, where the offset is calculated by the dividing the color offset bias parameter by the standard deviation of the ROI. Then, using the statistical information, color limits are calculated. Color limits are numerical values of the parametric data that correspond to the first and last indices in the color map. Color limits may be defined in relation to the standard deviation of the computational ROI about a computed or user-supplied reference parameter, such as a midpoint. In an embodiment, color limits may be defined in relation to the standard deviation of the computational ROI about its mean. In an embodiment, color limits are defined in relation to a measure of contrast, such as the RMS contrast, Michelson contrast, Weber contrast, a local image contrast metric (contrast compared against a filtered image) or other measure of contrast, where the color limits are solved to optimize or maximize the measure of contrast in the computational ROI and thereby permit the display of an Adaptive Qualitative Image. In an exemplary embodiment, the RMS contrast is used. In an embodiment, upper and lower limit values are equal to the mean plus or minus the standard deviation times a color-contrast parameter. In an embodiment, the mapping to colors may be achieved by relating the lower limit value to the first value in the color map and the upper limit value to the last value in the color map, and linearly mapping the intermediate values of the grayscale image between such endpoints.

In an illustrative embodiment, the color mapping may be performed by the following steps, which may be expressed in more detail in the Appendix:
   a. Compute the standard deviation of the region of interest
   b. Set the color reference point to the mean of the region of interest plus the bias parameter divided by the standard deviation
   c. Set the lower color limit to the color reference point minus the standard deviation times the color contrast parameter
   d. Set the upper color limit to the color reference point plus the standard deviation times the color contrast parameter
   e. Linearly map each pixel in the grayscale image to a color value in the color map, the lower limit value corresponding to the first index in the color map, the upper limit value corresponding to the last index in the color map, with values beyond the upper and lower limits saturating at the boundary colors, and the in-between values linearly interpolated between the upper and lower limits.

In the (optional) interpolating step, the color map is interpolated. In an embodiment, the color map is interpolated to smoothly map the intermediate color values and thus, prevent a choppy display. Using the color limits, the interpolating step rescales the parametric image onto the color map. In an embodiment, the color of each pixel is set for intermediate values by using linear interpolation between the two corresponding adjacent colors in the map. In an embodiment, the color map is provided in sufficient depth so that the rescaling does not require interpolation, but may provide the resolution required to use a direct look-up.

The following processing steps are an illustrative embodiment of linear mapping and interpolating the color map, as expressed in more detail in the Appendix:
   a. Set maximum color map index to corresponding to the last entry in the color map (i.e., the number of colors):
      i. maximum_colormap_index=NumRGBColors−1
   b. Rescale the image so that the intensities correspond to the same numerical range as color palette for each pixel by row and column in the parametric map

--- i. B[row][col] = (parametric_map[row][col] - lower_color_limit_range) * (maximum_colormap_index)/(upper_color_limit_range-lower_color_limit_range)
ii. B[row][col] = min(max(B[row][col],0), maximum_colormap_index)

--- c. Compute the palette indices of each pixel of B by using the floor function and call the resulting array "index":
      i. index[row][col]=min(floor(B[row][col]), maximum_colormap_index)
   d. If the color map has sufficient color depth, so that the effect of the interpolation would be negligible, the RGB value of the corresponding color map index may be computed as rgb_out[row][col][component]=colormap (index[row][col], component). However, if this color map does not have sufficient color depth, the following steps may be performed:
      i. Compute the remainder which is the difference between B and index and call the resulting array "delta":
         1. delta[row][col]=B[row][col]−index[row][col]
      ii. Use the value of delta to interpolate the RGB color channels onto the provided color map:
         1. For each color channel component (red, green, blue), set the color component of each pixel in rgb_out[row][col] to:

--- a. rgb_out[row][col][component] = colormap(index[row][col], component) * (1-delta[row][col]) + colormap(index + 1, component) * delta[row][col]

--- e. Ensure that the values for the RGB colors are between 0.0 and 1.0 if the RGB values are represented by floating point values.

In the generating a transparency mask step, the transparency mask is generated to identify transparent portions of the map. The parameters lower_transparancy_threshold and upper_transparancy_threshold define the transparency threshold based on the color limits calculated in the interpolation step and the values present in the parametric image. In an embodiment, intermediate levels of transparency are used for pixel values falling around the lower_transparency_threshold or upper_transparency_threshold so that a gradual fade from transparent to opaque is provided rather than a hard cutoff. In an embodiment, a parameter for opacity is used as a smoothing parameter, to smoothly render pixels in the map rather than having a hard threshold. As shown in the Appendix, the transparency may be smoothly transitioned using a calculate_transparency_mask subfunction. A predefined or computed mask may be used to make the map transparent in specific locations. In an embodiment, a mask called display_roi (having dimensions the same as the map) would be false (e.g., have a zero value) in locations corresponding to pixels in a map that are to be completely transparent. In an embodiment, a pixel in display_roi is false when it falls outside the ROI. In an embodiment, a pixel in display_roi can be set to false to obscure the corresponding data in the map, if the display overlay should not be shown, such as, for example, where it falls outside of boundary margins which may be set for edges of the image.

In an embodiment, the output of the statistical color mapping (740) process comprises a 4 matrices that each comprise the same number of pixels as the grayscale map, one for a values of red, green and blue (RGB), and one as an alpha channel (A) or transparency layer. Thus, in an embodiment, the statistical color mapping (740) process receives one matrix in the form of a grayscale map, and returns four, that may be referred to collectively as a RGBA data, or a color map. Accordingly, the grayscale oxygenation map (725) is processed by statistical color mapping (740) to produce the RGBA data that collectively are referred to as the oxygenation map (250), and the grayscale hemoglobin map (730) is processed by statistical color mapping (740) to produce the RGBA data that collectively are referred to as the hemoglobin map (255).

The reference names, oxygenation map and hemoglobin map are not intended to suggest that the maps show all, or only, of the namesake material. Instead, they are being used for reference only. More specifically, although blood oxygenation is a significant tissue property displayed by the oxygenation map, and perhaps, but not necessarily the most significant tissue property displayed by the oxygenation map, it is within the scope of the present disclosure that the oxygenation map display no other tissue properties, and it is within the scope of the present disclosure that the oxygenation map display substantial additional tissue properties. Likewise, the hemoglobin map is so named only for reference, and the name is not intended as a limitation on the content. Instead, although hemoglobin is a strong optical absorber in tissue, it is within the scope of the present disclosure that the hemoglobin map display no other tissue properties, and it is within the scope of the present disclosure that the hemoglobin map display substantial additional tissue properties. In other words, the names are not intended to be limitations, however, they are believed to be representative of at least a substantial portion of the molecular indicators reflected in the map. In an embodiment, the statistical map technique may be used to display other indicators of the tissue as sources of contrast. In an embodiment, the statistical map technique may be used to display qualitative contrast based on a computed spatially dependent image representing the speed-of-sound, the optical absorption, the optical scattering, the density or other such computed parameter of the tissue. In sum, the present disclosure section, as its name implies, concerns statistical color mapping as part of generating parametric—or parameter-based—images. The examples showing an oxygenation map and a hemoglobin map are just provided for illustration.

Thus, as described above and detailed further below, a statistical mapping method is provided for producing a qualitative image. A qualitative image in this respect is an image substantially without numerical values specified, as opposed to a quantitative image that has numerical values specified.

In an embodiment, a system is provided that produces qualitative images using relative contrast, where the energy fluence profile in the volume is sufficiently unknown or not measurable, or may sufficiently deviate from a mathematical or computer model of it. This situation consequently results in an underdetermined set of equations, or loss of accuracy, and consequently prevents an accurate quantitative numerical solution of the solved-for parameter, or results in the case where the quantitative accuracy of the computed parametric value is substantially insufficient to support assigning a specific indicative (diagnostic) color to specific levels of a solved-for tissue parameter such as the absolute or relative concentration of a molecule. One problem that may arise is that the accuracy of the computed concentration of a specific local position may be dependent on the rates of absorption and scattering of each optical wavelength, which varies across subjects and with imaging depth. When such a computation is performed independently for each spatial position, the computed value may deviate from the true value enough to inaccurately display color when a fixed or non-statistical mapping is used. To handle this situation, a reference level is determined statistically against the ordinary background material contained in the volume within a region of interest. In one embodiment, sufficiently ordinary or reference breast tissue is used, the breast tissue having a specific amount of oxygenation (for example, above 80%), so the statistics of such background tissue are used to qualitatively compare the rest of the colorization against it, the mean of the region of interest representing the average background amount. It should be noted that some phantoms with no background absorption make the reference level procedure only affix to items in the foreground and not the background. However, the background in true tissue actively aids in being able to use reference level. The statistics of the background are also used to assign the upper and lower limits for the color.

The method in accordance with an embodiment of the invention includes depositing electromagnetic energy that is subject to variability into a volume, measuring an acoustic return signal from energy deposited in the volume, and computing a parametric map that estimates values of at least one parameter as spatially represented in the volume. At least one region of interest of the parametric map is defined. The region of interest may represent a subset of the parametric map, or the entire map. The method produces a mapping configuration to adjust for the effects resulting from at least some of the variability in the spatial profile of the deposited energy. The mapping configuration is produced by determining a reference level within the region of interest of the parametric map and then specifying an upper color map limit and a lower color map limit, with at least one of the upper color map limit or the lower color map limit being determined in relation to the reference level. The reference level may be offset by an offset value, and the offset value may be tunable by the user or fixed. The parametric map is then rendered in the palette of a color map by mapping estimated values of the parametric map onto the color map according to the upper and lower color map limits of the mapping configuration to produce a rendered parametric map, in accordance with the procedures described above. The rendered parametric map may then be displayed to the user. The rendered parametric map may be a representation of oxygen saturation, total opto-acoustic return signal intensity, or other property. In an embodiment, the rendered parametric map is displayed as a qualitative image, and consequently numerical values of the colorized representation need not be displayed with the image. That is, the colorscale of the parametric map is displayed alongside the parametric map bearing no numerical reference values to associate against the colors.

Two or more wavelengths of energy can be applied by one or more energy sources to the volume so as to provide a source of molecular contrast for the parametric map. Where dual wavelengths are utilized, computing of the parametric map may include the steps of computing a spatial representation of the volume based on the acoustic return signals for the first of the two electromagnetic energy wavelengths, computing a spatial representation of the volume based on the acoustic return signal for the second of the two electromagnetic energy wavelengths, balancing the relationship between the computed spatial representations for the two electromagnetic energy wavelengths, estimating the values of at least one parameter as spatially represented in the volume based on the balanced spatial representations of volume for each of the at least two wavelengths, and outputting the estimated values of the at least one spatially represented parameter. In this respect, the balancing may be performed based on a mathematical characteristic applied to the region of interest of at least one of the computed spatial representations and then applying the result of the mathematical characteristic to normalize at least one of the computed spatial representations, thereby producing balanced spatial representations of the volume for each of the at least two wavelengths. The mathematical characteristic of the balancing may be a statistical function, and the normalization may be performed by multiplying the computed spatial representations in proportion to the result of statistical function. In an embodiment, the statistical function is the reciprocal of the standard deviation of the region of interest. In an embodiment, the result of the statistical function is a scalar value and the value that is used for multiplication is constant throughout the region of interest. The result of the statistical function may be a scalar value, and the value that is used for multiplication may vary spatially throughout the region of interest based on the result of the statistical function and according to a pre-determined relationship. Such pre-determined relationship is based on an assumed spatial energy distribution. In an embodiment, the mathematical characteristic of the balancing is the scalar projection of the estimated values in the region of interest for a first of the two wavelengths onto the estimated values in the region of interest for a second of the two wavelengths, and the normalization is performed by multiplying at least one of the computed spatial representations in proportion to the result of the scalar projection.

The parametric map may be computed by applying an implicit or explicit model of, or theoretical basis for, distribution of electromagnetic energy fluence within the volume pertaining to the two wavelengths. This may involve multiplying, dividing or weighting the respective return signals or image substantially by the energy fluence model as a function of depth or distance. The distribution of energy is responsible for the intensity of the optoacoustic return signal. The actual electromagnetic energy fluence caused by each wavelength, as distributed throughout the volume, has a propensity, due to variability within the volume or variability within a population of volumes, to differ from the modeled or theoretical electromagnetic energy fluence. The reference level may be determined using a statistical function of the numerical values of the parametric map within the region of interest. The color map may consist of one or more channels and the mapping step may include mapping numerical values of the parametric map onto each channel of the color map according to the upper and lower color map limits. The determination of the reference level may use a particular mathematical characteristic of the numerical values of the parametric map within the region of interest. The particular mathematical characteristic for determining the reference level may be, e.g., the mean of numerical values of pixels within the region of interest or a fixed constant. The particular mathematical characteristic for determining the reference level also may be a statistical function, such a standard deviation, a histogram, a maximum, a minimum, a median, a maximum-minimum/2, the proportion above a threshold, the kurtosis, the skewness, the variance, a range, or based on a measure of contrast such as Michelson, Weber, local or RMS contrast. Two or more wavelengths of electromagnetic energy may be deposited into the volume, and the step of computing a parametric map may be performed after the statistical mapping. By applying a theoretical basis of distribution of electromagnetic energy fluence within the volume pertaining to the two wavelengths, the distribution of energy responsible for intensity of the optoacoustic return signal may be factored into the computation. The rendered map may be masked with a transparency, and may be co-registered with an ultrasound image. The co-registration may involve motion estimation. User input may be used to specify the region of interest, such as by allowing the user to define a rectangle on an image. In this respect, the user input, which may be received via a graphical user interface, may be input defining a top and bottom depth, or a depth and a height which serve to define the top and bottom depth. The operator may adjust the region of interest in real time via the user interface. The upper and lower color map limits can be determined by computing a statistical function of the numerical values of the pixels of the region(s) of interest. Such statistical function may be the standard deviation or other such statistical function. The result of the statistical function is used to proportion the relationship that the upper and lower color map limits are from the reference level. The upper color limit may be defined as the reference level plus a first constant times the standard deviation of the region of interest, and the lower color limit may be defined as the reference level minus a second constant times the standard deviation of the region of interest. Of course, the first constant and the second constant may be the same constant.

The reference level may be fixed, and the computation of the parametric map may be pre-calibrated or adjusted by using fluence-compensation on a per-wavelength basis. A transparency map and the upper and lower color map limits may be defined in relation to the reference level. The transparency map may be a single-channel color map reflecting a transparency channel. The color map may include a plurality of colors, or may be a single-channel greyscale map.

Generate Parametric Images (240)—Combine Transparency Mask (750)

It has been observed that the measured optoacoustic return signal from locations with high hemoglobin content are the strongest. Thus, the signal-to-noise ratio is highest in regions of high hemoglobin. Moreover, it has been observed that focusing on regions of high hemoglobin content may be diagnostically useful. Accordingly, the combine transparency mask (750) process is designed to permit a later display of oxygenation from the regions comprising higher concentration of hemoglobin, and thus, having a higher signal-to-noise ratio. In an embodiment, parametric maps, may be combined synergistically with information being presented in the combined output that is not otherwise readily apparent or observable in the uncombined parametric maps, or obtainable from the uncombined parametric maps independently.

In an embodiment, the combine transparency mask (750) process calculates a separate alpha channel, i.e., transparency mask, for the oxygenation data that will constrain a specific display of the oxygenation data to regions of higher hemoglobin content, and thus to regions having higher signal-to-noise ratio. In an embodiment, the separately calculated alpha channel (A) may be combined with the RGB data in the oxygenation map (250) to form an RGBA masked oxygenation map (260).

To calculate the separate alpha channel, and thus, the transparency mask for the oxygenation data that will constrain a specific display of the oxygenation data to regions of higher hemoglobin content, the A channel (e.g., transparency mask) from the oxygenation map (250) and the hemoglobin map (255) are combined. In an embodiment, the RGB data from the oxygenation map may be replicated and stored with the combined transparency mask. In an embodiment, when the masked oxygenation map (260) is rendered, the RGB data from the oxygenation map (250) can be accessed.

In an embodiment, to calculate the separate alpha channel for the oxygenation data, the A channel (e.g., transparency mask) from the oxygenation map (250) and the hemoglobin map (255) may be weighted. In an embodiment, where the alpha channel from the oxygenation map (250) and the hemoglobin map (255) are stored as real values between 0 and 1, the oxygenation map (250) and/or the hemoglobin map (255) may weighted by a positive exponent, and the two weighted masks are then multiplied together to produce the masked oxygenation map (260) alpha channel. Where the alpha channel from the oxygenation map (250) and the hemoglobin map (255) are stored as integer values, in an embodiment, they may be scaled prior to exponent weighting and multiplication. In an embodiment, the oxygenation map (250) and the hemoglobin map (255) alpha channel data are weighted, multiplied and then scaled.

Coregister Maps with Ultrasound (265)

The coregister maps with ultrasound (265) process coregisters the parametric oxygenation map (250), hemoglobin map (255) and/or masked oxygenation map (260) with an acquired ultrasound image (step 215). In an embodiment, the parametric maps being co-registered and the acquired ultrasound image are scaled to fit the desired size of the final output, and then a blended overlay with the acquired ultrasound image, based on the alpha transparency channel of the respective parametric map. In an embodiment, the system performing processing on the optoacoustic data, and/or the system displaying the optoacoustic output—which may, but need not be the same as the system acquiring the sinogram—would provide the operator the ability to select a desired size of the final output.

The following processing steps are an illustrative embodiment of coregister maps with ultrasound, as expressed in more detail in the Appendix:
   a. The RGB ultrasound_image, which may be defined by a rectangle or other shape is interpolated or scaled to fit the co-registered output image.
   b. Each RGBA map (e.g., 250, 255 and/or 260) to be coregistered, is interpolated or scaled to fit the co-registered output image. The scaled RGBA map is overlaid on top of scaled ultrasound image using the blending function based on the associated alpha channel.

Method for Creating and Displaying Images

In an embodiment, the present disclosure includes a method for display of information within the optoacoustic return signal is provided. In an embodiment, a method for the qualitative display of molecular information reflected by an optoacoustic return signal is provided. In an embodiment, a method for the qualitative display of molecular information reflected by image statistics of an image reconstructed from an optoacoustic return signal is provided.

In an embodiment, the present disclosure includes a parametric map (a.k.a. parametric image) concerning molecular information in tissue that is computed (as an input to or component of this approach). Because of the variability in the nature of how light penetrates into tissue in vivo and/or due to an underdetermined set of equations from the measured data, however, the values in the resulting parametric map are difficult to calibrate. It is thus an objective that the molecular information may be displayed in a useful, and potentially clinically useful, qualitative fashion, based on relative values of a parametric map and/or statistical information of the parametric map. In an embodiment, an ideal parametric map may be the oxygenation saturation of hemoglobin in tissue, including, e.g., breast tissue. The purpose is to display clinically useful information and compensate for underdetermined set of equations resulting from a lack of complete information, such as, for example: having less information, or fewer lasers, than may be required to account for all unknowns in computation; and varying patient specific absorption/scattering, skin/tissue properties and morphology, physiology, structures, geometry, etc.

In an embodiment, the following steps may be used to implement a computer processing algorithm to accomplish the foregoing objective.
   a. Acquiring data including a plurality of short sinograms (205), long sinograms (210) and ultrasound images (215);
   b. Preprocessing the sinogram data (220)
   c. Reconstructing images from the processed sinogram data (225)
   d. Processing the reconstructed images (230), and producing long and short envelope images (232, 234);
   e. Creating parametric maps;
   f. Pre-processing of a parametric map may be done as a step (i.e. noise-removal, smoothing, statistical normalization)
   g. Calculating a color reference point based on statistical information of a region of the parametric image (for example, the mean of the region plus and adjustable bias offset).
   h. Determining a "color range" is calculated based on statistical information of a region of the parametric image (for example, the standard deviation of the region).
   i. Scaling and co-registering parametric map data onto a scaled ultrasound or other image; and
   j. Displaying diagnostic information concerning the tissue examined.

Algorithms and equations useful for implementation the foregoing are discussed above and in the Appendix.

In biological tissue, blood is a strong absorber in the NIR range. The calculation for oxygenation of hemoglobin in tissue may involve a normalization term in the denominator which makes the calculation less sensitive to error. This results from the approximation that oxy-hemoglobin and deoxy-hemoglobin (i.e., the primary optical absorbers in blood) are the full contributors to the return optoacoustic signal. From this, in an embodiment, it may be deduced that the oxygenation calculation is sensitive to the spatially dependent fluence-ratio between the wavelengths, and not the spatially dependent total fluence of each wavelength for a given point (or depth) in the tissue.

Consider, for example, a linear model of the molecular energy absorption containing a (spatially dependent smooth) miscalibration term, and the resulting model of the calculated parametric image. Since the model equation is linear (or approximately linear), the mean and standard deviation are affected linearly by the miscalibration term in the region of interest. Hence, a statistical method is a way to bypass the miscalibration term in a system modeled with a miscalibration term. This, in an embodiment, mean and standard deviation (and other potential mathematical functions) when transformed by the model remain stable in relation to the other data, and in the presence of a miscalibration. Thus, in an embodiment, even when the data is miscalibrated, (constant fluence, depth dependent fluence) the colorizations remain relatively stable.

In an embodiment, the foregoing approach can be applied with varied calibration methods. In an embodiment, the foregoing approach may also be applied when other various signal processing, noise reduction, or other filters are used. In an embodiment, the foregoing approach may be used when co-registration and overlay are performed with other modalities, such as ultrasound. In an embodiment, the foregoing approach is applicable even when varied methods, including more advanced methods, are used to calculate the parametric map. In an embodiment, the foregoing approach is applicable when the parametric map is well calibrated, but the unknowns such as light penetration or undetermined equations still exist. In an embodiment, the foregoing approach is applicable when the parametric map is well calibrated, but the unknowns such as light penetration or undetermined equations still exist, but are compensated for using another method, such as by estimating the unknowns; by explicitly solving for the unknowns; by solving a minimization problem to obtain the unknowns; or otherwise. In an embodiment, the foregoing approach is applicable to map quantitative images (i.e. a calibrated parametric map) where the reference point is fixed and not statistical. In an embodiment, the foregoing approach is applicable to map quantitative images (i.e. a calibrated parametric map) where the color range is fixed and not statistical. As discussed elsewhere herein, the addition of another laser wavelength, in effect, reduces the number of unknowns.

In summary, the foregoing approach provides statistical color mapping and relative (i.e., qualitative) images.

In an embodiment, the present disclosure includes a method for calibrating oxygenation or hemoglobin calculation in a dual wavelength optoacoustic system is provided by applying at least a plurality of the following steps:
  a. using reference points, or reference regions
  b. applying calculations—as described herein, or other such calculations that are extensions of the calculations described herein, or as will be apparent to one of skill in the art in view of the calculations described herein
  c. compensating for the effect of light passing through skin layer, coupling medium, tissue
  d. compensating for differences in scattering, absorption; penetration depth in a two dimensional image; a three dimensional volume of tissue with a two dimensional cross section from light bars, a predefined light distribution, or a dynamically measured light distribution;
  e. calibration from artifacts, including, differences in artifacts from arteries or vein
  f. applying an alternate detection scheme (automatic or manual) to find locations of veins or arteries in advance of calibration, which locations can be used for calculation
  g. using co-registered ultrasound data to provide information supplemental to the optoacoustic return signal and its derivatives
  h. compare the intensities in the regions or reference point at one wavelength (for one or more types of structures/tissues) against (at least) the regions or reference points at a second wavelength (and potentially additional wavelength(s)) and
  i. use the comparison to compensate for the intensity ratio (fluence ratio) between each wavelength with respect to depth and the absorption or scattering values of the tissue In an embodiment, for the step of using reference points or reference regions, such points or regions may correspond to: blood vessels; tissue; the skin layer; other known structures; depth; wavelength specific absorption of light through vessels (because light penetrates through arteries differently than through veins and hence can be identified and discriminated in an image); or a reference point in one or more different images. In an embodiment, the intensities in the regions or reference point at a plurality of wavelengths are compared for the purpose of compensating for at least one of the following: the intensity ratio (fluence ratio) between each wavelength with respect to depth (and/or position); and the absorption or scattering values of the tissue. In an embodiment the mean, standard deviation or other such mathematical characteristic of a reference region may be used in the calculation. In an embodiment, the characteristics of a region at one wavelength, are compared against the characteristics of a region at a second wavelength, and furthermore compared against known absorption parameters under presumptions of tissue composition; by fixing the presumptions of tissue composition, the system of equations becomes solvable to compensate for the unknown fluence or fluence ratio.

In an embodiment, presumptions of tissue composition may include using typical ranges or values for tissue properties such as arteries, veins, Vessels, background tissue, fat, muscle, or other known tissue or structures; the properties can include optical properties, mechanical properties, and/or other such known properties. These presumptions can yield assumptions about the nominal optical absorption for each wavelength. The nominal optical absorption can be useful in compensating for unknown fluence distribution. Thus, in an exemplary embodiment, presumptions may include that ordinary background breast tissue consists of blood which is predominantly at approximately 80% blood-oxygen saturation, and nominal amounts of water and no other significant absorbing molecules. In another exemplary embodiment, presumptions may include that the nominal blood-oxygenation values of arteries (90%+) and veins (60% to 80%), combined with the hematocrit levels and other physical properties of vessels yield values for the expected optoacoustic return signal at each wavelength, which can be used to calibrate for the unknown fluence distribution profile. For example, a blood-to-water ratio can be defined to represent the nominal proportion of blood to water in a vessel or it could also represent the ratio of blood to ordinary tissue under the assumption of tissue with optical absorption properties similar to water, for example tissue comprising 20% blood and 80% water. Further, if blood is assumed to be nominally oxygenated to a value such as 80%, then a nominal optical absorption coefficient can be found for each wavelength from the nominal proportions of water, oxy- and deoxy-hemoglobin, based on assumed tissue composition. Thus, in an embodiment, nominal optical absorption coefficients can be computed for each wavelength for a region with presumed composition by summing the weighted contributions from each of its constituents. For dual wavelengths, the ratio of nominal optical absorption can be computed. In an embodiment, for a local region that is presumed to conform to known tissue composition, the ratio of actual return signals can be multiplied with the nominal optical absorption ratio to serve as a fluence correction estimate factor. In an embodiment, the fluence correction estimate factor can be spatially smoothed, in order to form an estimate for spatial fluence compensation of the parametric map. Alternately, in an embodiment, vessel regions can be assumed to have known composition, and thus be used to calibrate the spatial fluence by curve fitting a fluence model to the determined fluence correction estimate factors. In an embodiment, such fluence compensation may also be done in other similar ways to this example. In an embodiment, the blood-to-water ratio or blood oxygenation may be adjustable by a user interface. In addition, this example helps to illustrate some concepts that may be applicable to using a statistical method of color mapping, if known composition may be variable. In an embodiment, other methods of fluence compensation models are also possible.

In an embodiment, the present disclosure includes a method for compensation of light distribution in a clinical optoacoustic imaging system is provided that performs such compensation using: one dimensional curves; simulated curves; measured curves; or a region of interest specific method. In an embodiment, the compensation may be fixed, or may be manually operated. Additional details of the compensation method are described above.

In an embodiment, a graphical user interface (GUI) is provided for operating a clinical optoacoustic system, the GUI including, without limitation: controls that permit operator selection of a region of interest or operator selection of the criteria for a region of interest; and to adjust display parameters. In an embodiment, such controls may include but are not limited to performing the following adjustments: the color contrast parameter; the selection of fluence compensation curves; the color reference point bias parameter; upper and lower color transparency thresholds; a parameter to adjust the amount of smoothing; other compensations for absorption, filter, reconstruction, and display parameters; and a gain parameter.

In an embodiment, a system is disclosed that does not attempt to fully determine the exact fluence profiles of the light as it penetrates into the tissue. Rather a simplification, using approximative parameters for the fluence model are used (as described above) to compensate for the light penetration. In an embodiment, the simple parameters are initially tuned to best approximate the light distribution for the majority of patients. If necessary, the parameters can be fine-tuned with a user-interface or using automatic methods. Collectively, the set of parameters that are used to compensate for how light penetrates into tissue (whether manually or automatically produced or tuned) are referred to as the "fluence assumptions". In this situation it is noted that the functional parameters displayed will be most precise in comparing the functional information of structures that are properly compensated by the fluence assumptions. Situations where the fluence assumptions may hold well include, without limitation:

a. where there are strong differences in oxygenation between two compared structures with respect to the ROI;
b. when two compared structures are near each other and can be assumed to have similar fluence, provided that the shadow of a strong optical absorber does not interfere with the fluence assumption;
c. when there is high contrast between the structure and the background tissue of the ROI;
d. when the structures being compared have high optical absorption;
e. when the presence or absence of other sources of high-contrast structures in ROI of the functional map are statistically common in the images which are compared;

In an embodiment, the system and method disclosed may detect relative or qualitative differences in oxygenation (or molecular concentrations) within the tissue. In an embodiment, where the displayed values are not mapped precisely in a calibrated manner on to a fixed value of blood oxygen saturation or blood volume (which would require full knowledge of the fluence profile) it is nonetheless possible to display the contrast of the functional parameters within the tissue, using methods as described above. In this manner, the methods and systems described above, are also able to produce clinically useful qualitative medical images. In an embodiment, the information may be displayed graphically, using color to display the quantity without presenting the operator with a numerical value corresponding to the color mapping, having a useful display of qualitative optoacoustic information, and without the direct presentation of corresponding numerical values. In an embodiment colors are displayed in a manner that they do not need to correspond to any particular fixed value, but rather, the colors may adjust automatically to display the maximized contrast based on information contained in the current image. For example, the color green need not correspond to a fixed value, e.g., 80% oxygenation, but instead, may be a representation of relative or of qualitative information. In an embodiment, the methods of fluence compensation and calibration can be used to produce more accurate quantitative images.

In an embodiment, the present disclosure includes an apparatus for detecting tumors or other structures or anomalies based on functional morphological information, rather than merely displaying colors. In an embodiment, the present disclosure includes an apparatus for qualitatively detecting tumors or other similar structures based on functional morphological information, rather than merely displaying colors.

In an embodiment, pattern classification or such techniques may be applied to the methods of calibration, qualitative imaging or relative imaging above. In an embodiment, a set of predetermined rules or guidelines may be used for interpretation of the images generated by the above systems and/or method. In an embodiment, a clinical system may include the rules or guidelines for the purpose of automatically applying the same, or for assisting an operator to manually apply them. In an embodiment, a system with a feature vector assembly module for assembling a feature vector concerning a lesion comprising an ordinal classification of a plurality of features of a lesion, the plurality features selected from the set of: 1) internal vascularity and de-oxygenation, 2) peri-tumoral boundary zone vascularity and deoxygenation, 3) internal deoxygenated blush, 4) internal total blood, 5) external peri-tumoral radiating vessels, and 6) interfering artifact; and a feature vector classifier for calculating a diagnostic measure of an outcome for a lesion based on a feature vector concerning the lesion. In an embodiment, the feature vector assembly module may contain an identification module for identifying the presence of each of the plurality of features of a lesion; and a quantification module for computing an ordinal classification for each of the plurality of features present in a lesion. In an embodiment, the lesion identification module may comprise a pattern search module for identifying, based on the characteristics of a lesion, the presence of a lesion in the at least one image. In an embodiment, a diagnositic outcome may be produced by inputting the produced feature-vector into a feature-vector classifier designed to operate on the feature vector. In an embodiment, a system for automatically analyzing an opto-acoustic image for the presence of features, involving a training phase, and a feature detection phase may be used to output the feature strength of each spatial position of an image to be used as input for the feature-vector assembly module.

Figure 10:
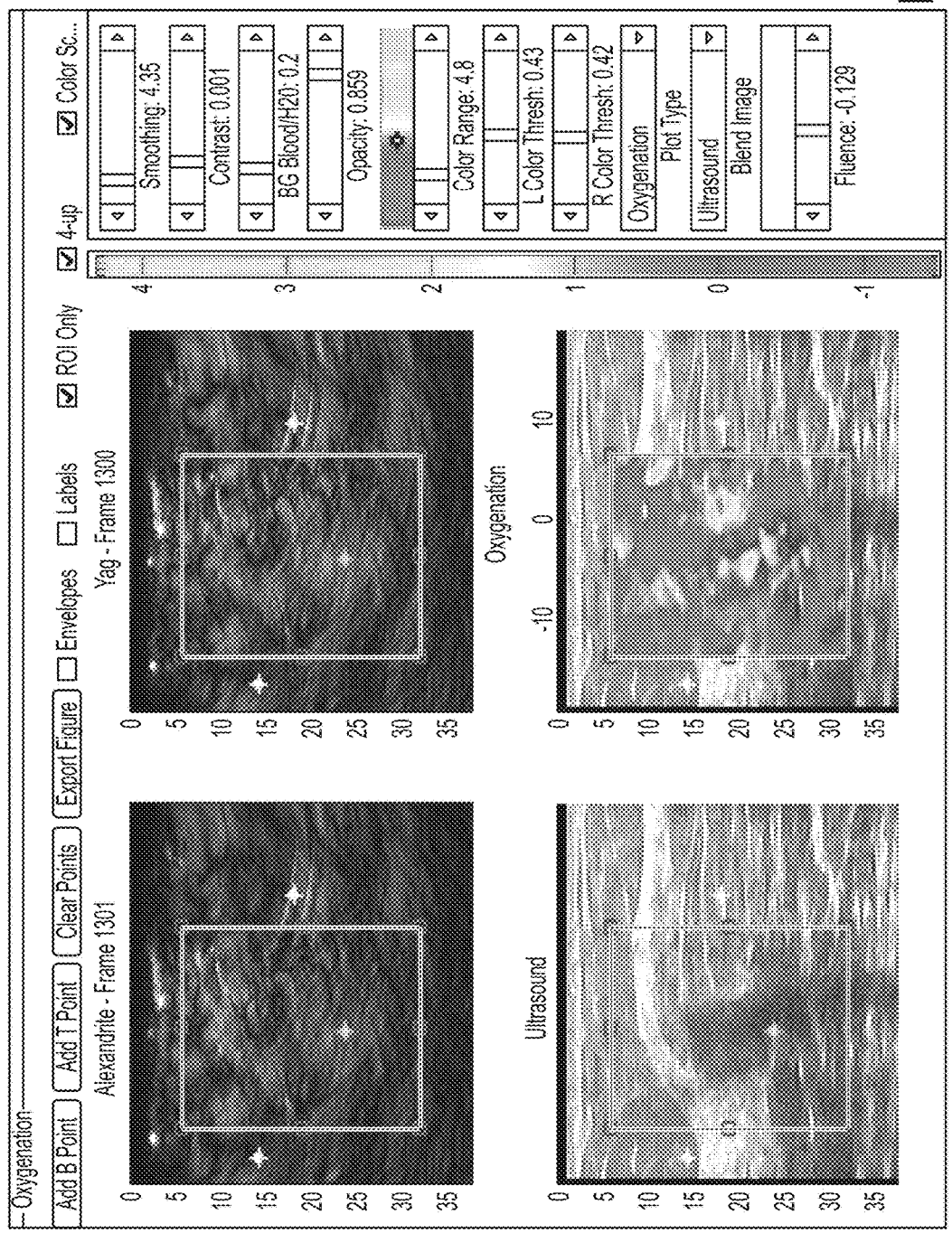
FIGS. 10-12 show an illustrative four-image displays with parameter input and display.
Figure 11:
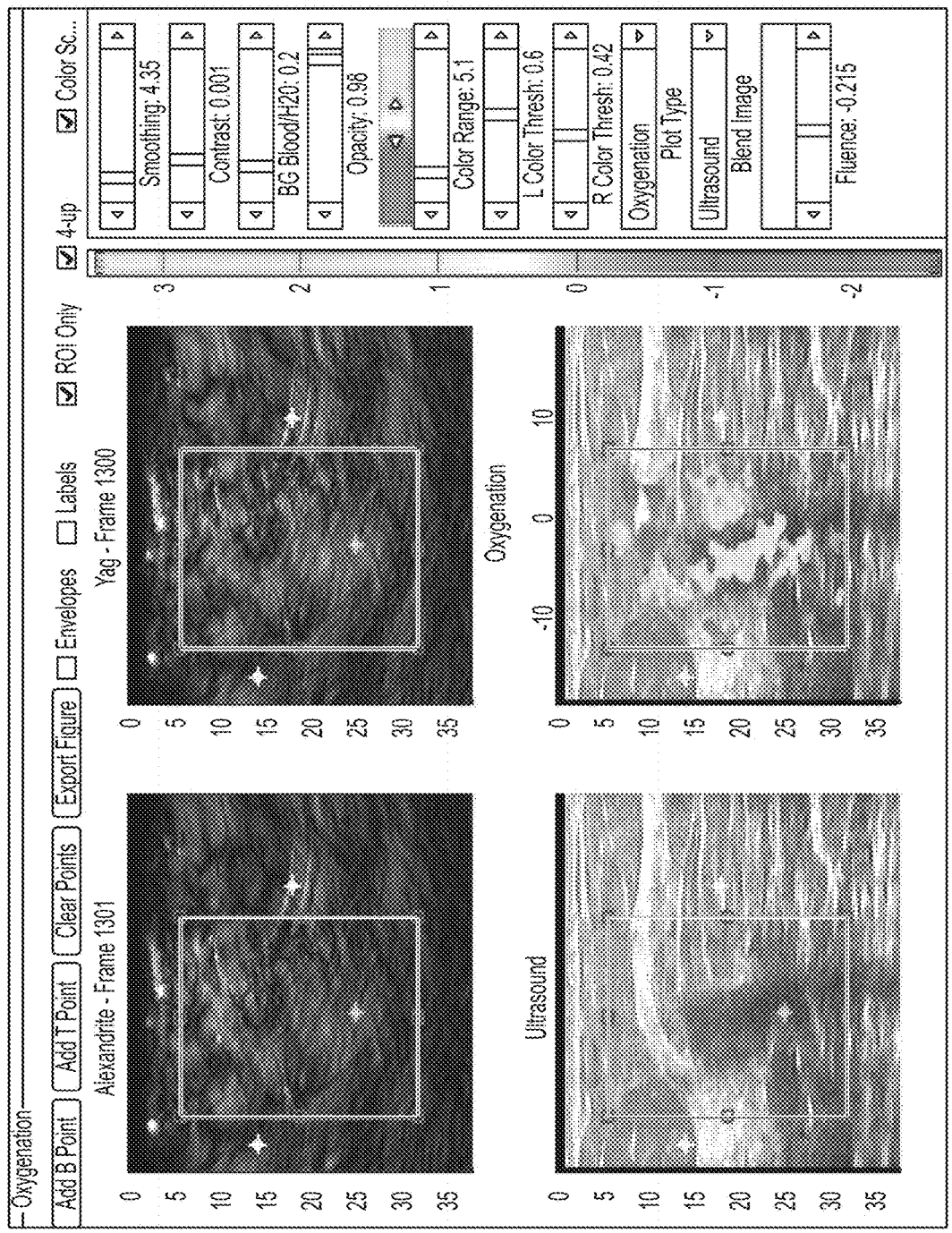
Figure 12:
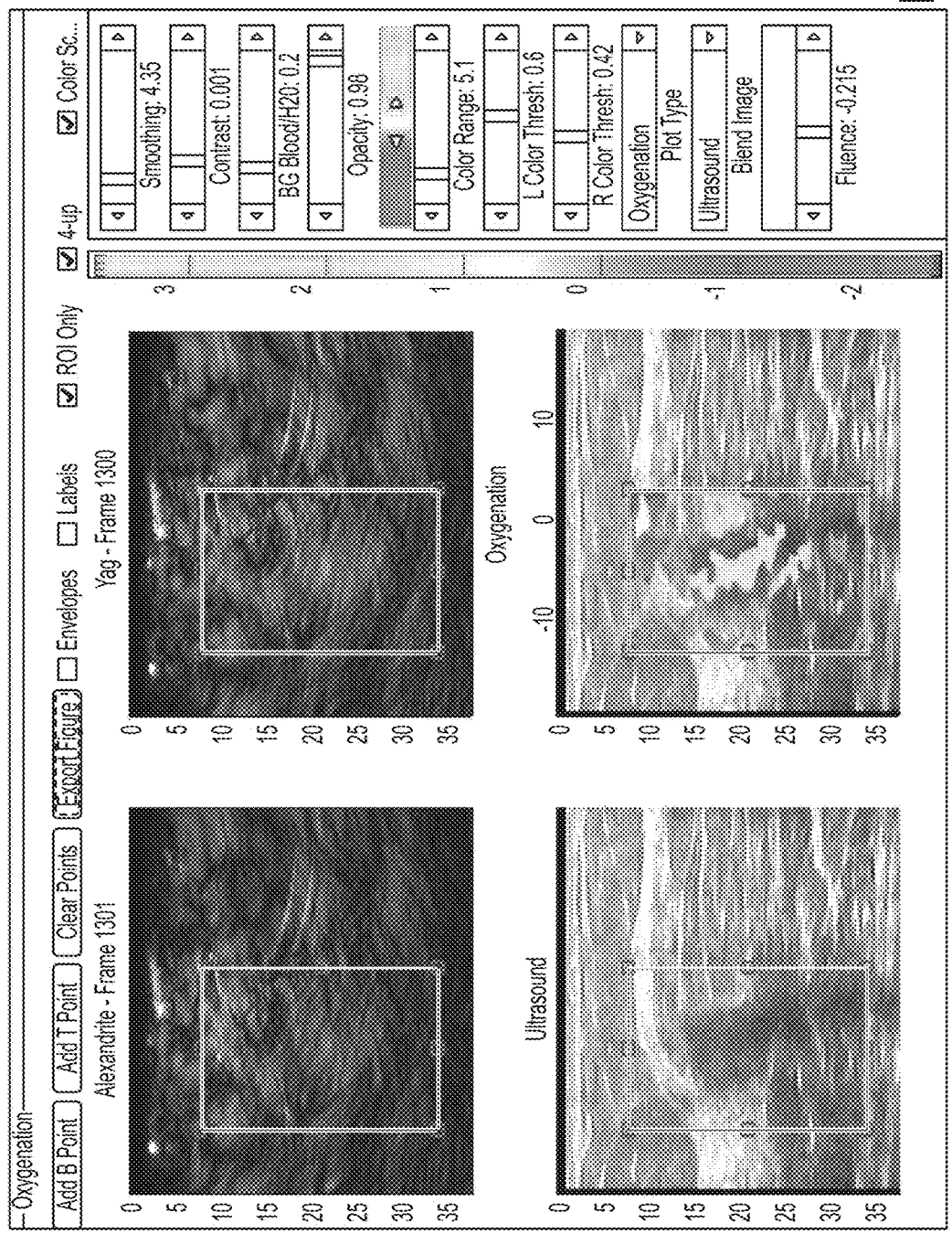

Turning now to FIGS. 10, 11 and 12, and with reference to FIG. 2 as well, four-image illustrative displays are shown. The image displayed in the upper left is an embodiment of short envelope image (232) with a identified rectangular region of interest. The image displayed in the upper right is an embodiment of a long envelope image (234) with the same identified rectangular region of interest. The image displayed in the lower left is an ultrasound image (295) also showing the identified rectangular region of interest. The image in the lower left is one embodiment of a display of coregistered ultrasound image and oxygenation map (275). On the right hand column of the four-image display are the value for various illustrative parameters that, in an embodiment, can be operator selected.

Figure 13:
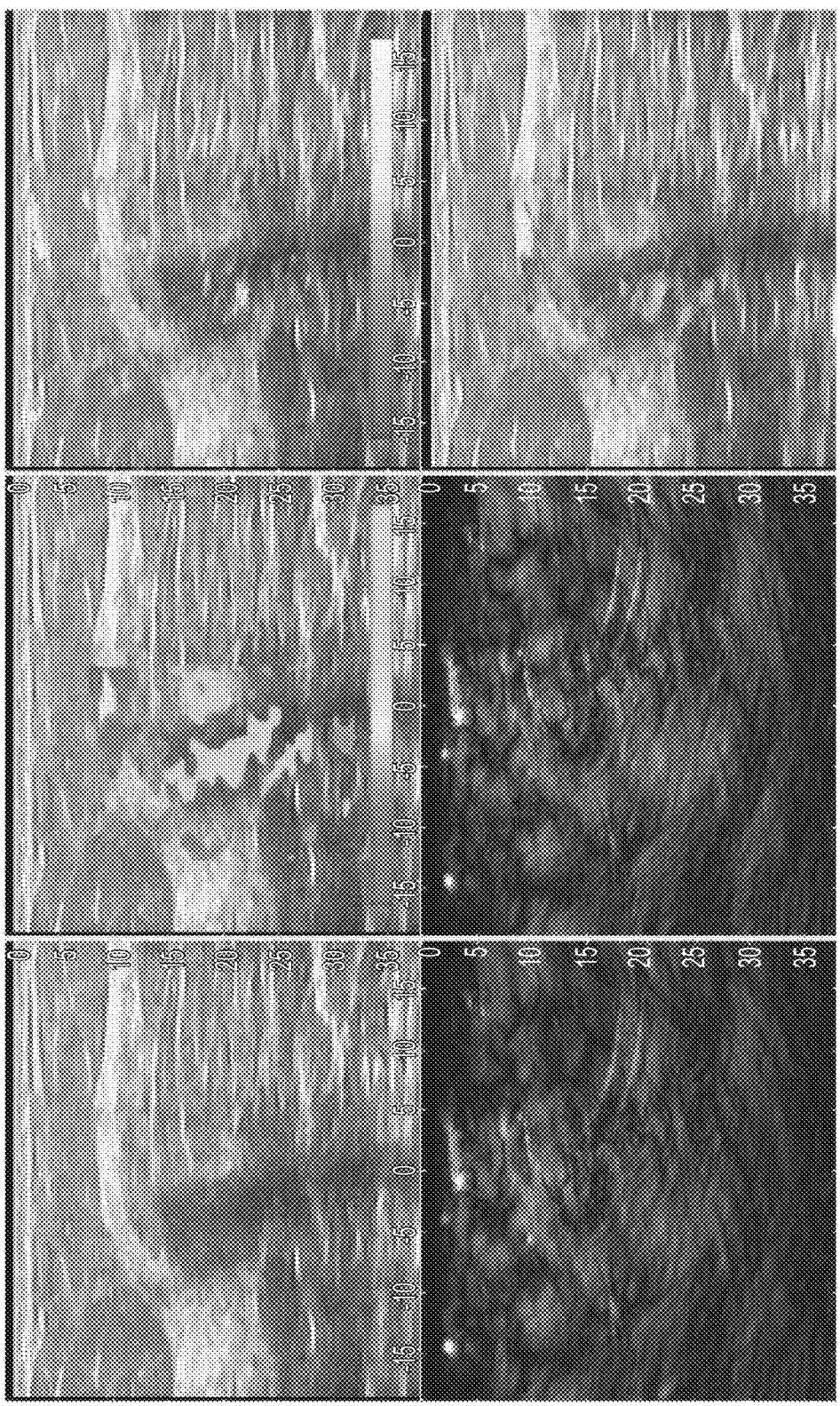
FIGS. 13-15 show illustrative six-image displays.
Figure 14:
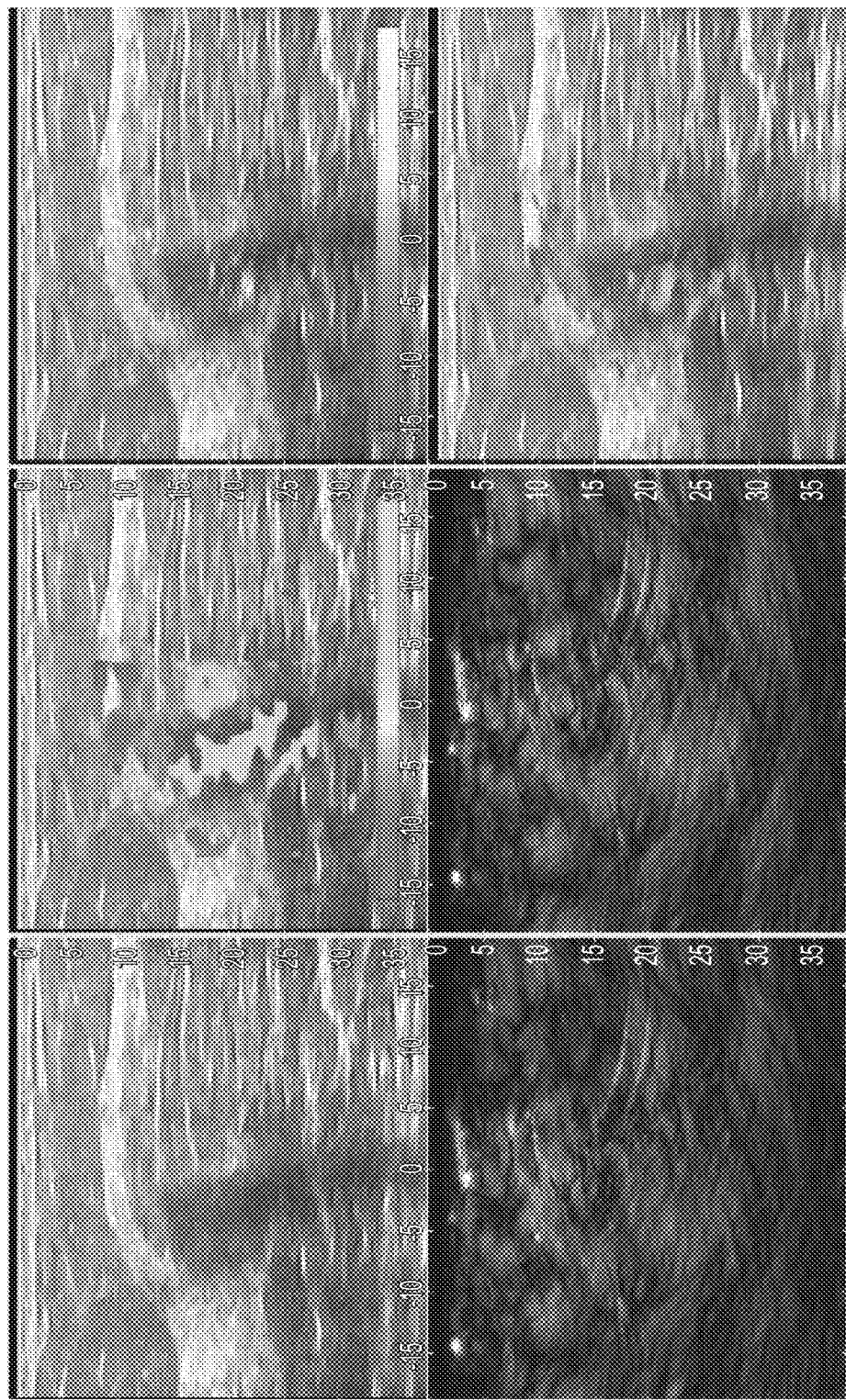
Figure 15:
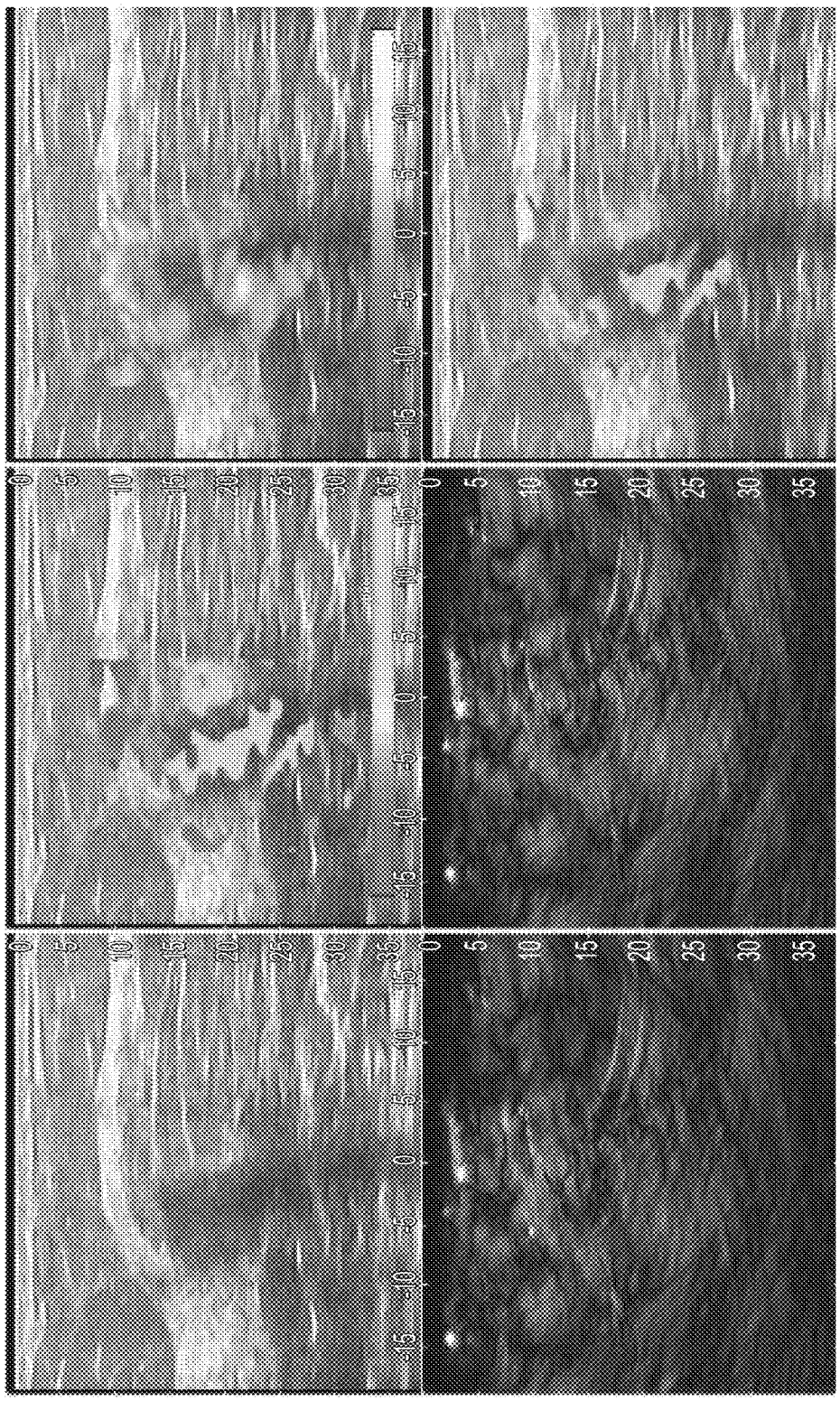

Turning now to FIGS. 13, 14 and 15, and with reference to FIG. 2 as well, six-image illustrative displays are shown. The top left is an ultrasound image (295), the bottom left and center are embodiments of short and long envelope images (270, 290). The top center image is an embodiment of a display of a coregistered ultrasound image and oxygenation map (275), the top right image is an embodiment of a display of a coregistered ultrasound image and hemoglobin map (280), and the bottom right image is an embodiment of a display of a coregistered ultrasound image and masked oxygenation map (285).

In an embodiment, colorization on an image shows relative oxygenation, thus, for example, red may mean an area is less oxygenated than the surrounding tissue and green may mean it's more oxygenated. In an embodiment, molecular optical contrast provides differentiation between hypoxic blood of breast carcinomas (which may be shown in red) and normally oxygenated blood in benign masses (which may be shown in green).

Playback Mode

As noted above, the Laser Optic Movie (LOM) is a collection of recorded data that may be recorded in groups of related files, or more preferably, in a single data file. In an embodiment, the disclosed system may include an offline (e.g., non-live) playback mode in addition to the live display modes described. In this respect, when the system is displaying data in the online mode, the live display may be paused, rewound to an earlier point in the LOM file described above, and an earlier portion of the LOM can be processed using one or more different system parameters and played back. Thus, the unprocessed data in the LOM can be used to playback the same scan as was previously viewed live, but with different processing so as to convey different information in the image than is displayed on the display during live mode. The user input devices 116 (FIG. 1) in the control panel of the control and display subsystem 2810 (FIG. 28) may include a trackball and various other input devices such as jog dials, buttons and conventional means for controlling video playback, as well as a graphical user interface (GUI), discussed above. A pause button may be included for pausing the live display and entering into playback mode. An "x seconds back" button may be provided for rewinding the time that is currently being displayed by x seconds. For example, if the system is in live mode and such button is configured as a "five-seconds back" button, then actuation of such button causes the system to enter playback mode and begin playback of images produced from data taken five seconds prior to the button being actuated.

For the playback mode, the raw data that has recently been acquired is stored in a large buffer. In an embodiment, when the user clicks "pause" in the GUI, the playback mode is initiated and the system can regenerate prior frames from raw data, while changing parameters to modify the processing used to generate the prior frames. Using the GUI in combination with the trackball or other user input device allows the user to scroll to select a frame or series of frames for playback. As the frame or frames are being played back in a loop, the user can adjust parameters or modes of the system in order to see the frames with different processing or in a different format. The resulting movie, (or an individual processed/re-processed frame), can be exported to a file. This can be done in a batch, which allows for offline processing from raw data. The raw data itself can be exported to a file. The playback mode can be configured to allow only a certain set of user-selected frames, selected using the trackball or other user input device, to be exported to a file. In an embodiment, the system stores raw and processed data on the optoacoustic electronics subsystem 2804 (FIG. 28), and then sends them over a network to the ultrasound subsystem 2802 (FIG. 28), which overlays them and displays the overlaid images to the user; a protocol can be provided that performs this process. The playback mode operation can be configured to allow a user to scan in one mode (e.g., the six-image display mode, shown in FIGS. 13-15 and discussed above), switch modes, and replay in another mode. One example of the use of playback mode with the six-image display mode is as follows. When the user is in six-image display mode and pauses the live display thereby entering playback mode, the system can switch to a different display mode such as a single-image display that allows the user to see a single, larger image and focus on a particular region of interest.

The playback mode further allows the user to apply different filters, tuned to find different physiological features, to the same stored data. The playback mode further allows a different reconstruction algorithm to be used during playback or export. One useful parameter that can be changed in the playback mode is the ROI depth, described above. It can also be configured to allow the interframe persistant artifact reduction, discussed above, to be applied to the paused buffer.

Optoacoustic System and Method

Returning to FIG. 1, generally, device 100 provides an optoacoustic system that may also be employed as multi-modality, combined optoacoustic and ultrasound system. In an embodiment, the device 100 includes a probe 102 connected via a light path 132 and an electrical path 108 to a system chassis 101. Within the system chassis 101 is housed a light subsystem 129 and a computing subsystem 128. The computing subsystem 128 includes one or more computing components for ultrasound control and analysis and optoacoustic control and analysis; these components may be separate, or integrated. In an embodiment, the computing subsystem comprises a relay system 110, an optoacoustic processing and overlay system 140 and an ultrasound instrument 150.

In an embodiment, the light system 129 is capable of producing pulses of light of at least two different wavelengths. In an embodiment, the light system 129 outputs should be capable of producing short pulses of light in each of those wavelengths, e.g., a pulse lasting less than about 100 ns, and potentially as short as about 5 ns. As will be apparent to one of ordinary skill in the art from this disclosure, the inventions disclosed herein may also be practiced using pulsed light comprising pulses lasting greater than 100 ns. In an embodiment, the light source 129 includes two separate lights 130, 131. The output of the light system 129 is delivered to the probe 102 via the optical path 132. In an embodiment, the lights 130, 131 are lasers producing light in the infrared, near-infrared, and/or visible spectrum. In an embodiment, light 130 and light 131 each produce light at a different wavelength in the infrared or near-infrared spectrum. In an embodiment, the optical path 132 used to deliver light from the light source 129 to the probe 102 is a fiber optic bundle comprising multiple strands of optical fiber. In an embodiment, the optical path 132 comprises sufficient optical fibers of sufficient size (diameter) to carry a short, high powered pulse of light to the distal end of the optical path 132. In an embodiment, the total pulse energy carried over the optical path 132 may be on the order of one or more millijoules. In an embodiment, the total energy per light pulse delivered from the optical path 132 is less than about 100 millijoules. In an embodiment, the total energy per light pulse carried over the optical path 132 is in the range of about 10-30 millijoules, and the optical path 132 comprises between about 1,000 and 2,000 optical fibers of between about 100 and 300 microns each. In an embodiment, a single fiber can be used as the optical path. In such embodiment, the fiber may be 1000-1500 microns in diameter. Of course, the diameter of such single fiber may be smaller, e.g., 400 microns. Given the required total pulse energy carried over the fiber, one skilled in the art can calculate the diameter required of the fiber accordingly.

In an illustrative embodiment, the light system 129 may use Nd:YAG and Alexandrite lasers as its two lights 130, 131, although other types or wavelengths, and additional lights, may also be used. Lights 130, 131 should be capable of producing a short pulse of light, e.g., a pulse lasting less than about 100 ns, and more preferably around 5 ns. In an embodiment, the two lights 130, 131 can be separately triggered. In an embodiment, the light output by the lights 130, 131 may be projected onto the same light path 132 through the use of an optical element 133 that generally permits one light 130 to pass through from a first side to a second side, while reflecting one light 131 that strikes the second side. The use of optical element 133 or a similar element permits the alignment of the output of two lights 130, 131 such as lasers onto proximal end of the light path 132. In an embodiment, optical elements 133 can align the light output from more than two lasers, for example, through the use of multiple optical elements 133.

Figure 39:
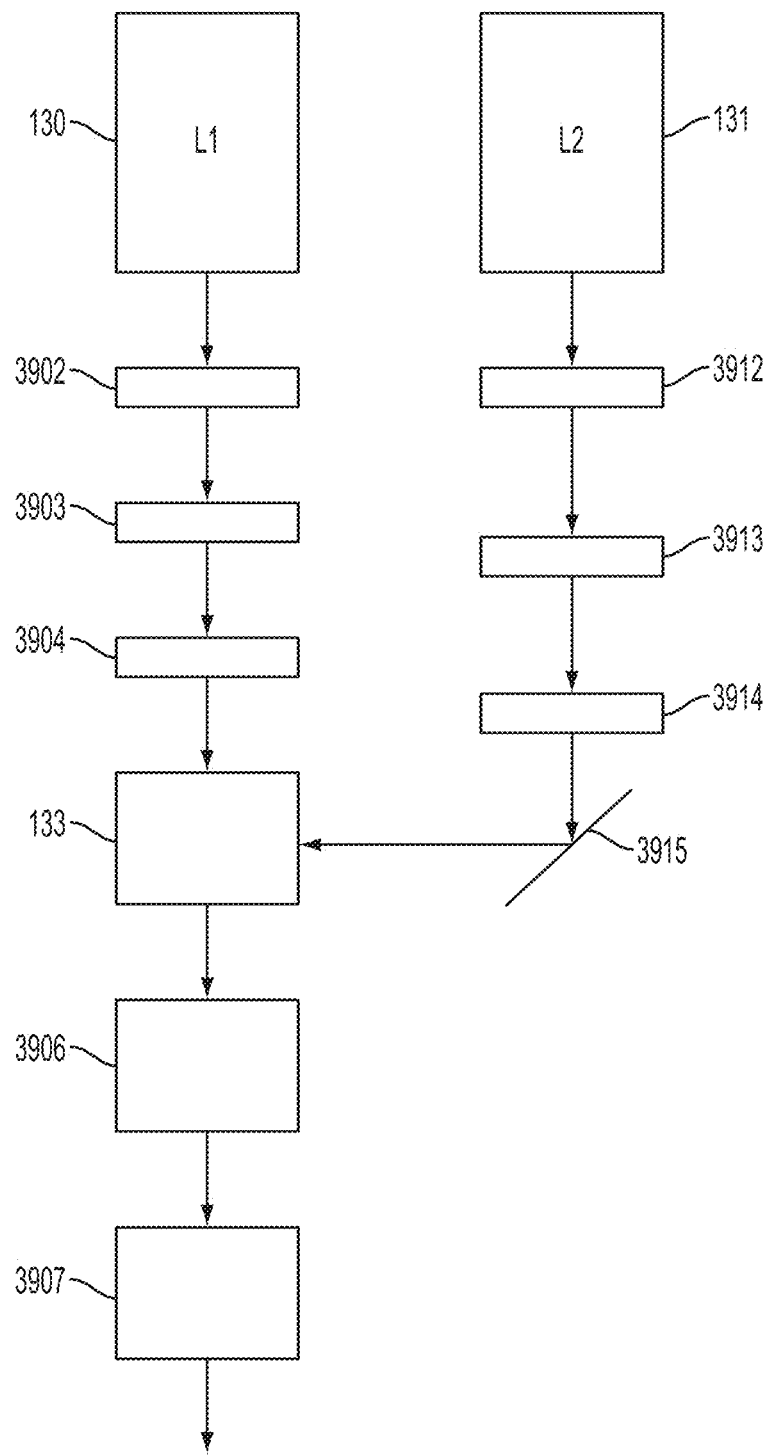
FIG. 39 is a schematic block diagram illustrating an embodiment of a light subsystem for use in a combined optoacoustic and ultrasound system.

Turning briefly to FIG. 39 there is shown a schematic block diagram illustrating an embodiment of a light subsystem 129 for use in a combined optoacoustic and ultrasound system. In an embodiment, light subsystem 129 comprises two light sources 130, 131 each capable of generating a light pulse; the output of each of the two light sources 130, 131 is directed to an optical attenuator 3902, 3912, a sync detector 3903, 3913, and a power detector 3904, 3914. If the light is not already aligned at appropriate angles, one or both of the beams of light may be redirected, e.g., by mirror 3915, and then, the light originating at the light sources 130, 131 is passed into a combiner 133 that redirects the light onto a common path. The common light path may then be passed through a homogenizer 3906, and/or an aperture 3907. After exiting the aperture, if the combined light path is not already aligned at the appropriate angle and location to exit a light output port, the light may once-again be redirected by the use of one or more mirrors (not shown).

Generally, the optical attenuators 3902, 3912 may be provided to attenuate the light pulse generated by the light sources 130, 131. Typical light sources 130, 131, may include a Q-Switched Nd:YAG laser and an Alexandrite Q-Switched laser. Such lasers may not permit the kind of fine output attenuation required for an optoacoustic application as described herein. Accordingly, an optical attenuator 3902, 3912 is used. In an embodiment, the optical attenuators 3902, 3912 each comprise two layers of polarized material that are rotatably mounted with respect to each other. In an embodiment, an external signal controls a small motor, which in turn adjusts the angle of one layer with respect to the other, and thus, the amount of light that is transmitted there-through. In an embodiment, one layer is a fixed sheet of polarized glass and the second layer is a round piece of polarized glass that can be rotated under control of a small electric motor. In an embodiment, the attenuator motor is controlled by the optoacoustic processing and overlay system 140 in connection with its processes controlling light output from the probe 102.

The sync detectors 3903, 3913 may be provided to generate a signal when a light source pulses. As discussed above, typical light sources 130, 131, may include a Q-Switched Nd:YAG laser and an Alexandrite Q-Switched laser. When using such pulse lasers, which require certain conditions to be met before they emit a pulse of light, the command to fire cannot be relied upon for synchronization as there may be delay, and potentially an unpredictable delay, between the command to fire and the actual pulse of light. Because, as discussed elsewhere herein, the acoustic sampling to detect the optoacoustic effect lasts less than 100 microseconds, precise timing is required, and thus, sync detectors 3903, 3913 are placed in the optical path. In an embodiment, a beam splitter (not shown) is used to redirect a small portion of the optical pulse into the sync detectors 3903, 3913 and allowing the vast majority of the beam to continue on its path. Since one sync detector is used for each light source, separate sync signals may exist for each. In an embodiment, a single sync detector could be used. In an embodiment, a single sync detector could be used, but the single sync detector may be designed to distinguish between the two light sources, and thus, itself, could generate separate sync signals for each.

The power detectors 3904, 3914 may be provided to permit a relative or absolute determination of the amount of post-attenuation light that will travel through a light path 132. In an embodiment, a beam splitter (not shown) is used to redirect a small portion of the optical pulse into the power detectors 3903, 3913, but allowing the vast majority of the beam to continue on its path. In such an embodiment, the detected amount of power may be scaled to determine the emitted light source power.

The homogenizer 3906 may be provided to homogenize the beam of light across its section. In other words, that the fluence is approximately the same across a known areas of the beam. In an embodiment, the beam will be directed to a bundle of fiber optic cable, and thus, the beam is homogenized in an effort to ensure that the amount of light entering each strand of the fiber optic cable is reasonably the same as the amount of light entering each other strand.

An aperture 3907 may be provided to ensure the appropriate circumference of the light beam for incidence upon the entry point of the light path 132.

Returning to FIG. 1, in an embodiment, multiple light systems and light paths may be employed, with the light of each light system being carried on separate fibers or fiber groups that may be intermingled and/or randomized (discussed further below) and/or grouped at their distal ends. Intermingled, as used in this context, refers to the mapping of the fibers in the light path such that fibers are generally distributed in a relatively even manner in the distal groupings. Thus, a plurality of adjacent fibers on the proximal end of the light path would generally be about evenly divided in groupings on the distal end. As an illustrative example, where there are two distal groupings, any arbitrary selection of a sufficient group of adjacent fibers on the proximal end should be about evenly split between the two distal groupings. The randomization, intermingling and/or grouping need not take place at any specific location on the light path 132. In other words, for example, the division of a fiber cable from one proximal group to two distal groups can occur at any point along the light path 132, or along substantially the entire length of the light path 132. Similarly, the randomization and/or intermingling need not take place along the entire length of the light path, but rather, for example, may take along a the distance of, e.g., a few centimeters or more near either end of the light path, or anywhere else along the light path 132. Randomizing fibers between one end and the other end of a light path prevents a local anomaly affecting an adjacent group of the fibers on the input from affecting an significant adjacent group of the fibers on the output. Intermingling fibers between one end and the other end of a light path prevents a local anomaly affecting an adjacent group of the fibers on the input from disproportionately affecting one group or subgroup of fibers on the output.

Where the light path terminates in multiple groupings (or subgroupings) of fibers, the distal ends of the groupings (or subgroupings) may be fused, or lapped and polished, or just secured together (removably or otherwise). In an embodiment, the distal end of the light path is formed into a plurality of groups that are spaced in such a manner so as to permit light to emit on each side of the transducer array. In an embodiment, the distal end of the light path is formed into a plurality of groups that are spaced in such a manner so as to permit light to emit around the entire transducer array. In an embodiment, the distal end of the light path is formed into two or more groups, and the two or more groups subdivided into subgroups that are separately secured by a light bar guide, which light bar guide may be associated with the group. In an embodiment, optical elements 133 can consist of optical elements that are used to measure the light energy to determine energy per light pulse.

Although the total energy per light pulse carried over the optical path is in the order of tens of millijoules, because the pulse of lights 130, 131 is so short, the peak power output over the optical path 132 is frequently approaching or in the megawatt range. Accordingly, the output of lights 130, 131 has the capacity to cause the optical fibers and/or the cladding on the optical fibers to burn, discolor or otherwise degrade. Such degraded optical fibers and/or cladding, whether burnt, discolored, or otherwise, can exacerbate the problem as they begin to transmit less light power and cause more heating. Accordingly, in an embodiment, sufficient number and size optical fibers are present in the optical path 132 to permit handling of the peak power loads and avoid fiber burnout. To accommodate higher peak power, a larger fiber bundle can be used. It will be apparent to a person of skill in the art that the peak power capacity of a fiber bundle can be increased by increasing the number of optical fibers, or the diameter of optical fibers, or both. Notably, however, as the dimension of the fiber bundle increases, the weight and flexibility of the optical path 132 may become less desirable. Moreover, when using more optical fibers, or optical fibers of a larger diameter, the output of light source 129 must be delivered to the optical path 132 across the wider diameter of the larger bundle. In an embodiment, regardless of the ultimate size of the proximal end of light path 132, the output of light source 129 should be distributed sufficiently across its cross section to prevent burn out failures when operating in expected peak power ranges.

In an embodiment, the fibers of the proximal end of the light path 132 may be fused to form a fused entry point to the optical path 132 for the output of light source 129. In an embodiment, the fiber ends can be fused by applying heat. In an embodiment a fused end may be surrounded with a metal ring. In an embodiment a fused end may be surrounded with a stainless steel ring. Once the proximal end of optical path 132 has been fused, it will resist burnout at substantially higher peak power. For example, using a fused end light path 132 may permit carriage of three, four or even five times as much peak power. The ability to carry substantially higher peak power in a given optical path 132 permits use of a more flexible and lighter fiber optic bundle to carry the same peak power as an un-fused optical path 132. Thus, in an embodiment, where a ½" fiber optic bundle may have been required in an un-fused bundle of optical fibers forming an optical path, a ¼" fiber optic bundle with a fused proximal end may be used to carry the same peak power. A ¼" fiber optic bundle with a fused proximal end is approximately ¼ of the weight and much more flexible than a ½" fiber optic bundle. Moreover, fusing of the proximal end of light path 132 may produce an even smaller fused area to illuminate using light source 132 as the fusing removes the inter-fiber spaces that would have existed in the bundled end of the round-cross-section optical fibers. Accordingly, one or more of the following advantages may be attained by fusing the proximal end of the optical fibers comprising the light path 132: reduced weight of the light path; increased flexibility of the light path; reduced failure; increased reliability; higher peak power capacity.

In an embodiment, the proximal end of the light path 132 may be separated into separate groups for separate lights 130, 131 in a light source 132, and light output by the lights 130, 131 may be projected onto different proximal groups of the light path 132. More than two separate lights may be used, and the proximal end of the light path 132 may be separated into at least one group for each light. Each group of fibers at the proximal end of the light path 132 may be fused together to form a fused entry point to the optical path 132 for the light with which it is associated. In an embodiment, the fibers of a light path having multiple groups on the proximal and are intermingled with respect to the groups or subgroups on the proximal ends. In an embodiment, the fibers of a light path having multiple groups on the proximal and are randomized with respect to the groups or subgroups on the proximal ends. In an embodiment, a light path is provided with a fused proximal end (input) and at least two groups on its distal end (outputs), the fibers being intermingled and randomized, thus preventing a local anomaly affecting adjacent fibers at the input of the light path from: (i) causing an anomaly affecting a substantial number of adjacent fibers on an output; and (ii) disproportionately affecting one of the outputs. In an embodiment, a light path is provided with at least two groups on its proximal end (inputs) and at least two groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs. In an embodiment, a light path is provided with at least two fused groups on its proximal end (inputs) and at least two fused groups on its distal end (outputs), the fibers being intermingled and randomized, thus preventing a local anomaly affecting adjacent fibers at an input of the light path from: (i) causing an anomaly affecting a substantial number of adjacent fibers on an output; and (ii) disproportionately affecting one of the outputs.

In an embodiment, optical fiber of the type that may be used in light path 132 includes a transparent core surrounded by a transparent cladding material with a lower index of refraction. The core may be made from any transparent material, although excellent results have been observed using pure glass (i.e., silica). In an embodiment where a bundle of optical fibers are to be fused, the cladding may be removed in the area to be fused. In an embodiment, the cladding may be removed using a chemical process. For example, for some cladding, hot sulfuric acid or acetone may be used. The removal of cladding prior to fusing reduces the chance of particles of the cladding material becoming embedded in the fused end, as such particles may interfere with the light transmission across light path 132.

In an embodiment, the light output by the lights 130, 131 is sent towards a fused optical fiber bundle at the proximal end of light path 132 via an optical path, which may include optical element 133, internal to the light source 129. In an embodiment, light source 129 is a laser system capable of outputting laser light pulses, at one or a more wavelengths, onto light path 132. In an embodiment, light path 132 is a fiber optic bundle having a fused end proximal to the light source 129.

In an embodiment, the device 100 also comprises an electrical path 108 running to and/or from the probe 102 to the system chassis 101. In an embodiment, electrical path 108 runs to and/or from the probe 102 to a relay system 110 within the system chassis 101. The electrical path 108 may run near, alongside or coaxially with the optical path 132 from the probe 102 toward their respective connections on the system chassis 101. In an embodiment, the electrical path 108 comprises a plurality of separate coaxial wires. In an embodiment, the electrical path 108 is run in a common jacket with at least a portion of the optical path 132. Running electrical path 108 in a common jacket with at least a portion of the optical path 132 reduces the number of cables running from the system chassis 101 to the probe 102. Running electrical path 108 in a common jacket with at least a portion of the optical path 132 may minimize the diameter and weight of, and increase the durability of, the combined cables (i.e., optical path 132 and electrical path 108) running from the system chassis 101 to the probe 102.

In an embodiment, the plurality of coaxial wires is woven around at least a portion of the optical path 132. As discussed above, many considerations go into the number of separate optical fibers used in optical path 132. As discussed further below, numerous design considerations go into the number of separate electrical leads or traces forming the electrical path 108. In an embodiment, there are about 256 leads (corresponding to 256 transducers) forming the electrical path 108 and approximately 1,000 separate optical fibers forming the optical path 132, making the fiber:lead ratio about 4:1. As will be apparent, it is possible to commingle the optical fibers and leads or traces in the electrical path in a variety of ways, including, for example, bundling a group of individual fibers with a single electrical lead or trace, or bundling proportionally larger groupings of fibers and leads together. In an embodiment, the bundling of fibers and leads or traces would be done generally in the proportion of fibers:leads in the system.

One or more displays 112, 114, which may be touch screen displays, are provided for displaying images and all or portions of the device 100 user interface. One or more other user input devices 116 such as a keyboard, mouse, trackball, and various other input devices (e.g., dials, buttons and switches) may be provided for receiving input from an operator. As an option, power and control signal lines 109 carry power to the probe 102 and control signals between the probe 102 and the computing subsystem 128.

In an embodiment, the connections between the probe 102 and the system chassis 101 may be formed into a flexible cable, which may consist of the light path 132, the control line(s) 109 and the electrical path 108. The flexible cable may be covered in a common outer jacket or sheath for convenience and ease of use. In an embodiment, a medial portion of the light path 132 form's the core of the single flexible cable, and medial portions of the electrical path 108 and/or control line(s) 109, if any, may be wrapped or braided about the medial portion of the light path 132. In an embodiment, a common outer jacket or sheathing encloses a fiber optic bundle forming a medial portion of the light path 132, a coaxial bundle forming a medial portion of the electrical path 108, and control line(s) 109, if any. In an embodiment, the fibers forming a medial portion of the light path, and the wires forming a medial portion of the electrical path 108, as well as control line(s) 109, if any, may be intertwined or intermingled with each other along the medial portion of the connections between the probe 102 and the system chassis 101.

In an embodiment, the distal end of the flexible cable(s) connecting the probe 102 and the system chassis 101 is associated with, and non-removably integrated as part of the probe 102. In an alternative embodiment, the distal end of the flexible cable(s) connecting the probe 102 and the system chassis 101 is removably associated with the probe 102. To removably associate the flexible cable(s) connecting the probe 102 and the system chassis 101 requires both optical fiber connection for the light path 102 and electrical connection for the electrical path 108 and control line(s) 109, if any.

In an embodiment, the light path 132 is split into two sections, and the two sections are brought together using an optical fiber connector in close proximity to the probe 102. The optical fiber connector may be physically located within the probe 102, or may span opening 404 (see FIG. 4), or be located outside the probe 102. In an embodiment, an optical fiber connector would mechanically couple and align the cores of the fibers making up the light path 132 so that light can pass from one section to the other without significant loss. In an embodiment, the facing ends of the two sections of the light path 132 are fused, and may be first stripped of cladding and then fused, to mitigate issues of core alignment. Regardless of whether the fiber ends are fused, the ends internal to light path 132 that are being connected by the optical fiber connector may be lapped and polished to improve light transmission. In an embodiment, probe 102 has a removable access panel that permits access to optical and/or electrical connectors located within the probe.

To support removability of the electrical path 108 and control line(s) 109, if any, removable electrical connectors may be provided. In an embodiment, flex circuit is elongated so that connectors 314 which are connected to the end of electrical path 108 are accessible from a removable access panel, thereby permitting the disconnection of electrical path 108. In an embodiment, electrical path 108 (and control path 109, if any) is split into two sections, and the two sections are brought together using an electrical connector in close proximity to the probe 102. The electrical connector may be physically located within the probe 102, or may span opening 404 (see FIG. 4), or be located outside the probe 102. In an embodiment, an electrical connector would electrically couple the two portions of the electrical path 108 so that signals can pass from one section to the other without significant loss.

In an embodiment, the signals carried on the probe-side portion of electrical path 108 are analog signals, and are terminated into an analog-to-digital converter, and the signals carried on the other portion of the electrical path—the portion that connects to the system chassis 101—are digitized representations of the analog signals carried on the probe-side portion of the electrical path 108. In an embodiment, the signals carried on the electrical path 108 are digital signals given that the analog-to-digital conversion is performed in the body of the probe handle In an embodiment, the optical connector(s) to connect the light path 132 to the system chassis, and the electrical connector(s) for the flexible cable(s) that operationally connects the system chassis 101 to the probe 102 may be integrated into a single connector that can be operated to quickly disconnect the probe 102 from the cable. In an embodiment, an optical connector connecting the light path 132 to the system chassis, and a multi-pin electrical connector for connecting the electrical path 108 and control line(s) 109 to the system chassis are provided as separate connectors. In an embodiment, the optical connector and the multi-pin electrical connector are designed to be hand operated permitting tool-free removal by an operator or maintenance personnel.

Figure 36:
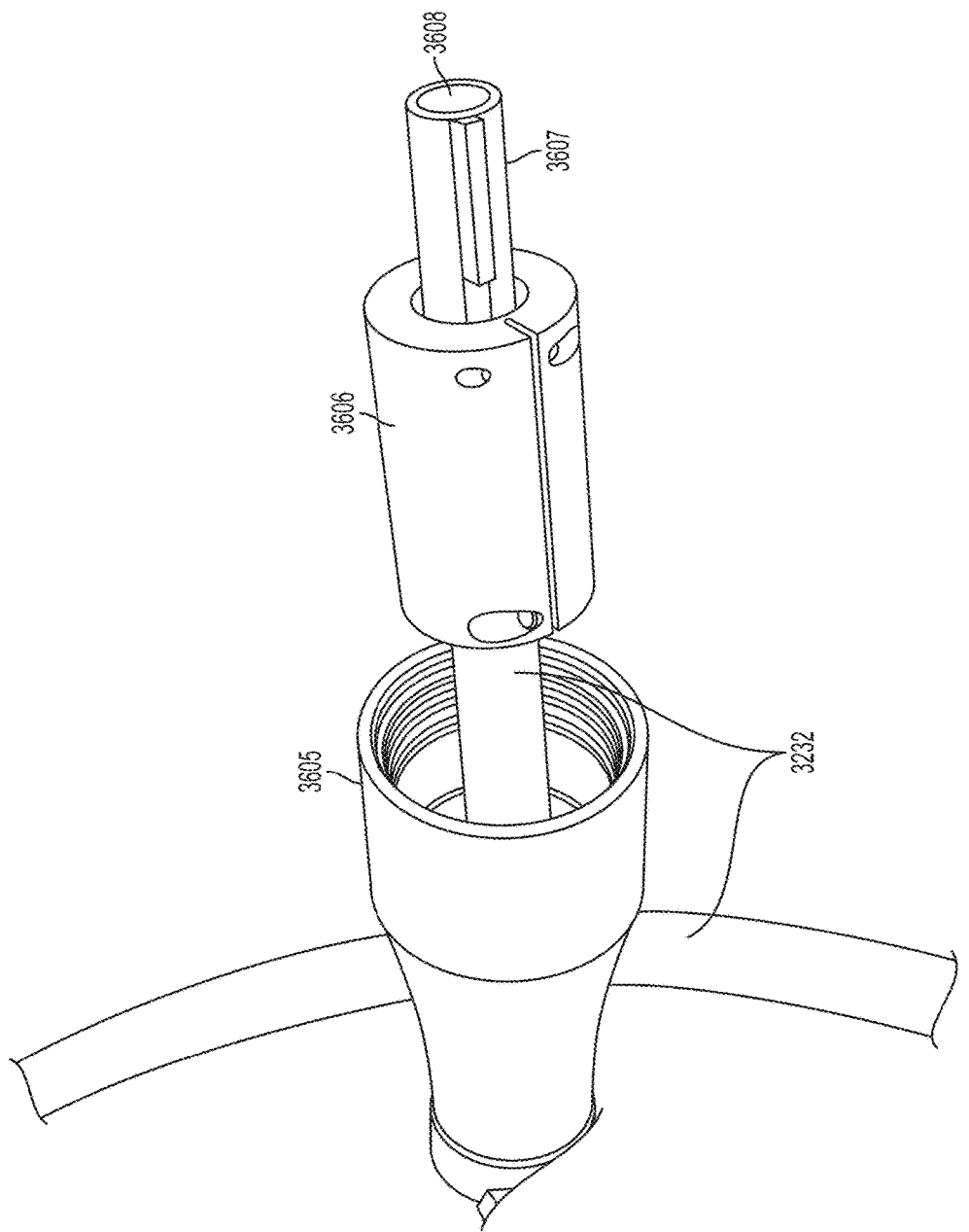
FIG. 36 shows an embodiment of a novel hand-operated fiber optic connector.
Figure 37:
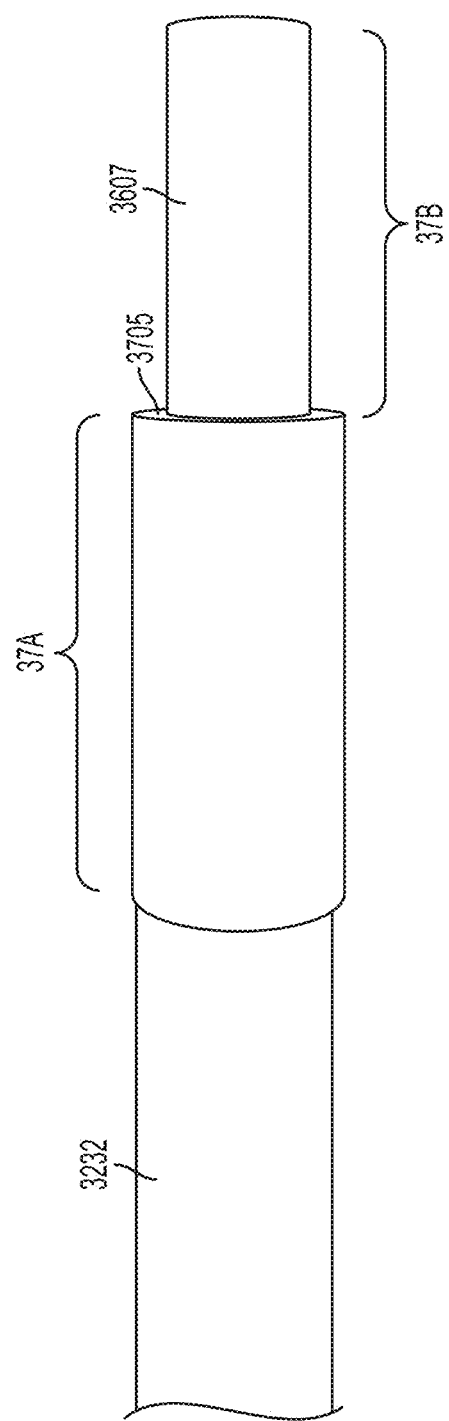
FIG. 37 shows a sheathed fiber optic bundle with one end of the fibers surrounded by a stepped ferrule as may be used in a novel hand-operated fiber optic connector.
Figure 38:
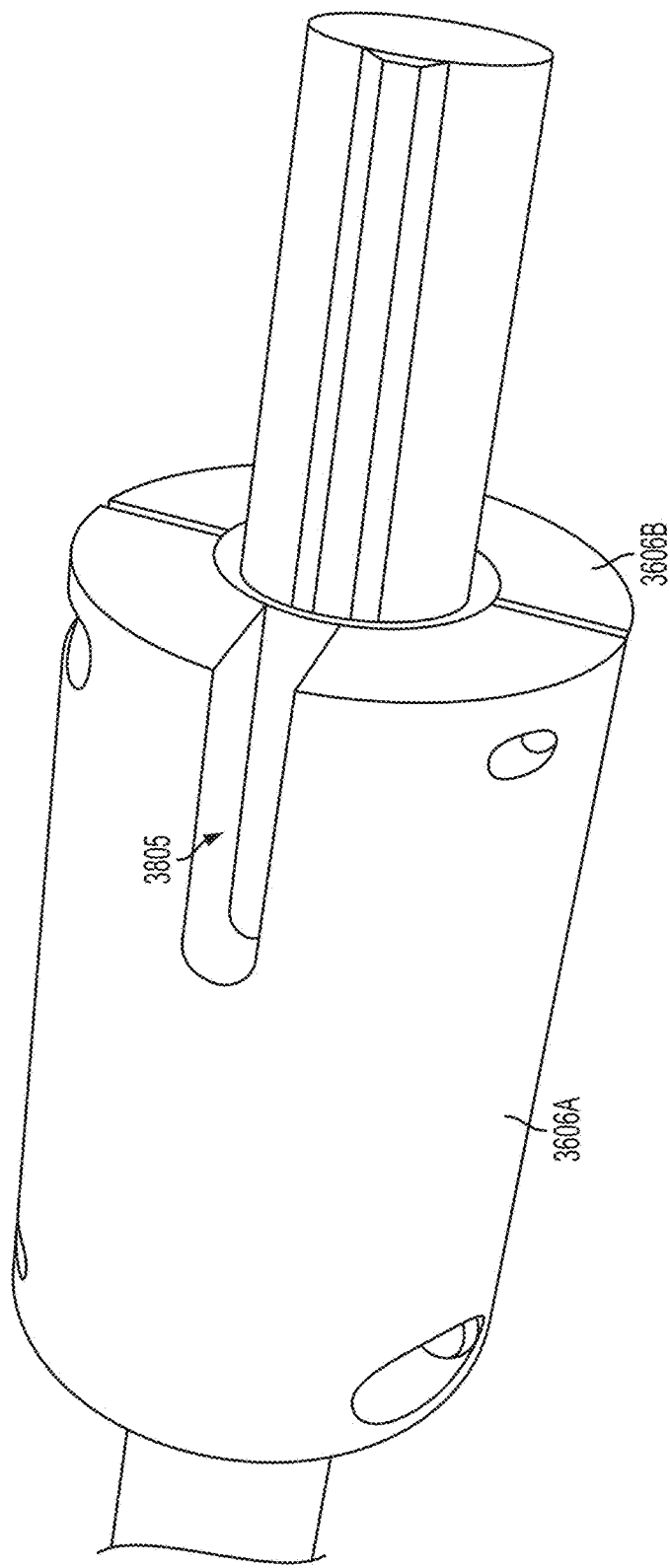
FIG. 38 shows a collared stepped ferrule as may be used in a novel hand-operated fiber optic connector.

Turning briefly to FIGS. 36, 37 and 38, an unconnected view of one embodiment of the cable side of a fiber optic connector, a detail view showing the ferrule of the connector, and another detail showing the collar of the connector, is shown. A light path 3232 is terminated at the distal end of a stepped ferrule 3607. In an embodiment, the distal end 3608 of the fiber bundle forming the light path 3232 is fused and/or lapped and polished. The stepped ferrule 3607 has an area of wider circumference 37A and an area of narrower circumference 37B which meet at the step. The area of narrower circumference is intended for insertion within the light output port (not shown) in the chassis side of the connector (not shown). A collar 3606 substantially surrounds the area of wider circumference 37A of the ferrule 3608. In an embodiment, a distal end of the collar 3606 is substantially flush with the step in the ferrule 3607, such that both the step and the distal end of the collar 3606 can come in contact with the chassis side of the connector (not shown). In an embodiment, the collar 3606 is made from two parts 3606A, 3606B that can be fastened together about the ferrule 3607. In an embodiment, the collar 3606 is made from semi-cylinders 3606A, 3606B that are fastened together with screws about the ferrule 3607. The cable side of the fiber optic connector also comprises a housing 3605, which may be internally threaded. In an embodiment, the chassis side of the connector comprises a cylindrical opening (light output port) permitting insertion of the area of narrower circumference 37B up to the step, a flat contact surface, and an externally threaded cylindrical protrusion.

The fiber optic connector is connected by: (i) inserting the area of narrower circumference 37B into the cylindrical opening until the step and/or distal end of the collar 3606 engage with the external surface of the chassis side of the connector; (ii) sliding the housing 3605 over the collar 3606 and engaging its threading with the threading of the chassis side of the connector; and (iii) screwing the threading on the housing together with the threading on the chassis side of the connector. In an embodiment, a rear portion of the housing 3605 applies pressure on the proximal end of the collar 3606 in the direction of the chassis, and thus urges secure contact between the collar 3606 and the chassis side of the connector (not shown).

In an embodiment, the fiber optic connector comprises a positioning means that ensures the that the light path can be repeatably rotationally aligned each time the connector is connected. In an embodiment, the positioning means consists of a slot 3805 in the collar 3606 and a key (not shown) that inserts into the slot 3805 when the area of narrower circumference 37B is being inserted into the cylindrical opening. In an embodiment, the positioning means may consist of at least one key and at least one slot, provided that if there is more than one key and slot, only one correct position will permit the connector to be secured. In an embodiment, the positioning means may consist of at least one post and at least one hole, provided again that if there is more than one post and hole, only one correct position will permit the connector to be secured. In an embodiment, the position means may consist of a contour or shape on one side of the connector and a complementary contour or shape on the other, such that there is only one correct position, and that the correct position can be manually located. The positioning means is intended to include all manner of positioning mechanisms that repeatable rotational alignment of the fiber optic bundle. In the foregoing embodiments, as will be apparent to one of skill in the art, the first step of connecting the fiber optic connector may additionally require rotating the collar until the positioning means properly engages.

Figure 16:
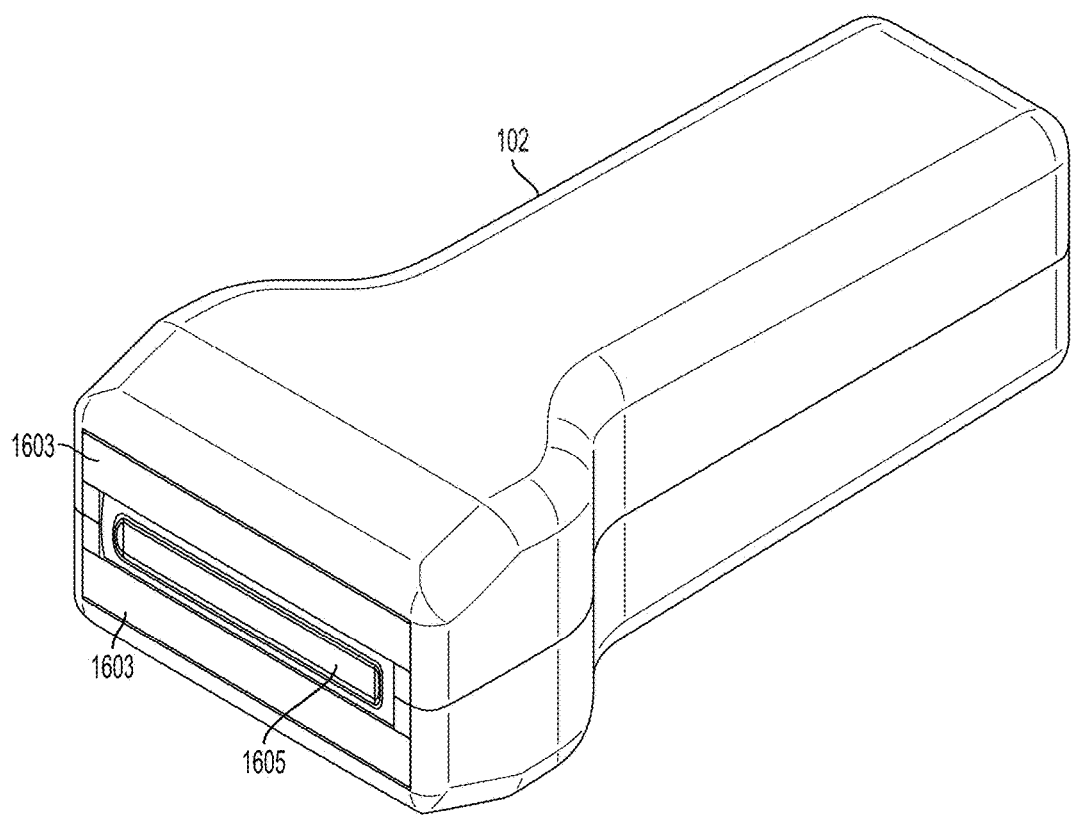
FIG. 16 shows a schematic orthogonal view of an embodiment of a probe that may be used in connection with the methods and other devices disclosed herein.

Turning now to FIG. 16, the probe 102 includes an array of ultrasound transducer elements forming an ultrasound transducer (not shown) covered by an acoustic lens 1605. In an embodiment the ultrasound transducer comprises an array of piezoelectric elements that can both transmit and receive acoustic energy. In an embodiment, at least some of the ultrasound transducer elements are capable of detecting ultrasound frequencies over a wide range. For example, ultrasound transducer elements may be capable of detecting ultrasound in the range from about 50 KHz to 20 MHz. This range can be achieved by applying a high impedance load (e.g., in the range of 5,000 to 50,000 ohms) to achieve a lower frequency response. The ultrasound transducer elements are capable of generating electrical energy in response to receiving ultrasound acoustic energy. The electrical energy generated by the ultrasound transducer elements receiving ultrasound is transmitted to the computing subsystem 128 via electrical path 108.

The probe 102 also includes one or more optical windows 1603 through which the light carried on optical path 132 can be transmitted to the surface of a three-dimensional volume 160. In an embodiment, it is desirable to locate one side of the optical window 1603 as close as practical to the acoustic lens 1605. The total area of an optical window 1603 is important to maximize energy for a given fluence incident on the surface of the volume 160.

In an embodiment, the multiple strands of optical fiber making up the optical path 132 are terminated in two light bars (not shown). In an embodiment, the ultrasound transducer elements (not shown) are arranged in an array that runs along a geometric plane and are generally spaced equidistant from each other. In an embodiment, the light bars (not shown) are oriented longitudinally, on each side of the planar array of ultrasound transducer elements. Preferably the ultrasound transducer elements generate electrical energy in response to both ultrasound acoustic energy received in response to stimulation caused by the pulsed light sources 130, 131 (i.e., the optoacoustic return signal) and to ultrasound acoustic energy received in response to acoustic output of the ultrasound transducer elements.

Referring back to FIG. 1, in use, the probe 102 may be placed in close proximity with organic tissue, phantom or other three-dimensional volume 160 that may have one or more localized inhomogenities 161, 162, such as e.g., a tumor, within. An ultrasound gel (not shown) or other material may be used to improve acoustic coupling between the probe 102 and the surface of the volume 160. The probe 102, when in proximity with the surface of the volume 160, can emit a pulse of a light through the optical windows 1603 or an ultrasound through acoustic lens 1605, and then generate electrical energy corresponding to ultrasound detected in response to the emitted light or sound.

In an embodiment, the computing subsystem 128 can trigger activity from light system 129 over control signal line 106. In an alternative embodiment, the light system 129 can create the trigger signal and inform the computing subsystem 128 of its activity over control signal line 106. Such information can be used to by the computing subsystem 128 to begin the data acquisition process. In this respect, it is noted that communication over control signal line 106 can flow both ways between the computing subsystem 128 (and/or the optoacoustic processing and overlay system 140 therein) and the light system 129.

In an embodiment, computing subsystem 128 can utilize control signal line 106 to control the start time and duration of light pulses from each light source 130, 131. The computing subsystem 128 can also trigger the probe 102 to emit ultrasound acoustic energy via the ultrasound transducer elements behind the acoustic lens 1605.

In an embodiment, the computing subsystem 128 receives electrical signals representative of the ultrasound detected by the ultrasound transducer elements, in response to an ultrasound transmitted signal or an optically generated ultrasound signal, behind the acoustic lens 1605 via electrical path 108. In an embodiment, the electrical signal representative of the ultrasound detected by the ultrasound transducer elements behind the acoustic lens 1605 is the analog electrical signal created by the elements themselves. In such embodiment, the electrical signals representative of the ultrasound detected by the ultrasound transducer elements behind the acoustic lens 1605 is transmitted to the computing subsystem via electrical path 108, and electrical path 108 is selectively directed by relay system 110 to the optoacoustic processing and overlay system 140 or the ultrasound instrument 150 for processing of the detected ultrasound. In such embodiment, the ultrasound instrument 150 can receive the same input (over the same connector) as it would receive from an ultrasound probe.

In another embodiment, the electrical signal representative of the ultrasound detected by the ultrasound transducer elements behind the acoustic lens 1605 is digitized by an analog-to-digital converter which can be housed in the probe 102. In such embodiment, time-resolved electrical signal representative of the ultrasound detected by the ultrasound transducer elements behind the acoustic lens 1605 is transmitted across the electrical path 108. Where the electrical signal is digitized at the probe 102, as will be apparent to one of skill in the art, the relay system 110 may be implemented to deliver digital data to the optoacoustic processing and overlay system 140 or the ultrasound instrument 150, or may not be needed at all.

The signal representative of the ultrasound detected by each of the plurality of ultrasound transducer elements behind the acoustic lens 1605 may be carried on a separate wire over the electrical path 108. Alternatively, the signal representative of the ultrasound detected by a plurality of ultrasound transducer elements behind the acoustic lens 1605, or even all of the ultrasound transducer elements behind the acoustic lens 1605, may be multiplexed (e.g., time division or frequency division) utilizing a multiplexer in the probe and a demultiplexer in the computing subsystem 128.

In an embodiment, the ultrasound instrument 150 processes ultrasound-induced acoustic signals to produce ultrasound images and the optoacoustic processing and overlay system 140 processes light-induced acoustic signals to produce optoacoustic images. In an embodiment, the ultrasound instrument 150 and optoacoustic processing and overlay system 140 can be combined into an integrated system performing the combined functions of both. As discussed above, in an embodiment, electrical signals representative of ultrasound detected by the probe 102 and delivered to the computing subsystem 128 via electrical path 108 is switched between the ultrasound instrument 150 and the optoacoustic instrument 140 via relay system 110 in accordance with whether the signal results from ultrasound stimulation or light stimulation.

In an embodiment, tomographic images reflecting the ultrasound-stimulated data may be generated by the ultrasound instrument 150 and tomographic images reflecting the light-stimulated data may be generated by the optoacoustic processing and overlay system 140.

Images, including tomographic images, produced by the optoacoustic processing and overlay system 140 can be stored in a computer memory in that system, along with data associated with sequence or time and date of the image data that was captured. Images, including tomographic images, produced by the ultrasound instrument 150 may be transmitted to the optoacoustic processing and overlay system 140 via a suitable interface 170, where they can be stored, along with images generated from the light-stimulated data, in a time-synchronized manner. In an embodiment, images stored in the memory of the optoacoustic processing and overlay system 140 can be recorded to another memory, e.g., a non-volatile memory internal to, or external to, the device.

In an embodiment, the optoacoustic processing and overlay system 140 can overlay images produced by the ultrasound instrument with images produced by optoacoustic instrument 140 for storage in the memory and/or display on one or more monitors 112, 114. In an embodiment, the overlayed optoacoustic image may be shown in a distinct color to distinguish it from the ultrasound image. In an embodiment, the overlaid optoacoustic image may contain colors that correspond to details discernable through optoacoustic imaging, such as, for example, blood oxygenation. In an embodiment, oxygenated blood is shown more in red than blue, while deoxygenated blood is shown in more blue than red. As used herein, the expression overlaid includes merging of the image by mixing as well as traditional overlaying of the image.

In an embodiment, the device 100 may be configured to operate in a cycle comprising a sequence of successively generating and acquiring data relating to one of the device's modalities, i.e., ultrasound or optoacoustic. The minimum time spacing between operation of the device's modalities depends on the device 100 components and their ability to fully execute and recycle for use. In an embodiment, a user can select between a variety of preprogrammed cycles such as, for example: ultrasound only; wavelength one only; wavelength two only; wavelength one and two (which may be caused, e.g., by separate lasers, or by a single, quickly tunable, laser); multiple iterations of wavelength one and two followed by ultrasound; and/or multiple iterations of ultrasound followed by wavelength one and/or two. Other and further combinations will be apparent to one of skill in the art. Moreover, where the device 100 is capable of generating more than two wavelengths, numerous additional preprogrammed cycles may be desirable. In an embodiment, additional cycles can be added by the machine operator. In an embodiment, the data collection of an entire cycle is generally intended to be directed to substantially the same portion of volume 160 and to be accomplished in rapid succession. In an embodiment, the device 100 cycles are normally in the range of 1 to 50 per second, and more typically in the range of 2 to 20 per second, as discussed above. The maximum cycle frequency is limited only by the capabilities of the cycle and modalities.

In an embodiment, the displays 112, 114 of device 100 can be configured to show various information depending upon the selected operating cycles. In an embodiment, any display 112, 144 or portion of the display can show at least one of the following: an ultrasound only image; a first wavelength response only image; a second wavelength response only image; a combined first and second wavelength response image; and/or an overlay ultrasound image and a wavelength response or combined wavelength response image. The combined first and second wavelength image may comprise a differential or other combinatorial means to provide the image. In an embodiment, an image can be displayed corresponding to each of the separate data collections in a cycle, or corresponding to the sum or difference between any or all of them.

In an embodiment, the device can be operated using a three-phase data collection operation, one phase generating and collecting data in response to ultrasound stimulus, one phase generating and collecting data in response to a first wavelength of light, and one phase generating and collecting data in response to a second wavelength of light. In an embodiment having a light source capable of generating more than two wavelengths, the device can be operated using a multi-phase data collection operation, one phase generating and collecting data in response to ultrasound stimulus, and one phase generating and collecting data in response to each wavelength of light. Other and further combinations will be apparent to one of skill in the art.

Using proper wavelength(s), optoacoustics is effective in identifying blood within a volume 160, and using multiple wavelengths can be used to readily distinguish between oxygenated and deoxygenated blood. Similarly, using proper wavelengths, optoacoustics is effective for measuring localized hemoglobin content within a volume 160. Thus, for example, a malignant tumor, which is characterized by increased blood concentration and decreased oxygenation, will appear very differently in an optoacoustic image than a benign growth, which is not characterized by such an increased blood concentration and has more normal oxygenation. Moreover, specific wavelengths of light can be selected to better distinguish between various biological tissues and organs. While a large spectrum of infrared, near-infrared and visible wavelengths can produce optoacoustic response in biological entities, oxygenated blood is more optoacoustically responsive than deoxygenated blood to a light source having a wavelength of about 1064 nm, while deoxygenated blood is more optoacoustically responsive than oxygenated blood to a light source having a wavelength of about 757 nm. The number and specific wavelength(s) of light used in the device 100 are selected in accordance with the makeup of the volume and the type of target that is of interest.

In an embodiment employing an ND:Yag laser to emit a pulse of light having a predominant wavelength of about 1064 nm and employing an Alexandrite laser to emit a pulse of light having a predominant wavelength of about 575 nm, the ND:Yag laser will be pulsed first, followed by a delay of about 50 milliseconds, followed by the pulsing of the Alexandrite laser. The cycle length before the following pulse of the ND:Yag laser may be 100 milliseconds or more. Thus, in an embodiment, the pulses/delays may be as follows: ND:Yag pulse, 50 millisecond delay, Alexandrite pulse, 50 millisecond delay, yielding a frequency of about 10 Hz, and a cycle time of about 100 milliseconds. Generally, regardless of the total cycle time, the time between the first and second light events should be as short as reasonably practical. Thus, in another embodiment, the pulses/delays may be as follows: ND:Yag pulse, 50 millisecond delay, Alexandrite pulse, 150 millisecond delay, yielding a frequency of about 5 Hz, and a cycle time of about 200 milliseconds. In yet another embodiment, the pulses/delays may be as follows: ND:Yag pulse, 50 millisecond delay, Alexandrite pulse, 250 millisecond delay, or a 450 millisecond delay, or a 950 millisecond delay, yielding, respectively, a frequency of about 3.33, 2 and 1 Hz, and cycle times of about 300, 500 and 1,000 milliseconds. In an embodiment, the Alexandrite laser may be pulsed before the ND:Yag. In an embodiment, a graphical user interface (GUI) is provided for operating a clinical optoacoustic system, the GUI including, without limitation: controls that permit operator selection of the cycle time and/or the order of light source pulsing.

Figure 17:
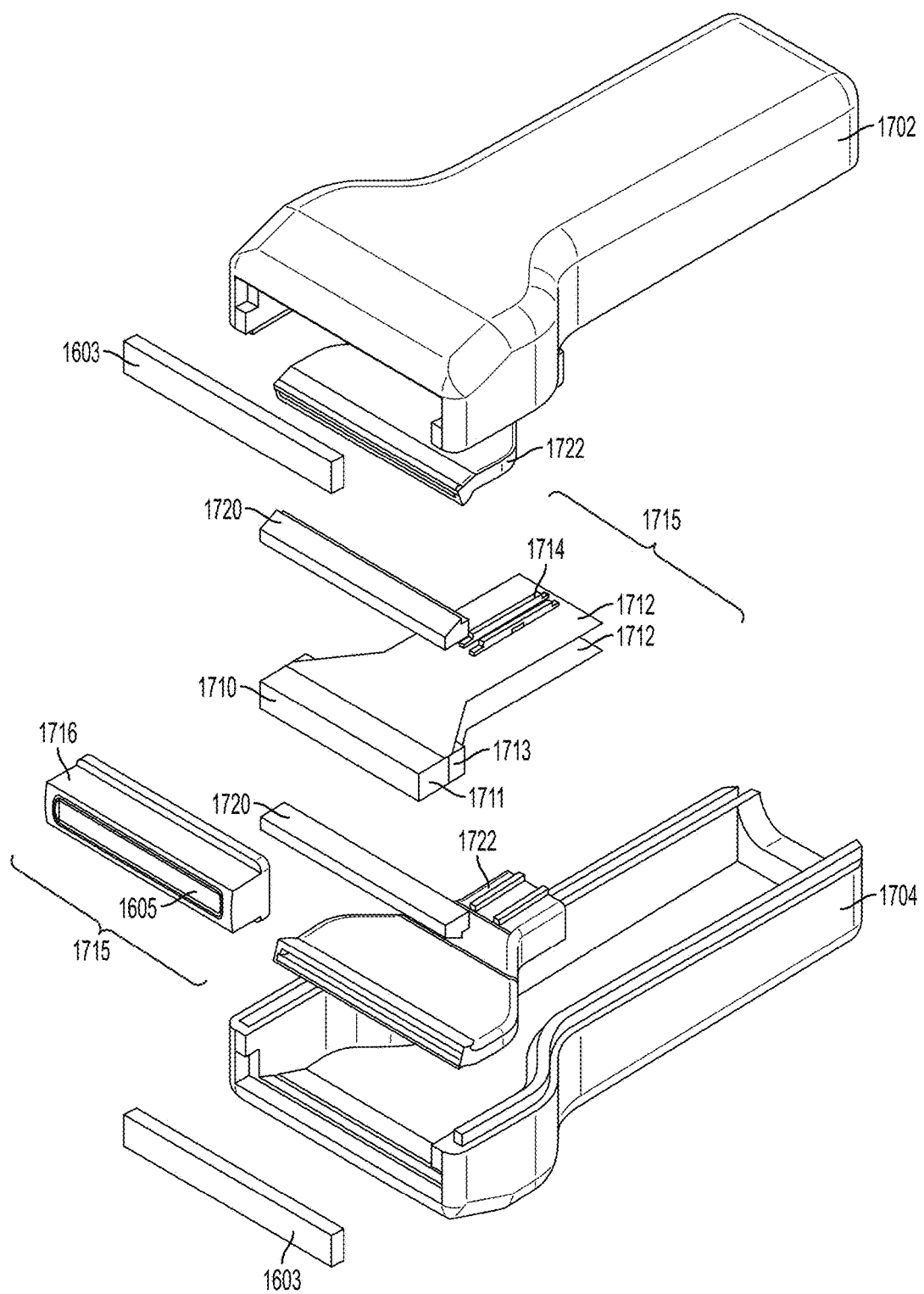
FIG. 17 shows an exploded view of an embodiment of the probe shown in FIG. 16.

FIG. 17 shows an exploded view of an embodiment of the probe 102 shown in FIG. 16. Shells 1702, 1704 are separated to show the components within the probe 102. The shells 1702, 1704 may be made from plastic or any other suitable material. The surfaces of the shells 1702, 1704 that may be exposed to light, and especially light generated by the light subsystem 129, are preferably both reflective (i.e., light colored) material and light scattering (i.e., having a scattering coefficient between 1 and 10). In an embodiment, the surfaces of the shells 1702, 1704 are highly reflective, i.e., more than 75% reflective. In an embodiment, the surfaces of the shells 1702, 1704 are very highly reflective, i.e., more than about 90% reflective. In an embodiment, the surfaces of the shells 1702, 1704 have low optical absorption, i.e., less than 25% absorptive. In an embodiment, the surfaces of the shells 1702, 1704 have very low optical absorption, i.e., less than about 10% absorptive. In addition, the material forming the shells 1702, 1704 should be acoustically absorbent to absorb, rather than reflect or transmit acoustic energy. In an embodiment, white plastic shells 1702, 1704 are used.

In an embodiment, flex circuit 1712 comprises a plurality of electrical traces (not shown) connecting cable connectors 1714 to an array of piezoelectric ultrasound transducer elements (not shown) forming ultrasound transducer 1710. In an embodiment, flex circuit 1712 is folded and wrapped around a backing 1711, and may be secured thereto using a bonding agent such as silicon. In an embodiment, a block 1713 is affixed to the backing 1711 opposite the array of piezoelectric ultrasound transducer elements. In an embodiment, the ultrasound transducer 1710 comprises at least 128 transducer element, although it may be desirable to have a greater number of transducer elements, as additional elements may reduce distortion, and/or increase resolution, accuracy and/or depth of imaging of the device 100. The cable connectors 1714 operatively connect the electrical traces, and thus, the ultrasound transducer 1710, to the electrical path 108. In an embodiment, the electrical path 108 includes a coaxial wire for each ultrasound transducer element in the ultrasound transducer array 1710.

The ultrasound transducer 1710 fits within housing 1716 so that the transducer elements are in close proximity to, or in contact with an acoustic lens 1605. The acoustic lens 1605 may comprise a silicon rubber, such as a room temperature vulcanization (RTV) silicon rubber. In an embodiment, the housing 1716 and the acoustic lens 1605 are formed as a single unit, from the same RTV silicon rubber material. In an embodiment, the ultrasound transducer 1710, portions of the flex circuit 1712, backing 1711 and block 1713 are secured within the housing 1716 including an acoustic lens 1605 using a suitable adhesive such as silicon to form a transducer assembly 1715. The block 1713 can be used to affix or secure the transducer assembly 1715 to other components.

To whiten, and reduce the optoacoustic effect of light generated by the light subsystem 129 on an RTV silicon rubber acoustic lens 1605 and/or the transducer assembly 1715, in an embodiment, the RTV silicon rubber forming the acoustic lens 1605 and/or the transducer assembly 1715 may be doped with $TiO_2$. In an embodiment, the RTV silicon rubber forming the acoustic lens 1605 and/or the transducer assembly 1715 may be doped with approximately 4% $TiO_2$. In an embodiment, the outer surface of the acoustic lens 1605 and/or the outer surface of the transducer assembly 1715 may additionally be, or alternatively be, coated with a thin layer of metal such as brass, aluminum, copper or gold. Gold, however, has been found to have a tendency to flake or crack off of RTV silicon rubber. In an embodiment, the RTV silicon may be first coated with perylene, then coated with nickel, then coated with gold, and finally, again, coated with perylene. In an embodiment, the RTV silicon may be first coated with nickel, then coated with perylene, then coated with gold, and finally, again, coated with perylene. In an embodiment, the outermost coating of perylene may be omitted. The multiple layering provides a durable gold coating without any substantial adverse effect to the acoustic properties of the acoustic lens 1605, and without any substantial adverse effect to the transducer assembly 1715 to detect ultrasound. In practice, it has been found that the perylene coatings adjacent to the nickel and the gold layers, may curl at the edges rather than adhering well to the metals or rubber upon which it is deposited. Thus, as discussed in more detail below, in an embodiment, the portions of the acoustic lens 1603 and/or transducer assembly 1715 having an edge capable of being mechanically secured against other components to prevent curling or peeling. In an embodiment, substantially the entire outer surface of the transducer assembly 1715, including the acoustic lens 1605, are coated with continuous layers of nickel, then perylene, then gold and then perylene again.

In an embodiment, a reflective material surrounds the transducer assembly 1715 from the rear edge of the housing 1716 to the end of the flex circuit 1712 to reflect any light from the light path 132 that may be incident upon its surfaces. In an embodiment, an electromagnetic shield for RF energy surrounds the transducer assembly 1715 from the rear edge of the housing 1716 to the end of the flex circuit 1712. In an embodiment, the lights 130, 131, may draw substantial energy (e.g., more than 1,000 volts for a few nanoseconds) creating substantial electromagnetic RF energy in the area of the probe 102. In an embodiment, the transducer assembly 1715 from the rear edge of the housing 1716 to the end of the flex circuit 1712 is surrounded by a foil, which may act as a reflective material and an RF energy shield. In an embodiment, the foil is selected from the group: copper, gold, silver. In an embodiment, the foil is tied into the device's 100 electrical ground.

Spacers 1720 space and position the light bar guide 1722 with respect to the transducer assembly 1715. Spacers are preferably made from materials that reduce its optoacoustic response to light generated by the light subsystem 129. In an embodiment, the spacers 1720 are made from a material similar to the light contacting portions of the shells 1702, 1704. In an embodiment, the light bar guide 1722 encases optical fibers that are part of the light path 132. In an embodiment, the optical fibers making up the light path 132 may be randomly (or pseudo-randomly) distributed throughout the light bar guide 1722, thus making specific locations on the light receiving end of the fiber optic bundle at least pseudo-random with respect to corresponding specific locations on the light emitting end of the optical fibers retained by the light bar guide 1722. As used herein the term randomly (or pseudo-randomly) distributed optical fibers making up the light path 132 means that the mapping of fibers from the proximal end to the distal end is done such that a localized interference in the light path 132 (e.g., burnout of a group of adjacent optical fibers) or a localized phenomenon (e.g., non-uniform light at the entry point to the optical path 132) will have an effect on the overall power transmitted, but will not have an operationally significant effect on any specific part of the distal end of the light path 132. Thus, two optical fibers adjacent at the proximal end are unlikely to be adjacent at the distal end of the optical path 132. Where optical fiber bundles are fused at the proximal and distal ends, the randomization must be done before at least one end is fused. As used herein the term randomly (or pseudo-randomly) distributed optical fibers does not mean that two different optical paths 132—i.e., for different devices 100—must differ from each other. In other words, a single "random" mapping may be reproduced in the light path of different devices 100 while still meeting the criteria of being a randomized. Because light generally behaves in a Gaussian manner, the entry point to the light path 132 is typically less than perfectly uniform. Randomization, as discussed above, may accommodate for the non-uniform entry of light into the light path 132. Randomization may also provide homogenization of light fluence over area illuminated, as it may aid in more evenly distributing the light fluence.

In an embodiment, the optical fibers encased by a light bar guide 1722 all end on substantially the same geometric surface, e.g., a curved or flat plane. In an embodiment, the fibers at the distal end, within a given light bar, may be grouped and subgrouped in a manner that may help hold the fibers in position during manufacturing. Such grouping (such as in groups for the two light bars) and subgroupings (e.g., having subgroups per lightbar) may further the even distributing over the geometric surface. Any number of subgroups may be used. In an embodiment, the number of subgroups is selected to be practical for fabrication and manufacturing. In an embodiment, the number of subgroups is selected to facilitate the manufacturing process. In an embodiment, the number of subgroups may be between 5 and 20, and may be 15. In an embodiment, the fiber groups are formed by placing fiber subgroups between physical channels that are molded or machined into light bar guide 1722, or its internal and/or external surfaces.

In one embodiment, after the fibers have been attached to the light bar guide 1722, the fiber ends may be lapped and polished to provide for a more uniform angle of light emission. In an embodiment, the light bar guide 1722, as installed in the assembled probe 102, directs the light emitting there-from at an angle slightly less than normal to the distal face of the probe 102, and specifically, at small angle inwards, towards the plane normal to and intersecting the center of the acoustic transducer array 1710. In an embodiment, the distal end(s) of the optical path 132 should match—or closely approximate the shape of the acoustic transducer array 132.

The term bar, as used in "light bar guide" herein is not intended to import a specific shape. For example, the light bar guide 1722 may guide the distal ends of optical fibers into substantially any shape such as, without limitation, a whole or part of a circle, oval, triangle, square, rectangle or any irregular shape.

In an embodiment, one or more light bar guides 1722 and optical windows 1603 are external to the shells 1702, 1704 housing the acoustic transducer assembly 1715, and are adapted to be attached to the outer sides of one or more of the shells 1702, 1704.

In an embodiment, the angle of light emitting from the optical window 1603 may be adjustable. In an embodiment, the light emitting from the optical window 1603 may be adjustable across a range. At one end of the range, light may emit from the optical window 1603 in a direction normal to the distal face of the probe 102, and at the other end of the range light may emit from the optical window 1603 at an inward angle of up to 45 degrees or more towards the plane normal to and intersecting the center of the acoustic transducer array 1710. The range can be smaller or larger. In this respect, a lower bound of the range could be set to be not less than 45 and a higher bound of the range could be set to be not greater than 90 degrees.

In an embodiment wherein a probe has two optical windows 1603, the angle of light emitting from both optical windows 1603 can be adjustable, individually, or together. Where adjusting the angle of light emitting from both optical windows 1603 together, the light direction would, in each case increase or decrease the angle of inward projection, that is, projection towards the plane normal to and intersecting the center of the acoustic transducer array 1710. In this manner, a larger light fluence can be directed deeper into the volume 160 (by angling toward normal), or shallower (by angling more inwardly).

Controlling the direction of the light angle can be done by moving the light bar guide 1722, or it can be accomplished optically through the use of post-light path 132 optics. In this respect, the movable light bar guide and the optical window may be provided external to the shell housing the acoustic transducer assembly, and may be adapted to be attached to an outer side of the shell. A second movable light bar guide may also be operatively connected to the shell housing the acoustic transducer assembly of the probe, and may movably retain the distal end of a second set of optical fibers. The first movable light bar guide and the second movable light bar guide may be capable of varying the angle of light transmission of a first set of optical fibers and varying the angle of light transmission of the second set of optical fibers independently of one another. Optical solutions may include the use of one or more lenses and/or prisms to re-direct the light that has been transmitted through the light path 132, or by using an optical element having a variable index of refraction, such as, for example, an optical element having an index of refraction controlled in response to electric fields. Re-directed light can be directed to illuminate a desired area, such as an area directly beneath the transducer elements 1710. Controlling the direction of light transmitted by the probe 102 is useful to maintain safe and optimize the direction of the light with respect to the skin and the transducers.

Control line 109 may be used to send commands redirecting light and/or to report the actual direction of light at the time a light pulse is emitted from the light path 132. The angle of the light emitting from the optical window 1603 may be important data to consider when interpreting acoustic information resulting from the light pulse. In embodiment that include a second movable light bar guide and second set of fibers, such light bar guide may be capable of varying the angle of light transmission of the second set of optical fibers in response to at least a second command.

In an embodiment, the device 100 can adjust the angle of incident laser light emitting from the probe 102. Adjustment of the angle of incident laser light emitting from the probe 102 may be carried out under the control of commands which may be sent via control line 109, or may be manually carried out, e.g., by an adjustment mechanism located on the probe. In an embodiment, a standoff may be used, e.g., to help direct incident laser light to the desired depth, or closer to the surface than can be achieved without a standoff. In an embodiment, the standoff is relatively transparent to both acoustic and light, and preferably to acoustics in the ultrasound range and light one or more of the wavelengths utilized by the light source 129. While the use of standoffs is known in ultrasound applications to aid in imaging of objects close to the surface of the volume 160 because ultrasound resolution lacks the capability to detect objects at a nominal distance from its transducers, the use of a standoff in the present application is for a different purpose, namely, to allow the light sources to be aimed directly under the transducer elements 1710. In an embodiment, the standoff is separate from the probe 102, and placed between the volume 160, and the distal end of the probe 102 comprising the acoustic lens 1605 and one or more optical windows 1603. In an embodiment, the standoff may be integral to the probe, and may be move into place and withdrawn as desired.

Optical windows 1603 may also be part of the probe 102 assembly. In an embodiment, the optical windows 1603 is spaced from the end of the light bar guide 1722, and thus, from the ends of the optical fibers making up the light path 132. The term optical window, as used here, is not limited to mechanically or optically flat optical matter, or solely to transparent optical matter. Instead, the term is used to refer to an optical element that may or may not effect light passing there-through, but will permit at least a substantial portion of the light incident on the side of the window proximal to the light path 132 to exit the probe assembly 102 in a manner that is dependent on the properties of the optical element. In an embodiment, the optical window 1603 may be transparent, which permits transmission of light, and specifically light emitted from the end of the light path 132, to volume 160 when the distal end of the probe 102 is in contact with or close proximity to that volume 160. In an embodiment, the optical window 1603 may be translucent, permitting diffusion and transmission of light, and specifically light emitted from the end of the light path 132, to volume 160 when the distal end of the probe 102 is in contact with or close proximity to that volume 160. In an embodiment, the optical window 1603 may be a lens, permitting the shaping and directing of light, and specifically light emitted from the end of the light path 132, to volume 160 when the distal end of the probe 102 is in contact with or close proximity to that volume 160.

In the assembled probe 102, one edge of the optical window 1603 is in close proximity to, or in contact with, the transducer assembly 1715. The proximity of the optical window 1603 to the transducer assembly 1715 allows light emitted from the optical window 1603 to be emitted from a location close to the acoustic lens 1605, and thus close to the plane of the transducer array 1710.

In use, a coupling agent (e.g., gel) may be used to improve the acoustic contact between the distal end of probe 102 and the volume 160. If the coupling agent makes contact with the distal end of the optical fibers forming the light path 132, extraneous acoustic signal may be generated in response to light transmission over the light path 132. In an embodiment, the distal end of the probe 102, including optical window 1603, mitigates the potential acoustic effect of a coupling agent in response to light emitting from the light path 132 by creating a gap between the coupling agent and the distal end of the optical fibers.

Figure 18:
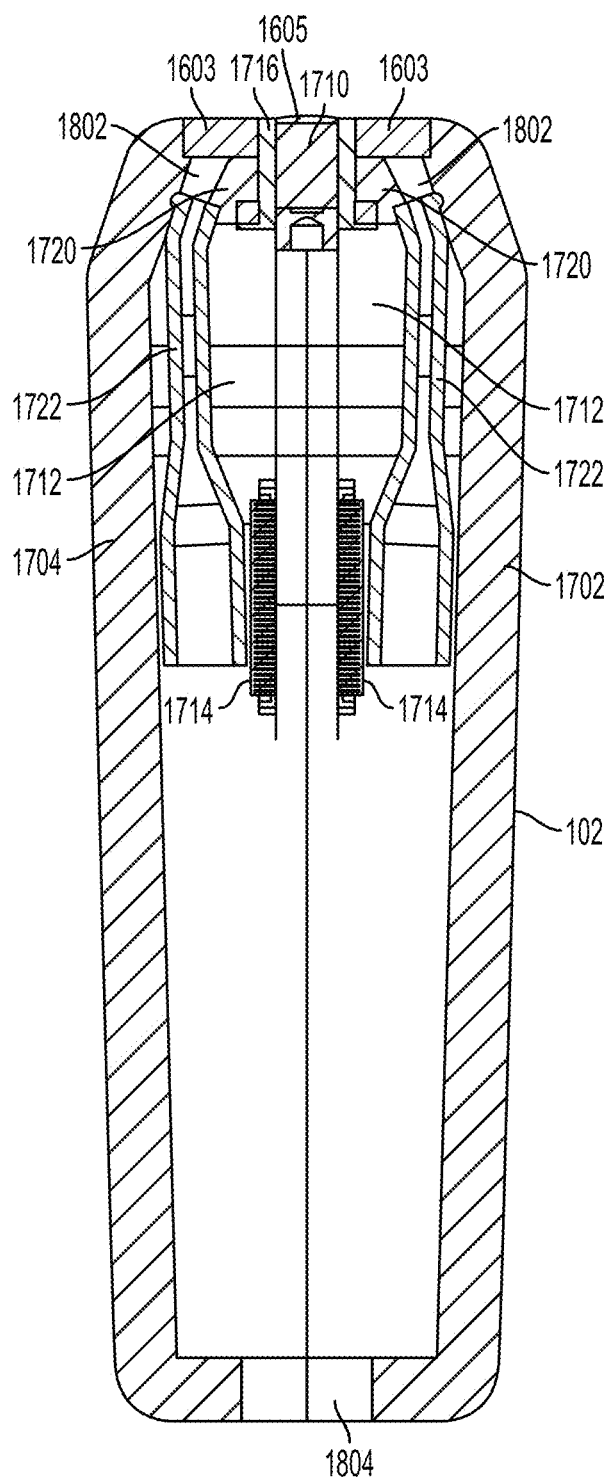
FIG. 18 shows a cutaway view taken along the centerline of the wider side of the probe shown in FIG. 16.

FIG. 18 shows a cutaway view taken along the centerline of the wider face of one embodiment of an assembled probe 102 such as the probe shown in FIG. 16. Shells 1702, 1704 support optical windows 1603 and transducer assembly 1715 at the distal end of the probe 102. Spacers 1720 supported by transducer assembly 1715 and shells 1702, 1704 aid in the positioning of optical widows 1603 and light bar guides 1722, and in maintaining gap 1802 between light bar guides 1722 and the optical windows 1603.

The distal ends of the optical fibers making up the light path 132 may be positioned such that they do not create a physical sound conduction path to the volume 160 or to the acoustic transducers 1710. In an embodiment, the gap 1802 serves the purpose of preventing high frequency sound conduction path between the distal ends of the optical fibers making up the light path 132 and the volume 160 or the acoustic transducers 1710. Specially selected materials, as discussed below, can be used to ensure that the light bar guide 1722 reduces and/or minimizes the physical sound conduction path between the distal end of the light path 132 and the volume 160 or the acoustic transducers 1710.

Flex circuit 1712, with piezoelectric transducer elements (not shown) thereon, wraps around backing 1711, and electrically connects the piezoelectric transducer elements with the cable connectors 1714 at each end of the flex circuit.

Opening 1804 in the shells 1702, 1704 provides an opening for optical path 132 (FIG. 1), electrical path 108 (FIG. 1) and optional power and control lines 109 (FIG. 1) to enter the inside of the probe 102. In an embodiment, a rubber grommet (not shown) may be used to provide stability and strain relief to the paths or lines passing into the probe 102 through opening 1804.

Figure 34:
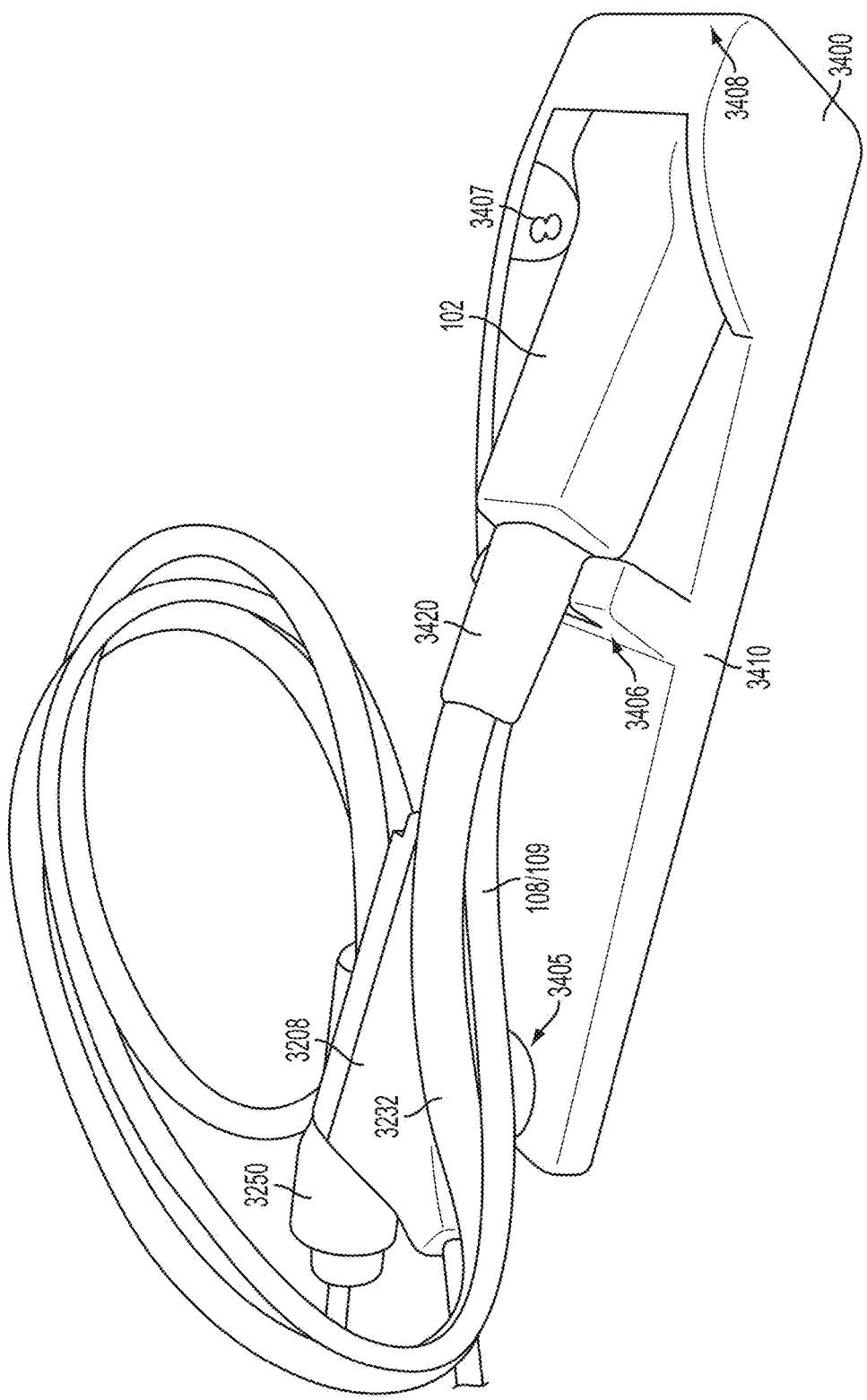
FIG. 34 shows a front view of a probe including a light path and light path connector, and a combined electrical path and control lines with a multi-pin connector therefor, resting in an embodiment of a probe holder.
Figure 35:
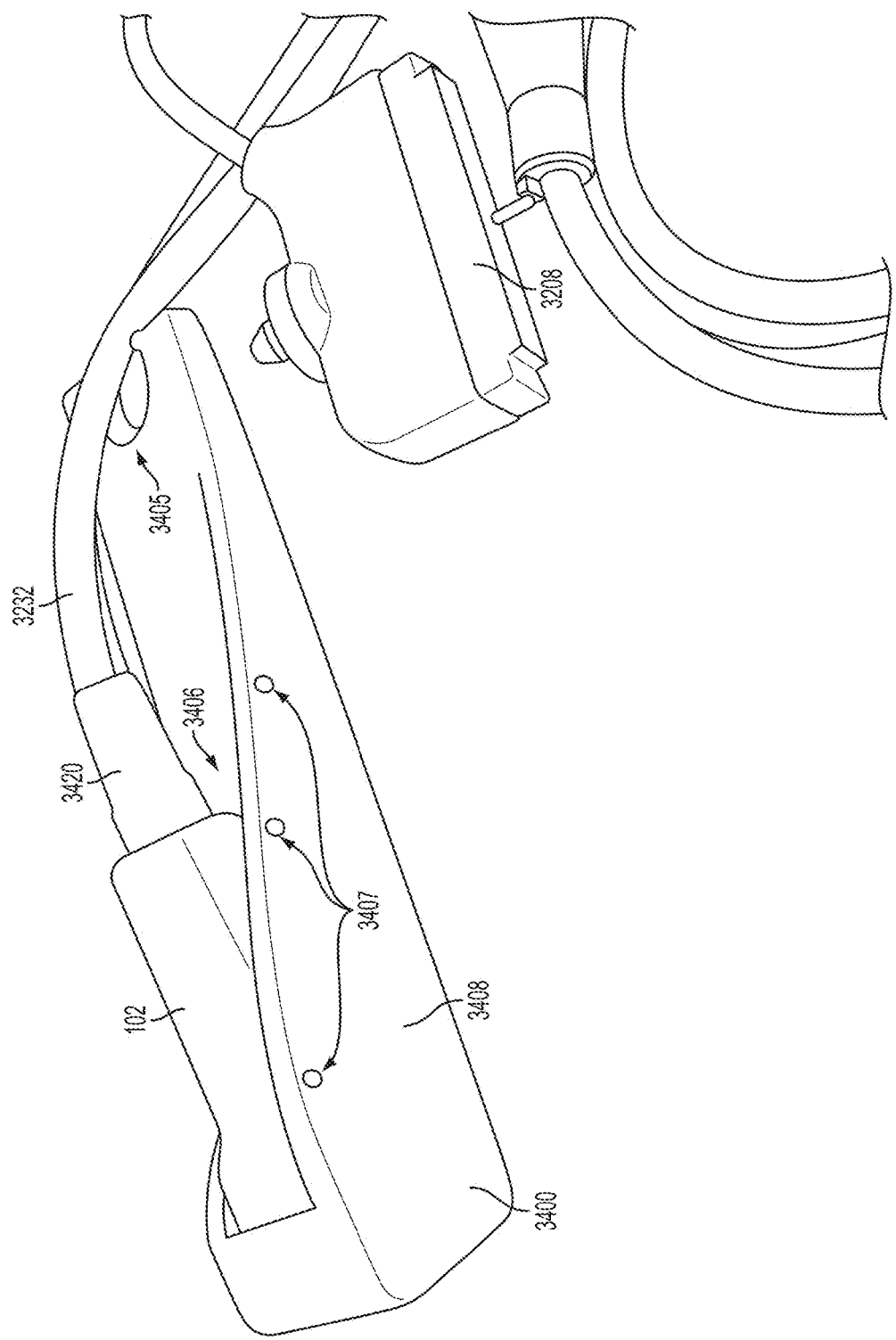
FIG. 35 shows a reverse view of a probe including a light path and light path connector, and a combined electrical path and control lines with a multi-pin connector therefor, resting in an embodiment of a probe holder.

Referring briefly to FIGS. 34 and 35, a probe holder 3400 is shown. The novel probe holder 3400 differs from a more typical probe face-up design that is used for an ultrasound probe. In an embodiment, the probe holder comprises a wire support 3405 and a probe support 3406, a rear wall 3408 with screw holes 3407 for securing the probe holder to a cart or other component of an optoacoustic system. The probe-end enclosing portion of the probe holder 3400 operates to encircle the active (distal) end of the probe 102. In an embodiment, the probe-end enclosing portion of the probe holder 3400 is made of materials that are substantially opaque to the light emanating from the light subsystem 129, thus reducing the risk of laser light leakage when the probe is in the probe holder. Moreover, in an embodiment, the probe-end enclosing portion of the probe holder 3400 is designed to provide a snug fit with the outer walls of the probe housing, again reducing the risk of laser light leakage when the probe is in the probe holder.

As is apparent from the figures, probe support 3406 both supports the probe in a position that it can be easily removed manually—by spacing it from the probe holder bottom 3410—but also is positioned behind the housing in such a manner as to inhibit the probe from sliding backwards and out of the probe holder 3400. In an embodiment, probe support 3406 may be used to support the probe 102 by its strain relief collar 3420. The wire guide 3405 is spaced from the probe support 3406 to reduce the pressure on the probe's 102 strain relief collar 3420 and soften the angle of curvature of the light path 132 and the integrated electrical path 108/109. In an embodiment, the probe holder will hold the probe 102 at an angle that is greater than parallel with the floor. In an embodiment, when seated in the probe holder 3400, the probe 102 will be maintained at an angle between 10 and 45 degrees with respect to horizontal.

On the interior distal end of the probe-end enclosing portion of the probe holder 3400, the distal end of the probe 102 may be supported from the probe's housing 1702/1704. In an embodiment, the design permits the probe to be securely positioned in a manner that the distal end of the probe's housing 1702/1704 (i.e., adjacent to the optical window 1603) may be in contact with the interior distal end of the probe-end enclosing portion of the probe holder 3400, but the optical windows 1603, acoustic lens 1605, and any other delicate or operational components at the active end of the probe 102 are either not in contact with the probe holder 3400, or in minimal contact therewith. In an embodiment, the interior distal end of the probe-end enclosing portion of the probe holder 3400 comprises a recess to permit secure seating of the probe 102 therein without contact between it and delicate probe components. Screw holes 3407 are provided to permit secure attachment of the probe holder 3400 to an appropriate location. In an embodiment, the probe holder 3400 can be securely fastened to a cart 3200. In an embodiment, a probe holder can be designed to be integral to a cart 3200, and need not be external thereto.

In an embodiment, a probe holder includes a sensor (e.g., a pressure sensor) to detect the presence of the properly-seated probe. Where such a sensor is employed, the output of the sensor can be used, for example, by the optoacoustic processing and overlay system 140 to override laser firing. In such an embodiment, this override can be alternative to, or in addition to forming the probe-end enclosing portion of the probe holder from materials that are substantially opaque to the light emitted from the optical window(s) of the probe. Alternatively, in an embodiment, the probe-end enclosing portion of the probe holder may maintain the active end of a properly inserted probe a short distance from an energy or power meter capable of measuring or inferring the total power or energy of the light emitting from the probe for calibration, maintenance or other purposes. In such an embodiment, where the probe holder also includes a sensor, the output of the sensor can be used by system software, such as for example, by the optoacoustic processing and overlay system 140 to engage laser firing for diagnostic, calibration, maintenance or other purposes.

Figure 19A:
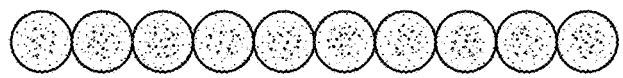
FIG. 19A is a side view not-to scale diagrammatic two dimensional representation of light exiting an optical fiber.
Figure 19B:
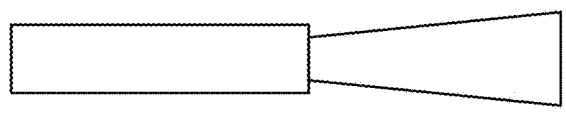
FIG. 19B shows an end view of a light pattern that may result on a surface from placement of optical fibers directly on to that surface.

Turning to FIG. 19A, a typical pattern of light striking a surface in close proximity to the ends of ten optical fibers is shown. Today, typical, reasonably flexible optical fibers have a diameter in the range of about 50 to 200 microns. Light exiting an optical fiber tends to expand slowly, see, for example, an illustrative example of light expanding after leaving the end of an optical fiber in FIG. 19B. The rate of expansion of the light beam leaving an optical fiber is a function of the diameter of the optical fiber and the refraction index of the optical fiber material, and may also be a function of the refraction index of the material to which the fiber is connected. When a group of optical fibers are placed in close proximity to a surface to be illuminated, a light pattern like that seen in FIG. 19A results.

In an embodiment, optical fibers having smaller diameters are employed to broaden the illuminated area and minimize weight and increase flexibility of the light path 132. Light diverges as it exits a fiber optic, and its divergence as it exits is inversely related to the diameter of the fiber—in other words, light diverges faster out of smaller diameter fiber optics. Thus, for example, optical fibers in the range of under 50 microns, and potentially less than 30 microns may be desirable to broaden the illuminated area, thus reducing, or potentially eliminating the need for a beam expander. In an embodiment, the distal end of one or more groups of the optical fibers comprising the light path 132 may be fused to avoid the characteristic pattern of light shown in FIG. 19A.

In an embodiment, an optoacoustic probe should produce a relatively uniform light distribution incident upon the surface of the illuminated volume. It may also be desirable for an optoacoustic probe to produce a relatively large area of light distribution. Providing a relatively large and uniform light distribution permits an optoacoustic probe to deliver a maximum amount of energy without exceeding a specific light fluence on any given area of the illuminated surface, which can maximize patient safety and/or improve the signal-to-noise ratio. For these reasons, it is not desirable to locate the optical fiber ends in too close proximity with the surface of the illuminated volume, and thus, obtain a small or uneven light distribution such as the one seen in FIG. 19A.

In an embodiment, the optical fibers may be moved away from the surface of a volume to be illuminated. Moving the end of the optical fibers away from the surface of the volume to be illuminated will cause the beams emitted from each optical fiber to expand, and produce a more uniform area of light distribution. One potential issue associated with moving the optical fibers away from the surface of the volume to be illuminated, is the optoacoustic effects caused by stray portions of the expanding beam. Another potential issue is the effect of enlarging the distance (between the end of the optical fibers and the surface to be illuminated) on the shape or size of a probe. Further, increasing the number of optical fibers (and thus enlarging the area of the fiber bundle emitting light) will increase the cost, weight and flexibility of the optical path 132 (FIG. 1), and may also affect the size of the probe.

Because the probe 102 is designed to be handheld, it is desirable to keep the probe head (the wider, distal portion of the probe 102) short so that the probe stem (the narrower, proximal portion of the probe 102) is relatively close to the surface of volume 160. Additionally, because the probe 102 is designed to be handheld, its total thickness is also a consideration for comfort, convenience and operational effectiveness. Accordingly, locating the distal ends of the fibers forming light path 132 at a sufficient distance from the optical window 1603 to permit expansion to fill the optical windows 1603 with uniform light fluence is not preferred. Similarly, using a very large number of fibers to enlarge the area of the fiber bundle held by the light bar guide 1722 at the distal end of the light path 132 and thereby attempting to permit expansion to fill the optical windows 1603 with uniform light fluence is also not preferred as it would, among other things cause undue weight, inflexibility, size and cost. Moreover, reducing the size of the optical window 1603 would reduce the total potential safe energy output of the device, and thus, is not preferred.

Figure 20A:
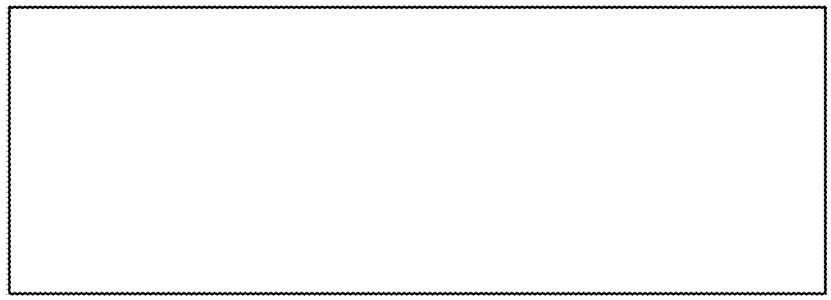
FIG. 20A shows an end view of a desirable light pattern for use in connection with the optoacoustic techniques discussed herein.
Figure 20B:
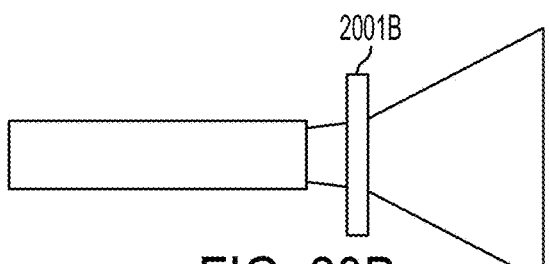
FIG. 20B shows a side view diagrammatic representation of an effect of a ground glass beam expander on the light emitting from a fiber shown in FIG. 19A.
Figure 20C:
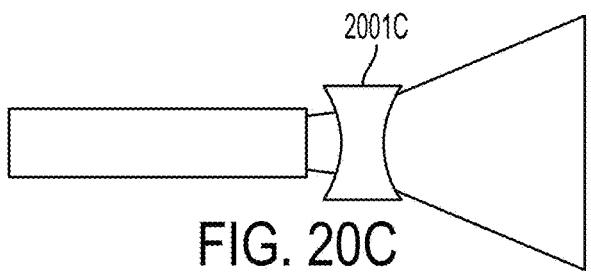
FIG. 20C shows a side view diagrammatic representation of an effect of a concave lens beam expander on the light emitting from a fiber shown in FIG. 19A.

Turning to FIGS. 20B and 20C, in an embodiment, a beam expander 2001b, 2001c may be used to expand the beam of light, causing it to become more uniform over a shorter distance. FIG. 20b shows the use of a ground or frosted glass beam expander 2001b, while FIG. 20C shows the use of a lens beam expander 2001c. In an embodiment, where the light bar guide 1722 is generally rectangular, a lens beam expander 2001c may be a cylindrical convex lens or a cylindrical concave lens. In an embodiment, a convex lens (not shown) may be used as a beam expander. It will be apparent to one of skill in the art that other lenses, lens systems or other optical systems or combinations thereof, can be used to spread and more evenly distribute the light.

Referring back to FIG. 18, in an embodiment, the light bar guides 1722 are angled inward toward the ultrasonic imaging plane on the end retaining the distal ends of the fibers. The inward angling of the distal end of the light bar guide 1722 permits the light emitting there-from to better fill, and thus, evenly illuminate the optical window 1603. Gap 1802, which may include a beam expander, may provide space for the light transmitted across the light path 132 to expand to fill the optical window 1603. The inward angling tends to cause the direction of the light incident on the surface of the volume 160 to strike the surface at an angle less than normal, and thus, potentially, to better propagate into the volume beneath the acoustic lens 1605 covering the ultrasound transducers 1710.

Turning back to FIG. 1, because the probe 102 is intended for handheld use, the weight and flexibility of the light path 132, the electrical path 108 and the optional power and control lines 109 is of consideration. In an embodiment, to make the light path 132 lighter and more flexible, the light path 132 is constructed from as few fibers as possible. A limiting factor to how few a number of fibers that can be used, is the amount of light carried across the optical path 132. The transmission of too much light over a fiber will damage the fiber. The light path 132 must carry the total amount of light that will be fluent on the surface of the volume 160, plus any light lost (e.g., absorbed or scattered) between the light source 129 and the surface of the volume 160 illuminated. Since the maximum area of illumination is known not to exceed the size of the optical window 1603, and because the area of illumination is subject to fluence limits per unit area, a total light energy carried by the light path 132 can be approximated by multiplying the fluence limit by the size of the optical windows 1603. The FDA provides numbers for the human safe level of fluence.

The volume 160 illuminated generally has its own optoacoustic response, which is especially apparent where light fluence is greatest, namely, at the surface of the volume 160. Increasing the area of illumination onto the surface of the volume 160 (e.g., by increasing the size of the optical window 1603 and beam) reduces the optoacoustic affect generated by the surface of the volume 160 itself, and thus may reduce the undesirable optoacoustic signal generated by the surface of the volume 160 itself as compared to a desired signal representing the inhomogenities 161, 162.

In addition to unwanted optoacoustic signal generated by the surface of the volume 160 itself, there may be other sources of unwanted optoacoustic signals that can be detected by the ultrasound transducer, such as the side walls surrounding the space between the optical windows 1605 and the respective light bar guides 1722, the acoustic lens 1605 and portions of the transducer housing 1716. The optical windows 1603 and any optional beam expander 2001B, 2001C may also be sources of unwanted optoacoustic signals that can be detected by the ultrasound transducer.

In an embodiment, the walls surrounding the space between the optical windows 1605 and the respective light bar guides 1722 may be made from a material that has high acoustic absorption properties and/or that is white and/or has high light scattering and/or reflecting properties. Using materials having these characteristics may reduce unwanted optoacoustic signals that can be detected by the ultrasound transducer. In an embodiment, the spacers 1722 can be made from a resin material such as Micro-Mark CR-600, a two part high performance casting resin that dries to a white color.

In an embodiment, a layer (not shown) of material that has high acoustic absorption properties and/or that is white and/or has high light scattering properties is placed between the transducer assembly 1715 and the light bar guides 1722 in the assembled probe 102. Alternatively, the layer may be applied directly to the transducer assembly 1715 or the light bar guide 1722 where the two parts contact in the assembled probe 102. This layer may reduce unwanted optoacoustic signals that can be detected by the ultrasound transducer. In an embodiment, the layer can be made from a resin material such as Micro-Mark CR-600, a two part high performance casting resin that dries to a white color. In an embodiment, the layer (not shown) may also comprise a reflective coating. In an embodiment a reflective coating of gold is applied to the layer to reflect light that might otherwise strike the layer.

In an embodiment, anti-reflective coatings may be used to reduce the optoacoustic signature of the optical window 1603 and/or the beam expander 2001B, 2001C. In an embodiment, magnesium fluoride may be used as an anti-reflective coating on the optical window 1603 and/or the beam expander 2001B, 2001C. Anti-reflective coatings may be used to reduce and/or minimize energy absorbed or reflected by the optical window 1603.

In an embodiment, the optoacoustic signature of the transducer assembly 1715 and/or acoustic lens 1605 can be reduced by whitening. In an embodiment, an acoustic lens 1605 comprising RTV silicon rubber may be whitened and have its optoacoustic signature reduced by being doped with about 4% $TiO_2$. It is believed that the $TiO_2$ doping increases the reflectivity of the acoustic lens and therefore the absorption, and also has a scattering effect that tends to diffuse the optoacoustic response of the RTV silicon rubber, bringing the response down to a lower frequency which can be more easily filtered. As discussed above, the outer surface of the transducer assembly 1715 and/or acoustic lens 1605 may be given a metal coating, such as gold, copper, aluminum or brass. In an embodiment, the metal coating, and in particular, gold, reduces the optoacoustic signature of the transducer assembly 1715 and/or acoustic lens 1605. It is believed that gold reduces the optoacoustic signature of the acoustic lens 1605 because of its high reflectivity in the light spectrum. In an embodiment, the acoustic lens may not be whitened and may retain its natural color, or be colored differently to minimize optical absorption at one or more particular wavelengths. In an embodiment, the acoustic lens may be made of materials other than RTV silicon rubber, such as, for example, buna-N rubber (i.e., nitrile rubber) or latex rubber.

As discussed above, the optical fibers at the end of the optical path 132 are retained by the light bar guide 1722 with all of the fiber ends retained by the light bar guide 1722 located on substantially the same plane. In an embodiment, the fiber ends may be fixed in place using mechanical force, an adhesive, or a combination of mechanical force and an adhesive. The fibers may be glued near their distal end to keep them in the desired location and pattern, and/or to reduce output of mechanical energy due to laser firing. In an embodiment, the spaces between optical fibers fixed within the light bar guide 1722 may be filled with a material having one or more of the following characteristics: sound absorbing, light scattering, white and/or light reflecting. In an embodiment, the optical fibers, which may be encased by a light bar guide 1722 at the distal end of the light path 132 are fused. Fusing fibers at the distal end of the light path 132 may permit the light emitting from the light path to be more uniform.

In an embodiment, a reflective coating is placed on areas of the shells 1702, 1704 where laser light emanating from the optical path 132 may strike it, including with the assembled probe, and in the areas designed to make skin contact, e.g., near the optical window 1603 and other portions of the distal end of the probe 102. In an embodiment, the shells 1702, 1704 are coated in gold where laser light emanating from the optical path 132 may, or is likely to strike it. In an embodiment, portions of the shell 1702, 1704 may be made from gold, although at present this may be cost prohibitive.

In an embodiment, a proximity detector system (not shown) is used to determine that the distal end of the probe 102 is on or very near the surface of a volume. Among the reasons such a proximity detector system is desirable is that it can be used to prevent pulsing of the light source 129 when the probe 102 is not in close proximity to a volume 160 under inspection, or to be inspected. This may be a safety issue as the light source 129 may produce light at levels that can be harmful, e.g., to the eyes. The proximity detector system may be implemented in the form of: a mechanical contact switch at the distal end of the probe; an optical switch looking at reflections of a non-harmful beam from the surface of the volume 160; a conductive switch that is closed by contact with the volume 160 and/or any acoustic gel or other materials between the volume 160 and the distal end of the probe; a conductive switch and a standoff comprising a conductive surface for contact with the distal end of the probe 102; a conductive switch and a thin, optically and acoustically transparent, conductive surface applied to the surface of the volume 160 of interest; an acoustic transducer switch that can detect close proximity of the volume 160 by transmitting and looking for the reflection of a sound within a specific time; an acoustic transducer switch that can detect close proximity of the volume 160 by using a narrow shape sound transmitter and receiver and using the reflection to detect proximity; using one or more of the transducers in the transducer array as a proximity detector by looking for a signal return; or by operating the device 100 in an ultrasound mode and looking for an ultrasound image.

In an embodiment, an optical detector (not shown) may be located in the probe 102 to take a measurement from which output energy can be estimated or deduced. In an embodiment, the optical detector will measure reflected energy such as energy reflected by the beam expander or optical window. In an embodiment, the optical detector will measure scattered energy such as energy scattered by the materials surrounding the gap 1802. The measurement of the optical detector can be transmitted to the system chassis 101 via control signal line 109, where it can be analyzed to deduce or estimate the light output of the probe 102. In an embodiment, control functionality in the system chassis 101 can control or regulate the light output of the light system 129, and thus the light output of the probe 102 based on a measurement made by the optical detector. In an embodiment, control functionality in the system chassis 101 can control or regulate the gain in the transducer receivers to compensate for variation of the light output of the probe 102 based on a measurement made by the optical detector. In an embodiment, the computing subsystem 128 can trigger differing activity from light system 129 over control signal line 106 based on a measurement made by the optical detector. In an embodiment, a measurement made by the optical detector can be used to control for variations in the electrical system or the power to the device 101. Similarly, in an embodiment, a measurement made by the optical detector can be used to control for variations in the optical path 132 or other optical elements of the device 100. In an embodiment, the optical detector can be used to cause the fluence of light output by the probe 102 to remain close to, but below, safe limits by accommodating for variations in electrical or optical characteristics that might otherwise cause the fluence of light output by the probe 102 to exceed or fall far below the safe limit.

In an embodiment, a safety feature would prevent disconnection of the probe 102 from the flexible cable when the system is in operation (e.g. when the laser is firing). To implement this safety feature, in an embodiment, the system 100 can use control line(s) 109 to operate a mechanical lock on the connector between the probe and the flexible connector. In an embodiment, a fail-secure mechanical lock would only permit disconnection of the probe 102 from the flexible cable when a specific control line(s) 109 was at voltage greater than a prespecified amount.

As discussed above, the device 100 comprises a probe 102 that, in an embodiment, is capable of transmitting both ultrasound and light to a volume 160, and is capable of receiving and processing an ultrasonic response to the transmitted ultrasound and light. The ultrasonic response to the transmitted ultrasound is typically a narrow bandwidth around the transmit frequency, with a percent bandwidth of about 70% and having no meaningful response below 2 Mhz, while the ultrasonic response to transmitted light is typically in a much broader range, such as the range of about 50 KHz to 20 MHz or more, typically centered in the range of 6 MHz to 8 MHz. In an embodiment, ultrasound is transmitted and received by the transducers 1710, while light is transmitted by a light 130, 131, across the optical path 132, and across the optical window 1603 or other aperture, the ultrasonic response thereto is received by separate transducers (not shown) tuned to receive the higher frequency range typically generated by the optoacoustic effect. The separate transducers are operated with high impedance amplifiers, e.g., having an impedance of more than 200 ohms, and preferably being about 500 ohms or more. Where the optoacoustic response is received by separate transducers, or by the same transducers using differing impedance loads from their use for ultrasound response, the signals representing the ultrasound response may be carried back to the system chassis 101 on separate wires of the electrical path 108 from the signals representing optoacoustic response.

In an embodiment, ultrasound is transmitted by the transducers 1710, and the ultrasonic response thereto is received by the transducers 1710, and light is transmitted by a light 130, 131, across the optical path 132, and out the optical window 1603, and the ultrasonic response thereto is also received by the transducers 1710. In such embodiment, the transducers 1710 are operated with high impedance amplifiers having an impedance of more than 1K ohm and less than about 100K ohms, and more preferably between 2K and 10K ohms input impedance. In an illustrative embodiment, the transducers 1710 may be operated with a 5K ohms input impedance amplifier.

In an embodiment where the probe 102 is equipped with ultrasound transducers 1710 and separate transducers (not shown) tuned to receive the higher (vs. broader) frequency range typically generated by the optoacoustic effect, the optoacoustic response for light that transmitted by a light 130, 131, across the optical path 132, and out the optical window 1603, may be received by both the transducers 1710 and by the separate transducers. Using both sets of transducers to receive ultrasound responsive to the optoacoustic effect may capture additional data that can be used to better analyze target 161, 162 within a volume 160.

Figure 21:
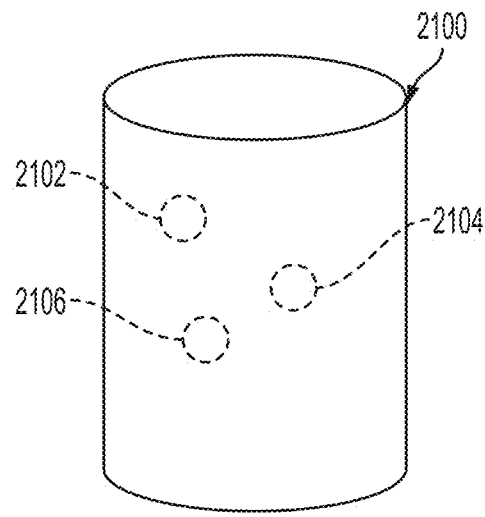
FIG. 21 is a representation of a phantom with a variety of targets therein that may be used in connection with calibration and testing of an optoacoustic device.
Figure 22:
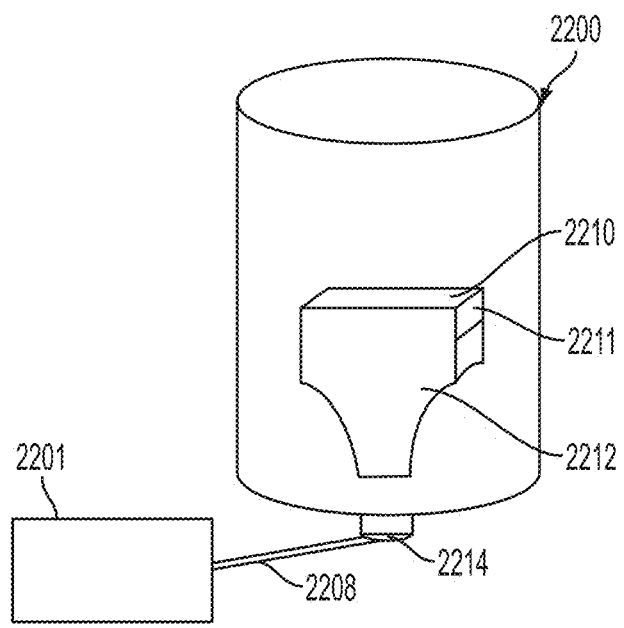
FIG. 22 is a representation of an active phantom that may be used in connection with calibration and testing of an optoacoustic device.
Figure 23:
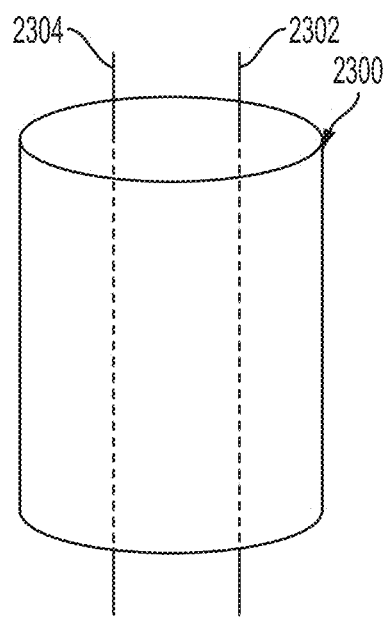
FIG. 23 is a representation of another phantom with a variety of targets therein that may be used in connection with calibration and testing of an optoacoustic device.

Turning to FIGS. 21-23, phantoms formed from plastisol are useful for registration and calibration. FIG. 21 shows a phantom 2100 for use in connection with an optoacoustic imaging device and/or a multimodal ultrasound and optoacoustic imaging device. The phantom 2100 comprises several targets 2102, 2104, 2106. In an embodiment, the targets 2102, 2104, 2106 are dissimilar, one being particularly responsive to a first stimuli but not a second, one being particularly responsive to a second stimuli but not the first, and one being particularly responsive to both the first and second stimuli. In an embodiment, the first stimuli may be an optoacoustic pulse at a first wavelength and the second stimuli may be an optoacoustic pulse at a second wavelength. In an embodiment, the first stimuli may be a traditional ultrasound signal and the second stimuli may be an optoacoustic pulse at one or more wavelengths. To make materials responsive to the various stimuli, doping is generally used. For optoacoustic response, material is doped with an absorber at the relevant frequency or frequencies. For ultrasound response, material is doped to be denser. Using phantom 2100 the response to the first or second stimuli can be demonstrated and or calibrated in response to the degree to which 2102, 2104, and/or 2106 targets are doped. This allows the determination of the doping percentages at which it is difficult to differentiate between target responses.

FIG. 23 shows a phantom 2300 for use in connection with an optoacoustic imaging device and/or a multimodal ultrasound and optoacoustic imaging device. The phantom 2300 comprises several targets 2302, 2302 embedded in plastisol. In an embodiment, the targets 2302, 2304 are generally linear and similar. In an embodiment, the targets 2302, 2304 are natural or synthetic horsehair. Using phantom 2300 multiple modalities such as optoacoustics and ultrasound can be co-registered. In an embodiment, a multimodality probe is coupled to the phantom, and an image showing the output of each modality is presented on the screen overlaid upon one another. Using a joystick or other input device, an operator can manually co-register the images, thus providing co-registration for the multimodality probe. In an embodiment, the images of each of the modalities are compared by a computer, and automatically co-registered.

FIG. 22 shows an active phantom 2200 for use in connection with an optoacoustic imaging device and/or a multimodal ultrasound and optoacoustic imaging device. The phantom 2200 comprises an active target 2212 embedded in plastisol and target control 2201. In an embodiment, active target 2212 comprises a linear array of transducers 2210 on a backing 2211; the transducers 2210 are operatively connected to target control 2201 through the body of the active target 2212, connector 2214 and by electrical path 2208. Target control 2201 can create signals that drive the transducers 2210. In an embodiment, target control 801 selectively creates signals to output a known ultrasound pattern and/or simulates an optoacoustic return signal. Using phantom 2200 permits testing and calibration of the optoacoustic return signal receiving and processing portions of an optoacoustic device 100 without concern for the integrity of the light output system.

Figure 24A:
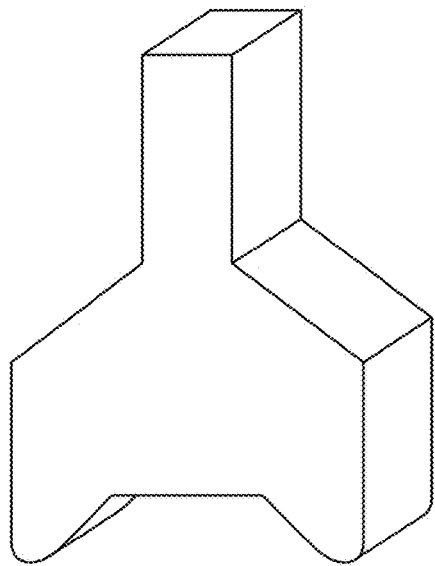
FIGS. 24A-24C show schematic orthogonal views of alternative embodiments of a probe that may be used in connection with the methods and other devices disclosed herein.
Figure 24B:
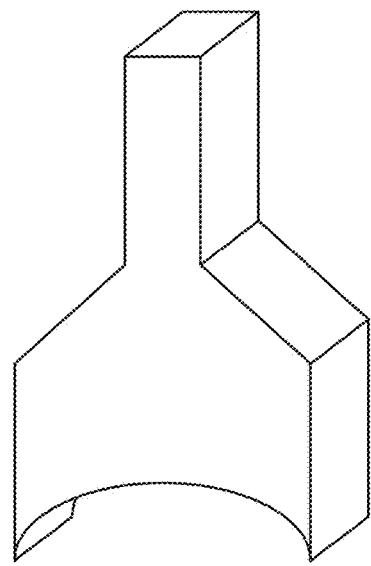
Figure 24C:
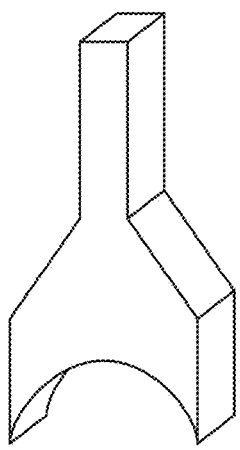

As discussed above and shown in the Figures discussed above, the probe 102 may have a linear array of transducers 1710 that are adapted to receive the optoacoustic return signal through an acoustic lens 1605. Other transducer geometries are also desirable. Turning to FIGS. 24A-C, in various embodiments, a linear transducer array may be oriented with sides that protrude at angles from the plane of the central portion of the array, or may be in the general shape of an ellipse or a semi-circle. Turning to FIGS. 25A-C, in various embodiments, a transducer array may be provided in a two dimensional shape as generally illustrated. Although the illustrations show only small numbers of transducers, e.g., 7 per line, in practice, many more transducers would be used. As discussed above, in an embodiment, 128 or more transducers per line, may be used. For example, in FIG. 25A, an illustrative array is shown comprising four generally linear arrays of transducers aligned on simple Cartesian coordinates in asterisk-type configuration ands sharing a common center transducer. In FIG. 25B, an illustrative array is shown comprising three generally linear arrays of transducers wherein the transducers are arranged similarly distant from one another on concentric rings in the various arrays, and also arranged in asterisk-type configuration and sharing a common center transducer. In FIG. 25C, an illustrative array is shown comprising three generally linear arrays of transducers arranged in a simple grid.

With respect to each of numerous geometries shown, to develop an image from the optoacoustic return signal requires (i) that the transducers are coupled to the volume 160 containing the target(s) of interest when used to detect an optoacoustic return signal, and (ii) that the detected optoacoustic return signal is processed using information relating the relative position of the transducers to each other in space. Transducers may be use in a flexible array that adapts to the shape of the volume 160 when coupled therewith, provided that the relative position of the transducers to each other in space is known, and used in processing the optoacoustic return signal.

In an embodiment, an optoacoustic probe can be used to detect the optoacoustic return signal by sampling the transducers for a period of time after the optoacoustic inducement, such as a laser, has been deployed. In an embodiment, at least some of the desired content of the optoacoustic return signal is in the frequency range of about 100 KHz to 12 MHz. Thus the optoacoustic return signal may be sampled at 30 MHz, which is a sufficient sampling rate for at least some of the desired content of the signal. In an embodiment, the sampling apparatus is capable of sampling up to 256 channels at 65 MHz. In an embodiment, an optoacoustic probe may have 128 or 256 transducers, and may be sampled at or around 30 MHz.

In an embodiment, an optoacoustic probe can detect the optoacoustic return signal by sweeping through multiple transducer elements or through multiple groups of transducer elements. For example turning to FIG. 25A, the 25 shown illustrated transducer elements are shown in four groups 2510, 2515, 2520, 2525 of seven, noting that each group shares a common center element. In an embodiment, after an optoacoustic pulse such as from a laser, a first cycle of the detection of the optoacoustic return signal can be conducted first through one group 2510, then a second group 2515, then a third group 2520, and then a fourth group 2525. Once that first cycle of the detection of the optoacoustic return signal is complete, a second cycle, a third cycle and so on may continue. The sampling apparatus discussed in an embodiment above capable of sampling up to 256 channels 65 MHz is also capable of sampling two separate arrays of 256 transducers at 30 MHz, or four arrays of 128 transducers at 30 MHz. Accordingly, in an embodiment as shown in FIGS. 25A-C, a sampling apparatus may be used to sweep through two or more groups of overlapping (e.g., FIGS. 25A-B) or unique (e.g., FIG. 25C) transducers and thus sample the optoacoustic return signal in response to a single optoacoustic event, such as the firing of a single laser pulse.

As will be apparent to one of skill in the art, sampling apparatus are capable of sampling at rates higher than the illustrative one discussed above. Using sampling apparatus that can sample more channels or at faster rates would permit a larger number of total samples to be generated in response to a single optoacoustic event. Accordingly, it is within the scope of this specification and the inventions disclosed herein, to use larger groups, and/or more groups, of transducers than are illustrated above, to be swept through in response to a single optoacoustic event.

Advantages exist in connection with each of the differing transducer geometries discussed above. The straight linear array is compact, cost efficient, easily handled, and is the most commonly used in standard ultrasound B-mode imaging. The curved or winged linear arrays may conform better to the irradiated volume, and thus, provide better coupling. The non-linear (multiple row, also known as 1.5 dimensional) arrays permit additional angles from which to resolve the optical return signal from a given voxel, which may improve resolution and/or add clarity and contrast to the image and/or may better support three-dimensional imaging applications. Flexible arrays may also provide better coupling with the volume. The non-linear arrays can allow transducer elements that are optimized for ultrasound to co-exist with transducer elements that are optimized for optoacoustics within the same probe. Different transducer elements are used to create either the US or OA images.

An optoacoustic return signal can be generally acquired within a window of less than about 100 microseconds. Using a generally accepted approximation for the speed of sound in tissue of around 1,500 m/s, a 100 microsecond acquisition window may correspond to a depth of up to about 15 centimeters. In an embodiment, an optoacoustic return signal can be acquired within a window of about 65 microseconds, and contain information from as deep as about 10 centimeters. In an embodiment, the frequency of light events is anticipated to be generally on the order of every 50 to 100 milliseconds (0.05 to 0.1 seconds). Accordingly, the data acquisition may occur less than 1% of the time, and closer to between 0.1% or 0.2% of the time, leaving more than 99% of the time where no data acquisition is occurring. Electrical noise may be created by powering the light subsystem 129 and/or other components of the system 100. Accordingly, in an embodiment, to prevent electrical noise from affecting the data acquisition, a synchronization is utilized to prevent powering unnecessary components during that period, leaving power only to the preamps, analog-to-digital converters and multiplexer. In an embodiment, the synchronization between power and data acquisition allows for the power system to be optimally electrically quiet during the acquisition time period. In an embodiment, this may be achieved by powering down noisy digital components during this period or allowing charged capacitors to power the acquisition hardware at this time. In an embodiment, this is triggered by the same trigger that starts the acquisition cycle and is controlled by the master processor to control the turning on/off of the peripheral components not involved with the acquisition cycle. In an embodiment, this takes from a few nanoseconds to a few microseconds. In an embodiment, the same synchronization signal can be used to synchronize one or more of the other switching power supplies within and/or associated with the OA system. By controlling one or more such switching power supply, electrical noise produced by the power supply (e.g., switching transients) can be caused to occur at the same time. In an embodiment, by using a synchronization signal, electrical noise produced by the power supplies in the OA system can be purposefully staggered, leaving temporal windows of electrical quiet during which data may be acquired.

In an embodiment, at least one switching power supply generating power for the light sources 130, 131 includes an external control for impeding operation of its switching operation—hereinafter a blanking signal—and the data acquisition is adapted to sample during a specific period after a pulse of light from a light source. For example, in an embodiment, sampling would begin 10 μS after the light pulse, and sampling would continue for approximately 65 μs at a sampling rate of 31.25 Mhz. In an embodiment, the sync detectors 3903, 3913 could be used to detect the light event. In another embodiment, sampling could begin 5 μs after a light pulse from the first light source, but 7 μs after a light pulse from the second light source, and could continue for approximately 65 μs at a sampling rate of 31.25 Mhz, for the first light source, or for approximately 63 μs at a sampling rate of 31.25 Mhz, for the second light source. Here too, the sync detectors 3903, 3913 could be used to detect the light event and distinguish the light sources.

In an embodiment, the optoacoustic processing and overlay system 140 can control the sequence of certain operations in the optoacoustic system, including initiating the light events from the light sources 130, 131, initiate the data sampling operation sampling the transducer data, and utilizing the blanking signal to impede the switching operation of a switching power supply during the period of data acquisition. In an embodiment, prior to initiating the acquisition of data, the optoacoustic processing and overlay system 140 causes the light event to occur, and initiates the blanking signal. Even at 20 frames per second, the period of data acquisition is just a small fraction of time, i.e., 20× about 65 µs or comfortably less than 0.2% of the total operation time of the switching power, a safety margin can be used, and the blanking signal can be issued before data sampling begins, e.g., without any delay after the sync detection, and may be maintained for up to 100 µs or more.

As discussed above, in an embodiment, the same transducers are used to receive acoustic-generated ultrasound and to receive the optoacoustic return signal. The geometry of acoustic-generated ultrasound transducers is not optimal for receiving the optoacoustic return signal. Accordingly, in an embodiment, separate transducers are used for the acoustic-generated ultrasound and the optoacoustic return signal. The acoustic-generated ultrasound transducers can have a narrower band because the transducer itself sends the signal that it needs to detect. The optoacoustic return signal transducer can have a wider band, such as, for example, 50 KHz to 20 MHz. This wider band is preferred, among other reasons, because gain falls faster with depth on the optoacoustic return signal. Thus, in an embodiment, a plurality of transducers is used to receive the acoustic-generated ultrasound and a separate plurality of transducers is used to receive the optoacoustic return signal. In an embodiment the plurality of transducers used to receive the acoustic-generated ultrasound and the separate plurality of transducers used to receive the optoacoustic return signal comprise approximately the same number of transducers. In an embodiment the plurality of transducers used to receive the acoustic-generated ultrasound and the separate plurality of transducers used to receive the optoacoustic return signal each comprise at least 128 transducers, and more preferably, would comprise at least 192 transducers. In an embodiment the plurality of transducers used to receive the acoustic-generated ultrasound and the separate plurality of transducers used to receive the optoacoustic return signal each comprise at least 256 transducers. In an embodiment, the transducers used to receive the optoacoustic return signal have a wider band frequency response than separate transducers used to receive the acoustic-generated ultrasound. In such an embodiment, the transducers used to receive the optoacoustic return signal have a frequency response from at least about 1 MHz to 5 MHz, and more preferably, from about 100 KHz to about 10 MHz, and even more preferably from about 50 KHz to about 20 Mhz. In such an embodiment, the transducers used to receive the optoacoustic return signal may use high impedance amplifiers, such as 1 KΩ or more, and more preferably, 5 KΩ or more. In such an embodiment, the transducers used to receive the acoustic-generate ultrasound would use amplifiers having an impedance of less than 1 KΩ, and more preferably about 200Ω. The use of separate transducers would eliminate the need for relay system 110, and the switching of the transducer outputs thereby between the optoacoustic processing and overlay system 140 and the ultrasound instrument 150.

As discussed above, in an embodiment, the same transducers are used to receive acoustic-generated ultrasound and to receive the optoacoustic return signal. Where the same transducers are used to receive acoustic-generated ultrasound and to receive the optoacoustic return signal, amplifiers should be used that have an impedance within the range of about 1-10 KΩ and more preferably amplifiers should be used that have an impedance of approximately 5 KΩ.

In an embodiment, the sampling of an optoacoustic return signal is performed in a variable manner, where the gain of the amplifiers associated with each of the sampled channels is adjusted over time, and is hereinafter referred to as time gain compensation or TGC. TGC ramps up gain on the acoustic input as the optoacoustic return signal becomes fainter, thus more accurately sampling the signal, and providing more normalized collected data and maintaining good signal-to-noise ratio as the signal become fainter. Optoacoustic return signal becomes fainter with time for several reasons, including that the later optoacoustic return signals have generally traveled further. Thus, generally optoacoustic return signal becomes fainter as the depth of a target increases. However, the magnitude (and thus needed gain) of optoacoustic return signals are also affected by the location and source of illumination. Generally, less light penetrates to deeper depths, and thus, the optoacoustic return signals are fainter because an optoacoustic event occurring at the surface of a volume generally induces a smaller response at a deeper depth. TGC is utilized to compensate for the later, fainter optoacoustic return signals.

The optoacoustic device 100 may comprise sensors (not shown) that can measure power and from that infer both total and peak power of the light subsystem 129, and performance and efficiency of the optical path 132. In an embodiment, sensors such as photo detectors can be placed within or in close proximity to the light subsystem 129 and within or in close proximity to the probe 102. In each case, the sensors would take a measurement during the illumination of a light 130, 131 which can be used to infer total and peak power. For this purpose, one or more sensors can be placed inside the probe 102 to measure reflection from the optical window. Similarly, one or more sensors can be placed within the light subsystem 129 to measure light reflected therein. Deviation over time in the measurements inferred between the two sensor locations may be indicative of anomalies in the light path 132.

Discussing now an embodiment of the system having sensors (not shown) such as photo detectors within or in close proximity to the probe 102. In an embodiment, one or more sensors may be placed within the probe, in the gap 1802 to measure reflection from the optical window. Alternatively, or additionally, in an embodiment, one or more sensors may be provided light directly from a component of the light path 132, such as from one or a small plurality of the optical fibers that make up the light path 132. Alternatively, or additionally, in an embodiment, one or more sensors may be provided light by another path provided within the probe. Thus, for example, one or more sensors could be located within the end of the probe opposite the optical windows 1603, and an auxiliary light path (not shown) can e.g., carry light directly from the light path 132 or reflected from the optical window or otherwise, to the one or more sensors. Alternatively, or additionally, in an embodiment, one or more sensors may be arranged to detect light originating in the light path 132 after it has been reflected from the surface of three-dimensional volume 160. Using information from sensors arranged to detect light reflected from the surface of three-dimensional volume 160, in combination with information concerning the light transmitted through the optical window 1603 towards the volume 160 (such as information from sensors measuring output from the light subsystem 129 or from the optical window 1603), can provide diagnostic information concerning the volume

160. Such diagnostic information may include the absorptiveness, or the darkness, of the volume 160.

In an embodiment, the foregoing sensors can be tuned to specific wavelengths through the use of an optical filter. Thus, for example, sensors within or in close proximity to the probe 102, sensors within or in close proximity to the light subsystem 129, sensors receiving light from an auxiliary light path and/or sensors arranged to detect light reflected from the surface of the volume 160, can be filtered to discriminate between the wavelengths of light produced by the light subsystem 129 and/or any extraneous light. Accordingly, sensors may be provided to detect (or potentially to reject) specific light frequencies, such as the light from one of the two light sources 130, 131.

In an embodiment, one or more sensors within or in close proximity to the probe 102 can be used as part of a triggering system and method for starting detection optoacoustic return signal data. In such a triggering system or method the detection of a specific threshold value of light by the one or more sensors can send a detection control signal to the computing subsystem 128. In an embodiment, the detection control signal is sent over the power and control signal lines 109 to the optoacoustic processing and overlay system 140. The detection control signal is used by the computing subsystem 128 to initiate (after any appropriate delay, if any) the process of obtaining the optoacoustic return signal data, for example, by "sampling" data from the ultrasound transducer elements. As discussed above, because the one or more sensors can be optically filtered to detect specific light frequencies, the detection control signal may be specific to one or more frequencies of light, and may initiate differing sampling rates, or delays, based upon the different frequency of light.

In an embodiment, one or more sensors within or in close proximity to the probe 102 can be used as part of a system and method for safely starting the optoacoustic system 100 and then bringing the laser to its safe power potential. Although laser light sources (e.g., 130, 131) generally have a controllable power output, many factors can affect the total power output by a light source regardless of its setting. Ambient temperature, for example, may affect the power output by a laser. Similarly, fluctuations in electrical power can also affect the power output by a laser. In addition, the light path 132 can negatively affect the light output of laser light sources (e.g., 130, 131). Fibers within the light path 132 can burn out, or lose transmissive properties as they age or are used. Moreover, fibers that are positioned in a bend can lose transmissive properties. Thus, the setting of a light source (e.g., 130, 131) to a particular output level is not necessarily determinative of the light that reaches the other end of the light path 132, and ultimately, the volume 160. Accordingly, in an embodiment, the light source (e.g., 130, 131) is set to a relatively low power. The relatively low power should be selected to be a power that, in the event everything is functioning at its peak output or transmissiveness, would not exceed a desired maximum fluence on the volume 160. Once the light source (e.g., 130, 131) is pulsed, a measurement from the one or more sensors is used to infer the fluence of light delivered to the volume 160. In the event that this inferred fluence is lower than the desired fluence level (or a desired range of fluence levels), the output from the light source can be increased, and the process repeated. Likewise, in the event that the inferred light fluence is higher than a desired maximum, the output from the light source can be decreased. Because the system 100 is capable of a significant number of laser events per second, the rate of increase to the light output, and thus, the potential increase in the fluence level between laser events, can be kept relatively small. In an embodiment, the amount of change in output from the light source may be larger when the inferred fluence is farther away from the desired fluence level (or a desired range of fluence levels), and smaller when the inferred fluence is closer to the desired fluence level.

In addition to providing a method for safely starting the optoacoustic system and bringing the laser to its safe power potential, the same process can be run as a closed loop control to ensure that the laser fluence is being monitored and controlled, and that to the extent it exceeds a predefined threshold such coming within some margin of a safety limit, its output power can be lowered. Similarly, operating the process as a closed loop control can also ensure that the laser output is being set to a maximum desirable setting even as the operating conditions of the system 100 (e.g., ambient temperature and electrical power) change, and regardless of the existing or changing condition of the light path 132. Keeping the laser at or close to its highest safe level permits the largest light fluence, and thus, strongest optical return signal. In an embodiment, one or more of the following: the target fluence level, the acceptable hysteresis around the target fluence level and a maximum fluence level, are user selectable, and when selected can be used by the processing running as a closed loop control to maintained the laser as specified. The closed loop control process can be used to normalize pulse-to-pulse power output.

In an embodiment, where the measurement taken at the one or more probe-proximate sensors falls below a predetermined threshold for a given laser output, as a failsafe, the lasers may be shut down. Such a level may reflect a failure or detachment of the light path 132, or other unsafe condition.

In an embodiment having one or more sensors within or in close proximity to the probe 102 and one or more sensors within or in close proximity to the light subsystem 129, the sensors can be utilized as part of a system for and method to detect faults in the light path 132 or to provide a safety control for faults in the light path. In an embodiment, the light output of the light subsystem 129 would be expected to be proportional to the light output of the light path 132 and the light fluence exiting the optical windows 1603. The use of one or more light subsystem-proximate sensors can permit detection of differences in the expected amount of the light incident on the several sensors. As discussed above, the light path 132 can negatively affect the light output by of laser light sources (e.g., 130, 131). For example, the light path 132 can be negatively affected by burn out, old or broken fibers within the bundle. Thus, setting a light source (e.g., 130, 131) to a particular output level is not necessarily determinative of the light that reaches the other end of the light path 132, and ultimately, the volume 160. By employing both one or more light subsystem-proximate sensors and one or more probe-proximate sensors, performance of the light path 132 can be detected and monitored.

In an embodiment, the one or more light subsystem-proximate sensors are used to measure the power of the light entering the light path 132 and one or more probe-proximate sensors are used to measure the power of the light that has been transmitted through the light path 132. The measurement taken at the one or more light subsystem-proximate sensors may be used to predict a measurement at the one or more probe-proximate sensors. In an embodiment, deviation from the predicted measurement at the one or more probe-proximate sensors can be used to identify potential problems with the light path 132. In an embodiment, the sensor readings are recorded with other data concerning the event.

In an embodiment, deviations are assessed to determine whether action needs to be taken, for example, whether the user needs to check the light path 132 connections, or whether the light path 132 is in need of maintenance (e.g., straightening, cleaning, lapping and polishing or other maintenance) or even replacement. In an embodiment, where the measurement taken at the one or more probe-proximate sensors deviates from its predicted measurement by more than a predetermined amount, as a failsafe, the lasers may be shut down. Such a deviation may represent a failure or detachment of the light path 132 or other fault or unsafe condition.

In an embodiment having one or more sensors within or in close proximity to the probe 102 and/or one or more sensors within or in close proximity to the light subsystem 129, the measurements from the sensors, along with the other settings of the machine (including the commanded light output) should be stored with the data other data associated with the light pulse, such as the optoacoustic return signal.

In an embodiment, a calibration phantom comprising one or more embedded photosensitive sensors is provided. As with the above-described sensors, the sensors in the phantom can be used to infer total and peak power, as well as light distribution. Deviation over time in the measurements inferred between the phantom sensors and the other sensors may similarly be indicative of anomalies. Moreover, changes over time between the readings of the various sensors within the phantom or within the probe may be indicative of issues with the evenness of light output of the probe. The use of such sensors rather than the system transducers avoids acoustic involvement, thus eliminating error introduced by the transducers themselves.

In an embodiment, a second calibration phantom may be provided with acoustic targets rather than sensors. The use of such a phantom eliminates any error that may be introduced by the sensors themselves. Calibration using both the acoustic target and sensor phantoms would provide a cross-check and mitigate the potential for calibration error. Time gain compensation must be properly calibrated.

Figure 40:
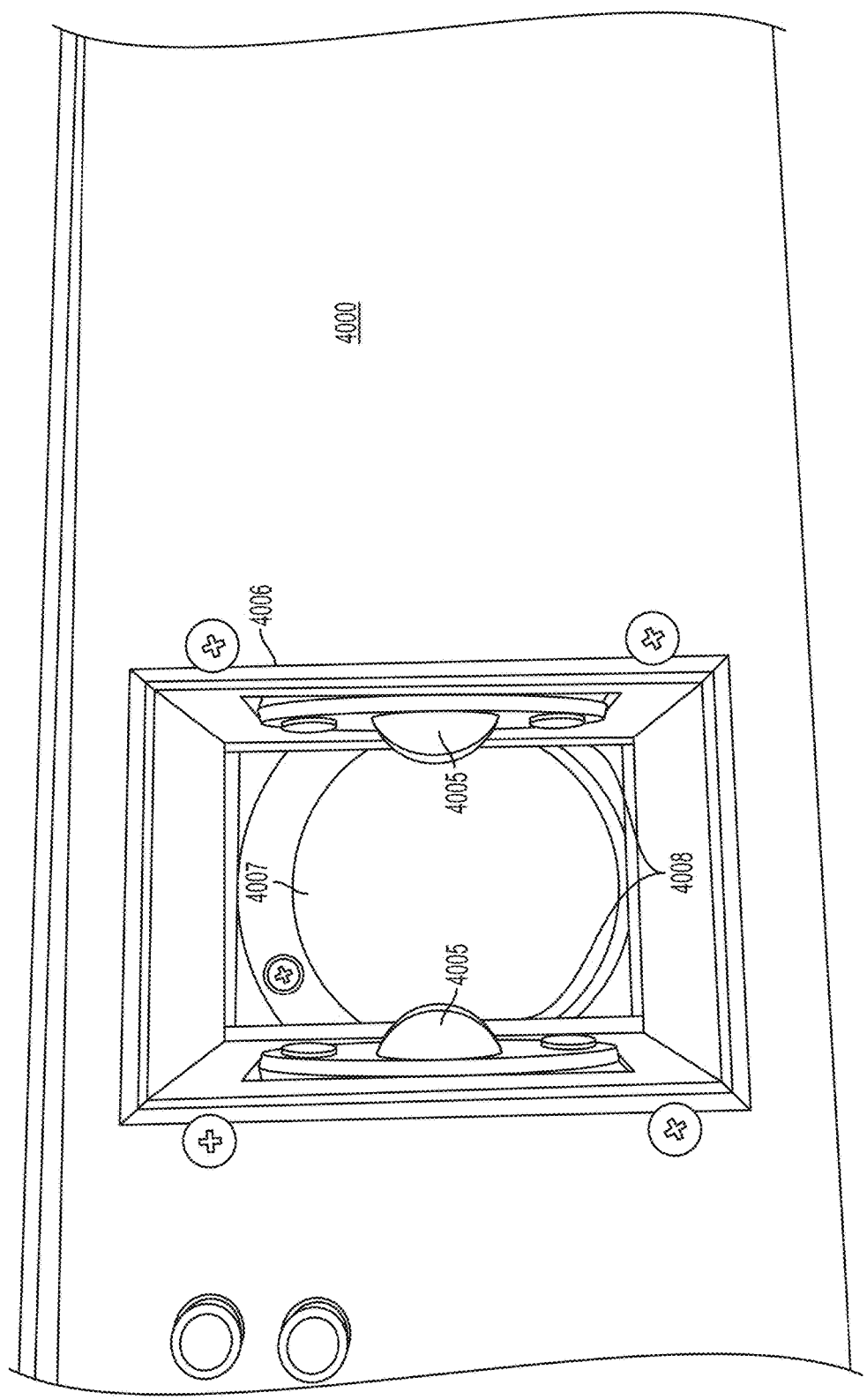
FIG. 40 shows an embodiment of a power meter for use in calibration of the optoacoustic system.

Turning briefly to FIG. 40, an embodiment of a calibration system receiving unit 4000 is shown. The calibration system receiving unit 4000 comprises an opening 4006 sufficient in height and width to receive a probe 102, sensors 4005 for sensing the presence of the probe 102 when it is inserted in the calibration system receiving unit, stops 4008 for preventing over insertion of the probe 102, and arresting its insertion at a fixed distance from a meter 4007. In an embodiment, meter 4007 is a sensor calibrated at each of the predominant wavelengths put out by the light subsystem 129. In an embodiment, meter 4007 is a sensor that can measure light energy and is calibrated for an ND:YAG laser and an Alexandrite laser. In an embodiment, the meter 4007 is a photo detector. In an embodiment, the meter 4007 is a thermal measurement device. In an embodiment, meter 4007 is large enough to measure the entire light output of the probe 102. In an embodiment (shown), the power meter is not large enough to measure the entire light output of the probe 102, but the total output is inferred based on the overlap of the area of the meter 4007 and the area of the optical window(s) 106. When the light subsystem outputs a pulse of light that the pulse emits from the distal (active) end of the probe, the sensor provides a measurement proportional to the light energy and/or power. In an embodiment, the voltage to the light subsystem and the Q-switch delay are constant, and thus, to adjust power output optical attenuator 3902, 3912 are employed.

In an embodiment, a calibration mode of the optoacoustic processing and overlay system 140 operates at least one of the light sources 130, 131 of the light subsystem 129 only if the probe sensors 4005 detect the presence of the probe 120 in the calibration system receiving unit 4000. After causing at least one of the light sources 130, 131 to cause a light event, the optoacoustic processing and overlay system 140 determines the power or energy measured by the meter 4007 and determines whether adjustment is appropriate. Where the power or energy measured at the probe 102 by the meter 4007 is either too high, or too low, adjustment may be made by adjusting (e.g., rotating) the optical attenuator 3902, 3912 associated with the light source 130, 131 requiring more or less output energy or power at the probe 102. In an embodiment, the output of sync detector 3903, 3904 may be used in calibration to determine which of the light sources 130, 131 caused a condition that requires adjustment, and permitting calibration function to then adjust the correct optical attenuator 3902, 3912.

In an embodiment the meter 4007 is calibrated to determine power at the first and second predominant wavelength and adapted to measure power at the first predominant wavelength in proximity to at least one optical window 106 after a sync signal reflecting a light event at the first light source is detected, and to measure power at the second predominant wavelength in proximity to at least one optical window 106 after a sync signal reflecting a light event at the second light source is detected; and the apparatus optoacoustic system to electrically attenuates appropriate optical attenuator, if necessary, based on the power measured by the power meter.

In an embodiment, a meter could be located proximal to the optical windows 106 or otherwise able to measure light output from the light path 132. In such an embodiment, the optoacoustic processing and overlay system 140 could obtain a measurement from the meter after each operation of a light source (or at such other convenient interval as is desired) and provide increased or decreased optical attenuation as appropriate based on such measurements. A meter operating in proximity to the optical window 106 may use internal reflection from the optical window to infer the total energy or power. A meter operating in a manner to measure light output from the light path 132 may use a dedicated fiber or plurality of fibers from the light path to infer the total energy or power. In an embodiment, the readings of a meter operating in a manner to measure or infer light output from the light path 132 can be compared to or monitored against the readings of a power meter 3904, 3914, as changes in the relative strength of these two measurements may be indicative of a maintenance or safety issue.

In an embodiment, calibration history is recorded for maintenance purposes. For example, using the calibration history can assist in knowing when or if an optical attenuator is nearing the end of its useful life, and thus requires replacement. Similarly, identifying sudden changes may indicate a system fault, e.g., burnt fibers in the light path or loss of alignment at the light output port.)

Figure 41:
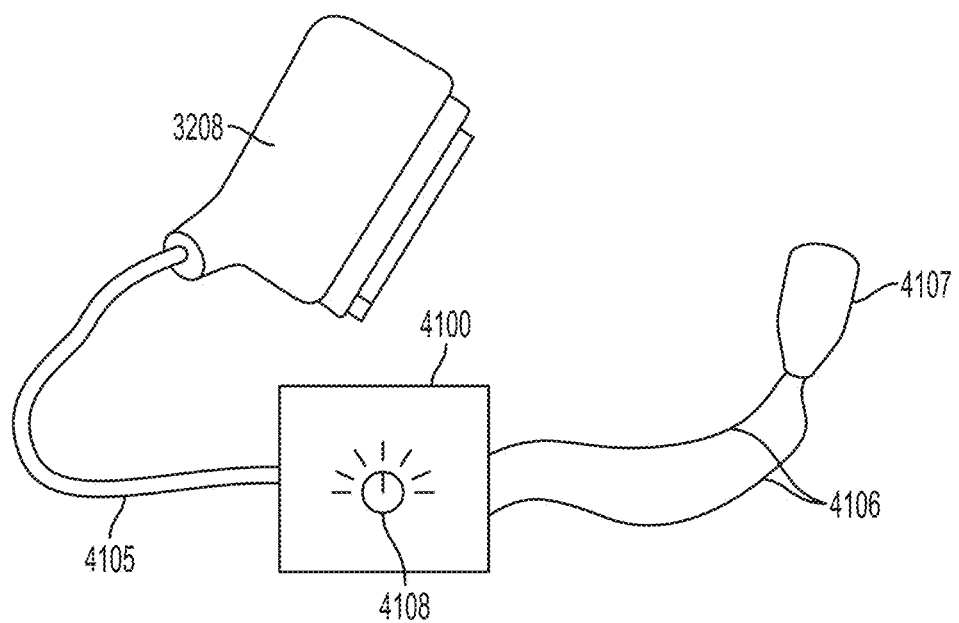
FIG. 41 is a schematic diagram illustrating an embodiment of a hardware testing system for use in testing certain portions of the optoacoustic system.

Turning now to FIG. 41 which shows a schematic diagram illustrating an embodiment of a hardware testing system for use in testing certain portions of the optoacoustic system. In an embodiment, the hardware testing system comprises a light pulse sensor 4107 adapted to sense a light pulse output from the light output port of the chassis of an optoacoustic system, e.g., cart 3200, and in response thereto to transmit signals over a plurality of conductors operatively connected to the optoacoustic processing and overlay system 140. In an embodiment, the plurality of conductors that are used by the hardware testing system are assembled into a bundle and terminated at a multi-pin connector having the same form factor as the multi-pin electrical connector for connecting the electrical path 108 and control line(s) 109 from the probe 102 to the system chassis. The hardware testing system also comprises a signal output unit 4100. In an embodiment, the signal output unit 4100 stores a plurality of signal sets and may output one of them in response to a triggering event. In an embodiment, the light pulse sensor 4107 can distinguish between light events occurring at different wavelengths, e.g., between a pulse from an ND:YAG laser and a pulse from an Alexandrite laser, and can send a corresponding trigger over one or more trigger wires 4106. In an embodiment, the light pulse sensor 4107 comprises two separate light sensors, one that sends a trigger over its trigger wire 4106 for the ND:YAG laser pulse, but not for the Alexandrite laser pulse, and the other that sends a trigger over its trigger wire 4106 for the Alexandrite laser pulse, but not for the ND:YAG laser pulse. In an embodiment, a single trigger wire carries the two separate distinguishable triggers. In an embodiment, the light pulse sensor may reside within signal output unit 4100, and a waveguide connected to the light output port may direct the light pulse to the light pulse sensor.

In an embodiment, at least some of the signal sets stored by the signal output unit 4100 may correspond to data that if received in the normal optoacoustic mode as a result of the triggering light source, would be resolved to a known optoacoustic image (e.g., an optoacoustic image of a specific mass in tissue). In an embodiment, the signal sets are in pairs, having one signal set respond to one light source and the other of the pair respond to the other light source, thereby providing information that, after one pulse of each light source would resolve to a known optoacoustic image and its associated parametric data—in other words, being essentially indistinguishable as viewed through the system from an actual live optoacoustic image, except that no probe 102 is used. The signal set should be transmitted in a manner that will not result in sampling error by the optoacoustic systems' ADC. In an embodiment, e.g., a digitally stored signal set should be transmitted at a rate that is at least twice the ADC sampling rate if it is asynchronous with the sampling. In an embodiment, signal set pairs can be created from sinograms comprising data actually received by the optoacoustic system in response to its operation on the tissue of a subject. In an embodiment, signal set pairs can be created by up-sampling sinograms comprising data actually received by the optoacoustic system in response to its operation on the tissue of a subject. The use of the optoacoustic device with these signal sets permits an external verification on the system's processing of known data, without variations that may be due to different tissue or other functional variations. Moreover, the use of the optoacoustic device with these signal sets controls for—by elimination—problems that may exist in the probe 102, light path 132 or electrical path 108.

In an embodiment, at least some of the signal sets stored by the signal output unit 4100 may correspond to data that could not reasonably result from operation of the optoacoustic system—hereinafter diagnostic signal sets. Examples of a diagnostic signal set may include a specific sine wave occurring on any one or group of the channels could not reasonably result from operation of the optoacoustic system. A near infinite number of other diagnostic signal sets can be created. In an embodiment, the optoacoustic processing and overlay system 140 can recognize one or more of these diagnostic signal sets, and in response thereto, perform one or more system diagnostics associated with the specific diagnostic signal set received.

In an embodiment, the signal output unit 4100 comprises a selector 4108. The selector 4108 can be used to select between signal sets, or between signal set pairs. The selector 4108 may be a mechanical switch, or implemented in software with an appropriate user interface, e.g., touchscreen. In an embodiment, a signal output unit has a variety of signal set pairs, at least some of the signal set pairs cause the optoacoustic system to display known images and parametric data in response to the operation of both light sources, and at least some of the signal set pairs cause the optoacoustic system to perform specific diagnostics in response to the operation of one or both of the light sources.

In an embodiment, the hardware testing system may also be adapted to receive and respond to ultrasound energy. In an embodiment, at least one ultrasound signal set reflecting a known ultrasound image is returned to the optoacoustic system in response to receiving ultrasound energy from the optoacoustic system via the multi-pin connector and electrical path 4105. In an embodiment, the an ultrasound signal set may correspond to one or more of the signal set pairs that are used to respond to optical pulses, and in this manner, the optoacoustic system can present overlaid images computed from the signals returned from the hardware testing system. In essence, the optoacoustic system need not recognize that the returned signals are coming from a testing system rather than from actual optoacoustic operation. Likewise, the selector 4108 on the signal output unit 4100 can be used to select between groups that include both a signal set pair which are sent in response to optical energy and an ultrasound signal set that is sent in response to ultrasound energy.

In an embodiment, at least some of the signal sets stored by the signal output unit 4100 may correspond to data that if received in the normal optoacoustic mode as a result of the triggering ultrasound energy, could be resolved to a known ultrasound image (e.g., by beamforming). The signal set should be transmitted in a manner that will not result in sampling error by the optoacoustic systems' ADC. In an embodiment, e.g., a digitally stored signal set should be transmitted at a rate that is at least twice the ADC sampling rate if it is asynchronous with the sampling. The use of the optoacoustic device with ultrasound signal sets permits an external verification on the system's processing of known data, without variations that may be due to different tissue or other functional variations. Moreover, the use of the optoacoustic device with these signal sets controls for—by elimination—problems that may exist in the ultrasound transducers or electrical path 108. In an embodiment, at least some of the diagnostic signal sets may be sent in response to ultrasound energy.

Figure 26:
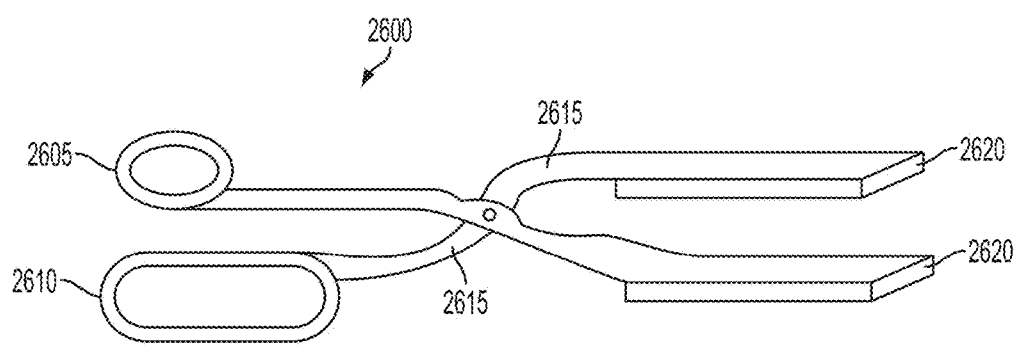
FIG. 26 is an illustrative example of a two-armed forceps-like probe having transducer arrays on its arms which can be physically positioned using finger grips.

In yet a further embodiment, linear or non-linear arrays may be physically separated from each other, but the data there-from may be recovered in response to the same optoacoustic event. Turning to FIG. 26, as an illustrative example, a two-armed (or more) forceps-like probe 2600 may contain linear or non-linear transducer arrays 2620 extending from arms 2615 that can be physically positioned using finger grips 2605, 2610 at the time of use, for example, on each side of a volume to be irradiated. In another example (not shown), two or more of the fingers of a glove could contain linear or non-linear arrays of transducers which can be manually positioned. In each case, although preferable, it is not necessary to know the orientation of one array with respect to the other in use. And while it is necessary that the optoacoustic event irradiate the volume sufficiently to permit the at least a portion of the transducer arrays coupled to the volume to detect an optoacoustic return signal, it is not necessary that the optoacoustic event is generated from the probe.

Figure 27:
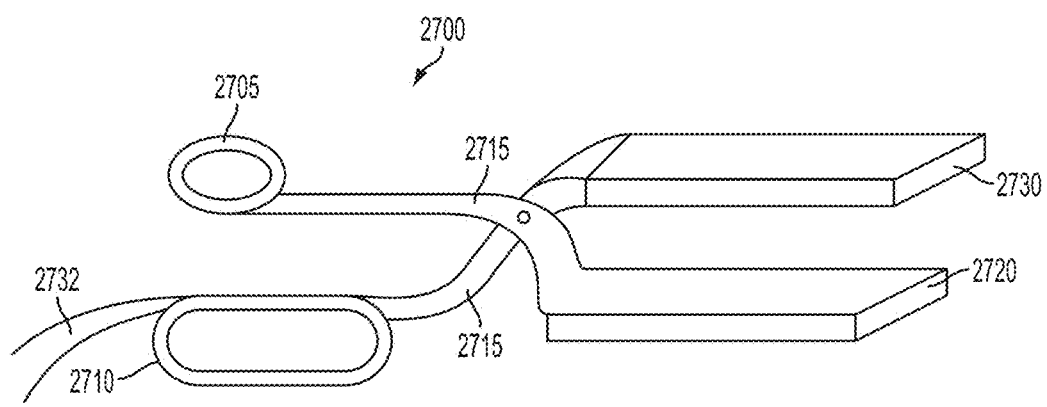
FIG. 27 is an illustrative example of a two-armed forceps-like probe having a transducer array on one arm and a light source on the other for use in forward transmission mode.

Turning to FIG. 27, a forceps-like probe 2700 for use in generating an optoacoustic image by acquiring data in a forward transmission mode is shown. The probe 2700 may contain a linear or non-linear transducer array 2720 situated across from an optical window 2730 that can project light output from a suitable light source such as a laser. The separation of the optical window from the transducer array mitigates numerous sources of noise that interfere with the sampling process of the optoacoustic return signal.

Each transducer in probe 102 may exhibit slight variations in operation. Accordingly, in an embodiment, once completed, probe 102 is tested in connection with one or more known test subjects such phantoms (see FIGS. 7-9) and the probe's measured response from the test subject is recorded. In an embodiment, the test subjects will produce a known optoacoustic return signal, either in response to a known optoacoustic event, or, by active control of the phantom. Variation from the known/expected optoacoustic return signal can be identified, and associated with each specific channel (e.g., transducer) comprising the variation. In this manner, the probe's own response characteristics—to the extent they may differ from probe to probe—can be accounted for, and may be normalized in later processing. Thus, if a particular transducer produces a signal that differs from the expected signal, that difference can be accounted for, and then later normalized.

In an embodiment, information associated with a probe's own response characteristics may be stored within the probe itself, and can be reported to the optoacoustic processing and overlay system 140 via power and control signal lines 109. In an alternative embodiment, information associated with a probe's own response characteristics may be stored outside the probe, and can be associated with a serial number or other identifier of the probe. The optoacoustic processing and overlay system 140 can obtain the probe response characteristics after identifying the probe for use. In an embodiment, the probe response characteristics may be stored in an network accessible location, either on a local disk, network, or on the Internet, and are made accessible to the optoacoustic processing and overlay system 140 via a connection (not shown) to that disk, network or the Internet. In an embodiment, the optoacoustic processing and overlay system 140 would obtain a unique identifier from the probe, and would thereafter query a database on the local device, network, or over the Internet, to obtain response characteristics for the probe associated with the unique identifier. Probe response characteristics may be recorded and stored at or near the time the probe is manufactured. In an embodiment, probe response characteristics may be updated by running a specialized test on the probe—the test having a known/expected response.

The probe identifier may be obtained by the optoacoustic processing and overlay system 140 after machine startup, but before engaging the light output. In an embodiment, the probe identifier is recorded on a bar code on the probe, and the bar code is scanned prior to the device causing light output. In an embodiment, the probe identifier is recorded on a computer-readable memory in the probe, and is queried by, or reported to the optoacoustic processing and overlay system 140 after startup, but prior to engaging the light output.

Because the probe identifier is known, the device can maintain statistics of probe usage. For example, in an embodiment, the device may maintain statistics of the operation of the probe in optoacoustic mode, including, e.g., the number and type of light output events that have occurred, and the number of ultrasound events that have occurred. Statistics can also be maintained concerning total light energy output from the probe (which may be deduced from an internal optical sensor, not shown). In an embodiment, the response characteristics of the probe and the probe statistics can be available to any device 100 on which the probe 102 is mounted. Thus, for example, such characteristics and statistics can be stored in a manner that they are accessible over the Internet. In an embodiment, a VPN is used for security on the Internet.

In an embodiment where the light path 132 is fixedly attached to the probe 102, the probe usage statistics may also be relevant to the fiber optics. For example, the fibers in the light path 132 may degrade with time and/or use resulting in some loss of transmission, e.g., broken or burned fibers. Accordingly, in an embodiment, the device can maintain statistics relevant to total light energy, peak light energy and the number of pulses passed through a light path 132. In an embodiment, sensors in the probe can detect information about the energy output of the light path, and sensors in the light subsystem 129 can detect information about the energy output of the light subsystem 129. By detecting variation in the sensors at the two ends over time, maintenance issues can be identified. For example, seeing a decrease at the probe-side sensors relative to the light subsystem-side sensors may indicate that the light path 132 is degrading and needs replacement. Moreover, a specific difference between the probe-side sensors and the light subsystem-side sensors may result in a condition that causes the device 100 to indicate that it is in need of maintenance. In an embodiment, where the difference is greater than a specific safety threshold, the device 100 may fail to continue to emit light events. In an embodiment, the information reported by these sensors may be stored with the usage statistics.

In an embodiment where the light path 132 is completely or partially detachable from the probe 102, the detachable portion of the light path may have its own unique identifier. Where the detachable portion of the light path has its own unique identifier, usage statistics that relate to that portion of the light path may be maintained in much the same manner as the usage statistics for the probe, but associated with the light path or portion.

In an embodiment, serialized components, that is, components such as a probe 102 or a light path 132 may comprise a memory for storing data concerning utilization of the serialized component. Log files can be written to such memory. In an embodiment the memory is affixed to the component and accessible to the optoacoustic processing and overlay system 140 via power and control signal lines 109. In an embodiment the memory is affixed to the component and accessible other software for reading and writing logs, which may execute on the optoacoustic processing and overlay system 140, via another electrical (e.g., conductive wires), optical (e.g., using a fiber optic waveguide or infrared transmission), radio frequency (e.g. Bluetooth or other radio frequency transmission), as would be apparent to one of skill in the art.

Figure 32:
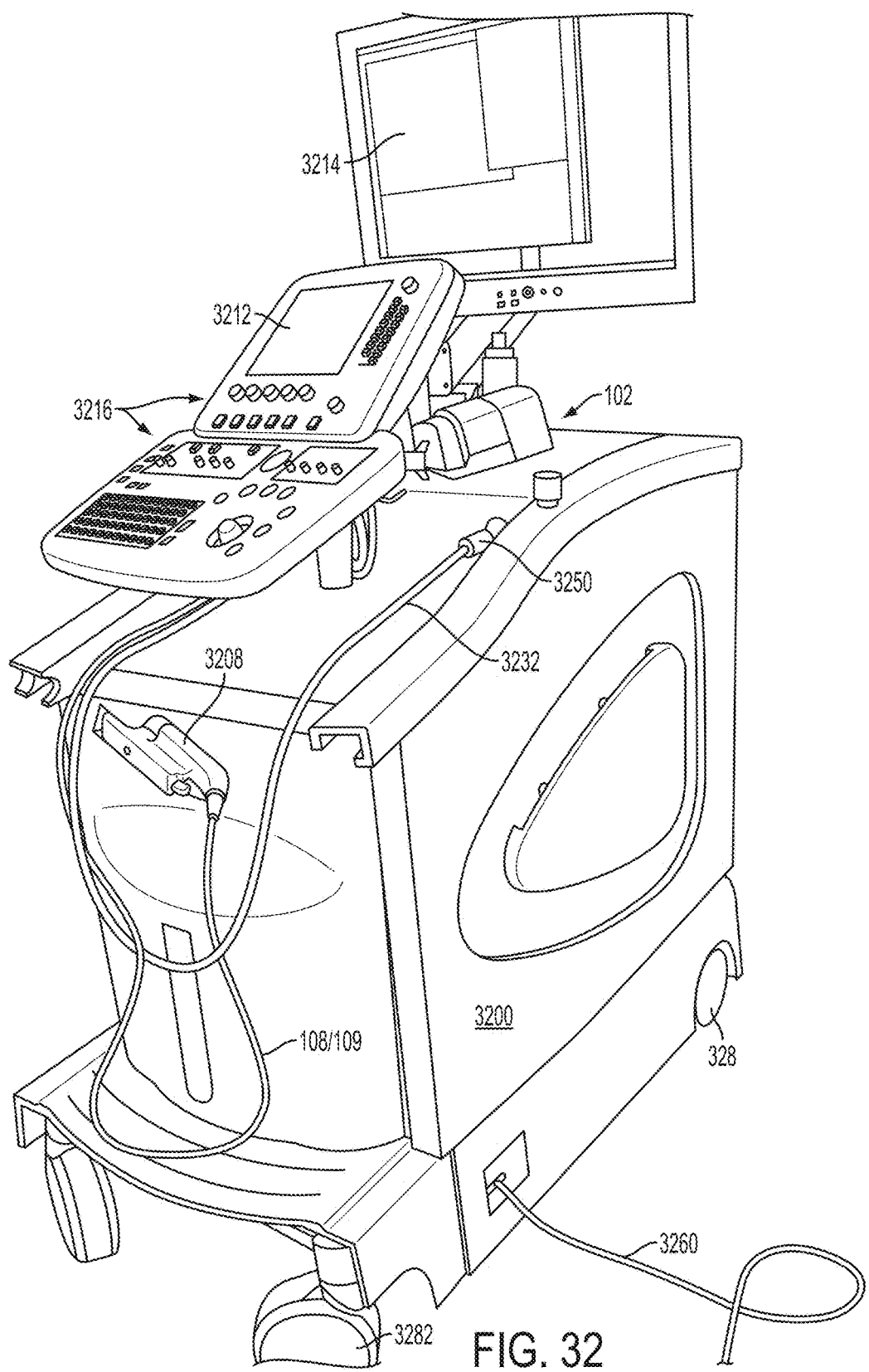
FIG. 32 shows an embodiment of a combined optoacoustic and ultrasound system with a probe (including a connected light path and connected combined electrical path and control lines).
Figure 33:
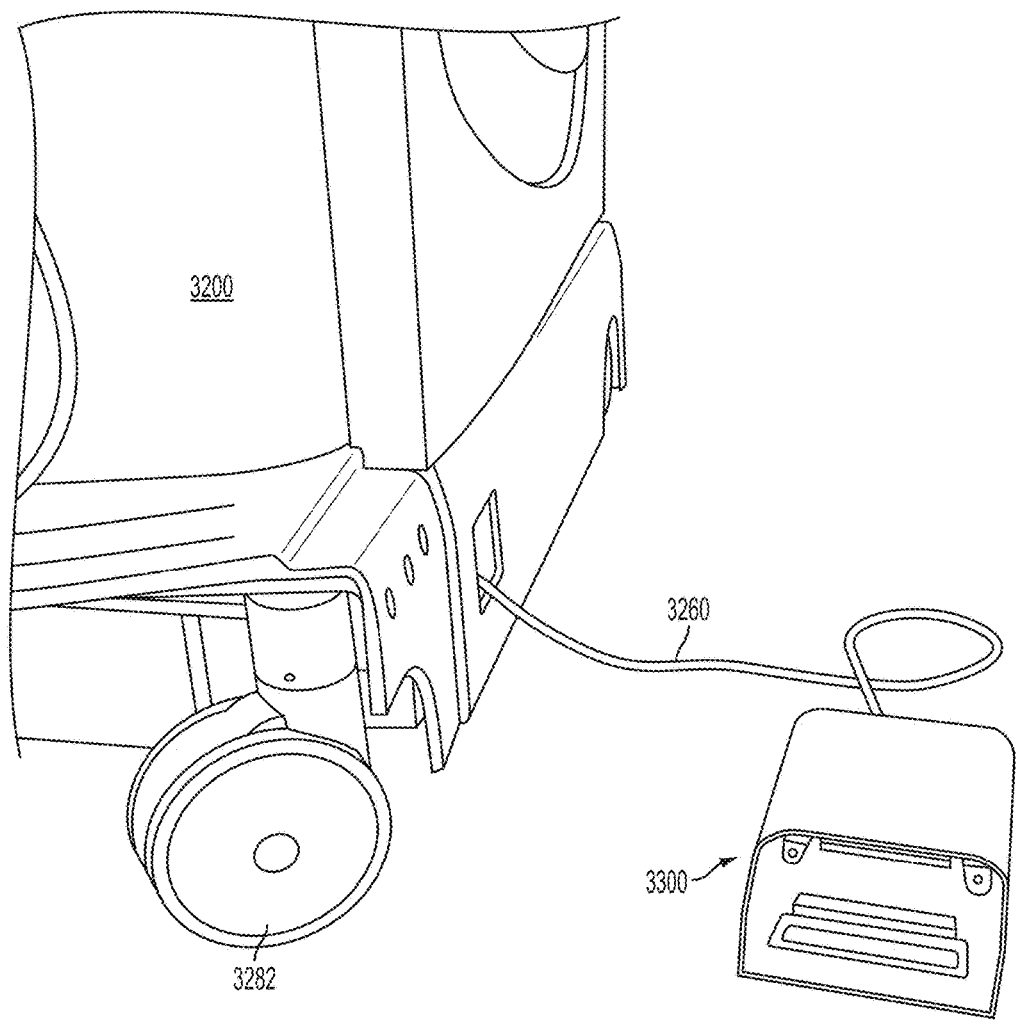
FIG. 33 shows an embodiment of a foot switch for use with a combined optoacoustic and ultrasound system.

Turning briefly to FIGS. 32 and 33, an embodiment of an optoacoustic system is implemented in the form of a cart 3200 having wheels 3282 for portability. The optoacoustic system comprises displays 3212, 3214 for some types of output to an operator, and user input devices 3216 including a keyboard and trackball as well as dials, buttons and switches provided for receiving input from an operator. Integrated electrical path and power and control signal lines 108/109 is connected to a probe 102 (largely obscured by a safety cover) on one end, and to the cart 3200 via a multi-pin connector 3208. Likewise, a sheathed light path 3232 is connected to probe 102 on one end, and to the cart 3200 via a fiber optic connector 3250. A foot switch 3300 is connected to the cart 3200 by a hardwired connection 3260, and provides for a hands-free means of engaging and disengaging the operation of the optoacoustic system.

In an embodiment, the probe component, consisting of the probe 102, the integrated electrical path 108/109 and its multi-pin connector 3208, the sheathed light path 3232 and its side of the fiber optic connector 3250, further comprises a memory (not shown). In an embodiment, the memory could be located within the probe 102 housing, within the multi-pin connector 3208 housing. In another embodiment, the memory could be located anywhere within or upon the probe component, or even external to the probe component. The memory is capable of storing data concerning utilization of the probe component. In an embodiment, a unique identifier is associated with the probe component, and may be stored in the memory, or in another memory associated with the probe component. In an embodiment, the unique identifier may be printed on the probe component, or placed on the probe component in the form of a bar code or other optically recognizable computer code. In an embodiment, the unique identifier may be stored in an RFID tag embedded in or associated with the probe component.

As the optoacoustic device operates, e.g., to create optoacoustic images, software which may operate in the optoacoustic processing and overlay system 140 or on another processor can accumulate information concerning the use and response of the probe component. Then, on command or at specific intervals, such information, or parts or summaries of that information may be written to the probe component memory as a log entry. In an embodiment, the specific intervals may comprise one or more of the following: each light event (i.e., pulse of light) traversing the light path 109; each time a pre-specified number of light events have traversed the light path; each interval during which the foot switch 3300 is used to operate the optoacoustic system; each patient session, which may be designated by the operator using the user input devices 3216; each power cycle of the optoacoustic system (i.e., from the time it is turned on until the time it is turned off); or upon elapsing of a time interval, such as, e.g., a second, a minute, or ten minutes.

In an embodiment, a log entry includes one or more of the following: time/date; unique identifier associated with the probe component; version information for any hardware or software comprising the optoacoustic system; counters, measurements or statistics relevant to total light energy, peak light energy and the number of pulses passed through a light path 132 during the interval, since a previously specified time (such as the last maintenance of the probe component) or since the probe component was placed into service; counters, measurements or statistics relevant to performance or characteristics of the light path or transmission loss from the cart's light output to the probe's light output; counters, measurements or statistics relevant to the performance or characteristics of the probe's ultrasound transducer array or its elements; or counters, measurements or statistics relevant to the performance or characteristics of any of the probe's other discrete components.

In an embodiment, previously written logs may be read and/or analyzed before normal operation of the optoacoustic system. The information read from previously written logs may be used to form a baseline for ensuring safe and efficient operation of the system, and to determine maintenance needs. In an embodiment, previously written logs may be read and analyzed as part of a maintenance function for the optoacoustic system. Significant changes in measurements or statistics relevant to performance or characteristics may indicate a need for maintenance. In an embodiment, significant changes in measurements or statistics relevant to performance or characteristics of the probe component or its constituent parts are reported to the system operator, or to maintenance personnel.

In an embodiment where a probe 102 is separable from a light path 132, electrical path 109 and/or power and control lines 108, any of these constituent parts may be separately serialized, and a separate memory may be maintained for the part itself, apart from the assembled probe component. For example, in an embodiment, a separable light path 132 comprises a unique identifier and memory separate from that of a probe component including an integrated electrical path 108/109 and its multi-pin connector 3208. In another example, in an embodiment, a separable light path 132, and electrical path 109 with its multi-pin connector 3208 each have a unique identifier and memory, separate from that of a probe component including power and control lines 108. In a similar manner, other components for which usage statistics or operational information is required may be separately serialized, and given their own unique identifier and memory.

One use of the device 100 is performing imaging examinations on humans for breast cancer detection. A clinical device 100 may be a multimodality system incorporating optoacoustic imaging capability and ultrasound imaging capability. An advantage of optoacoustic imaging over ultrasound imaging alone is that it provides very high contrast images which may provide for the direct functional evaluation of tumors.

Figure 28:
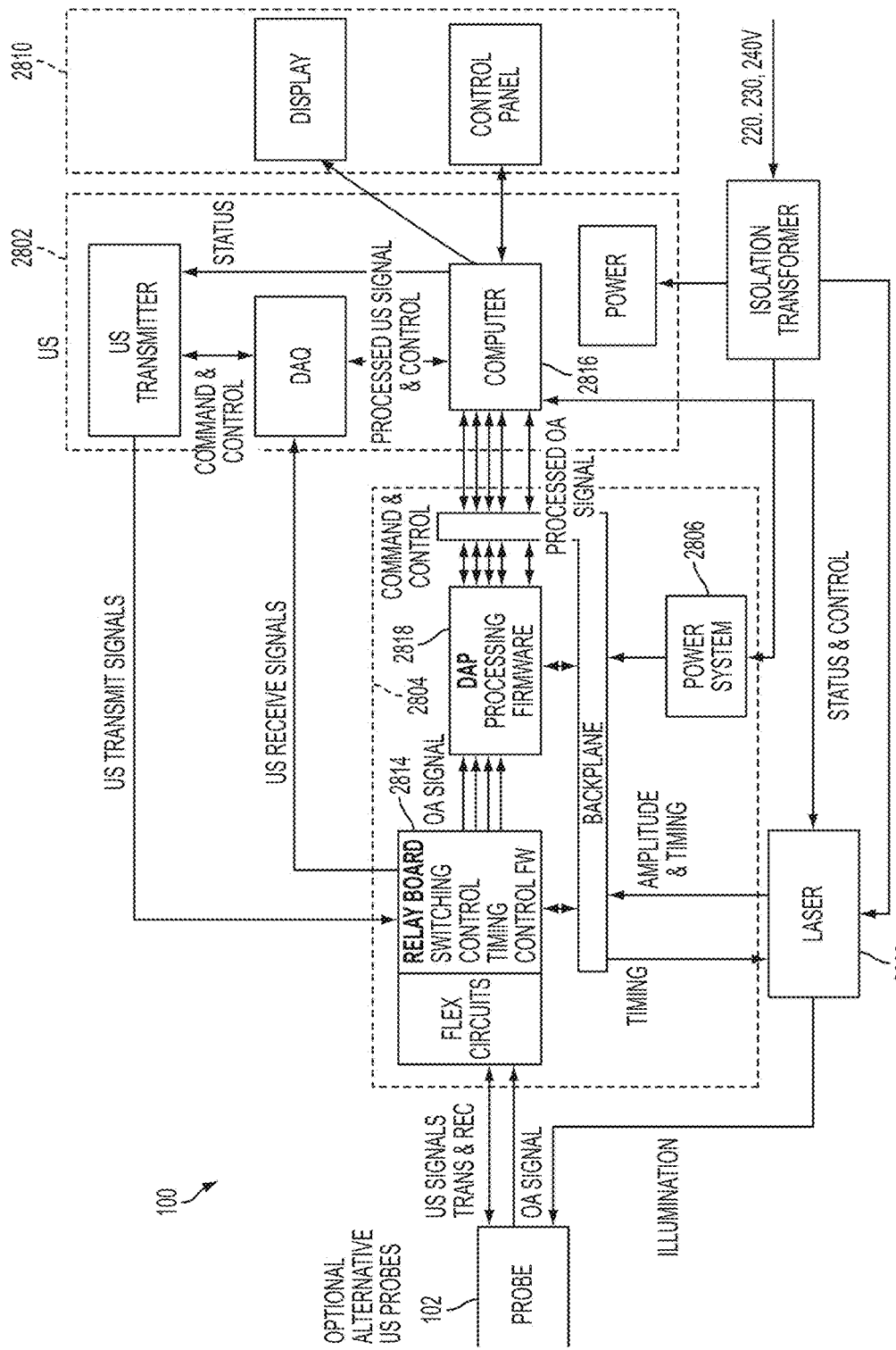
FIG. 28 is a schematic block diagram illustrating hardware components of the system.

A block diagram of an embodiment of the clinical system is shown in FIG. 28 that illustrates the interaction between major subsystems and the type of signals they represent. In an embodiment, device 100 provides an integrated system consisting of the following subsystems: ultrasound subsystem 2802, optoacoustic electronics subsystem 2804, power supply subsystem 2806, probe 102 and illumination/laser subsystem 2808, which may be housed in one console, and the control and display subsystem 2810 that can be attached to a console. The ultrasound subsystem 2802, the optoacoustic electronics subsystem 2804 and the control & display subsystem 2810 will be referred to hereinafter collectively as the UOA.

The ultrasound subsystem 2802 may be, e.g., a fully functional stand-alone ultrasound system. The ultrasound subsystem 2802 includes an ultrasound transmitter 2812 that outputs an ultrasound signal that is used to stimulate tissue. The ultrasound transmitter 2812 provides its output to a relay board 2814 in the optoacoustic electronics subsystem 2804 which switches the ultrasound signal to the probe 102. The ultrasound subsystem further includes a data acquisition board, or DAQ, that receives ultrasound signals from the relay board 2814 and processes them for transmission to and further processing by a computer 2816. The computer 2816 provides signal processing, user interface, and command and control functionality through software. The computer 2816 includes one or more computer-readable medium for storage of programming as well as data generated by the system. The computer-readable medium may be in the form of volatile and/or non-volatile RAM, ROM, solid state drive, optical media, magnetic media (e.g., hard drive) or other storage device. The memory and storage may be integrated into or physically separate from the remaining components of the computer. The computer 2816 further receives and transmits command and control signals to the DAQ for control of the data acquisition process and the ultrasound transmitter.

The optoacoustic electronics subsystem 284 includes a relay board 2814 that provides switching functionality for alternately switching received ultrasound signals to the DAQ of the ultrasound subsystem 2802 and received optoacoustic signals to a digital acquisition and processing (DAP) board 2818. The relay board 2814 includes firmware for both switching control and timing control. In an embodiment, flex circuits that form ultrasound transducers for both transmitting and receiving ultrasound signals are integrated into the relay board 2814. The DAP 2818 receives and processes the OA signal and outputs processed OA signals to the computer 2816. The computer 2816 provides command and control signals via a backplane to the DAP 2818 and the relay board 2814, and provides timing signals via the backplane to the illumination/laser subsystem 2808.

Figure 29:
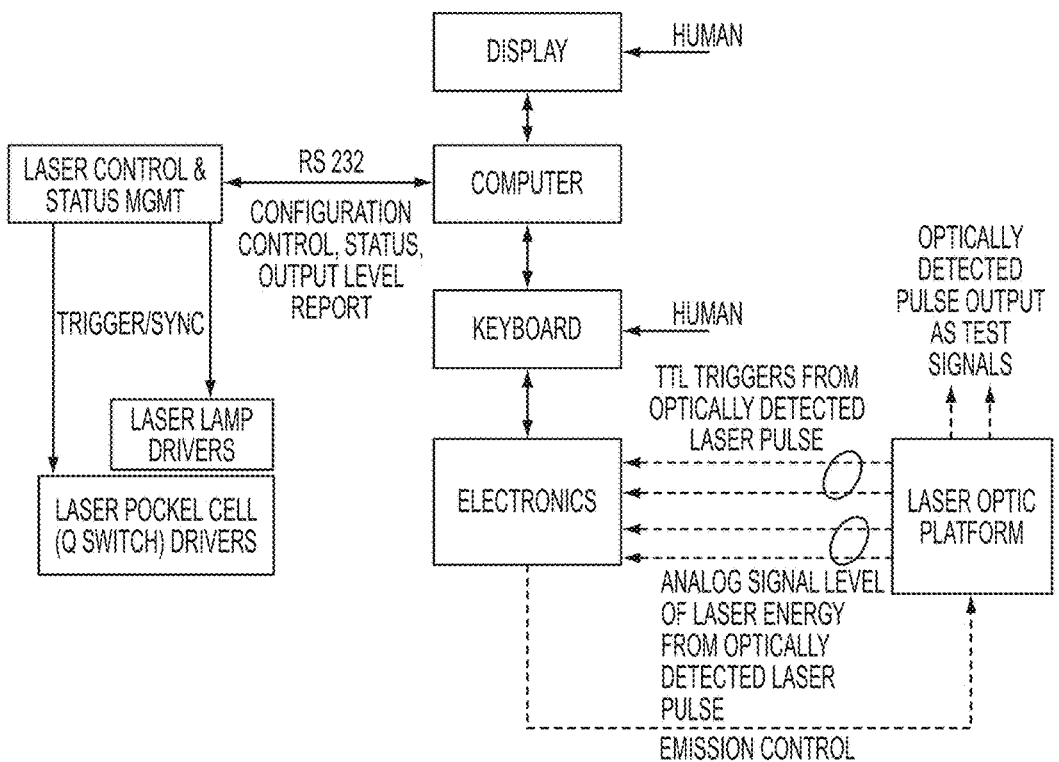
FIG. 29 is a block diagram illustrating the illumination subsystem and control interfaces of the system in accordance with an embodiment thereof.

FIG. 29 shows a block diagram illustrating the illumination subsystem 2808 and control interfaces of the system 100 in accordance with an embodiment thereof. Triggers are TTL positive for activation. Some of illumination subsystem external control and interfaces include interlocks, photo diode based outputs (6), grounds, RS232, power and optical port.

Figure 30:
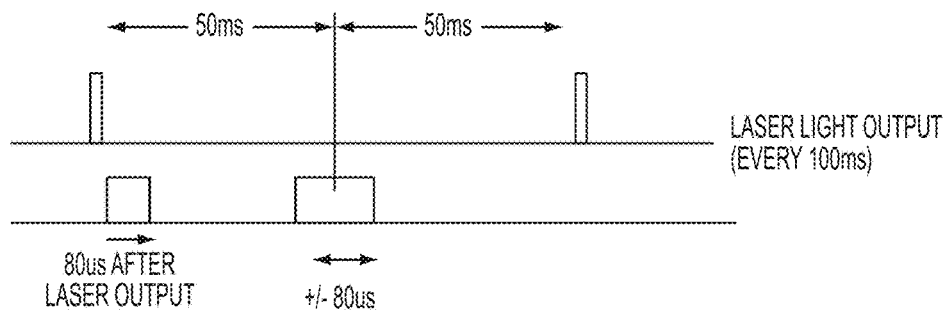
FIG. 30 is a pulse diagram illustrating a radiation restriction in the system.

FIG. 30 shows a pulse diagram illustrating a radiation restriction in the system 100.

In an embodiment the device 100 uses a hand held probe 102 including an array of transducers and an opening through which laser light can pass. In use, an operator manipulates controls and views the display as they move the probe 102 over the body or other volume to identify critical image characteristics. In an ultrasound mode the laser light source has no emission. In an optoacoustic mode the laser emits light according to specific preconfigured and/or operator set up parameters. In an embodiment the hand held probe may be manipulated in a similar fashion to the manipulation of an ultrasound probe. In an embodiment, the device 100 includes an operator selectable operational mode whereby an optoacoustic mode and ultrasound mode are interlaced.

In an embodiment the clinical device 100 includes an illumination source 1408 capable of providing two output wavelengths according to specific preconfigured and/or operator set up parameters. In an embodiment, the operator will be able to select either an Nd:YAG laser output at 1064 nm or an Alexandrite laser output at 757 nm, or to select the use of both laser outputs. When two wavelengths are selected, the laser subsystem, according to specific preconfigured and/or operator set up parameters, may alternate between the two wavelengths one after the other, or in other preconfigured or operator set up cycles. In an embodiment, laser operating parameters such as energy, pulse rate, and wavelength will be operator selectable, and subject, however, to specific preconfigured parameters.

In an embodiment, communication of the laser energy will be via a fiber optic bundle with a detachable mechanism. The detachable mechanism for interfacing the laser output to the fiber optic bundle includes a safety interlock/laser shutdown if disconnected. In an embodiment, the laser subsystem components include heat exchangers; pulse drivers; direct laser controls; laser power supplies; laser power management; laser head(s), cavities and optics; control and drive electronics; electronic interface ports; and a laser output port.

In an embodiment, the laser is completely controlled by the UOA control system. The clinical device may be powered ON/OFF by the use of a low current key switch located near the user control panel. Through the action of this low current switch, closure will cause the secondary output of an isolation transformer's 230 VAC to be applied to each of the subsystems, including the laser. Opening this switch removes power from each of the subsystems.

In an embodiment, the laser subsystem consists of a Q-Switched Nd:YAG laser and an Alexandrite Q-Switched laser with a common concentric output connector designed to have a fiber optic bundle attached. It contains all necessary electronics, cooling, power management, optics, and connections necessary to meet operational requirements.

As discussed above, according to specific preconfigured parameters, in an embodiment the operator will be able to select the clinical device 100 laser light output from the Nd:YAG (1064 nm) only or select laser light output from the Alexandrite (757 nm) only or alternating the laser light output of both wavelengths. In an embodiment, selection will be accomplished via RS232 commands from the UOA.

In an embodiment, the time between wavelength changes will preferably be less than 0.05 seconds, and the time delay to initiate the response to a wavelength change shall be less than 0.01 seconds (which is included in the 0.05 seconds to change wavelengths). This would allow a command to be 0.01 seconds before the actual wavelength change is made. These timing parameters will permit the device 100 to be capable of alternating the wavelength output at a rate up to 20 times per second so as to interleave each separate wavelength operating at 10 pulses per second.

In an embodiment, the laser output pulse width for the Nd:YAG laser is approximately 7 ns but as long as practical, and in any case should be less than 25 ns for the best pulse stability. The laser output pulse width for the Alexandrite laser may be less than approximately 60 ns and more preferably less than approximately 50 ns. In an embodiment, no satellite pulse (a secondary laser pulse occurring shortly after the primary pulse) is allowed for either laser. As discussed above, in an embodiment, one or more light sources other than the Nd:YAG or Alexandrite lasers may be employed. Thus, for example, in an embodiment, one quickly tunable laser could be deployed to create two or more separate wavelengths in sequential light pulses during operation of the device.

The pulse rate may be operator selectable. In an embodiment, the pulse rate is operator selectable from 2, 5, 10 PPS for each wavelength, and when interlace is selected the pulse rate will double to 4, 10, 20 PPS. In an embodiment, the maximum time to select between pulse rates will be 10 seconds. The pulse rate for each laser wavelength will be independent of single wavelength or interlace operation.

In an embodiment, the energy per pulse (laser output) that will be directed into the fiber bundle will be variable between 25 mJ to 250 mJ in a minimum of 15 steps for each wavelength. In an embodiment, the control will be via the RS232 port. Energy per pulse will be independently adjustable for each wavelength. In an embodiment, the maximum time for the output energy to be affected post selection will be approximately 2 seconds.

It is desirable to minimize the unintended pulse-to-pulse variation. Accordingly, in an embodiment, the (uncontrolled) pulse-to-pulse energy variation will be less than 3% RMS from the output of either laser after 50 laser pulses.

In an embodiment, a measure of the output energy of each pulse (both wavelengths) will be made and will be communicated with an analog output pulse to the UOA. In an embodiment, the pulse will be a stretched representation of the optically detected pulse. The amplitude will be a representation of the energy of each output pulse. In an embodiment, the amplitude will be 0 to 5 V peak with 5V peak equal to the maximum energy expected. In an embodiment, the driver for these signals may be DC coupled throughout and drive a 1000 ohm termination with 0 to 5 Volts. In an embodiment, the pulse may be peak detected and stretched by at least 200 ns but the peak must occur before 2 us to permit, that at least two samples are captures, when employing a 6.8 MHz anti aliasing filter at 20 M samples/sec. In an embodiment, a 20 M samples/sec sampling unit is located in the UOA electronics. Interface connectors may use BNC on the laser subsystem. The connector output can be provided on either a single BNC connector or a pair of BNC connectors, In an embodiment, each rising edge of the laser pulses will be detected and communicated to the UOA in a TTL format over a coax cable with a BNC connector. In an embodiment, separate signals, coax cables and connector may be used for each additional wavelength. In an embodiment, the signal will be a positive going TTL signal that will have a duration of at least 1 microsecond. In an embodiment, the UOA termination will be AC coupled into 50 Ohms.

In an embodiment, there will be a sync pulse jitter test. The test may use an oscilloscope with the trigger using the TTL sync pulse. The input will be the output of a wideband optical test detector that is sampling the output of the laser pulse. The RMS jitter of the optical detected waveform is preferably less than about 6 ns.

In an embodiment, each detected optical pulse for each wavelength is made available at two test connectors external to the laser system. In an embodiment, the test connectors will be BNC connectors, and the drivers for the signals should be able to drive a 50 Ohm scope load. These test signals may be used to support system testing and evaluation. In an embodiment, there is a separate output for each wavelength from the sync detectors to an analog driver for a 50 ohms output load—the amplitude can be a percentage of the actual pulse out of the optical detector.

In an embodiment, a fiber optical bundle interfaces to the output of the combined laser output port. In an embodiment, the optical output will be horizontal at the front-right of the optical unit. A quick disconnect connector may to be used to connect the fiber bundle to the laser output port.

In an embodiment, the mount for the fiber cable provides self-alignment to the laser energy output. In an embodiment, a ceramic disk with a 6 mm centered aperture will be installed at the output of the fiber optic mount to minimize damage to the fiber bundle. In an embodiment, a micro switch is engaged when the fiber bundle has made connection. The micro switch functions as a safety interlock and is used to ensure that the laser cannot be fired unless the micro switch is closed.

In an embodiment, the laser output beam shape will be circular. In an embodiment, the beam profile will be flattened to approximate a top hat shape to ensure homogeneous illumination of the optical fiber. In an embodiment, the beam width will be 6 mm in diameter at the 10% level. For safety and consistency, the beam shape should not substantially deviate from this shape; in an embodiment, the beam shape does not deviate from this shape by more than 3% RMS over time and from pulse-to-pulse.

In an embodiment, the output of each laser will be approximately 6.25 mm onto the fiber optics, and the beam should not have hot spot(s), including after extensive use. In an embodiment, both beam shapes (for the Nd:YAG and the Alexandrite) will be equal in diameter to within 5% of the 6 mm diameter. For the purposes herein, a hot spot is defined as a 15% variation in energy density over any 2 mm segment of the beam cross section. In an embodiment, the laser beam must be aimed at the output connector such that 98% of the output energy is transmitted into the fiber cable. In an embodiment, a mechanism is provided for achieving laser beam alignment in the field.

In an embodiment, the laser spectral width will be less than 30 nm at the FWHM (Full Wave Half Maximum) level, and the spectral characteristics are preferably stable and do not vary from pulse-to-pulse by more than 3 nm RMS.

In an embodiment, the major operating modes of the clinical device 100 are:
  a. Off mode: where all power has been turned off and no current should be flowing within the laser subsystem. This can be accomplished by turning OFF the main circuit breaker or by turning the power key switch to off. In this case power may still be connected to the isolation transformer.
  b. Sleep mode or ultrasound only mode: Almost all power is shut down for all operations but with sufficient energy to place the laser subsystem into the "on" mode. For example only the laser control unit is power up.
  c. On Mode: Warm Up Period: Places all necessary power ON to allow the laser to be warmed up. The laser will measure and report to the UOA the laser head temperature. Once the laser head temperature has reached a predetermined value the UOA will place the laser system into the "standby mode". In an embodiment, the laser subsystem will not be allowed to go into the "standby mode" until sufficient warm up has occurred.
  d. Standby Mode: Allows the laser to be placed into the "ready mode" quickly from a Ready Mode command.
  e. Ready Mode: Places the laser into the emission mode but the shutter remains closed. In an embodiment, the emission mode can be started a pre-specified interval, e.g., within 1 second or after 20 pulses, after the emission mode command.
  f. Emission mode: Provides specified output energy for as long as this mode is commanded. In this mode the laser provides for its lamp sync and driver, the Q-Switch delay and driver and the pulse rate as determined from external command. The wavelength output will be as determined from external command.

In an embodiment, the laser subsystem will have the capability to go from any operating mode to any lower operating mode directly: "off" being the lowest operating mode and "emission" being the highest operating mode. For example, in an embodiment, the operator will be able to go from the emission mode to the standby, on, sleep or off mode directly. Preferably, the operator will not be able to go from off to emission directly without first going through the modes between.

In an embodiment, the laser will operate with internal synchronism and the UOA will derive its synchronism from the laser via it sync signal outputs. In an embodiment, time sensitive interfaces (synchronism signals) will be interfaced using TTL signals, while computer interface information will be via RS232 interface. In an embodiment, the wavelength selection mode (single YAG, single ALEX, interlace mode) will be selected via RS232 and the control unit will produce the internal commands in interlace or single mode with the right timing. In an embodiment, electronics will validate the present laser emission thru energy photodiode and/or sync pulses and/or Q-Switch TTL sync outputs.

Figure 31:
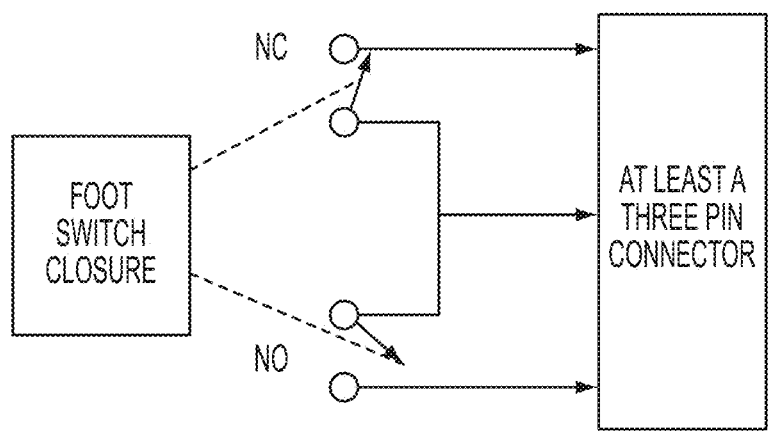
FIG. 31 is a schematic block diagram of one embodiment of a foot switch closure.

In an embodiment, a shutter will open to allow laser light to be emitted (defined as the emission mode). In an embodiment, the shutter will remain closed unless two conditions exist—a foot switch closure and an RS-232 command. But, as long as the foot switch remains closed and an RS232 command exists the emission will exist. Both the foot switch closure and the RS232 must both be present to achieve emissions. The foot switch closure may provide within the switch a double contact, NC and NO using a three-wire interface as shown in FIG. 31. When either or both the foot switch and RS232 command is changed emission will cease to exist via a closure of the shutter, preferably within about 0.5 seconds. The laser subsystem may remain in the Ready mode until commanded otherwise.

In an embodiment, the laser operating system shall keep a non-volatile time-stamped record of error codes, of lamp shots, and operational events, for the purpose of accountability and troubleshooting. The non-volatile record may be readable, and possibly erasable, via RS-232 commands. In an embodiment, erasure of the non-volatile record requires a password or other access device. In an embodiment, a log consisting of not less than 50 events may be sufficient. In an embodiment, the UOA can poll the number of messages and read them.

In an embodiment, the laser subsystem will monitor the temperature of the lasers heads and report each to the UOA on a periodic basis, permitting the UOA to avoid instructing the laser to go into the Ready Mode unless the laser head has reached an acceptable temperature, and automatically placing the laser subsystem into the off mode if the temperature is unexpectedly outside of its appropriate operating range.

In an embodiment, wires to pockels cell and all internal high radiated signals should be shielded. To mitigate electromagnetic radiation during the imaging time of the clinical device 100, the lamp driver recharging should be delayed by more than 70 microseconds after the Q-Switch. See FIG. 16. During recharge the electromagnetic radiation must be sufficiently low so as not to interfere with ultrasound or OA imaging.

In an alternative embodiment, a control signal can be used to suppress power supply switching noise during OA data acquisition, and also during US data acquisition. For example, a TTL, trigger from within the laser circuitry may be generated such that a logic HIGH would cause the internal switching power supply to stop its internal oscillator that drives the switching PWM (pulse width modulation) circuitry that powers the flash lamp circuits, and/or any other switching operation, and when at a logic LOW would resume normal operation. In an embodiment, this control may not be asserted for more than certain ON time (e.g., 100 microseconds), and to not exceed a certain duty cycle. In an embodiment, a trigger signal could be negative logic wherein a logic LOW would stop the oscillator and a logic HIGH would allow it to resume. In an embodiment, the trigger signal can be applied to one or more other switching power supplies within the laser and/or elsewhere in the OA system, which may suppress electrical noise from the power supply during the non-oscillatory interval. In an embodiment, the data acquisition period should be within the interval during which the one or more switching power supplies have the switching circuitry inhibited. Even where a switching power supply is of a type that is not PWM controlled, the trigger can in any event be used to inhibit operation of the internal oscillator used to control the switching functions.

In an embodiment, the user interface console will contain a "Panic Button" to place the laser into the off mode by removing all AC power to the laser system.

In an embodiment, the laser subsystem and all other subsystems will operate from 230+1−10% VAC, single phases, 60/50+/−3 Hz, 4000 VA max. In an embodiment, the mains voltage may be isolated from the various subsystems by the use of an isolation transformer such as part number 925.1202, manufactured by www.toroids.com, or equivalent, and protected with a switchable AC circuit breaker on the primary side. The secondary side of this transformer will provide AC power to each of the four (4) AC powered subsystems through a soft start isolation transformer to avoid inrush current problems. In an embodiment, the laser subsystem is adapted to accommodate a sudden loss of input power or brownout without causing damage, requiring realignment, tuning or causing unsafe operations.

In an embodiment, all operating system controls may be provided via UOA electronics.

The present system and methods are described above with reference to block diagrams and operational illustrations of methods and devices comprising an optoacoustic probe. It is understood that each block of the block diagrams or operational illustrations, and combinations of blocks in the block diagrams or operational illustrations, may be implemented by means of analog or digital hardware and computer program instructions. These computer program instructions may be provided to a processor of a general purpose computer, special purpose computer, ASIC, FPGA or other programmable data processing apparatus, such that the instructions, which execute via the processor of the computer or other programmable data processing apparatus, implements the functions/acts specified in the block diagrams or operational block or blocks. In some alternate implementations, the functions/acts noted in the blocks may occur out of the order noted in the operational illustrations. For example, two blocks shown in succession may in fact be executed substantially concurrently or the blocks may sometimes be executed in the reverse order, depending upon the functionality/acts involved.

As used in this description and in the following claims, "a" or "an" means "at least one" or "one or more" unless otherwise indicated. In addition, the singular forms "a", "an", and "the" include plural referents unless the content clearly dictates otherwise. Thus, for example, reference to a composition containing "a compound" includes a mixture of two or more compounds.

As used in this specification and the appended claims, the term "or" is generally employed in its sense including "and/or" unless the content clearly dictates otherwise.

The recitation herein of numerical ranges by endpoints includes all numbers subsumed within that range (e.g. 1 to 5 includes 1, 1.5, 2, 2.75, 3, 3.80, 4, and 5).

Unless otherwise indicated, all numbers expressing quantities of ingredients, measurement of properties and so forth used in the specification and claims are to be understood as being modified in all instances by the term "about," unless the context clearly dictates otherwise. Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the scope of the claims, each numerical parameter should at least be construed in light of the number of reported significant digits and by applying ordinary rounding techniques. Any numerical value, however, inherently contains certain errors necessarily resulting from the standard deviations found in their respective testing measurements.

Those skilled in the art will recognize that the methods and systems of the present disclosure may be implemented in many manners and as such are not to be limited by the foregoing exemplary embodiments and examples. In other words, functional elements being performed by single or multiple components, in various combinations of hardware and software or firmware, and individual functions, may be distributed among software applications at either the client level or server level or both. In this regard, any number of the features of the different embodiments described herein may be combined into single or multiple embodiments, and alternate embodiments having fewer than, or more than, all of the features described herein are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, as well as those variations and modifications that may be made to the hardware or software or firmware components described herein as would be understood by those skilled in the art now and hereafter.

Furthermore, the embodiments of methods presented and described as flowcharts in this disclosure are provided by way of example in order to provide a more complete understanding of the technology. The disclosed methods are not limited to the operations and logical flow presented herein. Alternative embodiments are contemplated in which the order of the various operations is altered and in which sub-operations described as being part of a larger operation are performed independently.

Various modifications and alterations to the invention will become apparent to those skilled in the art without departing from the scope and spirit of this invention. It should be understood that the invention is not intended to be unduly limited by the specific embodiments and examples set forth herein, and that such embodiments and examples are presented merely to illustrate the invention, with the scope of the invention intended to be limited only by the claims attached hereto. Thus, while the invention has been particularly shown and described with reference to a preferred embodiment thereof, it will be understood by those skilled in the art that various changes in form and details may be made therein without departing from the spirit and scope of the invention.

What is claimed is:

1. An optoacoustic imaging system for imaging tissue comprising:
    a first light source capable of generating pulses of light at a first wavelength, and a second light source capable of generating pulses of light at a second wavelength;
    a handheld probe having a distal end and a proximal end, the handheld probe comprising an optical window located at the distal end of the handheld probe, the optical window being in optical communication with the first light source and the second light source and capable to transmit the pulses of light to the tissue, and an ultrasound transducer array having an active end located at the distal end of the handheld probe, the ultrasound transducer array capable of receiving an acoustic return signal from the tissue;
    a computing subsystem for generating images from said acoustic return signal, said computing subsystem being configured to process and store a plurality of frames in a buffer, each frame of the plurality of frames comprising data including a sinogram; and an ultrasound image;
    a display for displaying the images generated by the computing subsystem; and
    a user input device;
    the optoacoustic imaging system being configured to switch, upon actuation of a playback mode via the user input device, from a live mode wherein images from the acoustic return signal are displayed in real time to the playback mode wherein at least one image is generated from at least one of the plurality of frames;
    the optoacoustic imaging system further being configured such that at least one parameter affecting the processing of said plurality of frames into an output image displayed upon said display can be enabled during the playback mode such that the output image displayed varies from an image generated from the frame when the optoacoustic imaging system is not in the playback mode;
    wherein, when the parameter is enabled, the output image displayed in playback mode is generated using interframe persistent artifact reduction processing;
    wherein the interframe persistent artifact reduction processing is configured to be performed on each of the plurality of frames generated from the pulses of light for each of the first wavelength and the second wavelength; and
    wherein each of the plurality of frames is grouped into groups, each group including one or more prior frames and one or more future frames of the same total light-energy.

2. The optoacoustic imaging system of claim 1, wherein the at least one parameter affecting processing of said plurality of frames into the output image comprises a parameter that engages a filter.

3. The optoacoustic imaging system of claim 1, wherein the at least one parameter affecting processing of said plurality of frames into the output image comprises a parameter that tunes a filter.

4. The optoacoustic imaging system of claim 1, wherein the at least one parameter affecting processing of said plurality of frames into the output image comprises a region-of-interest depth parameter.

5. The optoacoustic imaging system of claim 1, wherein the at least one parameter affecting processing of said plurality of frames into the output image comprises a parameter that causes a different reconstruction algorithm to be used to produce the output image than that which was used to produce a live output image.

6. The optoacoustic imaging system of claim 1, wherein the at least one parameter affecting processing of said plurality of frames into the output image comprises a parameter that causes an engaging of a filter tuned to highlight different physiological features than that which was used to produce a live output image.

7. The optoacoustic imaging system of claim 1, wherein the user input device comprises a pause button.

8. The optoacoustic imaging system of claim 1, wherein the user input device comprises an x-seconds-back button.

9. The optoacoustic imaging system of claim 1, wherein the playback mode comprises a six-image display mode.

10. A method of recording and playing back data associated with the operation of a combined ultrasound and optoacoustic imaging system, the method comprising the steps of:
    generating a light event comprising of pulses of light at least two wavelengths;

processing and storing a plurality of frames in a buffer, each frame of the plurality of frames comprising data including;
a sinogram; and
an ultrasound image;
switching upon activation of a playback mode via a user input device, from a live mode wherein images generated from an acoustic return signal are displayed in real time to the playback mode wherein at least one image is generated from at least one of the plurality of frames;
causing, in response to receipt of an input via the user input device, at least one parameter affecting the processing of said plurality of frames into an output image displayed upon a display to be enabled during the playback mode such that the output image displayed varies from an image generated from the frame when the optoacoustic imaging system was in the live mode;
wherein, when the parameter is enabled, the output image displayed in playback mode is generated using interframe persistent artifact reduction processing;
wherein the interframe persistent artifact reduction processing is configured to be performed on each of the plurality of frames generated from the pulses of light for each of the at least two wavelengths; and
wherein each of the plurality of frames is grouped into groups, each group including one or more prior frames and one or more future frames of the same total light-energy.

11. The method of claim 10, further comprising receiving an input via a user input device that selects a series of frames for playback in the playback mode and, in response thereto, plays back the selected frames from the buffer in a loop while allowing the at least one parameter affecting processing of said plurality of frames to be changed.

12. A non-transitory computer readable medium for controlling an optoacoustic imaging system, comprising data that, when accessed by a machine, cause the machine to perform operations comprising:
generating a light event comprising of pulses of light at least two wavelengths;
generating a plurality of sinograms comprising a sampled optoacoustic return signal each responsive to a light event;
generating one or more ultrasound images;
processing and storing a plurality of frames in a buffer, each frame of the plurality of frames comprising data including:
a sinogram; and
an ultrasound image;
switching upon activation of a playback mode via a user input device, from a live mode wherein images generated from an acoustic return signal are displayed in real time to the playback mode wherein at least one image is generated from at least one of the plurality of frames;
causing, in response to receipt of an input via the user input device, at least one parameter affecting the processing of said plurality of frames into an output image displayed upon a display to be enabled during the playback mode such that the output image displayed varies from an image generated from the frame when the optoacoustic imaging system was in the live mode;
wherein, when the parameter is enabled, the output image displayed in playback mode is generated using interframe persistent artifact reduction processing;
wherein the interframe persistent artifact reduction processing is configured to be performed on each of the plurality of frames generated from the pulses of light for each of the at least two wavelengths; and
wherein each of the plurality of frames is grouped into groups, each group including one or more prior frames and one or more future frames of the same total light-energy.

13. An optoacoustic imaging system comprising:
a first light source capable of generating pulses of light at a first wavelength, and a second light source capable of generating pulses of light at a second wavelength;
a handheld probe having a distal end and a proximal end, the handheld probe comprising an optical window located at the distal end of the handheld probe, the optical window being in optical communication with the first light source and the second light source and capable to transmit the pulses of light to the tissue, and an ultrasound transducer array having an active end located at the distal end of the handheld probe, the ultrasound transducer array capable of receiving an acoustic return signal from the tissue;
a computing subsystem for generating images from said acoustic return signal, said computing subsystem being configured to process and store a plurality of frames in a buffer, each frame of the plurality of frames comprising data including a sinogram; and an ultrasound image;
a display for displaying the images generated by the computing subsystem; and
a user input device;
the optoacoustic imaging system being configured, to switch upon actuation of a playback mode via the user input device, from a live mode wherein images from the acoustic return signal are displayed in real time to the playback mode wherein at least one image is generated from at least one of the plurality of frames
the optoacoustic imaging system further being configured such that at least one parameter affecting the processing of said plurality of frames into an output image displayed upon said display can be enabled during the playback mode such that the output image displayed varies from an image generated from the frame when the optoacoustic imaging system is not in the playback mode:
wherein, when the parameter is enabled, the output image displayed in playback mode is generated using interframe persistent artifact reduction processing;
wherein the interframe persistent artifact reduction processing is configured to be performed on each of the plurality of frames generated from the pulses of light for each of the first wavelengths and the second wavelength; and
wherein each of the plurality of frames is grouped into groups, each group including one or more prior frames and one or more future frames of the same total light-energy;
the optoacoustic imaging system further being configured to store in the buffer:
a plurality of frames used to generate a first real-time image among the plurality of the images displayed in real time; and,
at least one other frame used to generate at least one playback mode image, the at least one other frame being a future frame received and stored after a real-time display of the first real-time image.

* * * * *